United States Patent [19]
Suzuki et al.

[11] Patent Number: 6,139,797
[45] Date of Patent: Oct. 31, 2000

[54] IMMUNOASSAY APPARATUS

[75] Inventors: Kazuyasu Suzuki; Mitsuhiro Negami; Muneaki Nakamura, all of Shizuoka, Japan

[73] Assignee: Suzuki Motor Corporation, Hamamatsu, Japan

[21] Appl. No.: 09/137,185

[22] Filed: Aug. 20, 1998

[30] Foreign Application Priority Data

| Aug. 20, 1997 | [JP] | Japan | 9-239055 |
| Nov. 27, 1997 | [JP] | Japan | 9-342200 |
| Mar. 27, 1998 | [JP] | Japan | 10-100447 |
| May 29, 1998 | [JP] | Japan | 10-166325 |
| Jun. 12, 1998 | [JP] | Japan | 10-181693 |

[51] Int. Cl.[7] .................................................. G01N 21/17
[52] U.S. Cl. ............................. 422/82.05; 422/82.09; 422/82.11; 356/445
[58] Field of Search .................. 385/12; 250/229.11, 250/227.14; 356/445; 422/82.05, 82.09, 82.11; 436/524, 527, 805

[56] References Cited

U.S. PATENT DOCUMENTS

| 4,980,278 | 12/1990 | Yamada et al. . | |
| 5,327,225 | 7/1994 | Bender et al. | 356/445 |
| 5,359,681 | 10/1994 | Jorgenson et al. . | |
| 5,378,432 | 1/1995 | Bankert et al. | 422/82.07 |
| 5,449,625 | 9/1995 | Kobayashi et al. | 436/518 |
| 5,804,453 | 9/1998 | Chen | 436/518 |

FOREIGN PATENT DOCUMENTS

| 44 24 628 | 1/1996 | Germany . |
| 196 11 025 | 9/1997 | Germany . |
| 2185308 | 7/1987 | United Kingdom . |
| WO 97/15821 | 5/1997 | WIPO . |

OTHER PUBLICATIONS

Niggemann, et. al., "Remote sensing of tetrachloroethene with a micro-fibre optical gas sensor based on surface plasmon resonance spectroscopy", Sensors and Actuators B, vol. 34, Aug. 1996, pp. 328–333.

Jorgenson et al. "A fiber-optic chemical sensor based on surface plasmon resonance", Sensors and Actuators B, 12 (1993) pp. 213–220.

Biacore probe—Product Information Brochure.

Jorgenson, et. al., "Control of the dynamic range and sensitivity of a surface plasmon resonance based fiber optic sensor", 8253a Sensors and Actuators—A Physical, vol. A43, Nos. 1/3, May 1, 1994, pp. 44–48.

*Primary Examiner*—Jeffrey Snay
*Attorney, Agent, or Firm*—McGinn & Gibb, P.C.

[57] ABSTRACT

An immunoassay apparatus comprising: at least two optical fibers, each having a first end serving as an SPR sensor; a light source for emitting a predetermined light to a second end of said optical fibers; a spectrometer for analyzing a wavelength distribution of a reflected light reflected by the SPR sensors; a main control block for controlling operation of the light source and the spectrometer; and an apparatus main body for containing the aforementioned components.

37 Claims, 85 Drawing Sheets

FIG.9
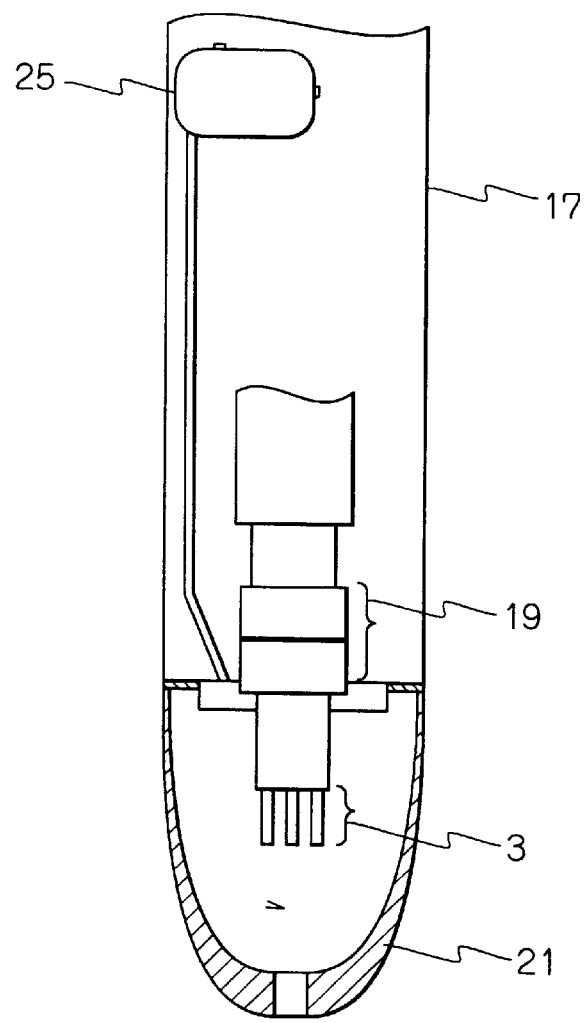
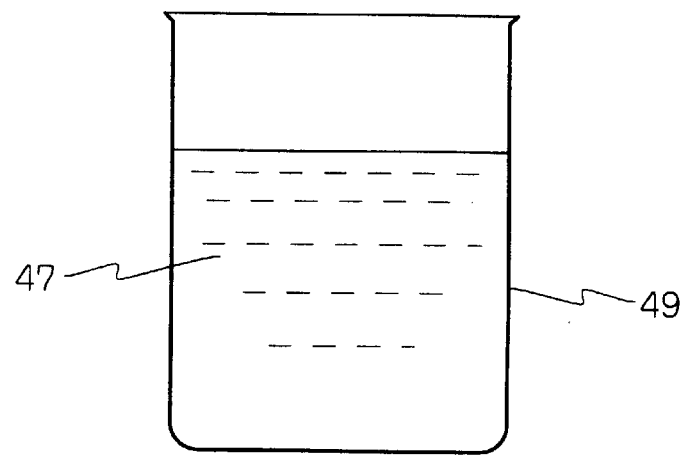
(500 μl)

FIG.19
(A)
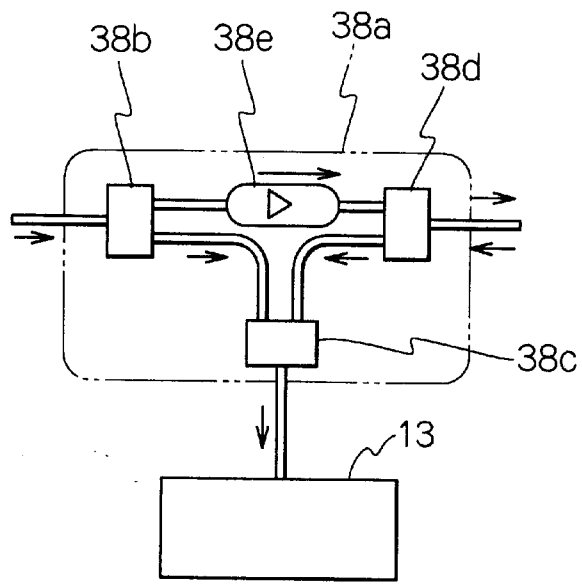
(B)
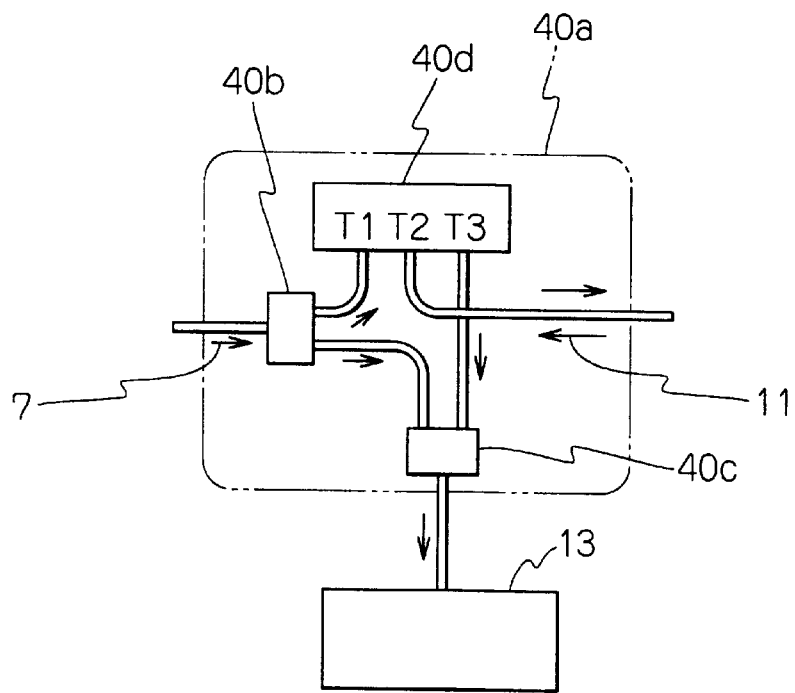

TO SPECTROMETER

TO SPECTROMETER

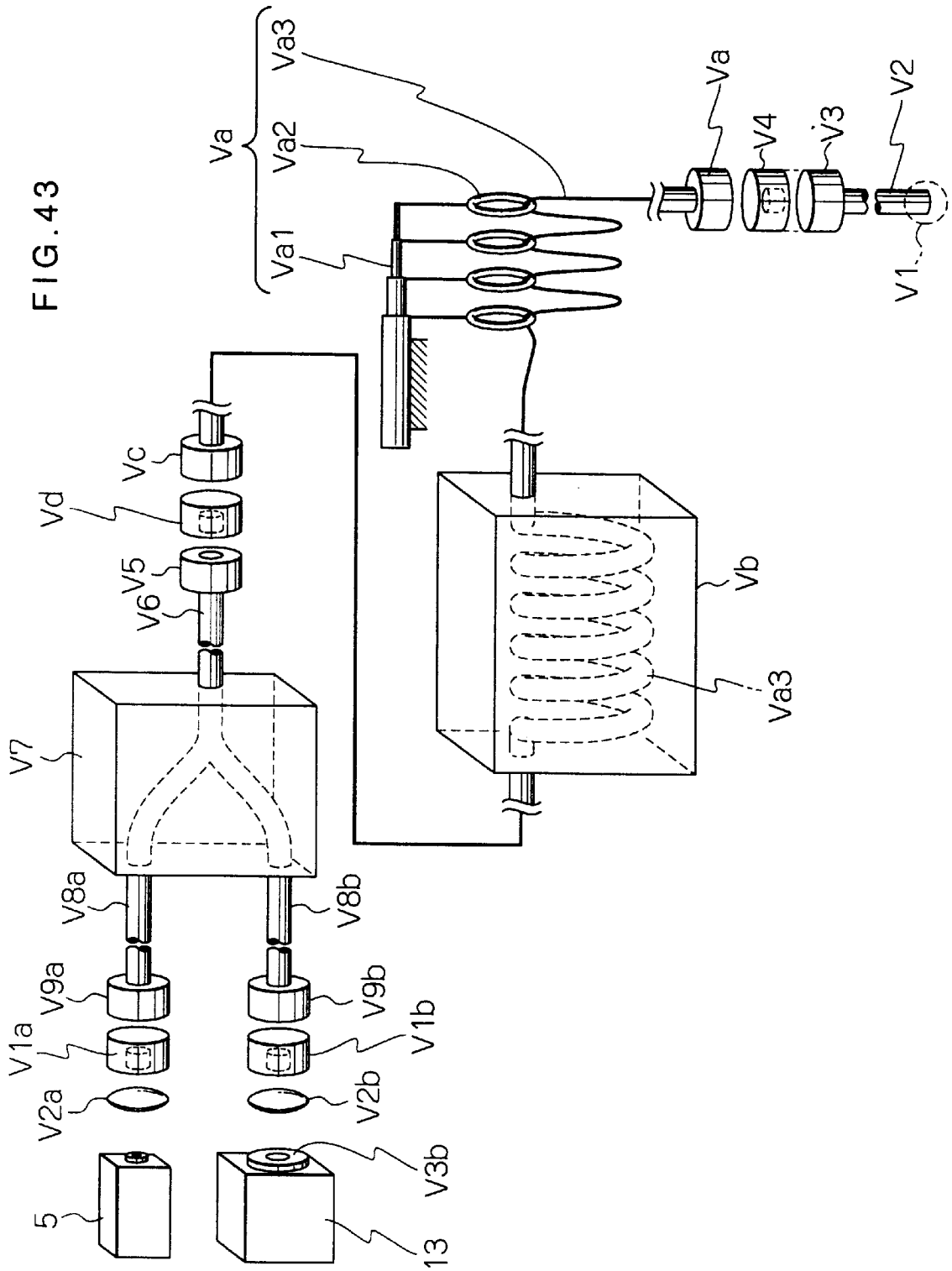
F I G. 43

IMMUNOASSAY APPARATUS

BACKGROUND OF THE INVENTION

1. Field of the Invention

The present invention relates to an immunoassay apparatus and in particular, to an immunoassay apparatus utilizing the surface plasmon resonance (hereinafter, referred to as SPR) phenomenon.

2. Description of the Related Art

Conventionally, in the field of biochemical analysis, an immunoassay has been used as a method for detecting a very small quantity of protein in a sample. This immunoassay utilizes a specific immune reaction between a so-called antigen (protein to be detected) and an antibody (antibody created by using the antigen) for quantitative analysis of a predetermined antigen concentration in a sample. This immunoassay can be applied even when a plurality of antigens are mixed in a sample, without isolating an antigen to be detected. This differs from a chemical quantitative analysis or a physical quantitative analysis.

Moreover, the immunoassay is realized in various ways.

(1) Radio immunoassay (RIA)

(2) Enzyme immunoassay (EIA)

(3) Fluoro immunoassay (FIA)

The RIA method requires a use of isotope and is not widely used recently. Moreover, the EIA method can easily carry out a quantitative analysis of an immune reaction and is widely used currently. Furthermore, the FIA method serves as an assay of a high sensitivity and a high accuracy. The EIA method which uses a solid phase for antibody quantitative analysis is called enzyme-linked immunosorbent assay (ELISA). There are two types of ELISA method.

a. Indirect method: using a solid phase of antigen b. Antibody catching method: using anti-IgM antibody for a solid phase The aforementioned ELISA method is used for quantitative analysis of an antibody for a specific causal organism (phatogen), quantitative analysis of an antibody for an allergen, and screening of monoclonal antibody. The ELISA method uses an assay kit including a micro-plate which generally has 96 indentations, enabling to carry out quantitative analysis of a number of samples simultaneously. These years, various types of automated immunoassay apparatuses are on market.

As the ELISA assay kit, various reagents are produced by number of reagent manufactures and available on market. For example, tPA is an enzyme which indirectly functions in a direction to dissolve fibrin related to blood clotting and thrombus in blood. Moreover, PAI-1 is an enzyme which functions in a direction to suppress tPA and form blood clotting and thrombus.

As a sensor used in the immunoassay apparatus, a so-called SPR sensor is known. This SPR sensor utilizes a surface plasmon resonance (SPR) phenomenon and carries out a quantitative analysis based on a principle as follows. That is, a thin metal (gold or silver) film having a thickness in the order of 50 nm is deposited on a bottom surface of a prism having a high refractive index. A predetermined light is introduced from the prism toward the metal thin film with an angle equal to or above a critical angle. The metal thin film having the thickness in the order of 50 nm is semi-transparent. The light coming from a prism side of the metal thin film passes through the metal thin film and reaches the opposite side of the metal thin film, where an evanescent field is generated.

By adjusting the angle of incidence of the light so that a wave number of the evanescent field is matched with a wave number of the surface plasmon resonance, it is possible to excite a surface plasmon resonance on the surface of the metal thin film. In this case, the wave number of the surface plasmon resonance depends on a dielectric constant of the metal thin film and a refractive index of a sample fixed on the thin metal surface. Accordingly, it is possible to determine a refractive ratio and a dielectric constant of he sample. Thus, an optical system is positioned opposite to a sample via a metal thin film, constituting a sensor.

By utilizing the aforementioned principle, an SPR sensor using an optical fiber for an immunoassay apparatus has been developed as a BIAcore by BIACORE Co., Ltd. The optical fiber used in the SPR sensor has an end portion prepared as follows. Firstly, a clad on the outer circumference of the end portion is removed and the end face is cut or polished before coated by silver. Moreover, the outer circumference of the end portion from which clad has been removed is coated by a thin metal (gold or silver) film. Furthermore, this metal thin film is covered with a dielectric film, onto which an antibody is fixed to be used for an immunoassay. Moreover, the other end of the optical fiber is provided with a predetermined light source for introducing a white light into the optical fiber.

Description will now be directed to an immunoassay analysis method of the SPR sensor having the aforementioned configuration. Firstly, the white light introduced into the optical fiber reaches the end portion, where waves of a particular wavelength in the white light excites a surface plasmon resonance. The wavelength which excites this surface plasmon resonance varies depending on a refractive index between the dielectric film and the antibody. Consequently, by comparing a wavelength having a maximum attenuation prior to an immune reaction with a wavelength having a maximum attenuation after the immune reaction. FIG. 1 is for explanation of the principle of the immunoassay apparatus 1z using the SPR sensor 3z.

It should be noted that the optical fiber is characterized in that the fiber itself is thin and the loss of light transferred in the optical fiber is small, which enables to make size of the immunoassay apparatus small and enables to carry out an analysis at a distance. These merits contribute to enhance the operationability of the immunoassay apparatus.

However, the aforementioned conventional method has disadvantages as follows. That is, in the enzyme immunoassay such as ELISA, a number of analysis steps are involved and a long period of time is required for the reaction. Accordingly, an analysis of one sample requires several hours or several tens of hours, disabling to increase the measurement efficiency. Moreover, in the enzyme immunoassay, for samples objects of a plurality of persons, an immunoassay is carried out for each of the analysis items. Accordingly, this cannot be applied for an all-at-once measurement of multiple analysis items for sample of a particular person.

Moreover, in the immunoassay apparatus using an SPR sensor including an optical fiber, it is necessary in advance to fix a particular antibody at the end of the optical fiber so as to be used for an immune reaction with an antigen in the sample to be analyzed. Accordingly, it is impossible to carry out a number of analysis items at once. Moreover, when changing the analysis items from one to another, it is necessary to exchange the entire optical fiber because the optical fiber is made as a unitary block.

Furthermore, in the SPR sensor using the optical fiber, there is no consideration on biohazard. That is, in the immunoassay, an infectious sample such as blood is used and accordingly, the area which is in contact with a sample, in principle, should be discarded and replaced with a new one. Actually, however, such a portion is repeatedly used by washing, which leaves a possibility that a part of antigen or antibody used for the immunoassay remains in the SPR sensor.

SUMMARY OF THE INVENTION

It is therefore an object of the present invention to provide an immunoassay apparatus which can eliminate the aforementioned disadvantages of the conventional methods and in particular, which can carry out at a real time a multiple items of measurement with a small quantity of a sample.

In order to achieve the aforementioned object, the immunoassay apparatus according to the present invention comprises: at least two optical fibers, each having a first end serving as an SPR sensor; a light source for emitting a predetermined light to a second end of the optical fibers; a spectrometer for analyzing a wavelength distribution of a reflected light reflected by the SPR sensors; a main control block for controlling operation of the light source and the spectrometer; and an apparatus main body for containing the aforementioned components. This immunoassay apparatus enables to carry out a plurality of immunoassays at once.

According to another aspect of the invention, the immunoassay apparatus further comprises optical path selecting means provided between the light source and the second end of the optical fibers. This enables to carry out an immunoassay with one of the optical fibers while cutting off a light to the other optical fibers.

According to still another aspect of the invention, the optical path selecting means is constituted by a liquid crystal mask having a function to transmit the light only to one of the optical fibers. By electrically controlling the liquid crystal mask, it is possible to apply a light only to one of the optical fibers.

According to yet another aspect of the invention, a multi-fiber connector is used for simultaneously disconnecting and connecting the optical fibers with the SPR sensors. This enables to rapidly replace the SPR sensors with another set of SPR sensors.

According to yet still another aspect of the invention, light switches are provided at the second end of the optical fibers for switching between transmission and cut-off of the light. This enables to apply a light only to one of the optical fibers.

According to still another aspect of the invention, branching means is provided between the light source and the light switches. This enables to introduce a light to the SPR sensors as well as to the spectrometer.

According to yet another aspect of the present invention, each of the SPR sensors is provided with a cap member having a suction hole for introducing a sample into the cap member; and a suction pump is provided at a predetermined position in the apparatus main body, for introducing the sample into the cap members. This enables to retain a predetermined quantity of a sample for an immunoassay.

According to still yet another aspect of the present invention, each of the cap members is filled with a preservation buffer. This enables to suppress denaturation of antibodies fixed on the SPR sensors.

According to yet still another aspect of the present invention, a predetermined transmission apparatus is provided in the apparatus main body and an output of the spectrometer is transmitted to the transmission apparatus so that the output of the spectrometer is transmitted from the transmission apparatus to an upper node apparatus. This enables to transmit measurement results to the upper node apparatus for various data processing.

According to still yet another aspect of the present invention, antibodies as a positive sensor and a negative sensor are fixed to the SPR sensors. This enables to make a decision as follows: if the positive control reacts normally, then the immunoassay system is normally, and if the negative control does not react, no non-specific reaction has occurred.

The present invention also provides an immunoassay apparatus comprising: at least two optical fibers, each having a first end serving as an SPR sensor; a light source for emitting a predetermined light to a second end of the optical fibers; a spectrometer for analyzing a wavelength distribution of a reflected light reflected by the SPR sensors; a main control block for controlling operation of the light source and the spectrometer; and optical path selecting means provided between the light source and the SPR sensors for introducing to the spectrometer one of a light from the light source or a reflected light from the SPR sensors. The optical path selecting means includes: a beam splitter provided on an optical path of the light from the light source to the SPR sensors; a first shutter provided at a downstream side of the beam splitter; and a second shutter and a mirror which are provided on a line intersecting at a right angle the optical path. The spectrometer is connected to a spectrometer optical fiber having an incident end on the line on which the beam splitter and the mirror are provided.

By controlling opening and closing of the first shutter and the second shutter, it is possible to alternately analyze a wavelength distribution from the light source and the light from the SPR sensors.

According to another aspect of the present invention, at least the SPR sensors of the optical fibers are connected via a predetermined connector to the optical path selecting means. Accordingly, when a series of immunoassays is complete, it is possible to remove the optical fibers having the SPR sensors from the optical selecting means and to connect another set of optical fibers having SPR sensors. That is, the SPR sensors can be used as a disposable type not requiring a washing step.

According to yet another aspect of the present invention, all the optical fibers connected to the optical path selecting means are connected via predetermined connectors. Thus, it is possible to easily replace any of the optical fibers including the SPR sensors, the optical fiber from the light source, and the optical fiber to the spectrometer. Accordingly, it is possible to assemble the immunoassay apparatus only when an immunoassay is to be carried out.

The present invention also provides an immunoassay apparatus comprising: at least two optical fibers, each having a first end serving as an SPR sensor; a light source for emitting a predetermined light to a second end of the optical fibers; and a spectrometer for analyzing a wavelength distribution of a reflected light reflected by the SPR sensors, wherein the second ends of the optical fibers are held on a predetermined shifting mechanism which positions one of the second ends of the optical fibers on an optical path leading to the spectrometer.

When an immunoassay with one of the SPR sensors is complete, the shifting mechanism operates to shift the positions of the SPR sensors so as to enable to introduce a reflected light from a following SPR sensor. Thus, it is possible to carry out a number of immunoassays by using a simple mechanism.

According to another aspect of the present invention, a predetermined converging lens is provided between the optical fibers and the optical path leading to the spectrometer. This converging lens enables to prevent diversion of light so as to be transmitted effectively.

According to still another aspect of the present invention, a plurality of converging lenses are held on the shifting mechanism so as to correspond to the second ends of the optical fibers. The converging lenses are moved together with the second ends of the respective optical fibers. Accordingly, it is possible to carry out optical positioning beforehand between the optical fibers, and the converging lenses, eliminating a necessity of complicated positioning control.

According to yet another aspect of the present invention, each of the optical fibers is divided into a sensor optical fiber having the SPR sensor and an intermediate optical fiber which are connected to each other by an optical fiber connector. Accordingly, when a series of immunoassays is complete, it is possible to disconnect only the sensor optical fibers having the SPR sensors from the apparatus and connect another set of optical fibers. That is, the sensor optical fibers can be used as a disposable type not requiring a washing step. Moreover, the apparatus can carry out a number of immunoassays in s short time.

According to still yet another aspect of the present invention, each of the sensor optical fibers has an optical fiber connector which is connected via an adapter to a corresponding optical fiber connector provided in each of the intermediate optical fibers.

According to still another aspect of the present invention, 19.

According to yet another aspect of the present invention, the intermediate optical fibers have an identical length. Accordingly, the optical path length does not change and there is no need of correction for the light intensity change depending on the optical fibers.

The present invention also provides an immunoassay apparatus comprising: a sensor optical fiber having at its first end an SPR sensor; a light source for emitting a predetermined light to second end of the sensor optical fiber; a spectrometer for receiving and analyzing a light reflected from the SPR sensor; and an optical coupler provided between the sensor optical fiber and the light source, the optical coupler having an optical path from the light source to the sensor optical fiber and an optical path from the sensor optical fiber to the spectrometer.

According to another aspect of the present invention, at least two sensor optical fibers are provided and the optical coupler has an optical path from the light source branched to the sensor optical fibers and optical paths leading from the sensor optical fibers to the spectrometer.

This enables to carry out a series of immunoassays with a simple configuration.

Moreover, when the optical coupler itself has an optical path selecting function, a predetermined control block issues an instruction to select a particular optical path so that a light is transmitted only to a sensor optical fiber corresponding to the optical path selected, enabling to carry out an immunoassay only with the sensor optical fiber According to yet another aspect of the present invention, each of the sensor optical fibers is provided with an optical fiber cable located between the sensor optical fiber and the optical coupler. This enables to pull the sensor optical fiber alone when the light source and the spectrometer are fixed at a predetermined position. Accordingly, it is possible to carry out an immunoassay with samples placed in a wide range.

According to still another aspect of the present invention, the sensor optical fiber is connected to a predetermined optical fiber connector which is connected via a predetermined adapter to the optical coupler. Accordingly, when an immunoassay of a predetermined sample is complete, the sensor optical fiber is disconnected from the optical fiber connector and another sensor optical fiber is attached. Thus, it is possible to carry out measurement of multiple items on a plurality of samples in a short time.

The present invention also provides an immunoassay apparatus comprising: at least two sensor optical fibers, each having at its first end an SPR sensor; light emitting means for emitting a predetermined light to second ends of the sensor optical fibers; and a spectrometer for receiving and analyzing a light returned from the SPR sensors, wherein the light emitting means is held on an optical path switching mechanism so that the light emitting means is positioned at the second end of one of the sensor optical fibers.

When an immunoassay with one of the SPR sensors is complete, the optical path switching mechanism operates to move the light emitting means to a position corresponding to a sensor optical fiber with which the next immunoassay is to be carried out. Thus, it is possible to carry out a number of immunoassay with a simple configuration.

According to still yet another aspect of the present invention, each of the sensor optical fibers is provided with a predetermined deflection mirror for reflecting the light from the sensor optical fiber, toward the spectrometer.

According to yet another aspect of the present invention, the deflection mirrors are concave mirrors.

According to still another aspect of the present invention, each of the sensor optical fibers is provided with a corresponding spectrometer optical fiber which is positioned according to the position of the sensor optical fiber and is connected to an optical coupler where the sensor optical fibers are united into a single optical path connected to the spectrometer.

According to still yet another aspect of the present invention, each of the spectrometer optical fibers is provided with a predetermined converging lens located between the spectrometer optical fiber and the light emitting means.

According to yet still another aspect of the present invention, a first deflection mirror is provided in the light emitting means and a second deflection mirror is provided in the vicinity of the spectrometer, wherein the first deflection mirror reflects a light from the sensor optical fibers, into a direction parallel to a shifting direction of the light emitting means, and the second deflection mirror reflects the light from the first deflection mirror, toward the spectrometer.

According to yet another aspect of the present invention, a total reflection mirror is provided in the vicinity of the sensor optical fibers, and a deflection mirror is provided between the light emitting means and the spectrometer, wherein the total reflection mirror totally reflects the light from the light emitting means, and the deflection mirror deflects the light reflected by the total reflection mirror, toward the spectrometer.

According to still another aspect of the present invention, the sensor optical fibers are arranged so as to arrange their cross sections in a circle; the light emitting means is constituted to be rotatable and has a rotary shaft matched with a center axis of the circle of the sensor optical fiber arrangement; and a light emitting member is provided in the light emitting means at a position corresponding to the sensor optical fibers, for emitting a light toward the sensor optical fibers.

According to yet another aspect of the present invention, spectrometer optical fibers are provided between the light emitting means and the spectrometer so as to correspond to the sensor optical fibers; and converging lenses are provided between the spectrometer optical fibers and the light emitting means so as to correspond to the spectrometer optical fibers.

According to still yet another aspect of the present invention, deflection mirrors are provided between the spectrometer optical fibers and the spectrometer, for deflecting the light from the spectrometer optical fibers, toward the spectrometer.

According to still yet another aspect of the present invention, the light emitting means comprises: a light source for emitting a light along the rotary shaft; a first deflection mirror for deflecting the light from the light source, toward the light emitting member; a second deflection mirror for deflecting the light from the SPR sensors toward the rotary shaft; and a third deflection mirror provided on the rotary shaft for deflecting the light toward the spectrometer.

According to yet another aspect of the present invention, the light emitting means comprises: a first deflection mirror for deflecting a light from a light source provided outside, along the rotary shaft to the SPR sensors; a second deflection mirror for deflecting the light advancing along the rotary shaft, toward the light emitting member; a third deflection mirror for deflecting the light from the SPR sensor toward the rotary shaft; and a fourth deflection mirror provided on the rotary shaft for deflecting the light toward the spectrometer.

According to still yet another aspect of the present invention, the light emitting means is connected to the spectrometer by a predetermined spectrometer optical fiber.

According to yet another aspect of the present invention, the sensor optical fibers are connected via predetermined optical fiber connectors to the immunoassay apparatus and the optical fibers are constituted so that they can be disconnected from the optical fiber connectors.

BRIEF DESCRIPTION OF THE DRAWINGS

FIG. 9 shows a step of suction of a sample into a cap member in the immunoassay procedure disclosed in FIG. 8.

FIG. 10A for a case of antibody P; FIG. 10B for a case of antibody N; FIG. 10C for a case of antibody A; FIG. 10D for a case of antibody B; and FIG. 10E for a case of antibody C.

FIGS. 19A and 19B are block diagrams showing modified examples of branching means disclosed in FIG. 17: FIG. 19A includes an optical switch, a splitter, and an isolator; FIG. 19B includes an optical switch, a splitter, and a circulator.

FIG. 35A shows the entire configuration of the apparatus, and FIG. 35B shows a modification of an optical coupler used in the apparatus.

FIG. 43 is a perspective view showing a configuration of an immunoassay apparatus according to an Embodiment 4.8 of the present invention.

DESCRIPTION OF PREFERRED EMBODIMENTS

[Embodiment 1.1]

Description will now be directed to an immunoassay apparatus according to Embodiment 1.1 with reference to the attached drawings.

Figure 1:
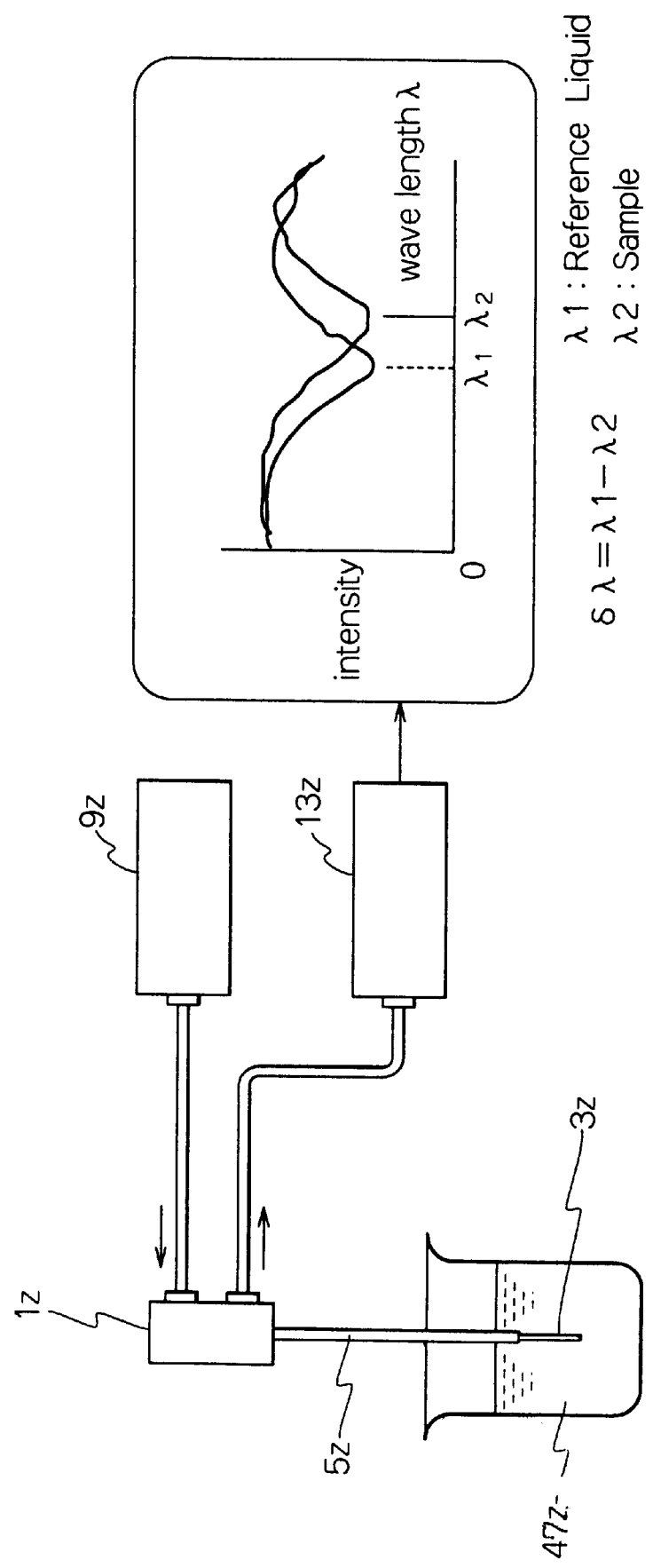
FIG. 1 explains a principle of a surface plasmon resonance.
Figure 2:
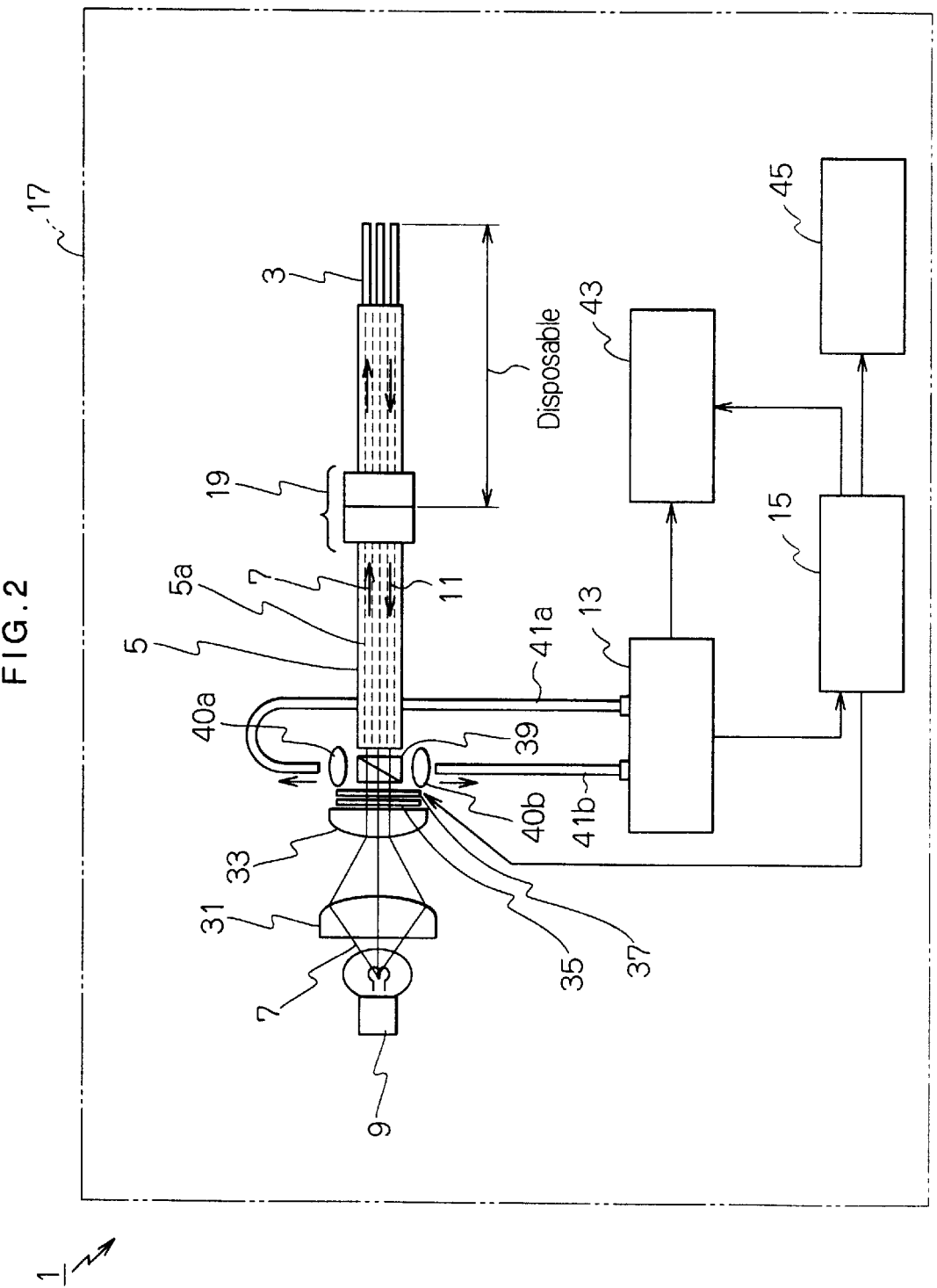
FIG. 2 is a block diagram showing an immunoassay apparatus according to an Embodiment 1.1 of the present invention.

As shown in FIG. 2, the immunoassay apparatus according to Embodiment 1.1 includes: an optical fiber $5a$ having an SPR sensor block 3 at one end thereof; a light source 9 for irradiating a predetermined white light 7 from the other end of this optical fiber $5a$; a spectrometer 13 for analyzing a wavelength distribution of a reflected light 11 from the SPR sensor block 3; a main control block 15 for controlling operation of the light source 9 and the spectrometer 13; and an apparatus main body for containing these components. There are provided at least two optical fibers $5a$.

[SPR Sensor Block]

Figure 3:
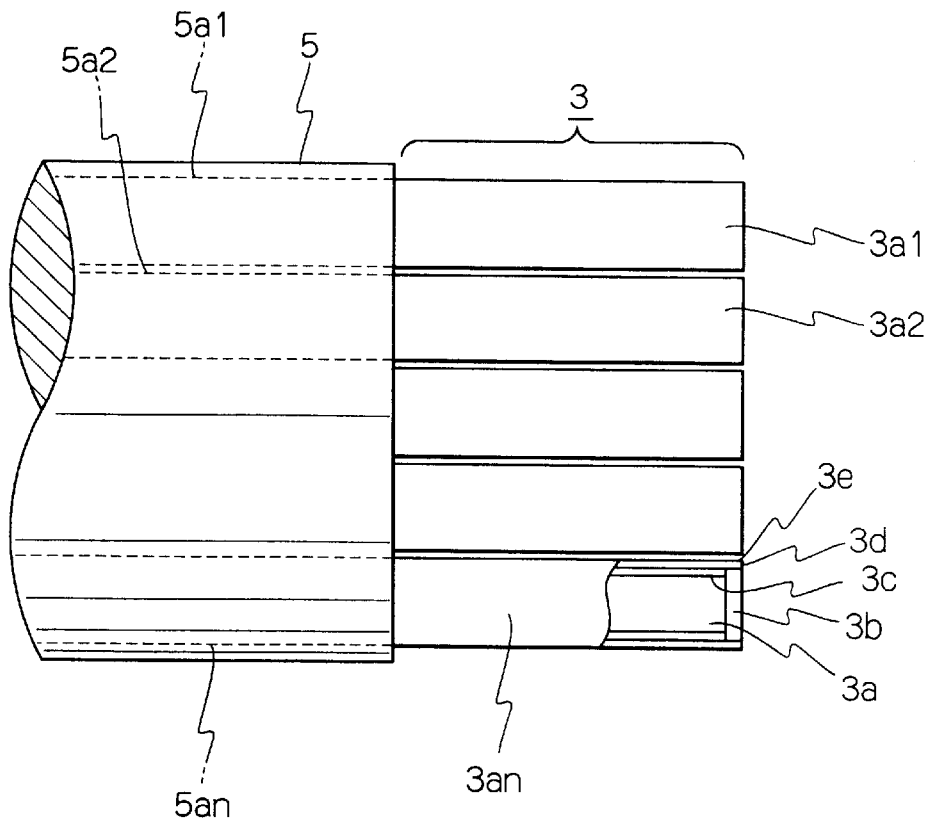
FIG. 3 is a side view showing an SPR sensor block of the immunoassay apparatus disclosed in FIG. 2 with a partially cut off portion.

Firstly, a plurality of optical fibers $5a$ made from quartz constitute a multi-optical fiber 5. An end portion of each of the optical fibers $5a$ functions as an SPR sensor constituting the SPR sensor block 3. This SPR sensor block 3 is detachably connected via a multi-fiber connector 19 to the remaining portions of the optical fibers $5a$. In the SPR sensor block 3, each of the optical fibers $5a$ has an end portion as shown in FIG. 2 and FIG. 3. Each of the optical fibers $5a$ has a core $3a$ whose end face is coated by silver, serving as a reflecting mirror $3b$. Moreover, the outer circumference of the core $3a$ is coated by a metal thin film $3c$ of silver or gold. This metal thin film $3c$ is covered by a dielectric film $3d$, on which an antibody $3e$ is fixed. It should be noted that there are various configurations of optical fiber. That is, the core is made from quartz or plastic (polymer), and the clad is made from quartz or plastic. Moreover, the SPR sensor block is made from quartz and plastic. Actually, these materials are used in an appropriate combination.

Figure 4:
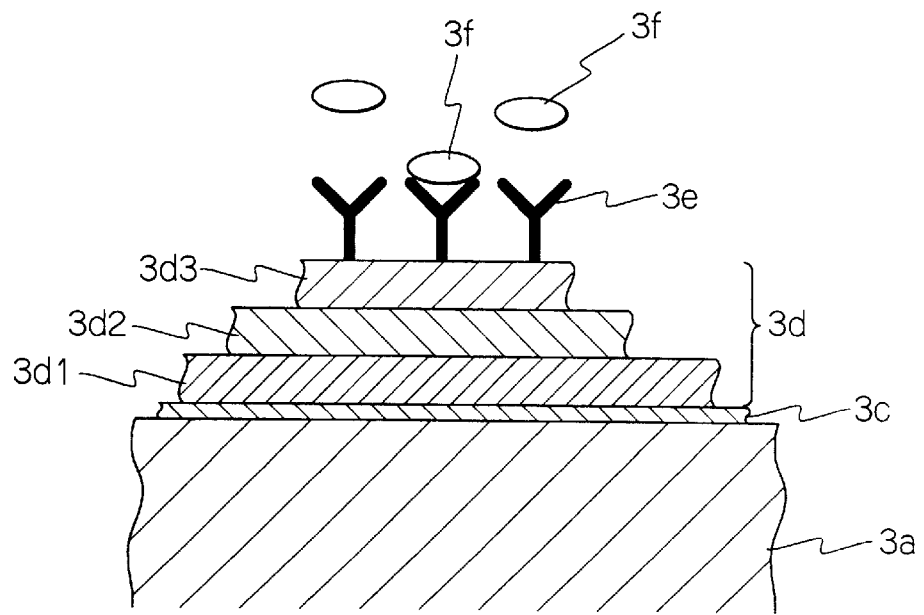
FIG. 4 is a cross sectional view showing a surface configuration of the SPR sensor disclosed in FIG. 3.

The dielectric film $3d$ functions as an adhesive for the antibody $3e$ to be fixed to the metal thin film $3c$. As for the specific configuration of this dielectric film $3d$, various configurations have been suggested. In this embodiment, as shown in FIG. 4, the metal thin film $3c$ is directly coated by a many-membered ring $3d1$ containing a sulfur atom (sulfide, disulfide, thiol, isonitryl, and the like). This many-membered ring $3d1$ is coated by a saturated hydrocarbon chain $3d2$ (12 to 30 atoms interrupted by a hetero atom without branching). Furthermore, the saturated hydrocarbon chain $3d3$ is covered by an active group $3d3$ (amino group, aldehyde group, epoxy group, carboxyl group, and the like). The antibody $3e$ is fixed to this active group $3d3$.

The type of the antibody $3e$ fixed to the dielectric film $3d$ is selected according to an antigen $3f$ in the sample to be analyzed. That is, when the antigen $3f$ in the sample to be analyzed is determined, a corresponding SPR sensor block is selected which has a plurality of antibodies $3e$ such as a protein, positive control, negative control, and the like which correspond to the antigen $3f$ to be analyzed. As has been described above, this SPR sensor block 3 is connected to the apparatus via the multi-fiber connector 19. Consequently, it is not difficult to replace an SPR sensor block with another SPR sensor block. Actually, the immunoassay apparatus 1 using this SPR sensor block 3 can be applied for a quantitative analysis for cancer, diabetes, bacteria (O-157), thrombus/head trauma, water quality inspection (toxin check), various endocrine checks.

As has been described above, when a plurality of antibodies $3e$ are fixed to the SPR sensor (in an example of FIG. 3, five types of antibody A, B, C, P, and N are used), multiple items can be analyzed through one operation. This is enabled by the variety of antibodies $3e$ fixed to the dielectric film $3d$ at the end portion of the optical fibers in the SPR sensor block 3 which are connected to specific proteins as respective antigens $3f$ contained in a sample. For example, for a cancer check, it is general to use a tumor maker as the check reagent. When a stomach cancer is considered, generally, three or four tumor markers are used in combination. In this case, these tumor markers are fixed to the respective optical fibers of the SPR sensor block 3 so that multiple check items can be checked through one measurement. This significantly enhances the measurement efficiency.

In the case of diabetes, in order to determine which endocrine is in an abnormal state, causing the diabetes, it is not sufficient to check the insulin concentration in a sample. In this case, it is important to carry out a quantitative analysis on secretion concentrations of respective proteins which have possibly caused the diabetes so as to enable to determine a treatment afterward and a medicine to be administered.

Moreover, in the immunoassay apparatus 1 according to this embodiment, as shown in FIG. 3, with the purpose of increasing a quantitative analysis accuracy, a positive control (antibody P) and a negative control (antibody N) are used as parts of the antibodies.

Here, the 'positive control' means an antibody which specifically reacts with a protein existing as an antigen in a sample. In a blood, urea, saliva, and the like, there may be contained a protein whose concentration is not much changed by a change of physical condition. The antibody P which reacts specifically with this protein is fixed on of one of the optical fibers 5a as a positive control.

On the contrary, the 'negative control' is an antibody N which corresponds to an antigen which cannot be contained in a sample. When the antibody N used as a negative control has caused a reaction, it is considered that a non-specific reaction has taken place and it is possible to take various countermeasures. It should be noted that as a negative control, it is possible to use an antibody which reacts with another type of antigen (protein) and accordingly, there is a wide range for negative control selection.

Moreover, if a sample contains no appropriate protein, there is a technique to add one to the sample. That is, it is possible to use a pair of proteins which specifically react as an antigen and an antibody to each other and which can easily be obtained. A predetermined quantity of the antigen is added to the sample prior to a quantitative analysis. The antibody corresponding to this antigen is fixed as a positive control to the SPR sensor block. Here, it is preferable that the antigen has affinity with a sample (blood, saliva, urea, and the like). This technique increases the operation procedure but increases the accuracy of the quantitative analysis as well. Note that each of the positive control and the negative control can be used solely or in combination.

[Cap Member]

Figure 5:
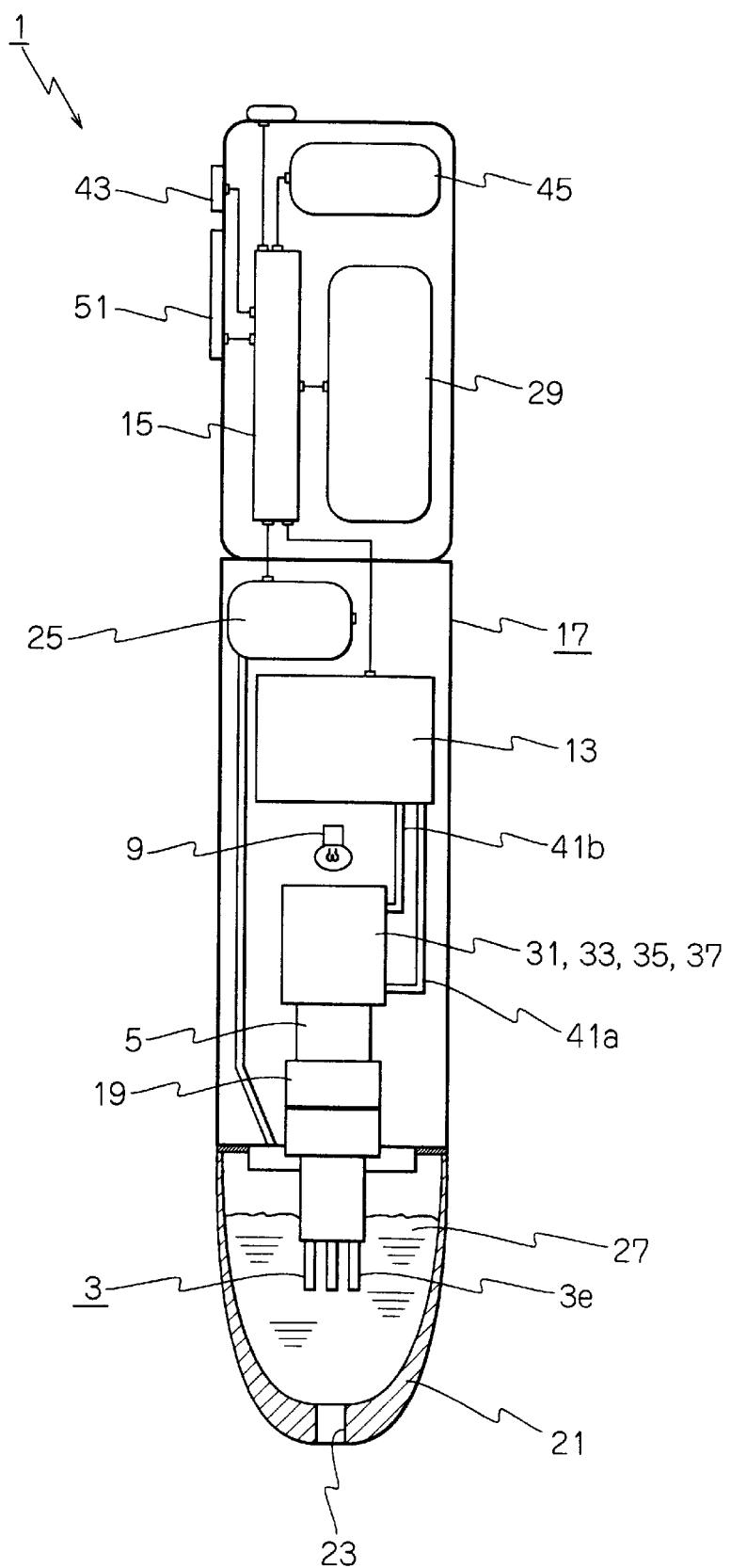
FIG. 5 is a cross sectional view showing an entire configuration of the immunoassay apparatus disclosed in FIG. 2.

As shown in FIG. 5, the SPR sensor block 3 is entirely covered by a predetermined cap member 21. This cap member 21 serves to temporarily retain a constant quantity of a sample for an immunoassay. The cap member 21 has a tip end where a suction hole 23 is formed for introducing a sample. Moreover, an inner space defined by the cap member 21 is connected to a suction pump 25 provided in an apparatus main body 17.

The cap member 21 is filled with a predetermined preservation buffer 27. The preservation buffer 27 serves to suppress denaturation of the antibody 3e prior to an immunoassay. More specifically, the preservation buffer is a phosphate buffer liquid, an acetate buffer liquid, and the like. It should be noted that when the cap member 21 is filled with a preservation buffer, the tip end of the cap member 21, i.e., the suction hole 23 is covered by a seal. When carrying out an immunoassay, this seal is peeled out. Because the suction hole 23 of the cap member 21 has a small diameter, the preservation buffer 27 will no come out easily even after the seal is removed. Moreover, this preservation buffer 27 can also be used for checking and correcting a characteristic of the respective SPR sensors 3 by applying a light with the cap member 21 filled with the preservation buffer so as to cause a surface plasmon resonance.

[Suction Pump]

The suction pump 25 connected to the inner space of the cap member 21 serves to introduce a sample through the suction hole 23 into the cap member 21. In the immunoassay apparatus according to this embodiment, suction of a sample is carried out automatically. This facilitates to introduce a constant quantity of a sample, which is indispensable to guarantee a quantitative analysis accuracy. Accordingly, the suction pump 25 is a small-size pump having a fine suction capacity and a high accuracy. The suction pump 25 is driven by a secondary battery 29. The secondary battery 29 may be a nickel-hydrogen battery, lithium ion battery, manganese dioxide-lithium battery, nickel-cadmium battery, or the like. In order to reduce the size of the entire apparatus main body 17, it is important to use a battery having a high energy density.

[Light Source]

The light source 9 applying light to the optical fibers 5a is a halogen lamp (see FIG. 2). The halogen lamp applies the light 7 consisting of lights of various wavelengths to the optical fibers 5a during an immunoassay. Note that the light source 9 is not to be limited to a halogen lamp but can be any lamp if it contains a light of a predetermined wavelength band. Moreover, if it is possible to predict a wavelength range of the light attenuated by an immune reaction, it is also possible to use a light source containing only the light of the presumed wavelength. It should be noted that operation of the light source 9 is controlled by a main control block 15 in the apparatus main body 17.

As shown in FIG. 2, at the downstream side of the light source 9, there are provided predetermined lenses 31 and 33. The lens 31 serves to converge the light 7 radiated from the light source 9. The light 7 after converted comes into the lens 33. The light introduced into the lens 33 is made into a parallel light, so that the parallel light 7 is applied to the optical fibers 5. It should be noted that when using a light source capable of radiating a parallel light, these lenses 31 and 33 are not required. At the downstream side of the lens 33, there is provided a polarizing plate 35 for polarizing the light 7 with P (parallel) polarization.

[Optical Path Selecting Means]

Figure 6:
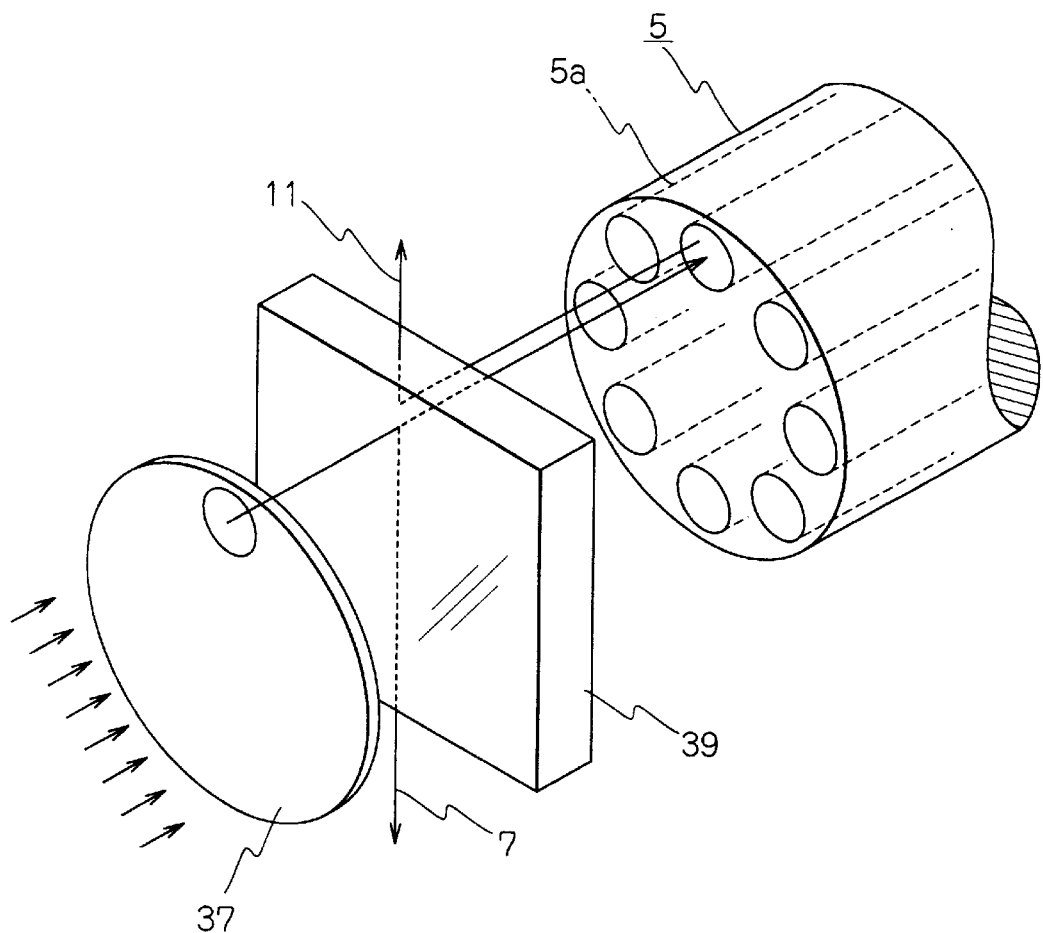
FIG. 6 is a perspective view showing an end of a multi-optical fiber from which light is introduced in the immunoassay apparatus disclosed in FIG. 2.

As shown in FIG. 2 and FIG. 6, at the downstream side of the light source 9 and further at the downstream side of the lenses 31 and 33, there is provided optical path selecting means (optical path selector) 37. This optical path selecting means passes the light 7 selectively to a plurality of the optical fibers 5a, thus allowing to carry out an immune reaction of respective antibodies 3e fixed on the SPR sensor block 3 one after another.

More specifically, the optical path selecting means 37 is made from a liquid crystal mask. This liquid crystal mask is controlled to pass the light 7 as a spot to the respective optical fibers 5a one after another. That is, when one optical fiber 5a is selected for introducing the light 7 for analyzing a spectrum pattern, the light 7 to the other optical fibers is cut off. It should be noted that the optical fibers 5a shown in FIG. 6 are arranged in a circular shape and accordingly, in the optical selecting means 37, a light transmission position is displaced in a circular shape. Operation of the optical path selecting means 37 is controlled by the main control block 15 provided in the apparatus main body 17. The optical path selecting means 37 using the liquid crystal mask has no mechanical drive block and can be made as a small component and reduce the trouble frequency. Moreover, it is possible to set an optical path with a high accuracy.

[Splitter]

As shown in FIG. 2 and FIG. 6, between the optical path selecting means 37 and the optical fibers 5a, there is provided a splitter 39 consisting of a half mirror. This splitter 39 divides the light 7 from the light source 9 into two directions. A part of the light is introduced directly into the optical fibers 5a, and the other part of the light is reflected by the splitter 39 into a direction different from the optical fibers 5a. In this embodiment, the part of the light 7 reflected by the splitter 39 is introduced into the spectrometer 13 which will be detailed later.

[Spectrometer]

As shown in FIG. 2 and FIG. 5, the immunoassay apparatus 1 according to the present invention includes a predetermined spectrometer 13. This spectrometer 13 is used to analyze a wavelength distribution (spectrum pattern) of the light 7 used in an immunoassay. Into this spectrometer 13 are introduced two lights. One is the light 7 emitted from the light source 9 to pass through the lenses 31 and 33, the polarizing plate 35, and the optical path selecting means and then reflected by the splitter 39. The other is the reflected light 11 which has been introduced into the optical fiber 5a and reflected by the SPR sensor block 3. In the spectrometer 39, the incident light 7 is compared to the reflected light 11 in the wavelength distribution so as to determine which wavelength of the reflected light 11 has been attenuated. It should be noted that the light is transferred from the splitter 39 to the spectrometer 13 via predetermined converging lenses 40a and 40b and optical guides (optical fibers) 41a and 41b.

[Main Control Block]

Figure 11:
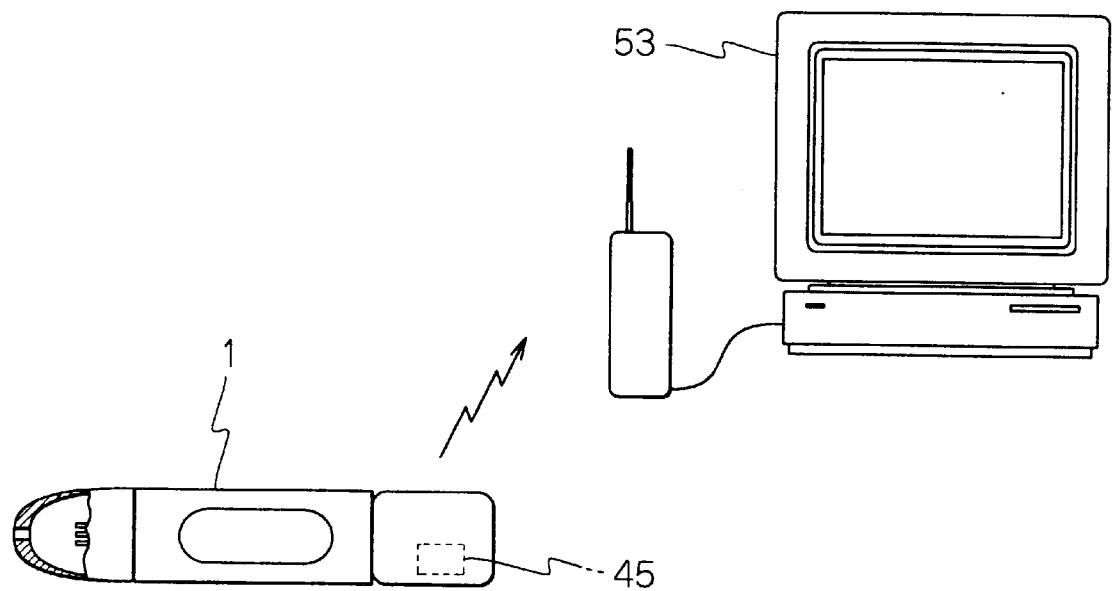
FIG. 11 shows a communication state between the immunoassay apparatus and an upper node apparatus.

As shown in FIG. 2 and FIG. 5, the main control block 15 provided in the apparatus main body 17, controls the light source 9, the optical path selecting means 37, the spectrometer 13, and the like. Moreover, the main control block 15 has a function to fetch an information relating to a wavelength distribution of the reflected light obtained by the spectrometer 13 and supply the information to the display block 43 and the transmitter 45 provided in the apparatus main body 17. Furthermore, the main control block 15 controls operation of the suction pump 25. Moreover, the transmitter 45 transmits an information of analysis results obtained by the spectrometer 13 to a receiver connected to an upper node apparatus (medical apparatus, computer, or the like) (see FIG. 11).

Next, description will be directed to operation of the immunoassay apparatus 1 having the aforementioned configuration.

[Outline of the Operation]

Firstly, as shown in FIG. 2, the light 7 emitted from the light source 9 passes through the lens 31 and the lens 33 and is made into a parallel light. After subjected to P polarization, the light is allowed to pass as a spot through a transmission position corresponding to one of the optical fibers 5a specified. After this, a part of the light 7 is reflected by the splitter 39 and introduced into the spectrometer 13 and the rest of the light gores into the SPR sensor block 3.

The light 7 introduced into the optical fiber advances in the SPR sensor block 3 while being reflected by the outer circumference of the end portion and is reflected by the reflecting mirror 3b (mirror coated by a gold or silver film) at the end face of the SPR sensor so as to be returned as the reflected light 11 through the optical fiber 5a. Here, in the SPR sensor block 3, a surface plasmon resonance is excited by the light 7, i.e., a light of a particular wavelength contained in the light 7. The light of this wavelength is attenuated. That is, the light is returned as the reflected light 11 with attenuation in this particular wavelength.

The reflected light 11 is again branched by the splitter 39 and introduced via the optical guide (optical fiber) 41b into the spectrometer 13. The spectrometer 13 analyzes the light 7 before introduced into the SPR sensor block 3 and the reflected light 11 reflected by the reflecting mirror 3b in the sensor block 3 so as to determine their wavelength distributions (spectrum patterns). The light 7 prior to the reflection is analyzed as a wavelength distribution of the halogen lamp itself having a wide wavelength band. However, the reflected light 11, as has been described above, shows an attenuation in a particular wavelength band due to the surface plasmon resonance caused between the metal thin film 3c and the dielectric film 3d in the SPR sensor block 3.

[Calibration]

Figure 7:
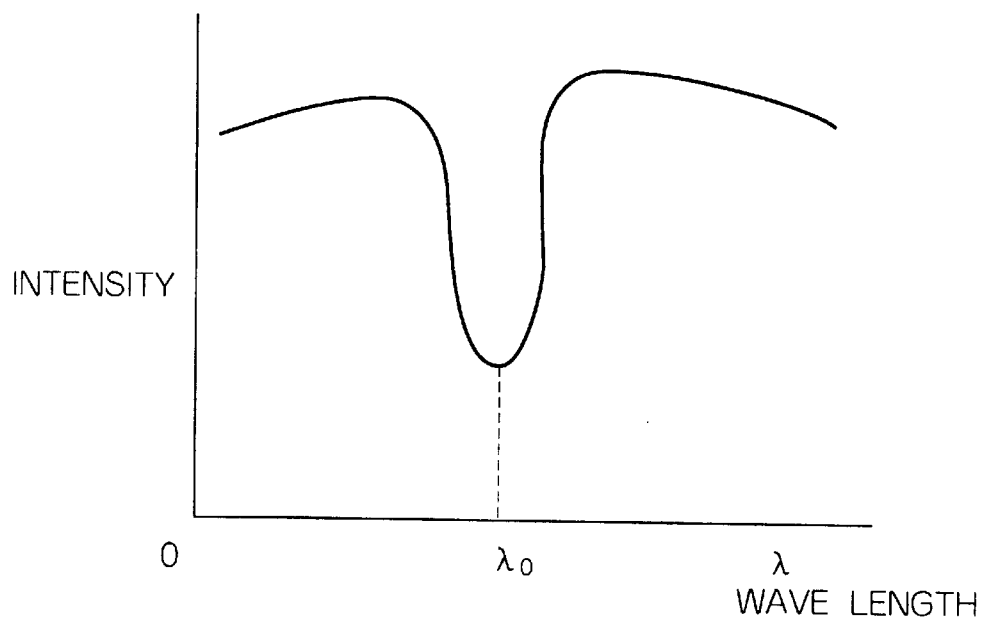
FIG. 7 shows an attenuation of a particular wavelength caused by a surface plasmon resonance.

Before carrying out an immunoassay, it is necessary to carry out a calibration of the SPR sensor block 3. That is, a dielectric film 3d (see FIG. 4) is formed on the surface of the SPR sensors 3. The reflected light 11 from the SPR sensor 3 is introduced into the spectrometer by the splitter 39. The spectrometer 13 analyzes the wavelength distribution of the reflected light 11. Thus, it is possible to obtain a wavelength distribution as shown in FIG. 7. As shown in this figure, intensity of a particular wavelength band is lowered.

From the wavelength distribution obtained, a wavelength having the minimum intensity is determined. This is the wavelength which has caused the surface plasmon resonance. Thus, it is possible to know the light wavelength which causes a surface plasmon resonance when no antibody 3e is fixed to the dielectric film 3d, thus enabling to carry out calibration of the SPR sensor block 3.

[Data Table Creation]

Next, a data table is created for the immunoassay apparatus 1 using the SPR sensor block 3. This data table shows a concentration dependency of the antibody 3f on various antibodies 3e. That is, if a sample has a high concentration of antigen, the light wavelength exiting a surface plasmon resonance varies according to the concentration. Consequently, by checking in advance a relationship between an antigen concentration corresponding to a particular antibody and a wavelength attenuated, it is possible to know an antigen concentration in an actual sample of the immunoassay.

[Immunoassay Procedure]

When carrying out an immunoassay, it is necessary to determine an antibody 3e to be fixed on the SPR sensor block 3. It is necessary to use an antibody which reacts specifically with an antigen which is considered to be contained in a sample.

Moreover, the immunoassay apparatus 1 according to the present invention also uses an antibody P serving as a positive control and an antibody N serving as a negative control. In general, a sample such as blood serum may contain a protein which almost does not change in quantity. In case no appropriate protein is contained, a cheap protein (such as albumin) is selected and a monoclonal antibody of this protein is used as the positive control. On the other hand, a protein serving as the negative control is any antibody which corresponds to an antigen not contained in the sample.

The antibody P and the antibody N are fixed to the SPR sensor block separately from each other. Besides, various antibodies A, B, and C are selected according to the check items and are fixed to the SPR sensor block 3 corresponding to the other optical fibers 5a (see FIG. 3). An actual immunoassay is carried out by using the SPR sensor having the fixed antibodies A, B, C, P, and N.

Figure 8:
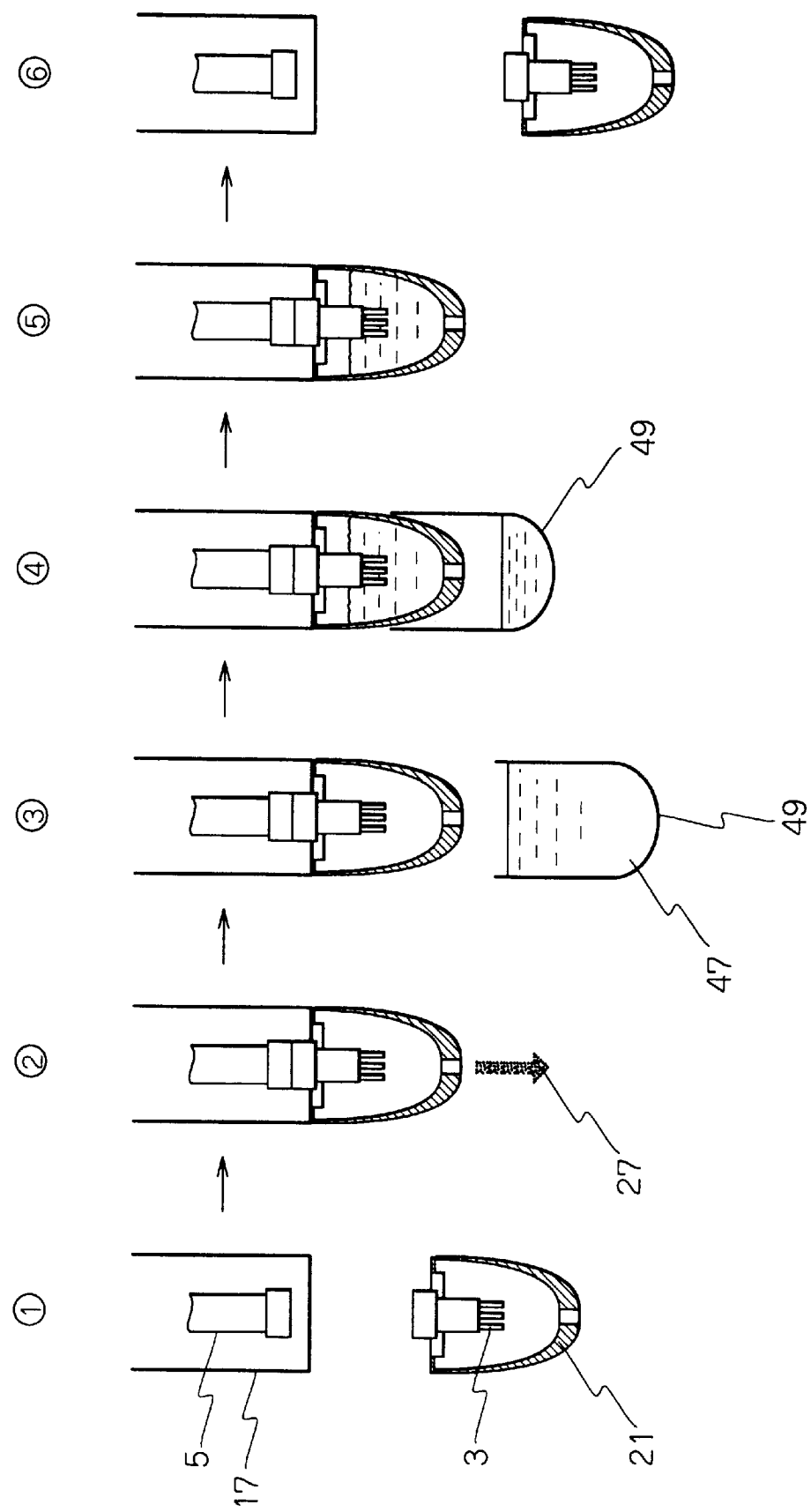
FIG. 8 shows steps of immunoassay procedure.

A shown in FIG. 8, the SPR sensor block having the fixed antibodies corresponding to a check item is connected via the multi-fiber connector to the apparatus. The buffer 27 is removed from the cap member 21. After this, a sample tube 49 filled with a sample 47 is prepared. The sample 47 is introduced from the sample tube 49 into the cap member 21 by way of suction using the aforementioned suction pump 25.

In general, the sample tube 49 is filled with a sample 47 in the order of 500 μl, from which only 100 μl or so is actually introduced into the cap member 21 (see FIG. 9).

With the cap member 21 filled with the sample 47, an immunoassay is carried out. More specifically, the light 7 is applied via the optical path selecting means 39 to one of the optical fibers 5a. The light reflected light 11 reflected by the SPR sensor block 3 is analyzed by the spectrometer 13 so as to determine a wavelength distribution. Next, the light 7 is applied via the optical selecting means 30 to another optical fiber 5a. The reflected light 11 reflected by the SPR sensor block 3 is analyzed by the spectrometer 13. Thus, the light 7 is applied to all of the optical fibers 5a one after another. Thus, analysis is carried out for all the optical fibers, i.e., all the antibodies fixed on the respective optical fibers in the SPR sensor block 3. When the immunoassay is complete, the SPR sensor block 3 is removed and another SPR sensor block 3 is connected for another immunoassay.

[Data Processing]

Figure 10:
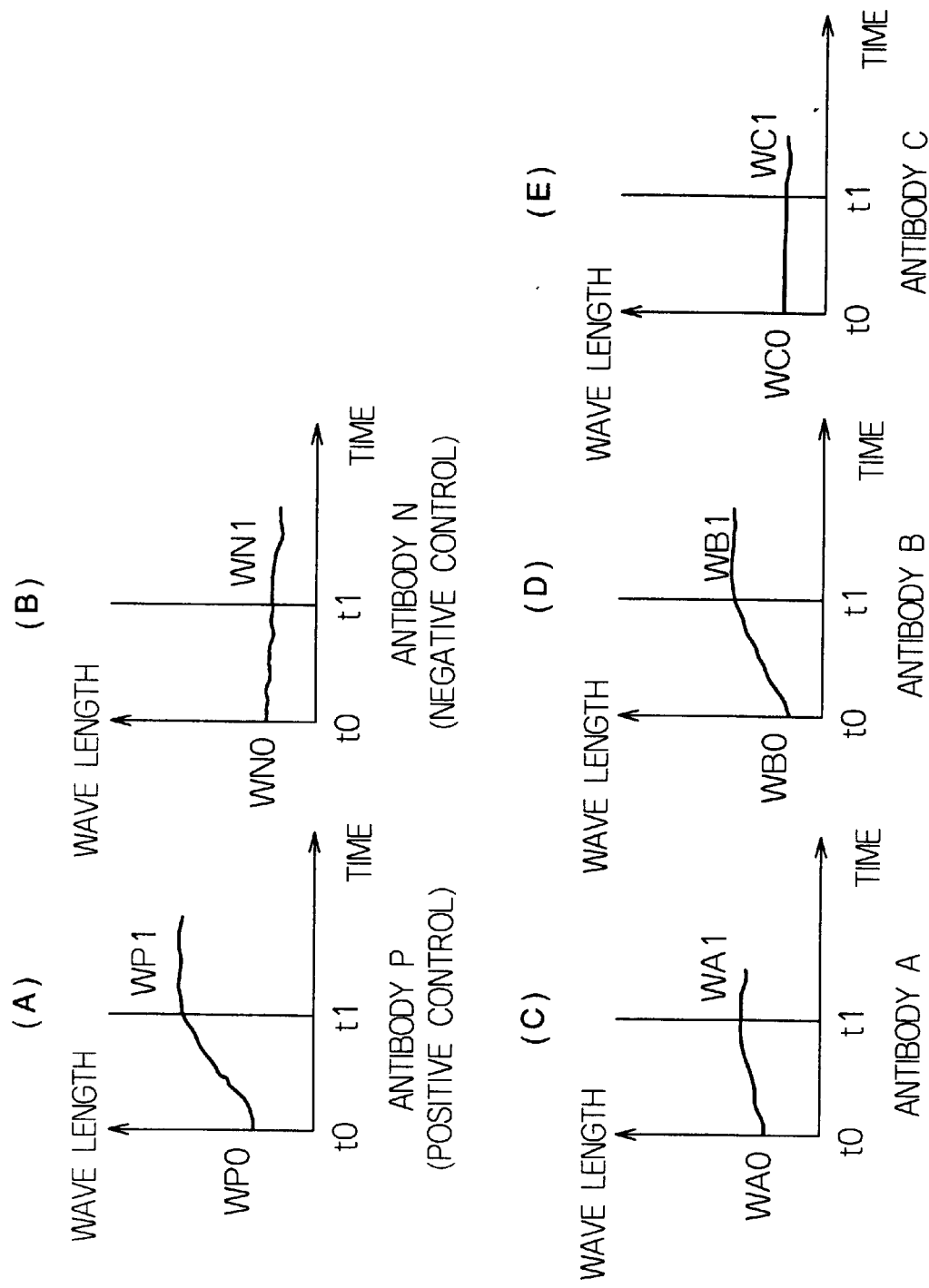
FIGS. 10A–10E shows a temporal change of an attenuated wavelength in an immunoassay.

Next, description will be directed to a data processing carried out according to the information obtained from the spectrometer 13. An example of immunoassay explained here uses an SPR sensor block 3 having an antibody P as the positive control, antibody N as the negative control, and three different antibodies A, B, and C. FIG. 10 shows results of the immunoassay of a sample. A vertical axis indicates a wavelength which has been attenuated most by the surface plasmon resonance. A horizontal axis represents a time lapse. FIG. 10A shows a wavelength attenuation for the antibody P. FIG. 10B shows such a wavelength attenuation for the antibody N. Moreover, FIG. 10C, FIG. 10D, and FIG. 10E shows the attenuated wavelength of the reflected light for the-antibody A, B, and C, respectively, according to the time t. It should be noted that the time t1 in FIG. 10 indicates a moment when an immune reaction is terminated.

An information obtained from an immunoassay is converted from an analog to a digital data by the main control block 15 and stored in a predetermined memory. When a series of immunoassays is complete, the data obtained is transmitted via the transmitter 45 to an upper node apparatus 53 (computer, see FIG. 11). These operations are specified through key operation on an operation panel 51 (see FIG. 6) of the immunoassay apparatus 1. Moreover, the display block 43 shows a currently obtained result of immunoassay. The display block uses an LCD or LED. It is also possible to additionally use a buzzer for indicating a start or end of each step of the immunoassay.

Figure 12:
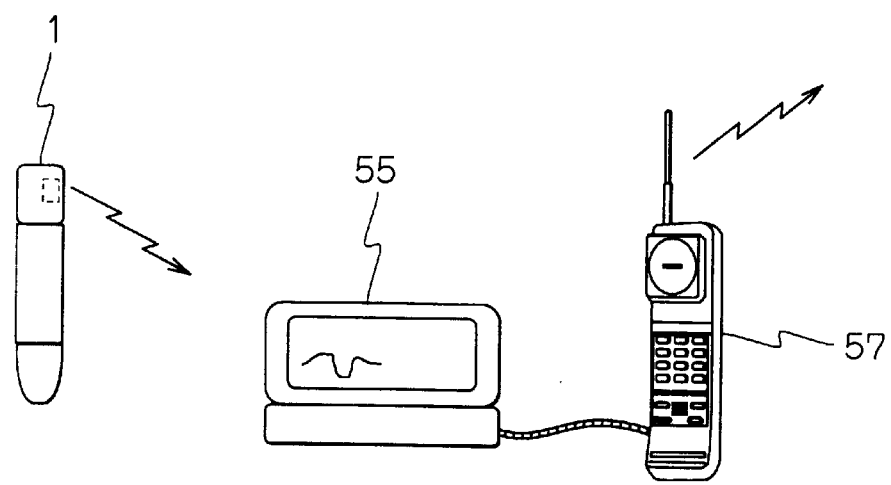
FIG. 12 shows another communication state between the immunoassay apparatus and an upper node apparatus.

The upper node apparatus analyzes the data received (including data correction and compensation) and displays a wavelength distribution obtained. According to a plurality of wavelength distributions obtained, the upper node apparatus 53 executes a quantitative analysis of concentration of the antigen contained in the sample and displays a result obtained. The upper node apparatus 53 is installed in a nurse center (see FIG. 11) so that the obtained information can be used for determining a treatment of a patient and a medicine to be administered. Moreover, as shown in FIG. 12, at a patient's residence or at a treatment site, a portable type computer 55 and a cellular telephone 57 are used in combination for transmitting an immunoassay result to a hospital.

Figure 13:
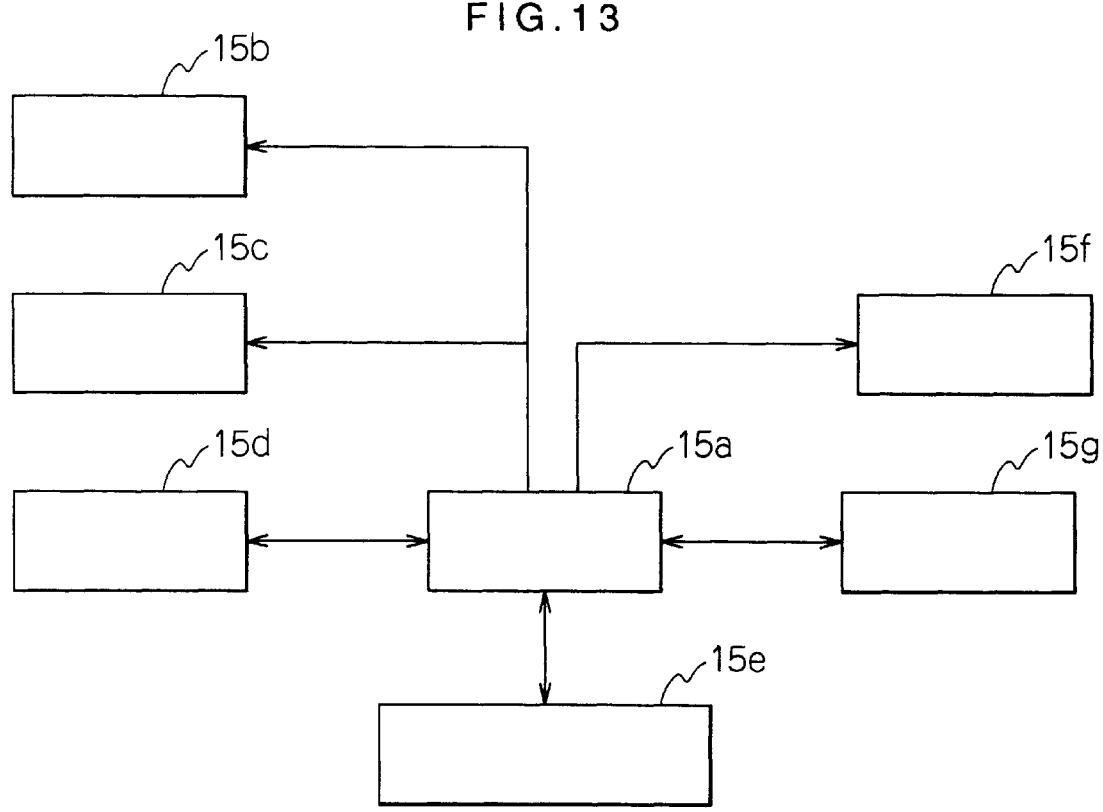
FIG. 13 is a block diagram showing an information flow in the immunoassay apparatus.

FIG. 13 is a block diagram showing a control data flow required for the main control block 15a of the immunoassay apparatus 1 for controlling operation of the respective blocks. As shown here, the main control block 15 issues a control instruction to an optical path selecting means control block 15b so that the optical path selecting means selects an optical path, and to a spectrometer control block 15c so that the spectrometer executes an analysis of a wavelength distribution of a reflected light. Moreover, the main control block 15 issues a control instruction to a data processing block 15d so that a data processing is executed according to a data obtained from the spectrometer 13. The data after processed is stored in a data base 15e. Furthermore, the main control block 15 issues a control instruction to a display control block 15f so that an immunoassay result appears on the display block 43, and to a transmission control block 15g so that the transmitter 45 transmits the data obtained.

Figure 14:
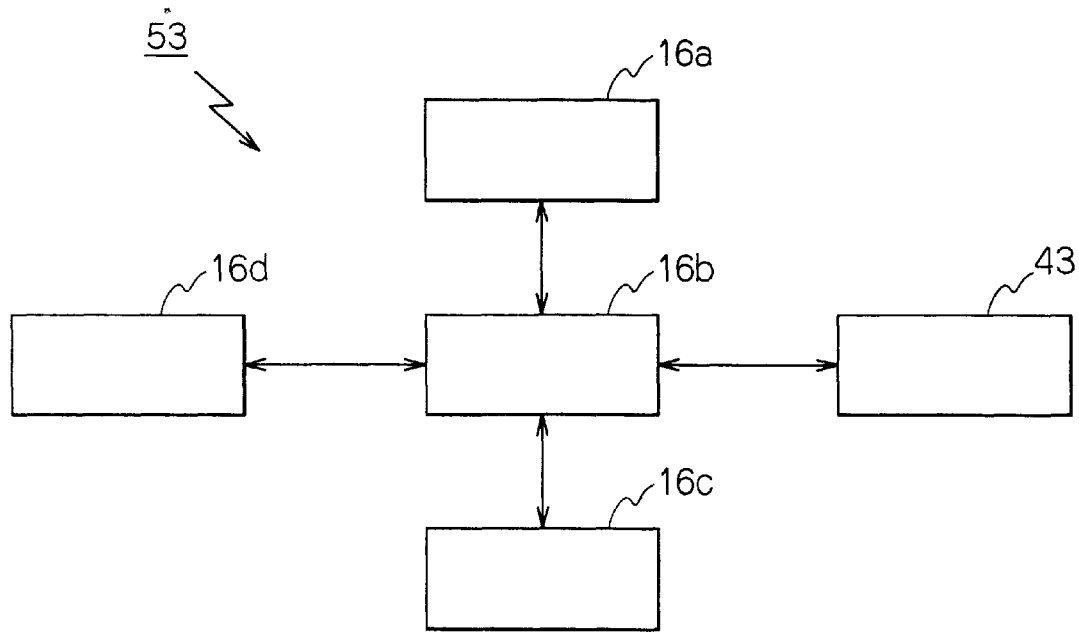
FIG. 14 is a block diagram showing an information flow in an upper node apparatus.

FIG. 14 is a block diagram showing a data flow in the upper node apparatus 53 (computer) to display results of an immunoassay. The immunoassay results received by the receiver 16d is stored in a data base 16c of the upper node apparatus (computer) 53 and transmitted to a data calculation block and a diagnosis block 16a for evaluating the immunoassay results. The evaluation results are displayed by the display block 43.

For example, the aforementioned FIG. 10 shows results of a normal immunoassay. When the attenuated wavelength is changed for the antibody P as the positive control as shown in FIG. 10, and if the change is matched with the change registered in the data table, it can be decided that a normal immunoassay is carried out. On the contrary, if there is a great difference between the change currently obtained and the change in the data table, it is considered that some defect is present in the immunoassay system.

Moreover, as shown in FIG. 10B, when an attenuated wavelength for the antibody N is almost unchanged, it is considered that a correct immunoassay is carried out. This is because an antibody used as a negative control is an antibody which reacts specifically with an antigen which cannot be contained in the sample. On the contrary, if the attenuated wavelength of the antibody N is greatly changed, then it is considered that a non-specific reaction has occurred and the immunoassay accuracy is not reliable.

When the antibodies A, B, and C exhibit attenuated wavelengths as shown in FIGS. 10C, 10D, and 10E, a conclusion can be made as follows. Because the attenuated wavelength for the antibody B changes most greatly, the sample has a highest concentration of an antigen which reacts specifically with the antibody B. Because the attenuated wavelength for the antibody A changes less than for the antibody B, the concentration of an antigen which reacts specifically with the antibody A is smaller. Because the attenuated wavelength for the antibody C almost does not change, the sample does not contain an antigen which reacts with the antibody C. It should be noted that the aforementioned series of immunoassay steps can be carried out with a single sample of a patient in three minutes or so.

For a cancer diagnosis, various tumor markers are used as the antibodies for the immunoassay. When a cancer is present, an abnormal state can be found in a particular protein secreted in blood. By using a monoclonal antibody of this protein as a tumor maker antibody, and the protein is subjected to a quantitative analysis. By using a plurality of tumor markers, it is possible to increase the analysis reliability. Moreover, in case of diabetes, a plurality of endocrine proteins associated with the diabetes change their concentrations. By carrying out a quantitative analysis of the endocrine proteins, it is possible to determine a treatment of a patient and a quantity of medicine to be administered. It concentrations of a plurality of antibodies can be determined by using a plurality of antibodies, it is possible to accurately identify a cause of the diabetes symptom. Furthermore, this immunoassay can be applied for various infectious diseases and blood trouble.

[Embodiment 1.2]

Next, description will be directed to another Embodiment 1.2 of the present invention.

Figure 15:
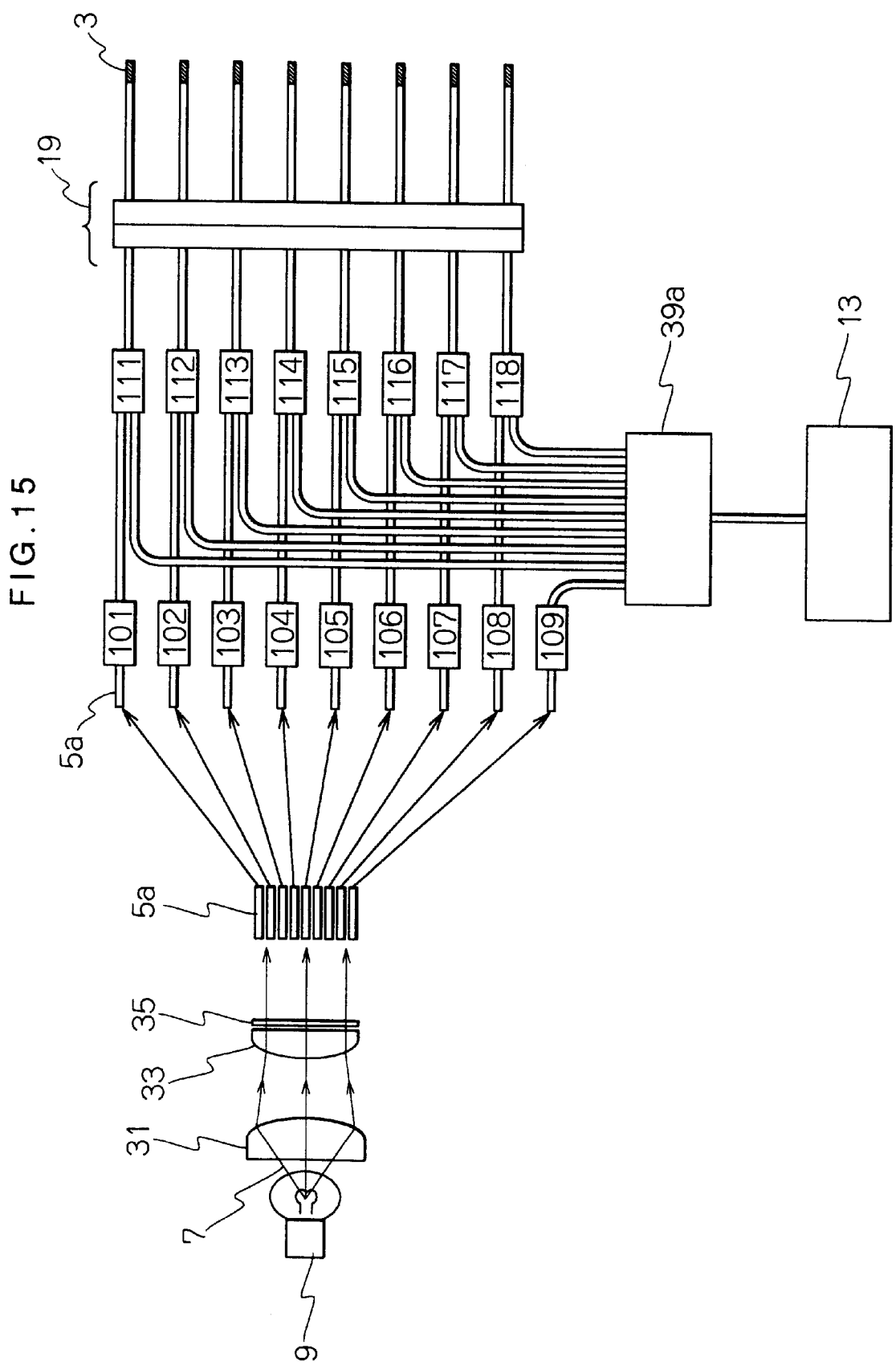
FIG. 15 is a block diagram showing an immunoassay apparatus according to an Embodiment 1.2 of the present invention with an optical fiber and an SPR sensor block enlarged.

FIG. 15 shows a configuration of the immunoassay apparatus according to Embodiment 1.2, which includes light switches 101, 102, 103, . . . 109 for switching between transmission and cut-off of the light 7 for respective optical fibers 5a. At the downstream side of the respective light switches 101, 102, 103, . . . 109, there are provided splitters 11, 112, 113, . . . 118 for branching the light 7 into the SPR sensor block 3 and into the spectrometer 13. Basically, Embodiment 1.2 has an identical configuration as the Embodiment 1.1 and explanation on the common parts will be omitted.

Unlike the Embodiment 1.1, the Embodiment 1.2 does not have any optical path selecting means as shown in FIG. 15. That is, the light switches 101, 102, 103, . . . 109 replace the optical path selecting means. These light switches 101, 102, 103, . . . 109 are operated according to control by the main control block 15 (see FIG. 16.). The splitters 111, 112, 113, . . . 118 provided at the downstream side of the light switches 101, 102, 103, . . . 109 are constituted by half mirrors.

The light 7 coming from a halogen lamp as the light source 9 passes through the converging lenses 31 and 33 so as to increase its density. Because the light intensity distribution tends to be irregular, an integrating sphere (not depicted) may be provided to suppress the intensity irregularity. The light 7 coming out of the integrating sphere passes through the polarizing plate 35 before introduced into one of the optical fibers 5a. The main control block 15 controls the light switches 101, 102, 103, . . . 109 provided for the respective optical fibers so that only one (for example, 101) of the light switches is turned ON simultaneously.

The light 7 which has passed through the light switch 101 which is ON further passes through the splitter 11, reaching the SPR sensor block 3. In this SPR sensor block 3, the light 7 is attenuated by a surface plasmon resonance. The light 7 is reflected by the end face of the SPR sensor 3 and returned as a reflected light 11 to the splitter 111. In the splitter 111, a part of the reflected light 11 is introduced via another splitter 39a to the spectrometer 13. Moreover, as shown in FIG. 15, among the plurality of optical fibers, the optical fiber having the light switch 109 is connected directly to the splitter 39a. This enables to compare the light 7 coming from the light source 9 to the reflected light 11 reflected from the SPR sensor block 3.

Figure 16:
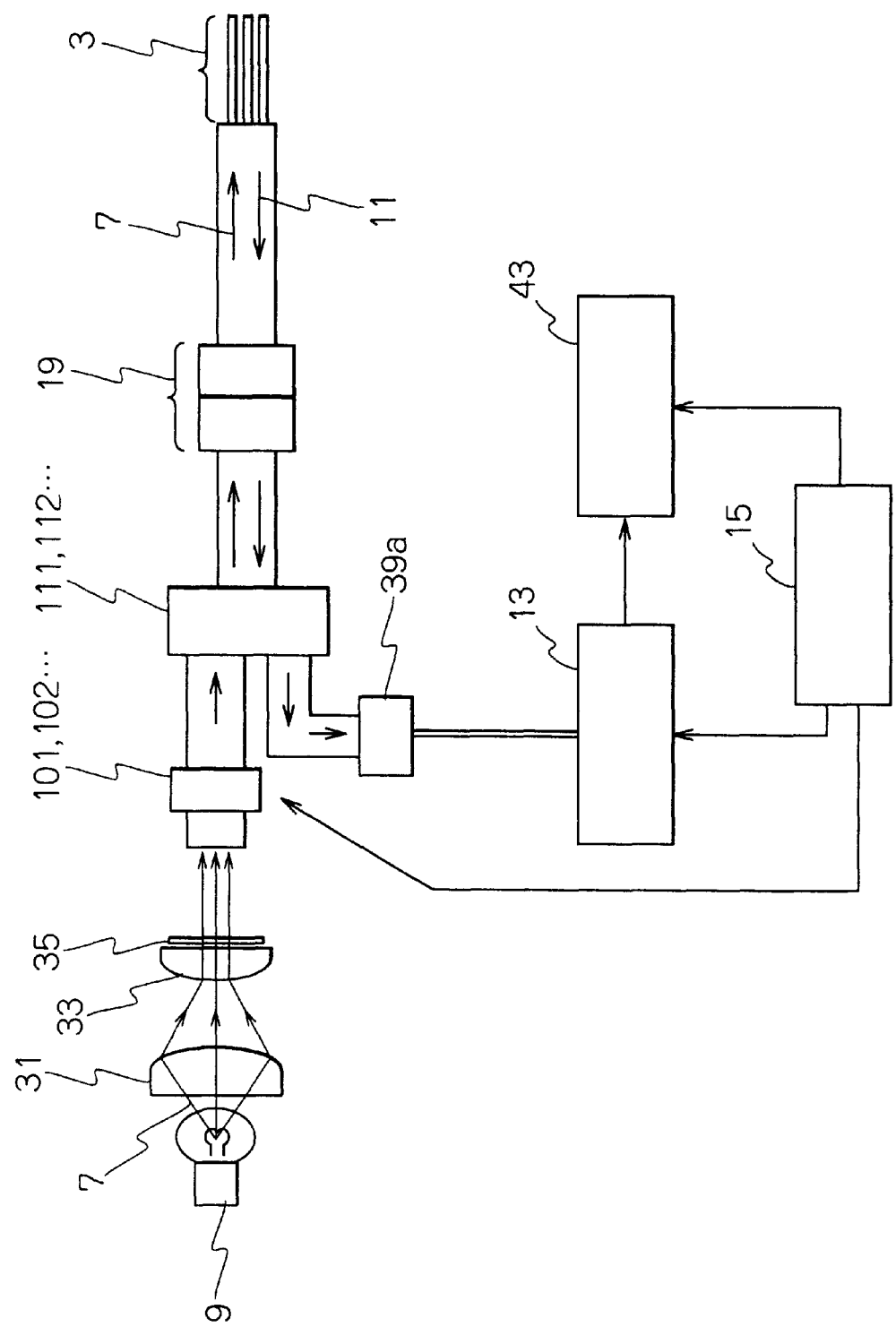
FIG. 16 is a block diagram showing an entire configuration of the immunoassay apparatus disclosed in FIG. 15.

It should be noted that FIG. 15 shows the optical fibers 5a arranged separately from each other but actually, the optical fibers 5a are banded into a single multi-optical fiber as shown in FIG. 16. Moreover, in the same way as Embodiment 1.1, the immunoassay apparatus of Embodiment 1.2 includes a predetermined display block 43.

[Embodiment 1.3]

Figure 17:
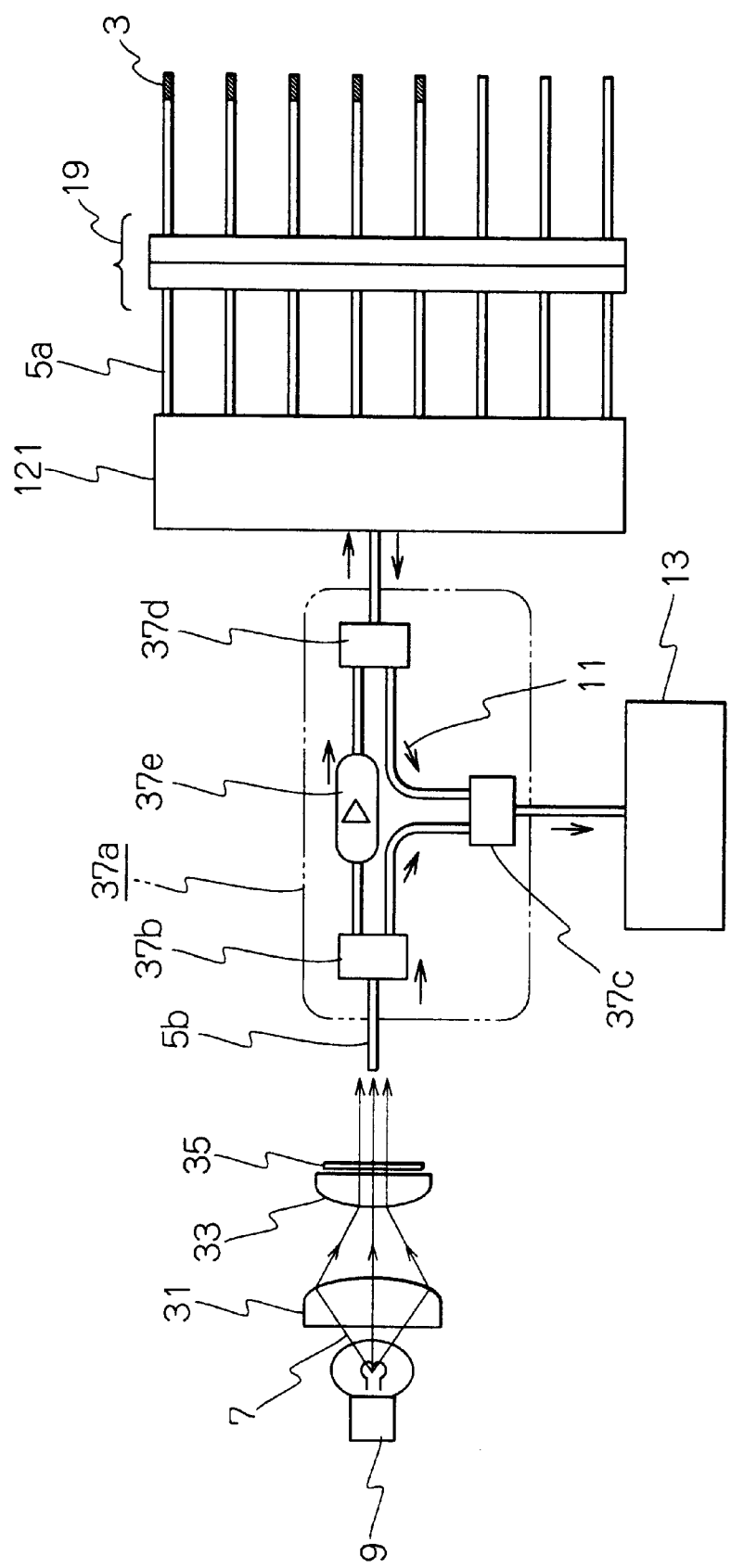
FIG. 17 is a block diagram showing an immunoassay apparatus according to an Embodiment 1.3 of the present invention with an optical fiber and an SPR sensor block enlarged.
Figure 18:
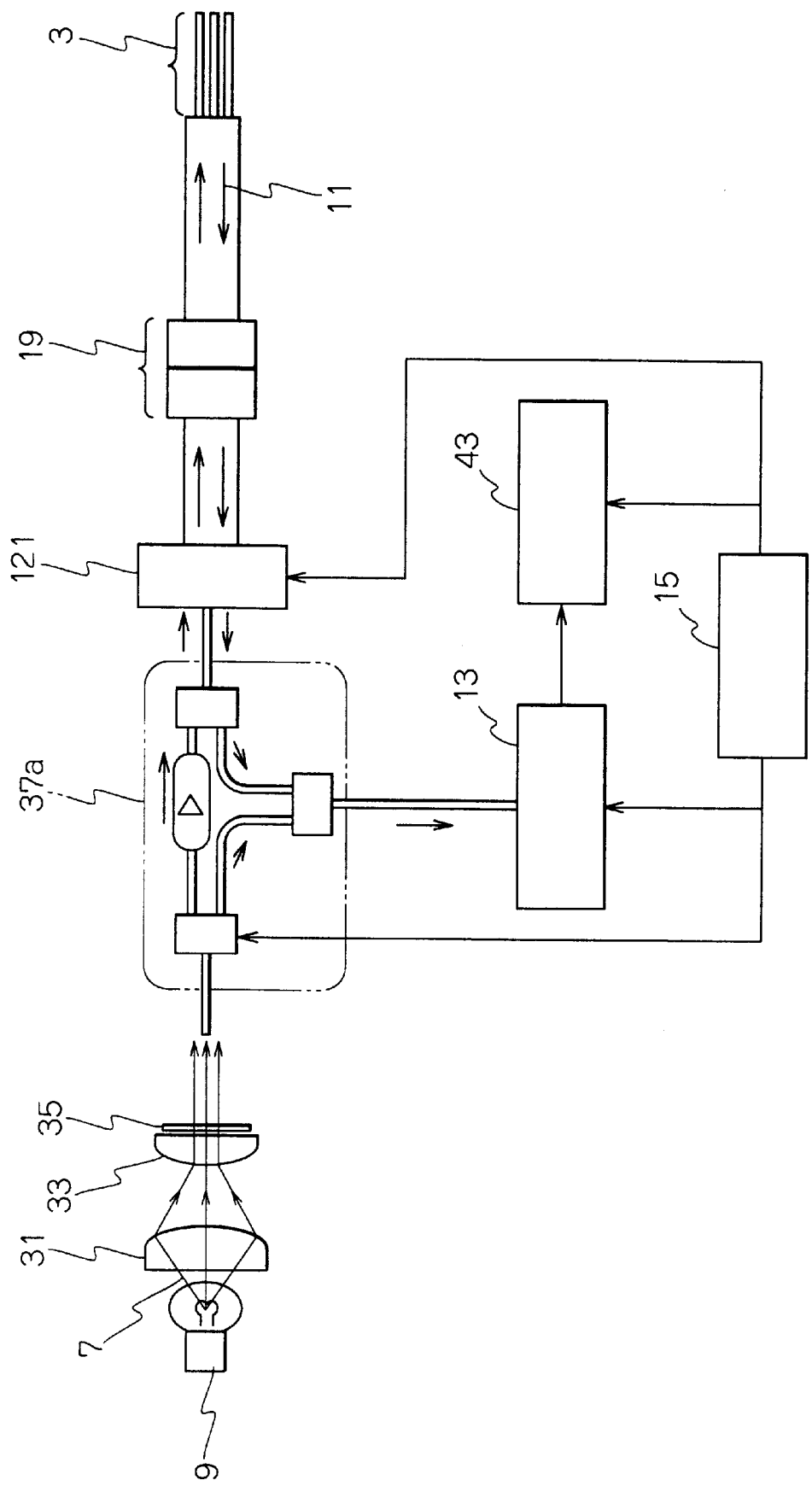
FIG. 18 is a block diagram showing an entire configuration of the immunoassay apparatus disclosed in FIG. 17.

Next, description will be directed to an Embodiment 1.3 of the present invention. As shown in FIG. 17, the immunoassay apparatus according to the Embodiment 1.3 includes a first light switch 121 for switching between transmission and cut-off of the light 7 and branching means 37 provided between the light source 9 and the first light switch 121, for branching the light 7 to the SPR sensor block 3 and to the spectrometer 13.

The branching means 37a has at the upstream side a second light switch 37b for switching introduction of the light 7 to the SPR sensor block 3 and to the spectrometer 15. At the downstream side of the second light switch 37b are provided an isolator 37e and a splitter 37d in this order. On the other hand, between the second light switch 37b and the spectrometer 13, there is provided another splitter 37c. The splitter 37d and the splitter 37c are connected to each other by a predetermined optical fiber.

In this embodiment, the first light switch 121 is used to select an SPR sensor and accordingly, the optical path at the upstream side of the first light switch 121 can be constituted by a single-core optical fiber. That is, the light 7 emitted from the light source 9 passes through the converging lenses 31 and 33, the integrating sphere 32, and the polarizing plate 35 and comes into the single-core optical fiber 5b in the branching means 37a. Here, the second light switch 37b selects an optical path to the SPR sensor block 3 or an optical path to the spectrometer 13. The light 7 which is introduced toward the SPR sensor block 3 passes through the isolator 37e and the splitter 37d, reaching the first light switch 121. Here, one of the optical fibers 5a is selected and the light 7 is introduced into that selected optical fiber 5a to reach the SPR sensor block 3.

In the SPR sensor block 3, the light 7 is partially attenuated by a surface plasmon resonance and returned as the reflected light 11 to the first light switch 121. The reflected light 11 is then branched by the splitter 37d. Here, the reflected light 11 is directly transmitted to the spectrometer but is not transmitted to the second light switch 37b because of the isolator 37e. The reflected light 11 introduced into the spectrometer 13 is subjected to a wavelength analysis. Moreover, the light 7 coming from the second light switch 37b is also introduced into the spectrometer 13 so that the (incident) light 7 is compared to the reflected light 11. It should be noted that the immunoassay apparatus according to this embodiment also includes a predetermined control block 15 and a display block 43.

Next, explanation will be given on modifications of the branching means 37a.

FIG. 19A shows a modification in which a third light switch 38c is provided at the upstream side of the spectrometer 13. By using this third light switch 38c, unlike the splitter, it is possible only the light from one direction and accordingly, there is no need of consideration on the other light state.

FIG. 19B shows a modification in which a circulator 40d is provided for switching the optical path. When an optical path of the second light switch 40b is selected by the circulator 40d, the light 7 is introduced to a terminal T1 of the circulator 40d and comes out from a terminal T2 of the circulator 40d. This light 7 is reflected by the SPR sensor block 3 (omitted in FIG. 19) and returned as the reflected light 11 to the terminal T2 of the circulator 40d. The reflected light 11 then comes out of a terminal T3 of the circulator 40d, and via the third light switch 40c, introduced to the spectrometer 13. Moreover, by switching by the second light switch 40b, the (incident) light 7 is directly introduced to the spectrometer 13. It should be noted that the second light switch 40b and the third light switch 40c are synchronized in operation. Thus, it is possible to compare the (incident) light 7 and the reflected light 11.

[Embodiment 1.4]

Figure 20:
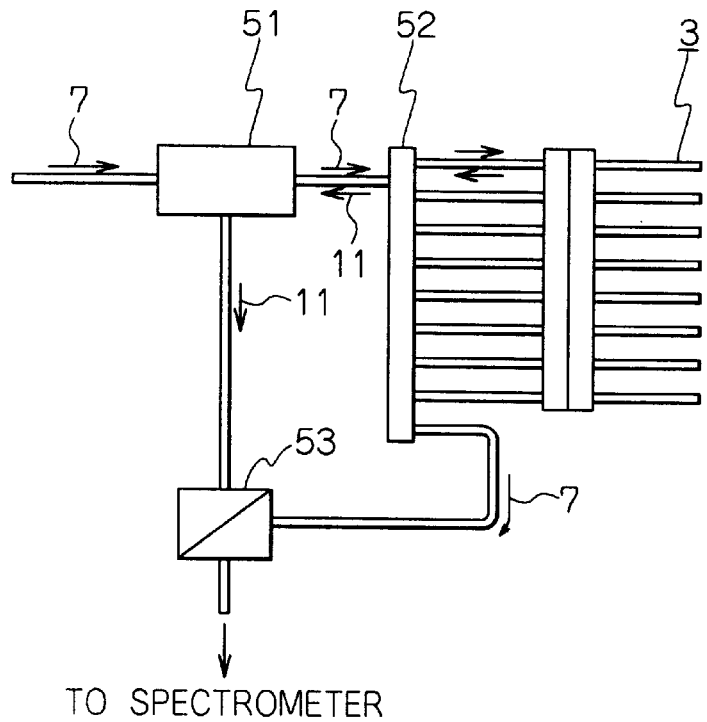
FIG. 20 is a block diagram showing branching means used in an immunoassay apparatus according to an embodiment 1.4 of the present invention.

Next, description will be directed to an embodiment 1.4. In the immunoassay apparatus according to the embodiment 1.4, as shown in FIG. 20, a circulator 51 is provided for branching the light 7 from the light source into two optical paths: one to the SPR sensor block 3, and the other to the spectrometer. These optical paths are switched to each other at a predetermined timing.

At the downstream side of the circulator 51 leading to the SPR sensor block 3, there is provided a light switch 52. This light switch 52 is connected to a single optical fiber for the incident light and to a number of optical fibers at the side of the SPR sensor block 3. Among the number of optical fibers provided at the side of the SPR sensor block 3, one optical fiber serves to transmit the light 7 from the light source to the spectrometer, and the remaining optical fibers respectively constitute SPR sensors 3 at their end portions.

On the other hand, the reflected light 11 reflected from the SPR sensor block 3 is returned by the light switch 52 to the circulator 51. That is, only the light reflected one of the optical fibers of the SPR sensor block 3 is returned to the circulator 51. The circulator 51 functions to transmit the reflected light 11 to the side of the spectrometer.

The light 7 coming light from the light switch 52 and the reflected light 11 coming from the circulator 51 are introduced to the splitter 53 which is provided at the upstream side of the spectrometer. The (incident) light 7 and the reflected light 11 are subjected to a wavelength distribution analysis by the spectrometer. It should be noted that the splitter 53 at the upstream side of the spectrometer may be replaced by a light switch.

Figure 21:
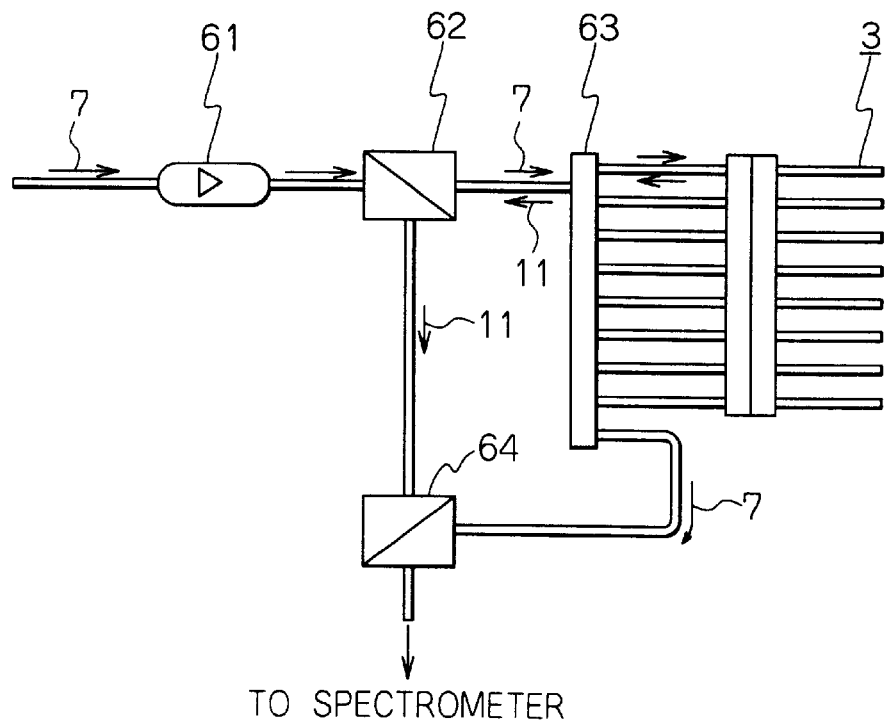
FIG. 21 a block diagram showing a modified example of the branching means disclosed in FIG. 20.

Next, explanation will be given on a modification of this embodiment. In this modification, as shown in FIG. 21, the aforementioned circulator 51 is replaced by a splitter 62, and an isolator 61 is provided at the upstream side of this splitter 62. The splitter 62 and the isolator 61, as separate devices, have the aforementioned functions.

The light 7 which has passed through the isolator 61 and the splitter 62 are transmitted to the SPR sensor block, and the reflected light 11 reflected by the SPR sensor block 3 is returned to the splitter 62. Here, as the isolator 61 is provided at the upstream side of the splitter 64, the reflected light 11 is not transmitted to the light source side. Moreover, the reflected light 11 returned to the splitter 62 is introduced into the splitter 64 provided at the upstream side of the spectrometer.

On the other hand, a part of the light coming out of the light switch 63 and not transmitted to the SPR sensor block 3 is directly introduced to the splitter 64. That is, the (incident) light 7 and the reflected light 11 are introduced via the splitter 64 to the spectrometer provided at the downstream side of the splitter 64. Thus, the (incident) light 7 and the reflected light 11 are subjected to a wavelength distribution analysis.

It should be noted that the immunoassay apparatus according to the present invention can also be applied to a quantitative analysis of bacteria, river and see water check, toxin check, meat and vegetable quality check, and the like.

[Embodiment 2.1]

Figure 22:
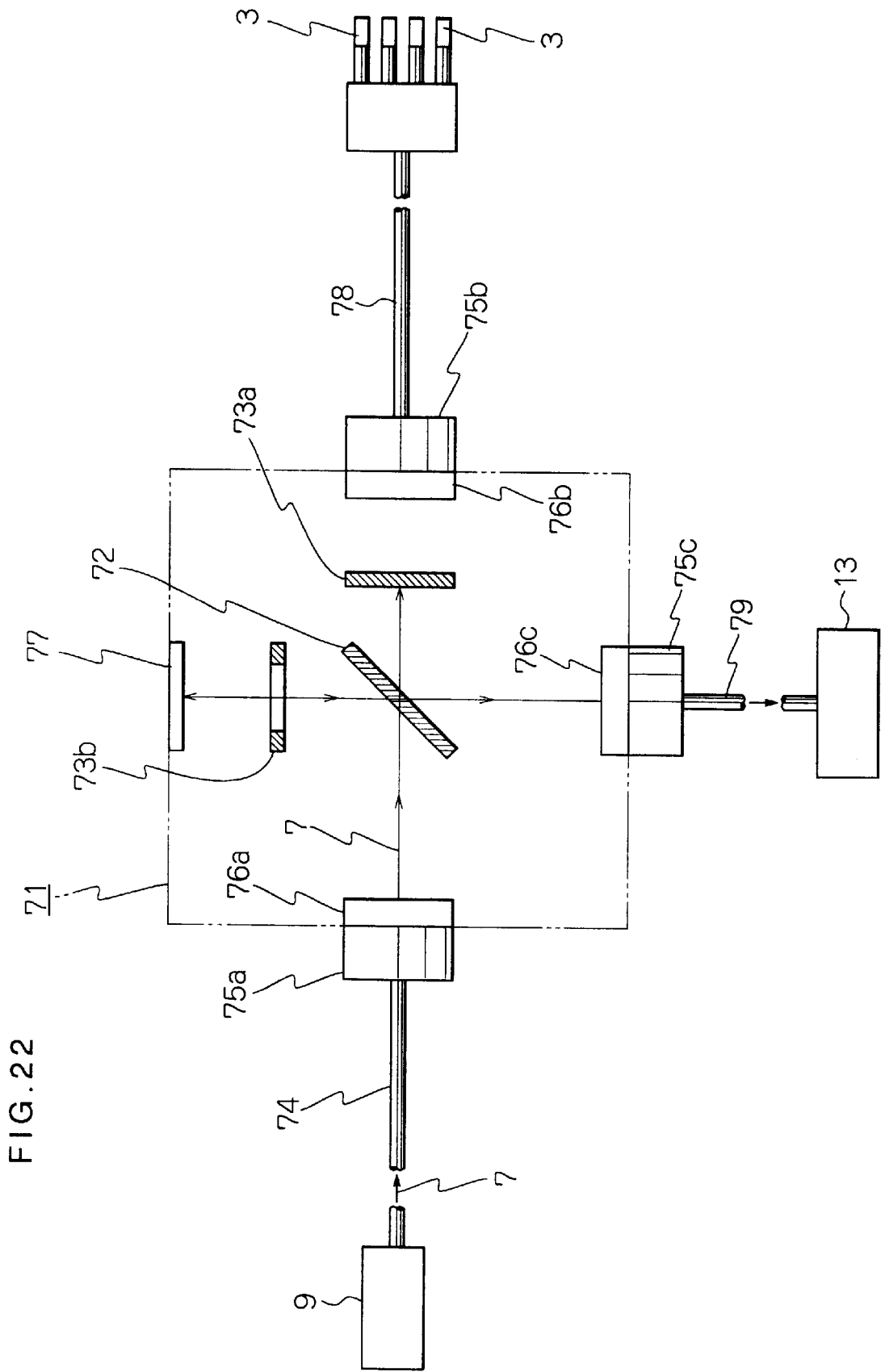
FIG. 22 is a block diagram showing a configuration of optical path selecting means used in an embodiment 2.1 of the present invention for a case when light from a light source is directly introduced to a spectrometer.
Figure 23:
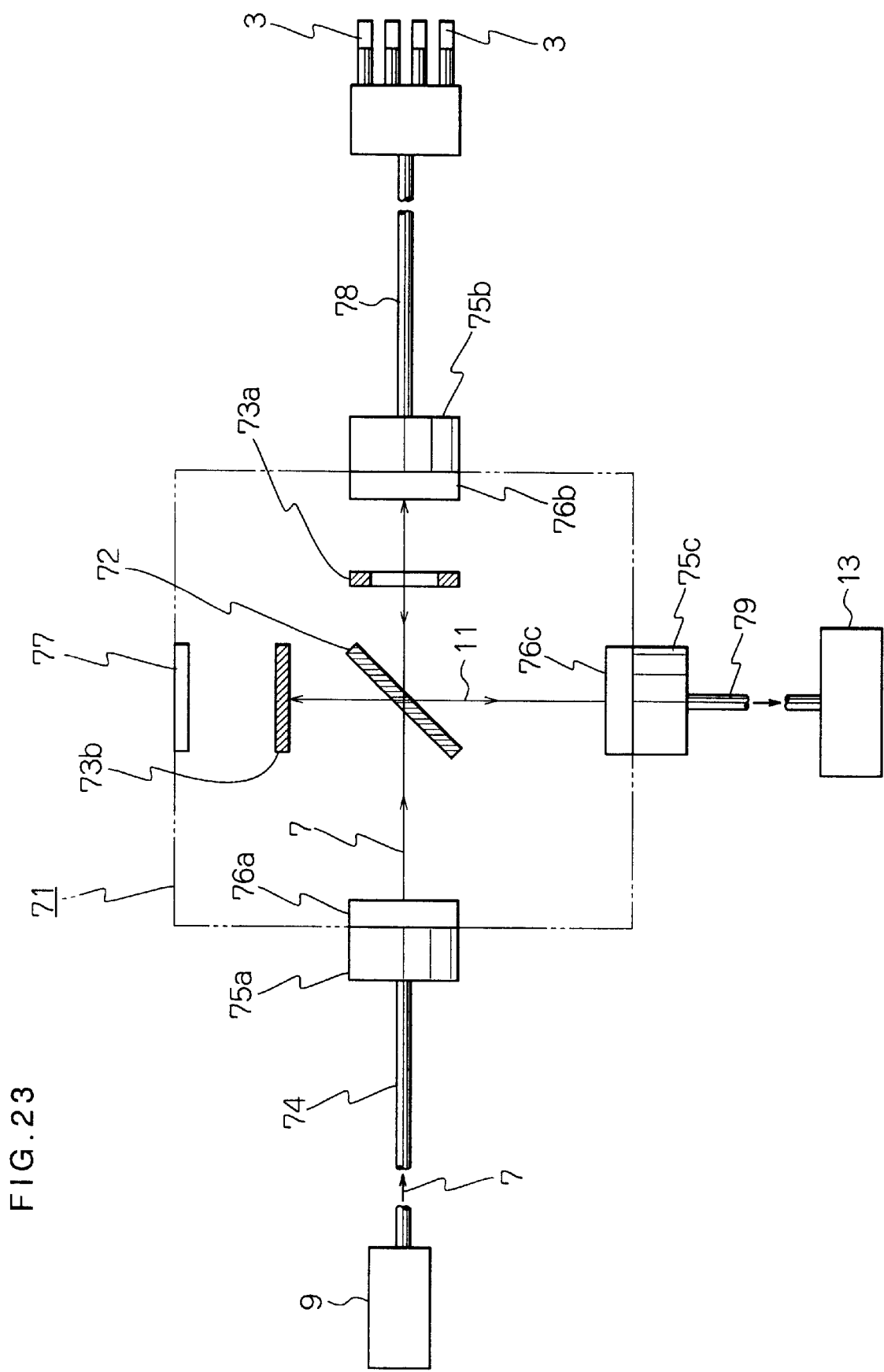
FIG. 23 shows the optical path selecting means disclosed in FIG. 22 for a case when a reflected light from an SPR sensor block is introduced to the spectrometer.

Next, description will be directed to an embodiment 2.1 of the present invention. The immunoassay apparatus according to the embodiment 2.1, as shown in FIG. 22 and FIG. 23, is characterized in using optical path selecting means having a predetermined beam splitter 72 and shutters 73a and 73b.

More specifically, the optical path selecting means 71 is connected via an optical fiber connector 75a to an optical fiber 74 for introducing the light 7 from the light source 9. This optical fiber connector 75a is connected via a connector receptacle 76a to the optical path selecting means. The optical fiber connector 75a can be removed from the connector receptacle 76a. However, the optical fiber connector 75a is not indispensable. That is, the optical path selecting means 71 can be connected directly to the optical fiber 74.

Moreover, the beam splitter 72 is arranged on the optical path leading to the light source 9. The beam splitter 72 transmits a part of the incident light and reflects the other part of the light. The beam splitter 72 is formed by a dielectric multi-layered film and a chrome film and is arranged with an angle of 45 degrees with respect to the light path of the light 7.

Furthermore, in the vicinity of the beam splitter 72, the shutter 73a is arranged at the downstream side of the optical path of the light 7. This shutter functions to control transmission and cut-off of the light 7 to the SPR sensor block 3.

The shutter 73a, for example, includes a liquid crystal panel for controlling the transmittance of the light 7 electrically. Moreover, it is also possible to employ a mechanical type shutter. The opening/closing operation of the shutter 73a may be automatically controlled by the main control block 15 of the immunoassay apparatus or manually switched for each immunoassay.

As has been described above, the optical path selecting means 71 includes the beam splitter 72 and the shutter 73 arranged on the optical path. Moreover, the shutter 73b is arranged in a direction which intersects the optical path at a right angle. This shutter 73b has an identical configuration as the aforementioned shutter 73 arranged on the optical path. Furthermore, a mirror 77 is provided behind the shutter 73b. As has been described above, the beam splitter 72 is arranged at an angle of 45 degrees with respect to the optical path of the light 7 and accordingly, a part of the light 7 reflected by the beam splitter 72 advances in the direction of the shutter 73b and the mirror 77.

On the line connecting the mirror 77 and the shutter 73b, but opposite side of the splitter 72, there is provided another connector receptacle 76c. The connector receptacle 76c is connected via an optical fiber connector 75c to an optical fiber 79c. This optical fiber 79 serves to introduce to a spectrometer 13, the light 7 or the reflected light 11 from the SPR sensor block 3. The optical fiber 79 together with the optical fiber connector 75c can be removed from the connector receptacle 76c.

On the optical path of the light 7, after the shutter 73a, there is provided a connector receptacle 76b. This connector receptacle 76b is connected to an optical fiber connector 75b. This optical fiber connector 75b serves to connect an optical fiber 78 leading to the SPR sensor block 3.

Next, explanation will be given on operation of the optical path selecting means having the aforementioned configuration.

FIG. 22 shows the light 7 directly introduced to the spectrometer 13. The light 7 from the light source 9 passes through the optical fiber 74, the optical fiber connector 75a, and the connector receptacle 76a, and is introduced into the optical path selecting means 71, reaching the beam splitter 72.

A part of the light 7 passes through the beam splitter 72 and reaches the shutter 73a. Here, the shutter 73a is automatically or manually controlled so as to cut-off the light 7. Accordingly, the light 7 will not reach the SPR sensor block.

On the other hand, the other part of the light 7 which has been reflected by the beam splitter 72 with a right angle is introduced to the shutter 73b. Here, the shutter 73b is in an open state for transmitting the light 7, and the light reaches the mirror 77 located behind the shutter 73b. The mirror 77 reflects the light 7 entirely so as to pass the shutter 73b again. The light 7 which has passed through the shutter 73b reaches the beam splitter 72. A part of the light 7 passes through the beam splitter 72 and reaches the optical fiber 79 leading to the spectrometer 13. This light 7 is subjected to a wavelength distribution analysis by the spectrometer 13. This is a case when the light 7 coming from the light source 9 is directly subjected to analysis by the spectrometer 13.

Next, explanation will be given on a case of an immune reaction at the SPR sensor block 3 with reference to FIG. 23. The light 7 from the light source 9 is introduced into the optical path selecting means via the optical fiber 74, the optical fiber connector 5a, and the connector receptacle 76a. A part of the light 7 which has reached the beam splitter 72 passes through the beam splitter 72 and reaches the shutter 73a. Here, the shutter 73a is automatically or manually controlled to transmit the light 7. Thus, the light 7 reaches the sensor block 3. The light reaching the SPR sensor block 3 is changes its wavelength distribution according to an immune reaction in the SPR sensor block.

A reflecting mirror (not depicted) is provided at the end face of the SPR sensor 3. The light 7 which has changed its wavelength distribution is reflected by this reflecting mirror an comes back as a reflected light to the optical path selecting means 71. The reflected light 11 passes through the optical fiber 78 and the shutter 73a, reaching the beam splitter 72. The reflected light 11 is introduced by the beam splitter 72 into the spectrometer 13.

On the other hand, a part of the (incident) light 7 from the light source 9 is reflected by the beam splitter 72 and reaches the shutter 73b. At this moment, the shutter 73b is controlled not to transmit the light 7. Thus, the light 7 will not reach the mirror 77 to be reflected. Thus, by controlling opening/closing of the shutters 73a and 73b, it is possible to alternately analyze a wavelength distribution of the (incident) light 7 from the light source 9 and the reflected light from the SPR sensor block 3. That is, with one spectrometer 13, it is possible to alternately analyze the incident light 7 and the reflected light 11.

As has been described above, the optical selecting means 71 in this embodiment, has a plurality of connector receptacles, to which a plurality of optical fibers can be connected vian optical fiber connectors. Consequently, the optical fibers can easily be removed when required. This facilitates disassembling and assembling of respective components, including replacement of the SPR sensor block for checking different antigens. Moreover, because of the shutters and the beam splitter, the optical path selecting means can have a simplified configuration and a reduced size. It should be noted that as shown in FIG. 22, by connecting a plurality of optical fibers via a light switch, it is possible to carry out a plurality of immunoassays in a short time.

[Embodiment 3.1]

Figure 24:
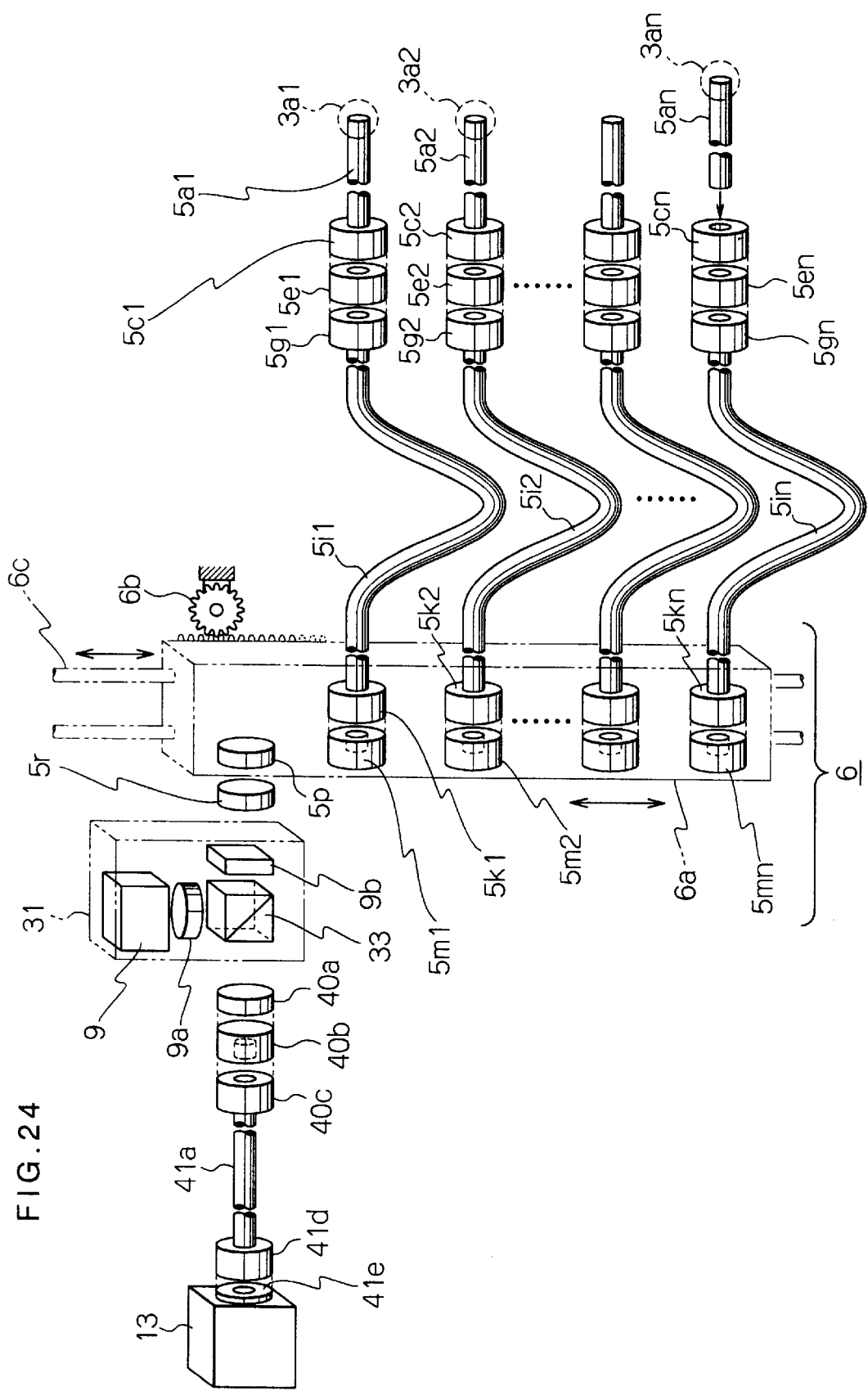
FIG. 24 is a perspective view showing a configuration of an immunoassay apparatus according to Embodiment 3.1.

The immunoassay apparatus according to Embodiment 3.1 is characterized by an optical path switching mechanism shown in FIG. 24. FIG. 24 schematically shows main components of the optical path switching mechanism according to this embodiment. This immunoassay apparatus includes: optical fibers 5a1, 5a2, ..., 5cn, having at one end, SPR sensors 3a1, 3a2, ..., 3an, respectively; light emitting means 31 for emitting a predetermined light; and a spectrometer 13 for detecting and analyzing a reflected light from the SPR sensors 3a1, 3a2, ..., 3an. That is, for the plurality of optical fibers 5a1, 5a2, 5an, each having the SPR sensors 3a1, 3a2, ..., 3an, there is provided only one light emitting means 31 and only one spectrometer 13.

These sensor optical fibers 5a1, 5a2, ..., 5an are introduced vian optical fiber connectors 5a1, 5c2, ..., 5cn, adapters 5e1, 5e2, ... 5en, and intermediate optical fibers 5i1, 5i2, ..., 5in, to the vicinity of the light emitting means 31. The light emitting means 31 is connected to the spectrometer 13 via a predetermined spectrometer optical fiber 41a. In the optical path switching mechanism according to this embodiment, the intermediate optical fibers 5i1, 5i2, ..., 5in have their ends movable with respect to the light emitting means 31 so as to introduce a reflected light from the plurality of the SPR sensors 3a1, 3a2, ..., 3an to the spectrometer 13.

It should be noted that FIG. 24 shows the optical fiber connectors 5c1, 5c2, ..., 5cn, the adapters 5e1, 5e2, ..., 5en, and the optical fiber connectors 5g1, 5g2, ..., 5gn separated from one another, but they are connected to one another in actual use.

Hereinafter, explanation will be given on a portable type immunoassay apparatus 1 (see FIG. 34) as an example of the present embodiment.

[SPR Sensors]

Figure 25:
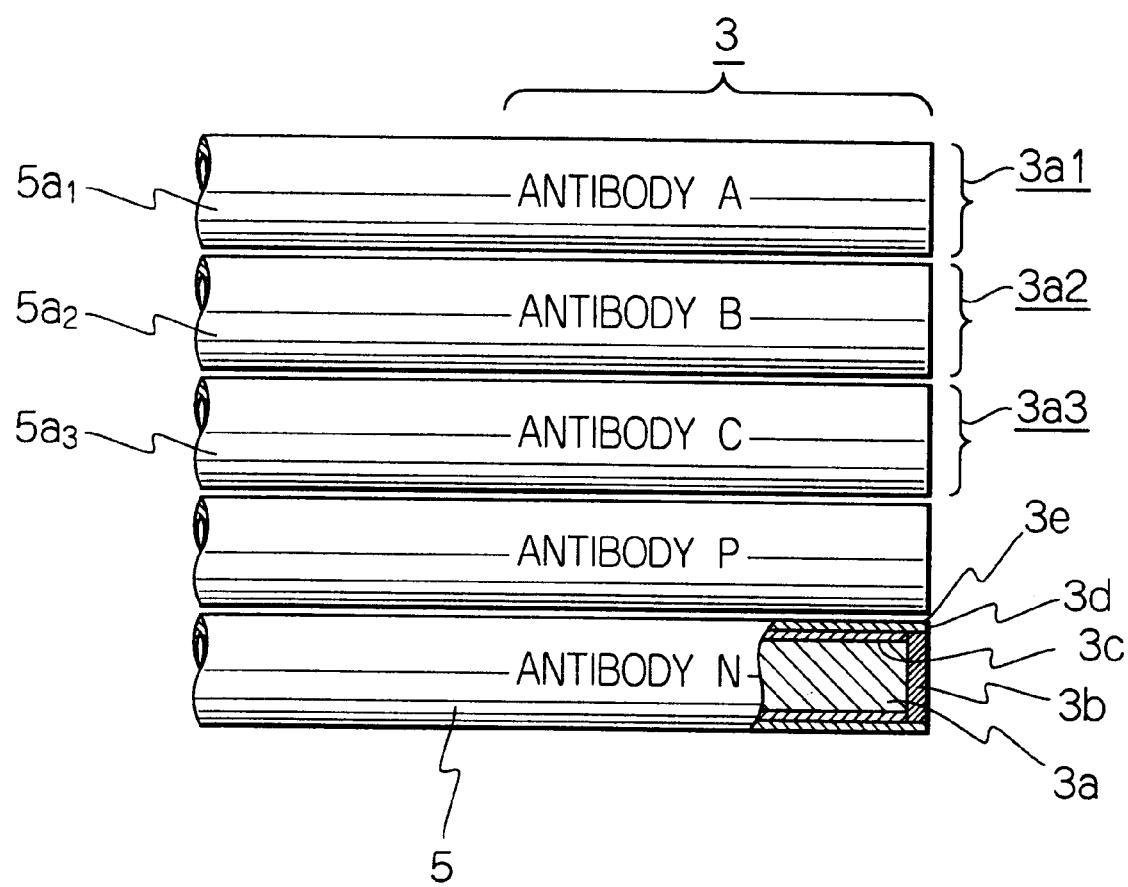
FIG. 25 is a side view showing SPR sensors disclosed in FIG. 25, partially cut-off.

As shown in FIG. 24 and FIG. 25, the immunoassay apparatus according to the present embodiment includes a plurality of sensor optical fibers 5a1, 5a2, ..., 5an whose end portions serving as the SPR sensors 3a1, 3a2, ..., 3an. As shown in FIG. 25, each of the sensor optical fibers 5a1 has a core 3a whose end face is coated by silver serving as a reflecting mirror 3b. The outer circumference of the core 3a at the end portion is coated by metal thin film 3c made from silver or gold. This metal thin film 3c is further covered by a dielectric film 3d, on which an antibody 3e is fixed.

[Light Emitting Means]

Next, the light emitting means 31 will be explained with reference to FIG. 24. The light emitting means 31 emits a light of a predetermined wavelength band. More specifically, as shown in FIG. 24, the light emitting means includes: a predetermined light source 9, a converging lens 9a, and a beam splitter 33. Moreover, the light emitting means may include a shutter 9b.

The light source 9 is a halogen lamp. The halogen lamp contains a light of various wavelengths and, during an immunoassay, emits a predetermined light to the sensor optical fibers 5a1, 5a2, ..., 5an. It should be noted that the light source 9 is not to be limited to a halogen lamp but can be other than a halogen lamp if a predetermined wavelength band of light can be obtained. Moreover, in case a wavelength to be attenuated by an immune reaction can be predicted, it is possible to use a light source which can emit a light containing only a wavelength near the predicted wavelength.

Moreover, the converging lens 9a converges the light emitted from the light source 9 with a predetermined ratio and introduces the light into the beam splitter 33 which will be detailed later. The converging lens 9a is selected according to the light from the light source 9. More specifically, if the light from the light source 9 is a divergent light, a lens having a function to converge the light is selected.

The beam splitter 33 arranged at the downstream side of the converging lens 9a functions to branch the incident light. More specifically, the beam splitter 33 has a surface for reflecting a part of the incident light from the light source 9 in inclined toward the SPR sensors 3a1, 3a2, ..., 3an. Accordingly, a part of the light from the light source 9 is reflected toward the SPR sensors 3a1, 3a2, ..., 3an. On the other hand, the remaining part of the light from the light source 9 transmits the beam splitter 33. This is because the beam splitter 33 consists of a half mirror or the like.

Moreover, the shutter 9b is arranged in the vicinity of the beam splitter 33 for controlling radiation/non-radiation of the light to the SPR sensors 3a1, 3a2, ..., 3an. The shutter 9b is, for example, a liquid crystal shutter.

[Spectrometer]

Figure 26:
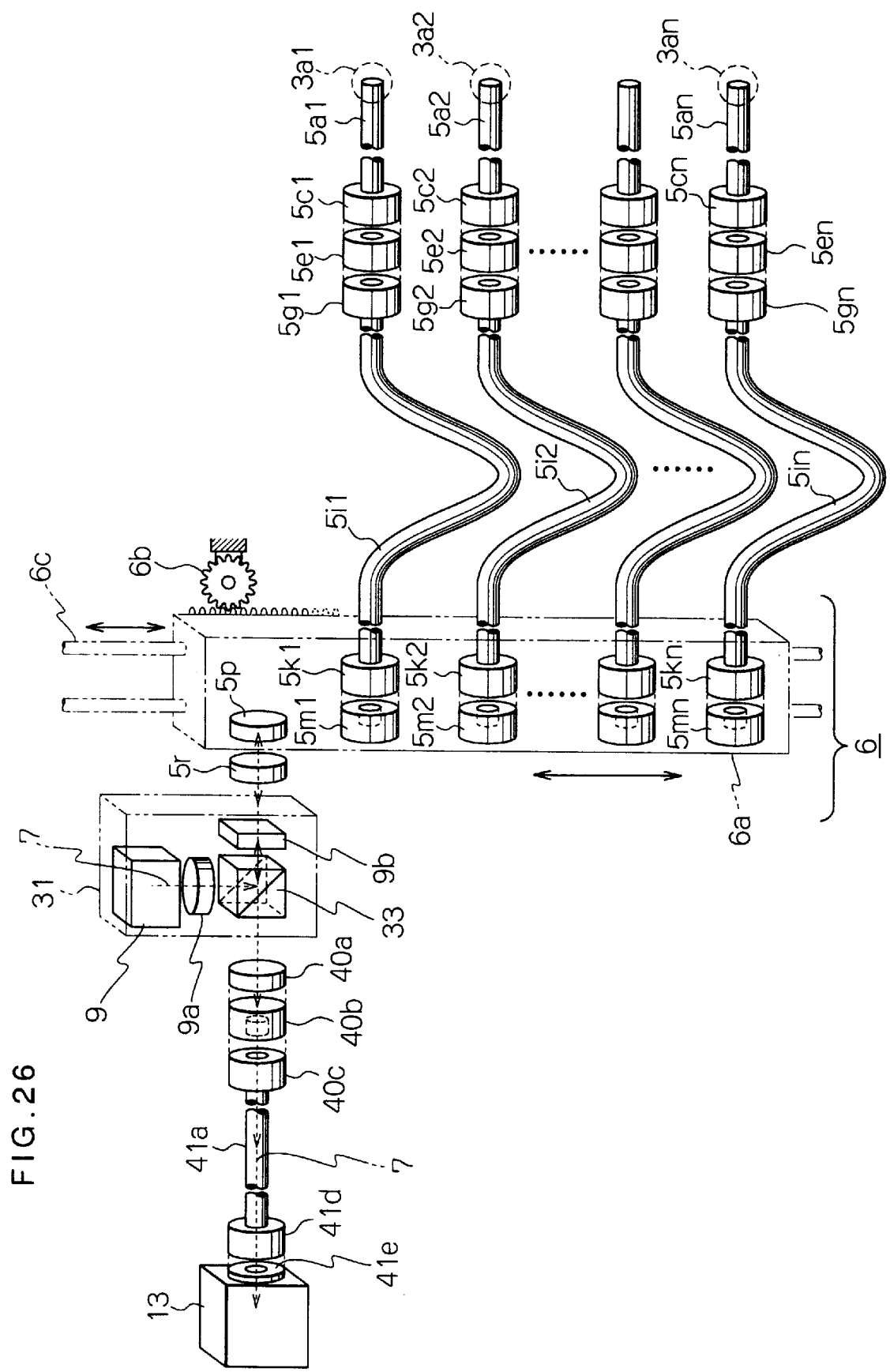
FIG. 26 shows the immunoassay apparatus in a state for carrying out a reference measurement.

As shown in FIG. 24 and FIG. 26, the immunoassay apparatus 1 according to the present embodiment includes the spectrometer 13. The spectrometer 13 is used for analyzing wavelength distribution (spectrum pattern of the light used for an immunoassay. Here, two lights are introduced to this spectrometer. One of the lights is emitted from the light source 9, which passes through the aforementioned converging lens 9a and the beam splitter 33 and is reflected by a total reflection mirror 5p which will be detailed later so as to pass the beam splitter 33. The other of the lights is reflected from the SPR sensors 3a1, 3a2, ..., 3an.

In the spectrometer 13, the incident light from the light source 9 is compared to the reflected light from the SPR sensors 3a1, 3a2, ..., 3anm in wavelength distribution so as to determine which wavelength is attenuated in the reflected light. It should be noted that the light from the light emitting means 31 is introduced to the spectrometer 13 via a predetermined converging lens 40a, a receptacle 40b, an optical fiber connector 40c, a spectrometer optical fiber 41a, and further an optical fiber connector 41d and a spectrometer adapter 41e. The present embodiment employs only one spectrometer 13, but it is also possible to provide two or more spectrometers if increase of a production cost is allowed.

[Optical Path Switching Mechanism]

Next, an explanation will be given on the configuration of the optical path switching mechanism for the plurality of the optical fibers. In order to use the one spectrometer 13 for the respective SPR sensors 3a1, 3a2, ..., 3an, by introducing the reflected light from the SPR sensors 3a1, 3a2, ..., 3an to the spectrometer one after another, the optical path is switched from one to another while moving the ends (left ends in the figure) of the intermediate fibers.

In this embodiment n sensor fibers 5a1, 5a2, ..., 5an are provided, respectively having at one end the SPR sensors 3a1, 3a2, ..., 3an, and at the other end, optical fiber connectors 5c1, 5c2, ..., 5cn.

The optical fiber connectors 5c1, 5c2, ..., 5cn are connected to the corresponding connectors 5e1, 5e2, ..., 5en. When an immunoassay at one of the SPR sensors is complete, the corresponding optical fiber alone can be removed with the optical fiber connector from the corresponding adapter. To the other side of the adapters 5e1, 5e1, ..., 5en are connected further optical fiber connectors 5g1, 5g2, ..., 5gn of the intermediate optical fibers 5i1, 5i2, ..., 5in for introducing the incident light from the light emitting means 31 to the SPR sensors 3a1, 3a2, ..., 3an as well as introducing the reflected light from the SPR sensors 3a1, 3a2, ..., 3an to the spectrometer 13. The optical fiber connectors 5g1, 5g2, ..., 5gn may be identical to the optical fiber connects 5c1, 5c2, ..., 5cn.

Moreover, the sensor optical fibers 5a1, 5a2, ..., 5an may be constituted so as to be removable from the optical fiber connectors 5c1, 5c2, ..., 5cn because the connectors are quite expensive. If the optical fiber connectors 5c1, 5c2, ..., 5cn can be reused by discarding the optical fibers alone, the immunoassay cost can be reduced, For example it is possible to form a predetermined through hole in the optical fiber connectors 5c1, 5c2, ..., 5cn so that the sensor optical fibers 5a1, 5a2, ..., 5an can be inserted into the holes.

It should be noted that the sensor optical fibers 5a can be connected to the intermediate optical fibers 5i1, 5i2, ..., 5in by connecting the connectors 5a1, 5c2, ..., 5cn directly to the connectors 5g1, 5g2, ..., 5gn without using the adapters.

Each of the intermediate optical fibers 5i1, 5i2, ..., 5in has a sufficient length compared to the distance between the light emitting means 31 and the adapters 5e1, 5e2, ..., 5en. The intermediate optical fibers has at their other ends, optical fiber connectors 5k1, 5k2, ..., 5kn which can be connected to and removed from receptacles 5m1, 5m2, ..., 5mn which serve for light transmission between the light emitting means 31 and the intermediate optical fibers 5i1, 5i2, ..., 5in.

In the immunoassay apparatus 1 according to the present embodiment, the sensor optical fibers 5a1, 5a2, ..., 5an together with the SPR sensors 3a1, 3a2, ..., 3an are arranged in one plane. The optical fiber connectors 5k1, 5k2, ..., 5kn of the intermediate fibers 5i1, 5i2, ..., 5in and the corresponding receptacles 5m1, 5m2, ..., 5mn are also arranged in one plane so as to oppose to the light emitting means 31. However, prior to an immunoassay, the total reflection mirror 5p is located to oppose the light emitting means 31 so that the light from the light emitting means 31 is directly introduced to the spectrometer 13. That is, a part of the light reflected by the beam splitter 33 is further reflected by the total reflection mirror 5p so as to pass through the beam splitter 33, reaching the spectrometer 13.

The total reflection mirror 5p, the optical fiber connectors 5k1, 5k2, ..., 5kn, and the receptacles 5m1, 5m2, ..., 5mn are supported on a predetermined shifting frame 6a in a shifting mechanism 6. The shifting frame 6a retains the optical fiber connector 5k1, 5k2, ..., 5kn of the intermediate fibers 5i1, 5i2, ..., 5in and the corresponding receptacles 5m1, 5m2, ..., 5mn as a unitary block, so as to shift these components all at once according to a control instruction from a main control block 15 which will be detailed later. More specifically, the shifting frame is shifted along a guide shaft 6c. However, the shifting mechanism 6 is not to be limited to this configuration. It should be noted that in this embodiment, cross sections of the sensor optical fibers 5a1, 5a2, ..., 5an are arranged in a single straight line but can also be arranged in matrix or circle. The same applies to the intermediate fibers 5i1, 5i2, ..., 5in.

[Immunoassay Procedure]

(1) Reference measurement

Firstly, for a reference measurement, the light from the light source is directly subjected to a wavelength distribution analysis. This reference measurement is carried out for evaluation of the operation of the immunoassay apparatus itself. As shown in FIG. 26, the light 7 from the light source 9 passes through the converging lens 9a and reaches the beam splitter 33. In the beam splitter 33, a part of the light 7 is reflected to pass the converging lens 5r and reaches the total reflection mirror 5p. The light is totally reflected by this total reflection mirror 5p to return through the previous optical path, reaching the beam splitter 33. The light passes through the beam splitter and then the converging lens 40a, the receptacle 40b, the optical fiber connector 40c, and the spectrometer optical fiber 41a to reach the spectrometer 13. Thus, it is possible to obtain a wavelength distribution of the light 7 emitted from the light source 9.

(2) Sample analysis

For actual analysis of a predetermined sample, the SPR sensors 3a1, 3a2, ..., 3an corresponding to check items are used. Connection of these sensors, i.e., the optical fiber connectors 5c1, 5c2, ..., 5cn is carried out independently from one another. However, it is also possible to use a multi-fiber connector so as to connect a plurality of optical fibers all at once.

The preservation buffer 27 is discharged from the cap member 21. The sample 47 is introduced from the sample tube 49 into the cap member by way of suction. This suction is carried out by using the aforementioned suction pump 25. The sample tube 49 contains 500 μl of the sample 47, from which only about 100 μl is actually introduced into the cap member 21.

Figure 27:
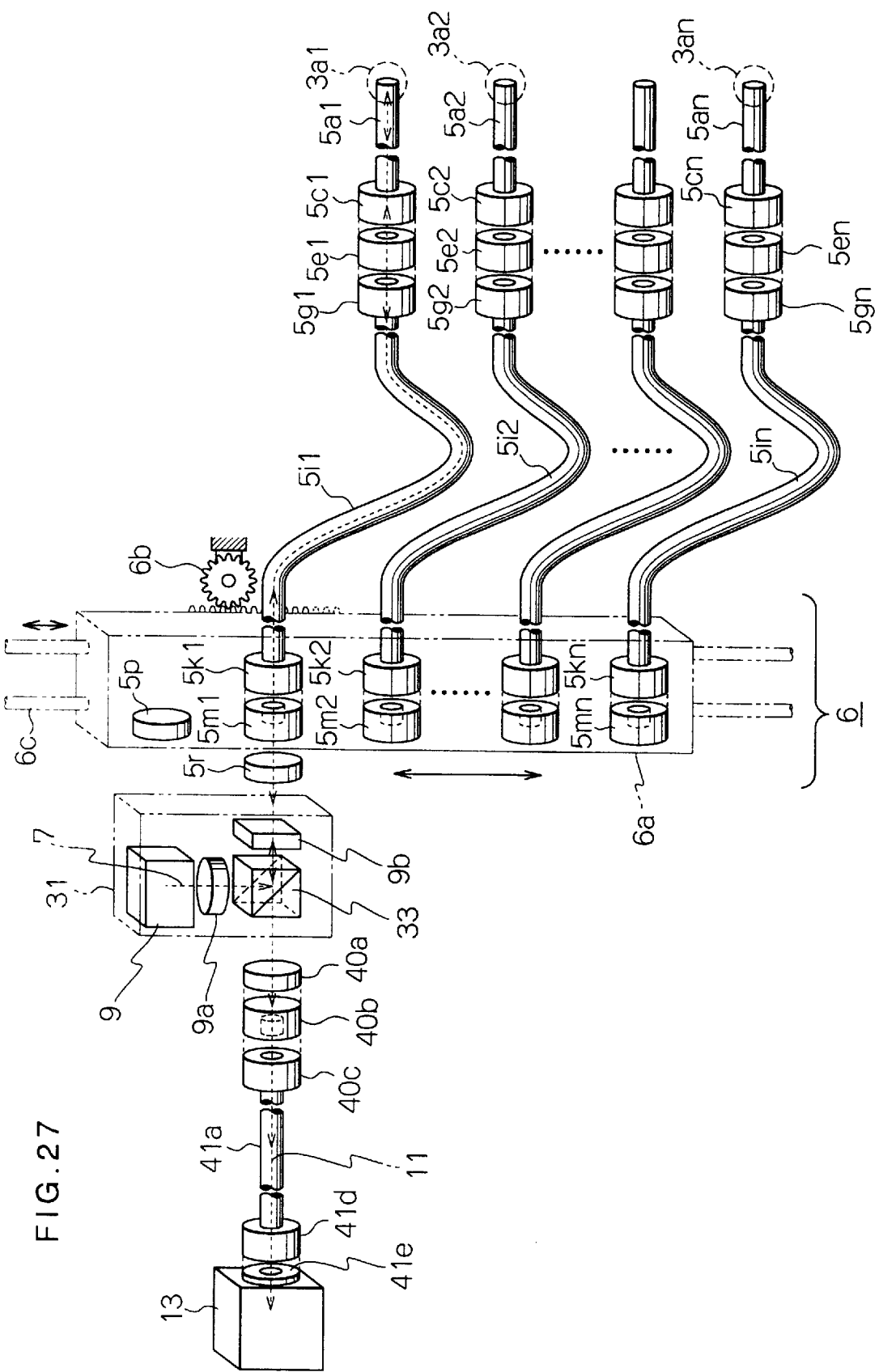
FIG. 27 shows the immunoassay apparatus in a state for carrying out an immunoassay with a first SPR sensor.

When the cap member 21 is filled with the sample 47, an immunoassay can be carried out. More specifically, as shown in FIG. 27, the shifting frame 6a is shifted so that the optical path of the light emitting means 31 is matched with the optical path of the receptacle 5m1 connected to the first intermediate optical fiber 5i1. Here, the total reflection mirror 5p is moved away from the optical path. Note that the SPR sensor block 3a remains at a fixed position, and only the intermediate optical fibers 5i1, 5i2, ..., 5in having one end fixed to the shifting frame are moved. Because the intermediate optical fibers 5i1, 5i2, ..., 5in have a sufficient length, the shifting frame 6a can be moved freely.

The light 7 from the light source 9 is reflected by the beam splitter 33 and introduced via the receptacle 5m1 and the optical fiber connector 5k1 to the intermediate optical fiber 5i1. The light 7 passing through this intermediate optical fiber 5i1 further passes through the optical fiber connector 5g1, the adapter 5e1, and the optical fiber connector 5c1, reaching the SPR sensor 3a1. Here, the light 7 advances while being reflected by the outer circumference of the end portion of the SPR sensor 3a1 and is reflected by the reflective mirror 3b (mirror coated by gold or silver) at the end face of the SPR sensor 3a1, so as to be returned as a reflected light 11 through the sensor optical fiber 5a1. Here, the light 7 excites a surface plasmon resonance. That is, a light of a particular wavelength contained in the light 7 excites the surface plasmon resonance, and this light of the particular wavelength is attenuated in intensity. The reflected light 11 returns with this particular wavelength attenuated.

The reflected light 11 passes through the intermediate optical fiber 5i1, reaching the light emitting means 31. A part of the reflected light 11 passes through the beam splitter 33 and, via the spectrometer optical fiber 41a, comes into the spectrometer 13. The reflected light 11 is subjected to a wavelength distribution analysis by the spectrometer 13. Thus, the immunoassay of the first SPR sensor 3a1 is complete.

Figure 28:
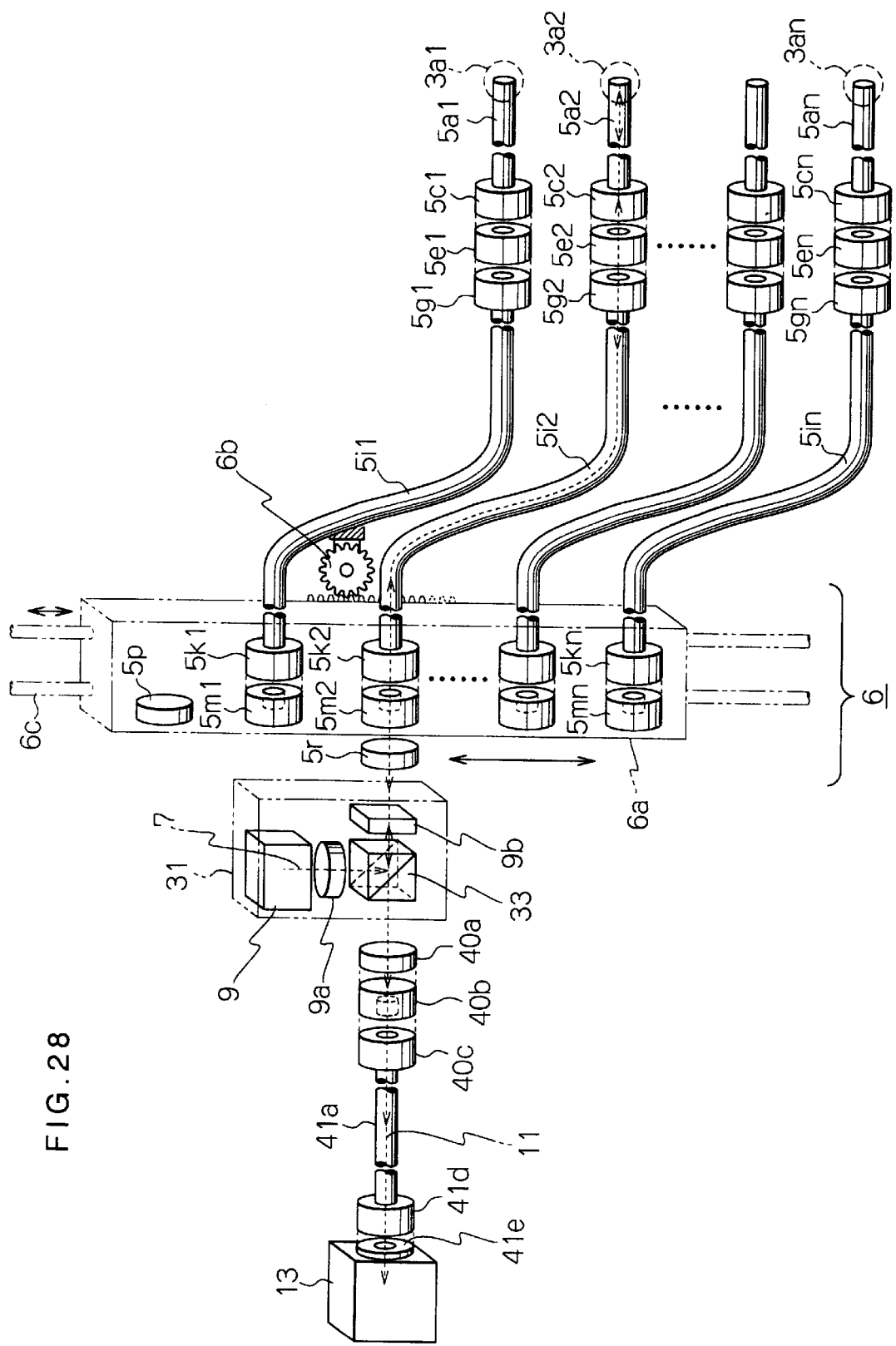
FIG. 28 shows the immunoassay apparatus in a state for carrying out an immunoassay with a second SPR sensor.

Next, an immunoassay of the second optical fiber having having the second SPR sensor is carried out. More specifically, as shown in FIG. 28, the shifting frame 6a is shifted so that the optical path of the light emitting means 31 is matched with the receptacle 5k2 corresponding to the second intermediate optical fiber 5i2. The light 7 from the light source 9, in the same way as for the aforementioned first SPR sensor, reaches the second SPR sensor 3a2. The reflected light 11 is introduced to the spectrometer 13. Because the second SPR sensor 3a2 has an antibody different from that of the first SPR sensor 3a1, it is possible to detect concentration of an antigen different from that of the first SPR sensor 3a1.

Figure 29:
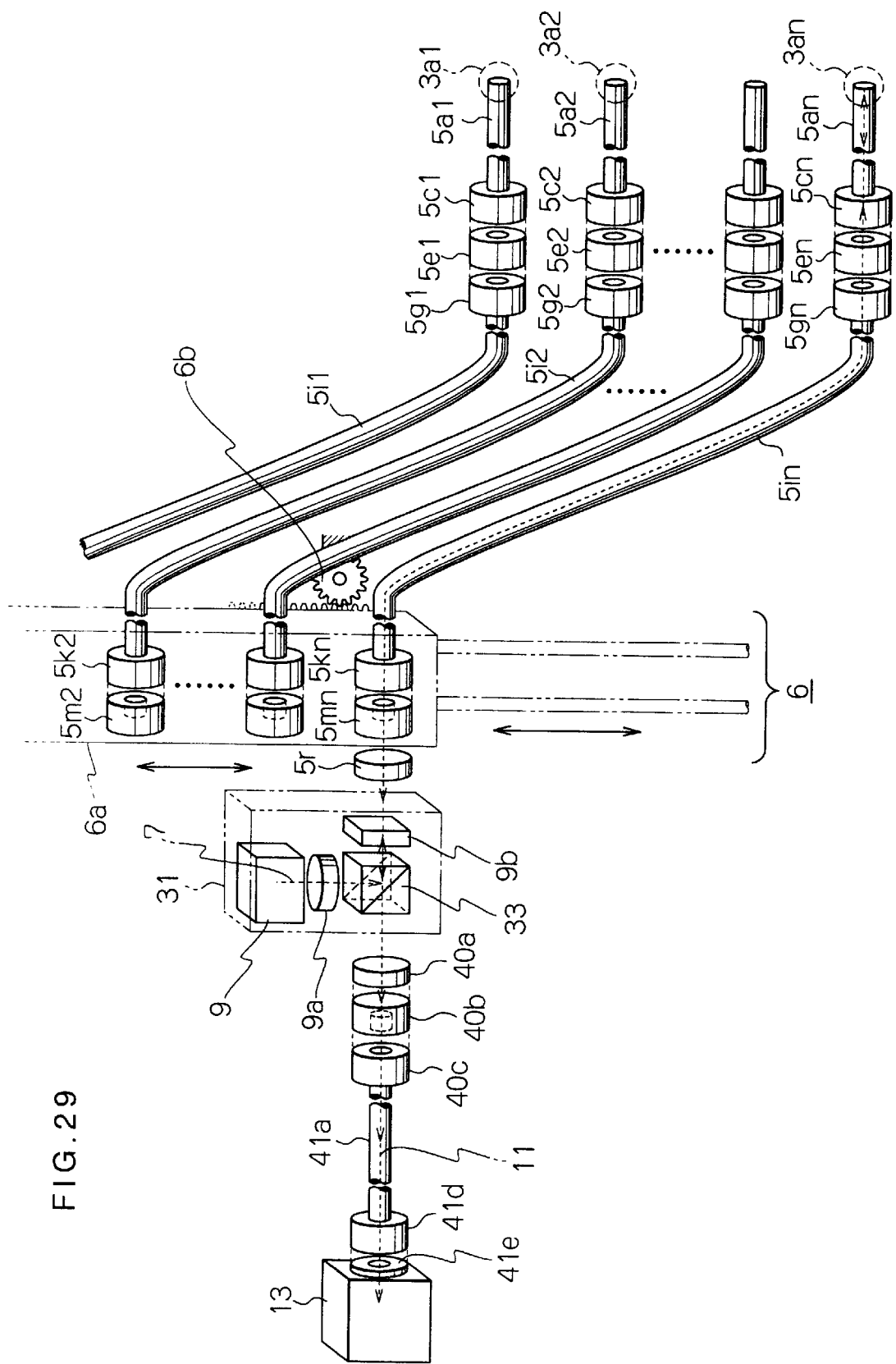
FIG. 29 shows the immunoassay apparatus in a state for carrying out an immunoassay with an n-th SPR sensor.
Figure 30:
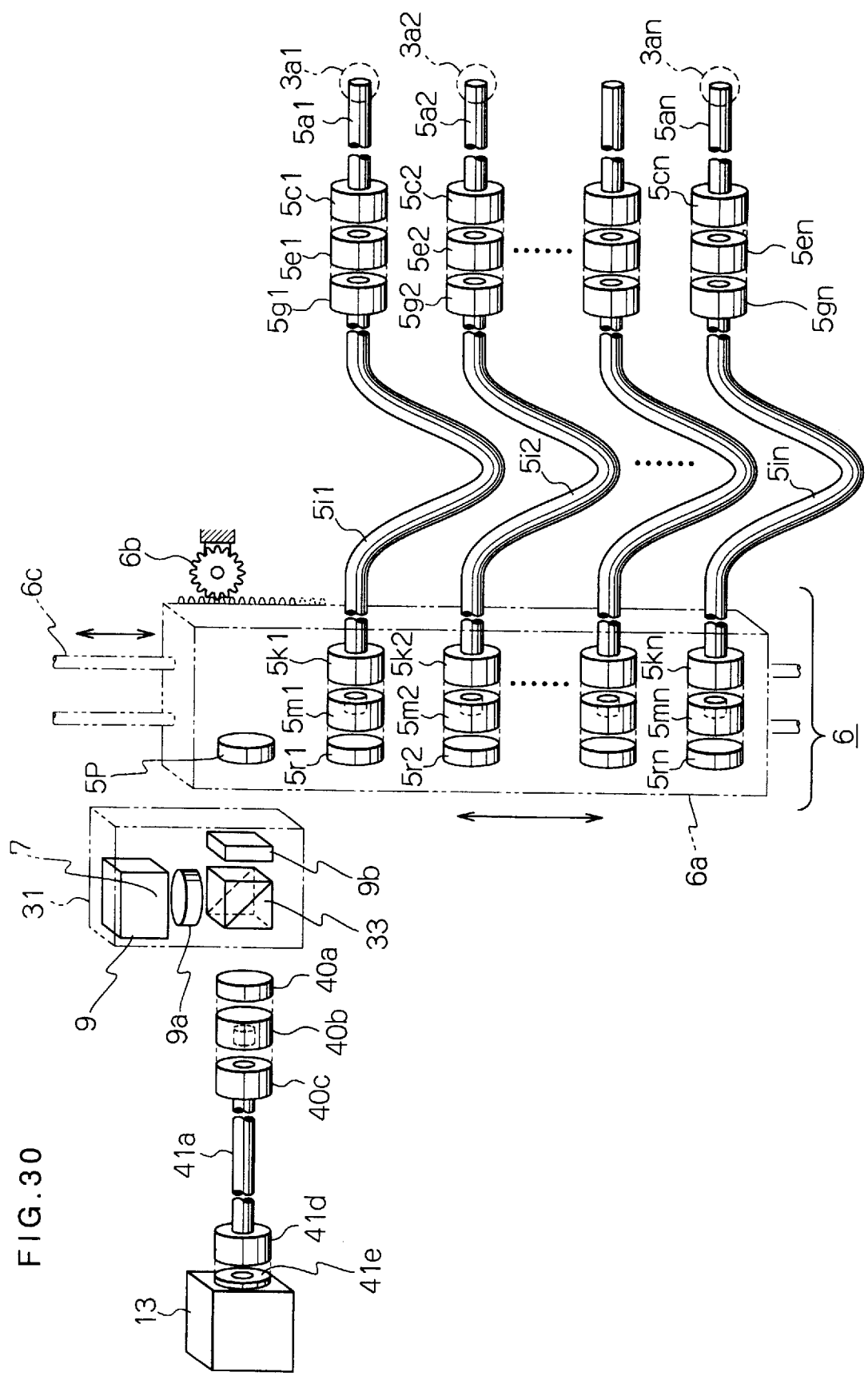
FIG. 30 shows an immunoassay apparatus according to an Embodiment 3.2.
Figure 31:
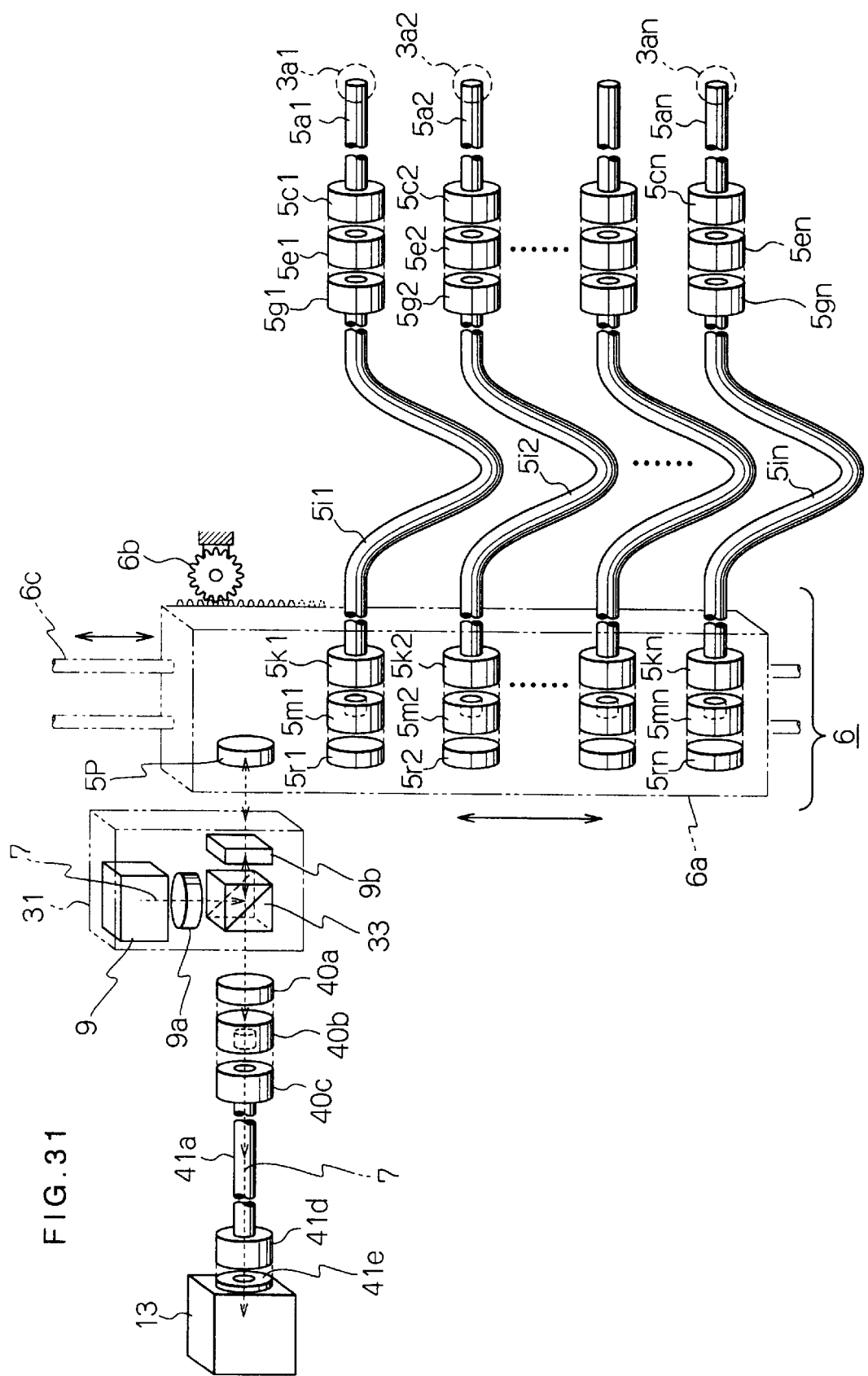
FIG. 31 shows the immunoassay apparatus of FIG. 30 in a state for carrying out a reference measurement.
Figure 32:
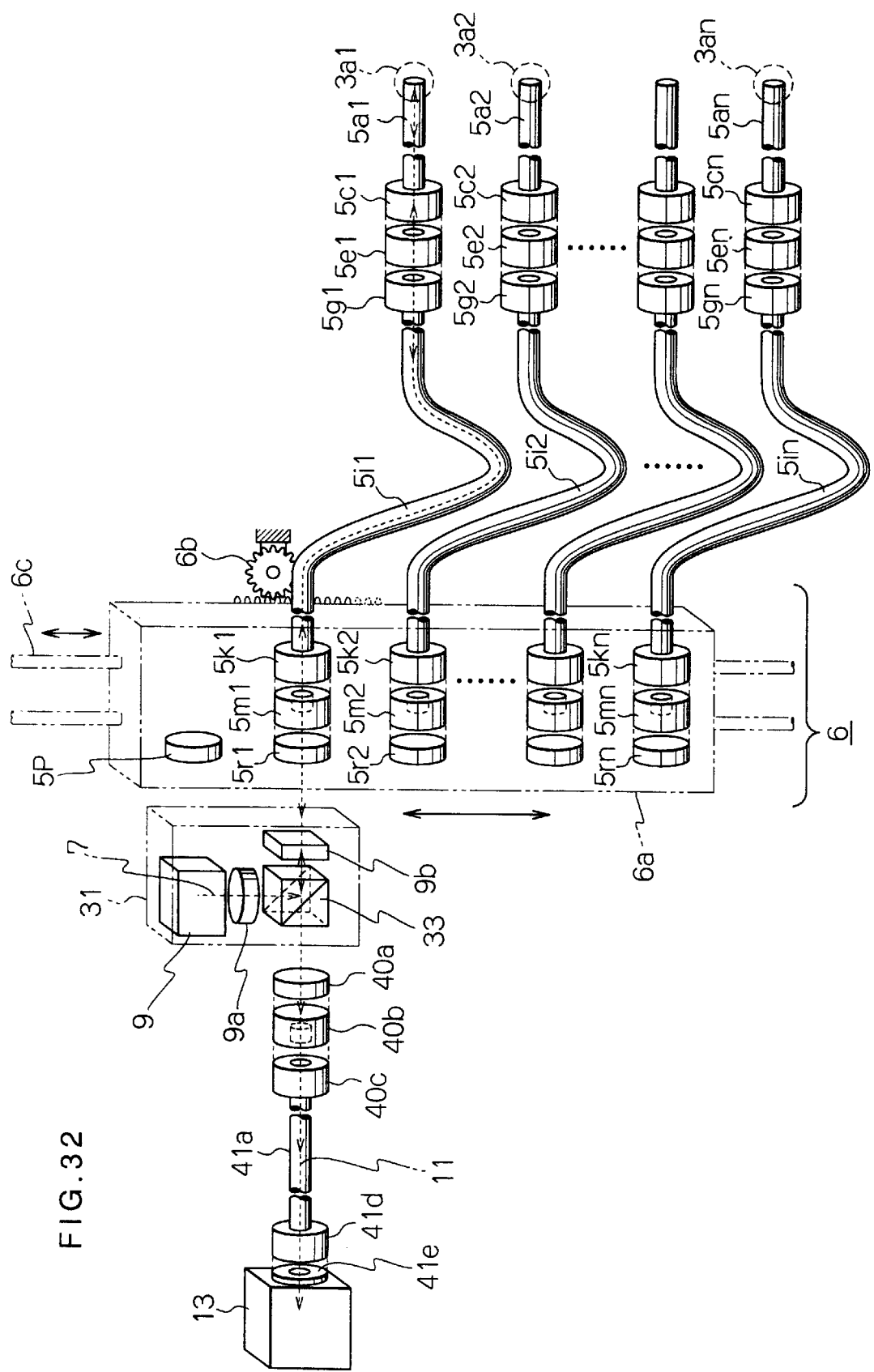
FIG. 32 shows the immunoassay apparatus of FIG. 30 in a state for carrying out an immunoassay with a first SPR sensor.

FIG. 29 shows an immunoassay by the SPR sensor 3an formed on the n-th sensor optical fiber. In this case also, the shifting frame 6a is shifted so that the receptacle 5mn corresponding to the n-th intermediate optical fiber 5in is matched with the optical path of the light emitting means 31.

Thus, the optical path is switched by the shifting mechanism 6 without changing the entire optical path length for the optical fibers. Accordingly, there is no need of correction for light intensity change for the respective optical fibers.

When a series of immunoassays is complete, the SPR sensors 3a1, 3a2, . . . , 3an are removed, and another set of optical fibers are connected for the next immunoassay. In this present embodiment, the sensor optical fibers 5a1, 5a2, . . . , 5an constituting the SPR sensors 3a1, 3a2, . . . , 3an can be separated via the adapters 5e1, 5e2, . . . , 5en, from the intermediate optical fibers 5i1, 5i2, . . . , 5in. Consequently, the optical fiber length to be discarded is reduced to be minimum, suppressing the assay costs.

[Embodiment 3.2]

The Embodiment 3.2 differs from the Embodiment 3.1 in that converging lenses 5r1, 5r2, . . . , 5rn are provided for the respective intermediate optical fibers 5i1, 5i2, . . . , 5in. In this embodiment it is assumed that n optical fibers are used.

Firstly, attention is paid on a first optical fiber 5a1 having at one end an SPR sensor 3a1 and at the other end a connector 5c1. The connector 5c1 is to be connected to a corresponding adapter 5e1. When an immunoassay with the SPR sensor 3a1 is complete, the optical fiber 5a1 alone can be removed so as to be discarded. Moreover, the adapter 5e1 is further connected to an optical fiber connector 5g1 of an intermediate optical fiber 5i1. The intermediate optical fiber 5i1 has at the other end a connector 5k1. The connector 5k1 may be identical as the connector 5g1. This connector 5k1 is to be connected to a corresponding receptacle 5m1. In the vicinity of the receptacle 5m1, there is arranged the converging lens 5r1. The converging lens 5r1 serves to converge the light so as to enhance the light transmission efficiency.

The rest of the optical fibers 5a2 to 5an also have the aforementioned connection configuration up to the corresponding converging lenses 5r2 to 5rn.

Because a converging lens is provided for each of the optical fibers, it is possible to increase an optical system positioning accuracy. That is, in case a single fixed converging lens 5r is used, the receptacles 5m1, 5m2, . . . , 5mn connected to the connectors 5k1, 5k2, . . . , 5kn mounted on the shifting frame 6a should be shifted so as to match the optical axis of the converging lens 5r accurately with the optical axis of a particular receptacle. On the other hand, when a converging lens is provided for each of the optical fibers, a positioning between the respective converging lenses 5r1, 5r1, . . . , 5rn and the corresponding receptacles 5m1, 5m2, . . . , 5mn can be fixed beforehand. Accordingly, there is no need of a complicated positioning control. What is required to is to match the optical axis of the light emitting means 31 with the optical axis of the respective converging lenses 5r1, 5r2, . . . , 5rn.

The aforementioned total reflection mirror 5p, the converging lenses 5r1, 5r2, . . . , 5rn, the receptacles 5m1, 5m2, . . . , 5mn, the connectors 5k1, 5k2, . . . , 5kn are held on a shifting frame 6a. The shifting frame 6a is shifted by an instruction from the main control block 15.

Next, explanation will given on a specific operation of the present embodiment with reference to FIG. 31 to FIG. 34.

(1) Reference measurement

Firstly, for reference measurement, the light emitted from a light source is directly subjected to a wavelength distribution analysis. The shifting frame 6a is positioned so that the optical path of the light emitting means 31 is matched with the total reflection mirror 5p. The light from the light source 9 passes through the converging lens 9a and reaches the beam splitter 33. A part of the light 7 is reflected by the beam splitter 33 to pass through the converging lens 9b, reaching the total reflection mirror 5p. The light is totally reflected by this total reflection mirror so as to return through the previous optical path, reaching the beam splitter 33. A part of the light which has reached the beam splitter 33 passes the beam splitter 33 and then the converging lens 40a, the receptacle 40b, and the spectrometer optical fiber 41a to reach the spectrometer 13. Thus, it is possible to carry out a wavelength distribution analysis of the light 7 emitted from the light source 9.

(2) Immunoassay using a SPR sensor

The SPR sensors 3a1, 3a2, . . . , 3an are connected one by one via the connectors 5c1, 5c2, . . . , 5cn. The shifting frame 6a is shifted so that the optical path of the light emitting means 31 is matched with the optical path of the receptacle 5m1 connected to the first intermediate optical fiber 5i1. Here, the total reflection mirror 5p is removed from the optical path. Moreover, the SPR sensor 3a1 is at a fixed position and only one end of the intermediate optical fiber 5i1 is moved.

The light emitted from the light source 9 is reflected by the beam splitter 33 and passes through the converging lens 5r1, the receptacle 5m1, and the connector 5k1 to enter the intermediate optical fiber 5i1. The light further advances through the connector 5g1, the adapter 5e1, reaching the SPR sensor 3a1. In the SPR sensor 3a1, the light 7 advances while being reflected by the outer circumference of the end portion of the SPR sensor 3a1, and is reflected by the reflective mirror 3b (mirror coated by gold or silver) at the end face of the SPR sensor 3a1 and return as a reflected light 11 through the optical fiber 5a. Here, the light 7 excites a surface plasmon resonance in the SPR sensor 3a1. This surface plasmon resonance is excited by a particular wavelength of light in the light 7. Consequently, the reflected light 7 returns with this particular wavelength attenuated.

The reflected light 11 from the SPR sensor 3a1 returns via the intermediate optical fiber 5i1 to the light emitting means 31. A part of the reflected light 11 passes through the beam splitter 33 and the spectrometer optical fiber 41a to enter the spectrometer 13. Here, the wavelength distribution of the reflected light is analyzed by the spectrometer 13.

Figure 33:
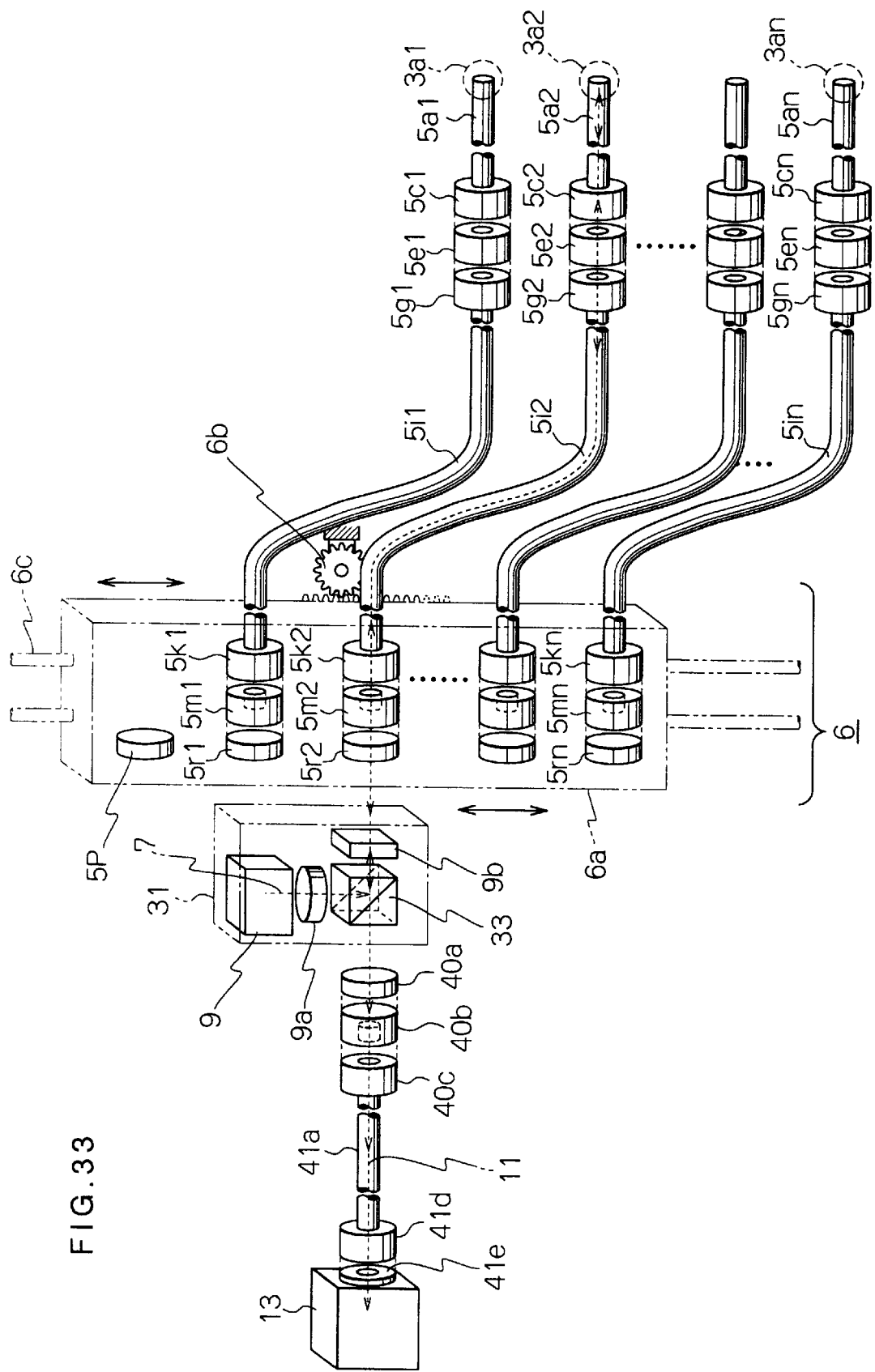
FIG. 33 shows the immunoassay apparatus of FIG. 30 in a state for carrying out an immunoassay with a second SPR sensor.

Next, as shown in FIG. 33, an immunoassay is carried out with the second optical fiber 5a2. The shifting frame 6a is positioned so that the optical path of the light emitting means 31 is matched with the receptacle 5m2 which corresponds to the second intermediate optical fiber 5i2. The light 7 emitted from the light source 9, in the same way as the in the first optical fiber, reaches the second SPR sensor 3a2. The reflected light 11 is returned to enter the spectrometer 13. Because the second SPR sensor 3a2 has an antibody different from that of the first SPR sensor 3a1, it is possible to detect a concentration of an antigen different from that of the first immunoassay.

Figure 34:
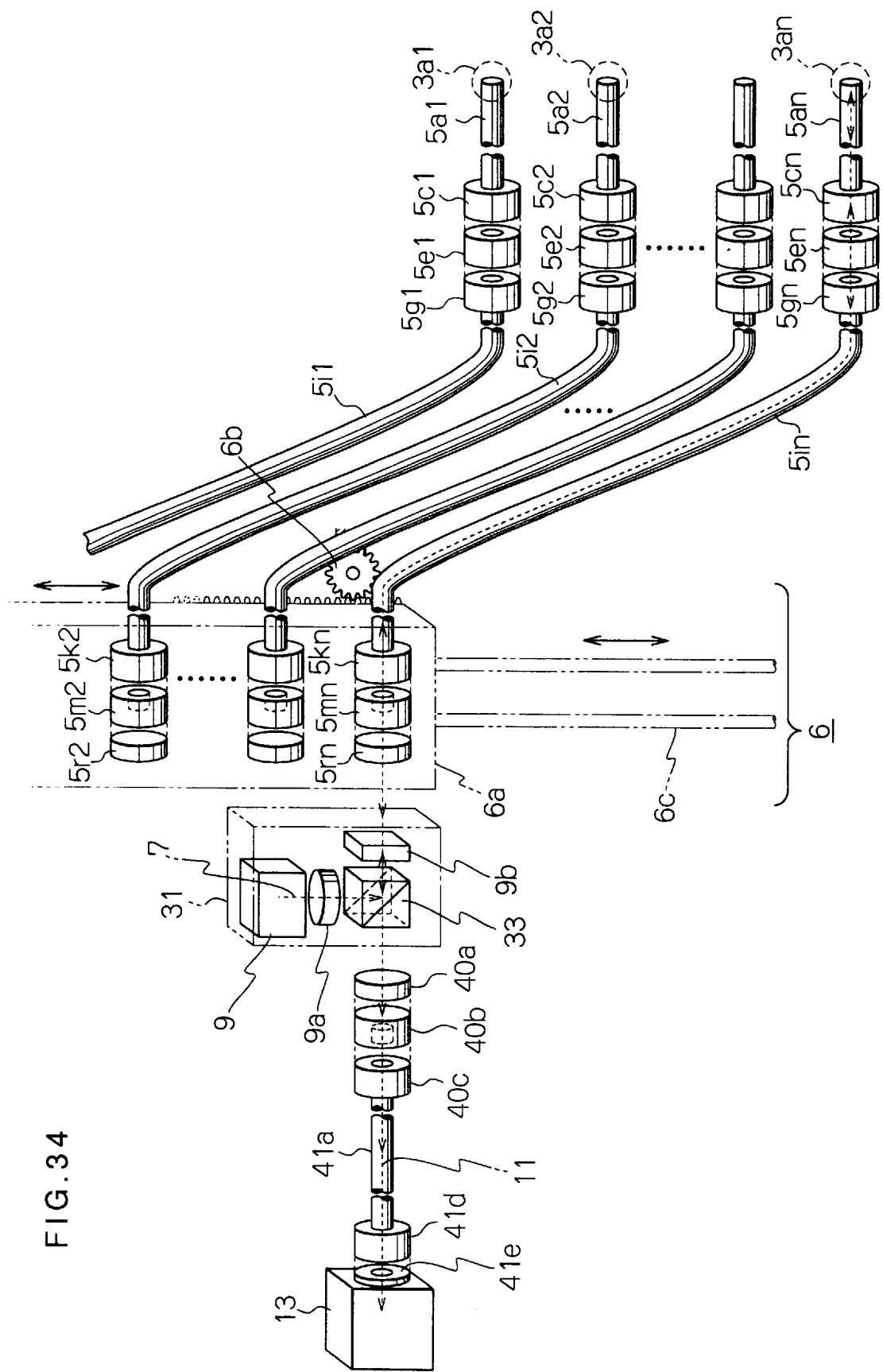
FIG. 34 shows the immunoassay apparatus of FIG. 30 in a state for carrying out an immunoassay with an n-th SPR sensor.

FIG. 34 shows an immunoassay with the n-th optical fiber having the n-th SPR sensor 3an. In this case also, the shifting frame 6a is moved to be positioned so that the optical path of the light emitting means 31 is matched with the optical path of the receptacle 5mn which corresponds to the n-th optical fiber.

When a series of immunoassays is complete, the SPR sensors 3a1, 3a2, . . . , 3an are removed and another set of SPR sensors 3a1, 3a2, . . . , 3an are connected for the next immunoassay.

In this embodiment, the optical fibers 5a1, 5a2, . . . , 5an can be disconnected via the adapters 5e1, 5e2, . . . , 5en from the intermediate fibers 5i1, 5i2, . . . , 5in. Consequently, it is possible to minimize the optical fibers to be thrown away.

It should be noted that in the aforementioned embodiments, cross sections of the optical fibers are arranged in a straight line but the present invention is not to be limited to this configuration. The cross sections of the optical fibers can also be arranged in a matrix with the shifting frame 6a movable over the matrix.

[Embodiment 4.1]

Description will now be directed to an Embodiment 4.1 of the present invention.

Figure 35:
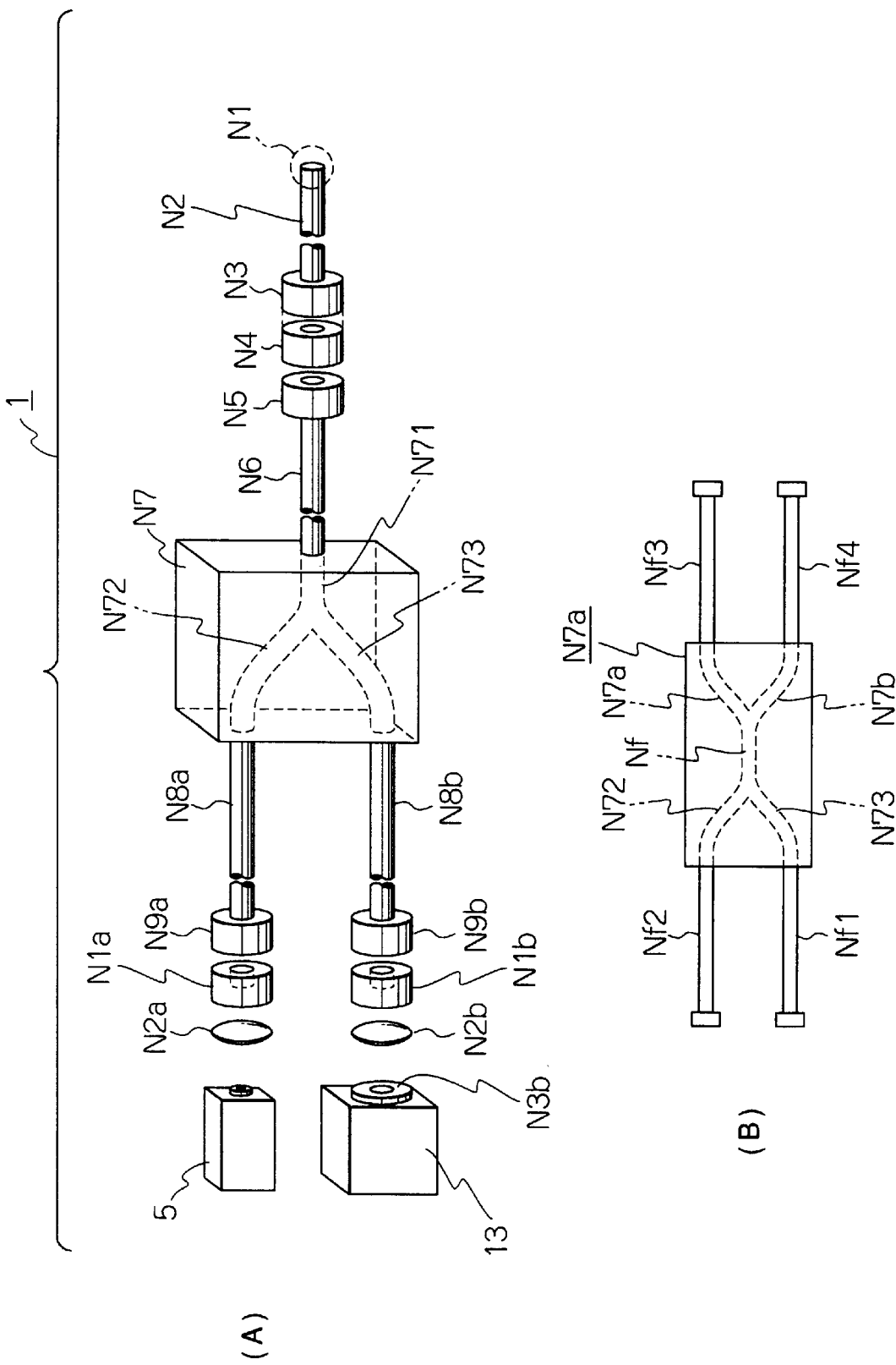
FIG. 35 is a perspective view showing a configuration of an immunoassay apparatus according to an Embodiment 4.1 of the present invention.

FIG. 35 schematically shows a configuration of the immunoassay apparatus according to the Embodiment 4.1. This immunoassay apparatus comprises as main components a sensor optical fiber N2 having a sensor N1, light source 5 for emitting a predetermined light, a spectrometer 13 for detecting and analyzing the light reflected from the SPR sensor N1, and an optical coupler N7 provided between the spectrometer 13 and the sensor optical fiber N2.

The sensor optical fiber N2 is connected to the optical coupler N7 via a connector N3 and an adapter N4. Between the optical coupler N7 and the light source 5, there are provided a receptacle N1a and a converging lens N2a. Between the optical coupler and the spectrometer 13, there are provided a receptacle N1b and a converging lens N2b. It should be noted that the sensor optical fiber N2 may be detachable together with the connector N3. If the sensor optical fiber N2 is detachable from the connector N3, it is possible to replace only the sensor optical fiber, reusing the connector N3. This contributes to reduce the assay cost. Moreover, it is preferable that the connector N3 be subjected to treatment for water-proof and corrosion-proof.

[Optical Coupler]

Next, explanation will be given on the optical coupler. The optical coupler N7 is connected to an optical fiber for the sensor optical fiber N2, an optical fiber leading to the light source 5, and an optical fiber leading the spectrometer. The optical coupler transmits the light emitted from the light source 5, to the sensor optical fiber 2, and introduces to the spectrometer 13 the light reflected from the SPR sensor.

There are several types of optical coupler in use such as a melting type, photoelectric effect type, temperature control type, and stress control type. The melting type means two optical paths melted into a single optical path. In the optical coupler N7 shown in FIG. 35, theoretically, I the light emitted from the light source 5 into the optical path N72 has intensity of 100 for example, the light is transmitted through the optical path N71 with an intensity of about 100. The same applies to the light introduced to the optical path N73 having an intensity of 100. On the other hand, the light reflected by the SPR sensor N73 is divided in the optical coupler N7 into two direction: one for the light source 5 and the other for the spectrometer 13. If the division ratio is identical for these two directions, a reflected light having an intensity of about 50 is introduced to the optical path N72 and to the optical path N73. Actually, however, a predetermined loss is caused at the point between the optical fiber and at the point where two lights are combined or one light is diverged into two parts. Accordingly, even if the light coming from the optical path N72 to the optical path N71 has an intensity of 100 for example, after reflected by the SPR sensor N1 and divided into the optical paths N72 and N73, the divided light parts respectively have an intensity in the order of about 35 due to the loss at the connection point of the optical fiber N6 and at the branching point of the optical coupler N7. A specific loss value varies depending on various conditions. For example a test on an optical coupler shows that a loss in the diverging direction is 1.5 dB or below, whereas a loss in the converging direction is 4.5 dB. It should be noted that the light division ratio may be other than 50:50, such as 60:40.

As shown in FIG. 35B, it is possible to use an optical coupler having four optical paths N7a, N7b, N72, and N73. This coupler is to be used when using two sensor optical fibers. That is, when a plurality of sensor optical fibers N2 are used, it is necessary to use an optical coupler N7a having optical paths N72 and N73 to be connected to the optical fiber Nf1 for the light source 5 and the optical fiber Nf2 for the spectrometer 13 and the number of optical paths corresponding to the number of the sensor optical fibers.

In the aforementioned optical coupler N7a having four optical paths N7a, N7b, N72, and N73, if it is assumed that the light emitted from the light source 5 has an intensity of 100, the light coming into one sensor optical fiber Nf3 has an intensity of about 50. After reflected by the SPR sensor, the light is divided into half, i.e., an intensity of about 25 before entering the spectrometer.

The photoelectric effect type optical coupler changes a wavelength characteristic by applying a voltage to a photoelectric crystal, so as to control light division and optical path selection. Moreover, the temperature control type optical coupler uses silicone around the joints of optical paths so as to adjust temperature by a Peltier element, thus changing a wavelength characteristic. Furthermore, the stress control type optical coupler changes a wavelength characteristic by applying a twist or bending to an optical path within the optical coupler.

Next, an explanation will be given on operation of the immunoassay apparatus 1 having the aforementioned configuration.

[Embodiment 4.2]

Figure 36:
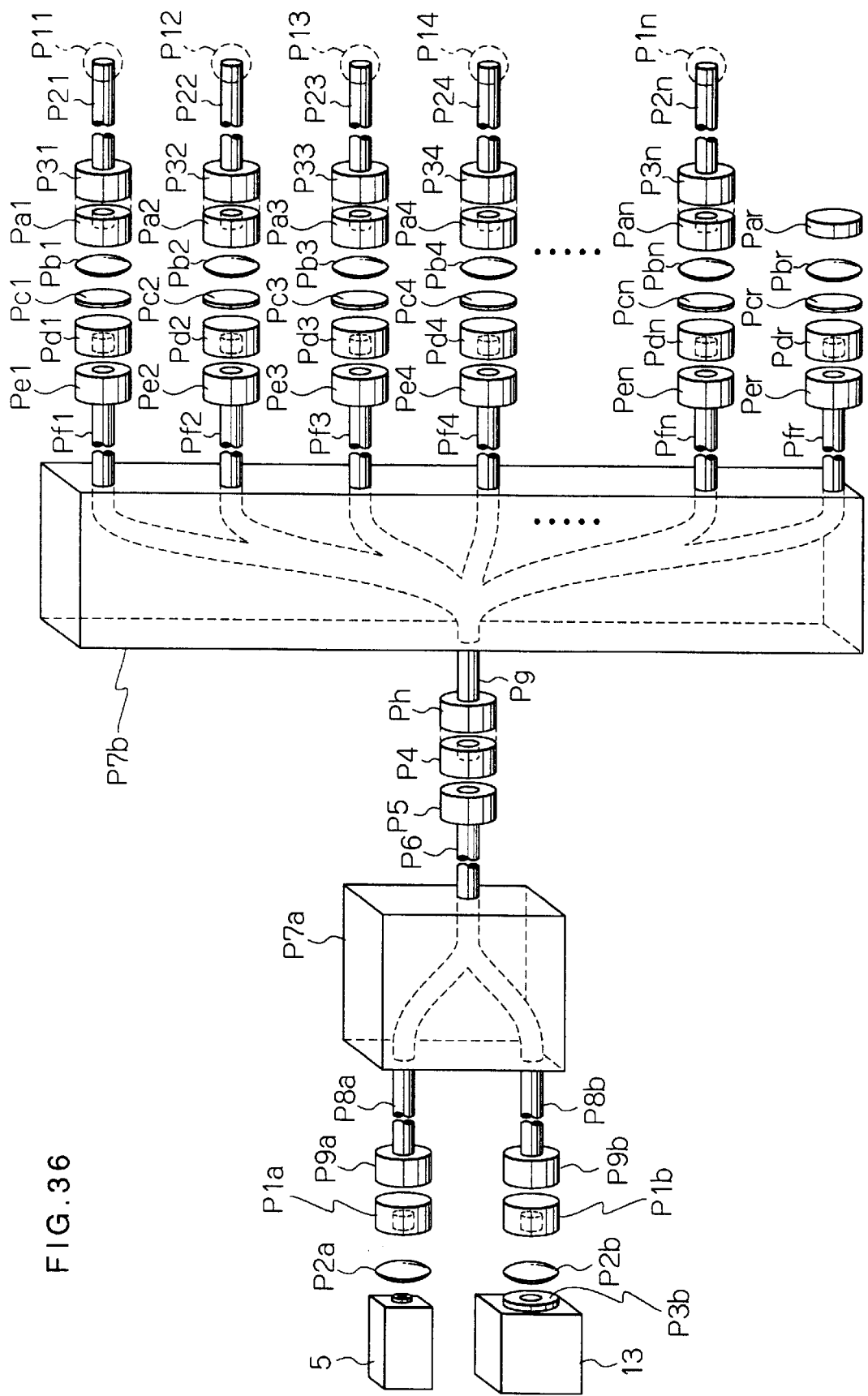
FIG. 36 is a perspective view showing a configuration of an immunoassay apparatus according to an Embodiment 4.2 of the present invention.

The Embodiment 4.2 will be detailed below with reference to FIG. 36.

This embodiment differs from the Embodiment 4.1 in that two optical couplers are used. That is, between an optical coupler P7a and a plurality of sensor optical fibers P21, P22, ..., P2, there is provided a second optical coupler P7b. Between the second optical coupler P7b and the respective sensor optical fibers P21, P22, p2n there are arranged receptacles Pd1, Pd2, ..., Pdn, shutters Pc1, Pc2, ..., Pcn, the converging lenses Pb1, Pb2, ..., Pbn, and receptacles Pa1, Pa2, ..., Pan in this order.

The second optical coupler P7b converges n+1 optical paths into one optical path. The number n corresponds to the number of sensor optical fibers used. For the last n+1-th optical path, there is provided a reflecting mirror Par instead of the sensor optical path. In the second optical coupler P7b, the optical path converging the n+1 optical paths is connected via the optical fiber Pg to the optical coupler p7a.

Next, explanation will be given on an actual immunoassay procedure. Firstly, a reference measurement if carried out if necessary. In the reference measurement, the light emitted from the light source 5 is directly subjected to a wavelength distribution analysis. That is, the shutter Pc corresponding to the reflection mirror Par is opened and the remaining shutter Pc1, Pc2, ..., Pcn are all closed. Thus, the light from the light source 5 is reflected by the reflection mirror Par and passes through the second optical coupler P7b and the optical coupler P7a to enter the spectrometer 13. Thus, the spectrometer 13 detects a wavelength distribution of the light from the light source 5.

Next, an actual immunoassay is carried out with the first SPR sensor P11. For this, only the first (uppermost) shutter Pc1 is opened and all the other shutters Pc2, ..., Pcn, Pcr are closed. Accordingly, the light emitted from the light source 5 passes through the converging lens P2a and the receptacle P1a to enter the optical coupler P7a, from which the light is introduced to the second optical coupler P7b. In the second optical coupler P7b, the light is branched into the n+1 optical paths, but only the first shutter Pc1 is open. Consequently, the light passes through the receptacle Pd1, the shutter Pc1, the converging lens Pb1, and the receptacle Pa1 to reach first SPR sensor P11. The light is reflected by the end face of the SPR sensor P11 to return as the reflected light 11. The reflected light 11 enters the second optical coupler P7b and is introduced to the spectrometer 13 for analysis.

The above-given explanation also applies to the second SPR sensor and after.

Figure 37:
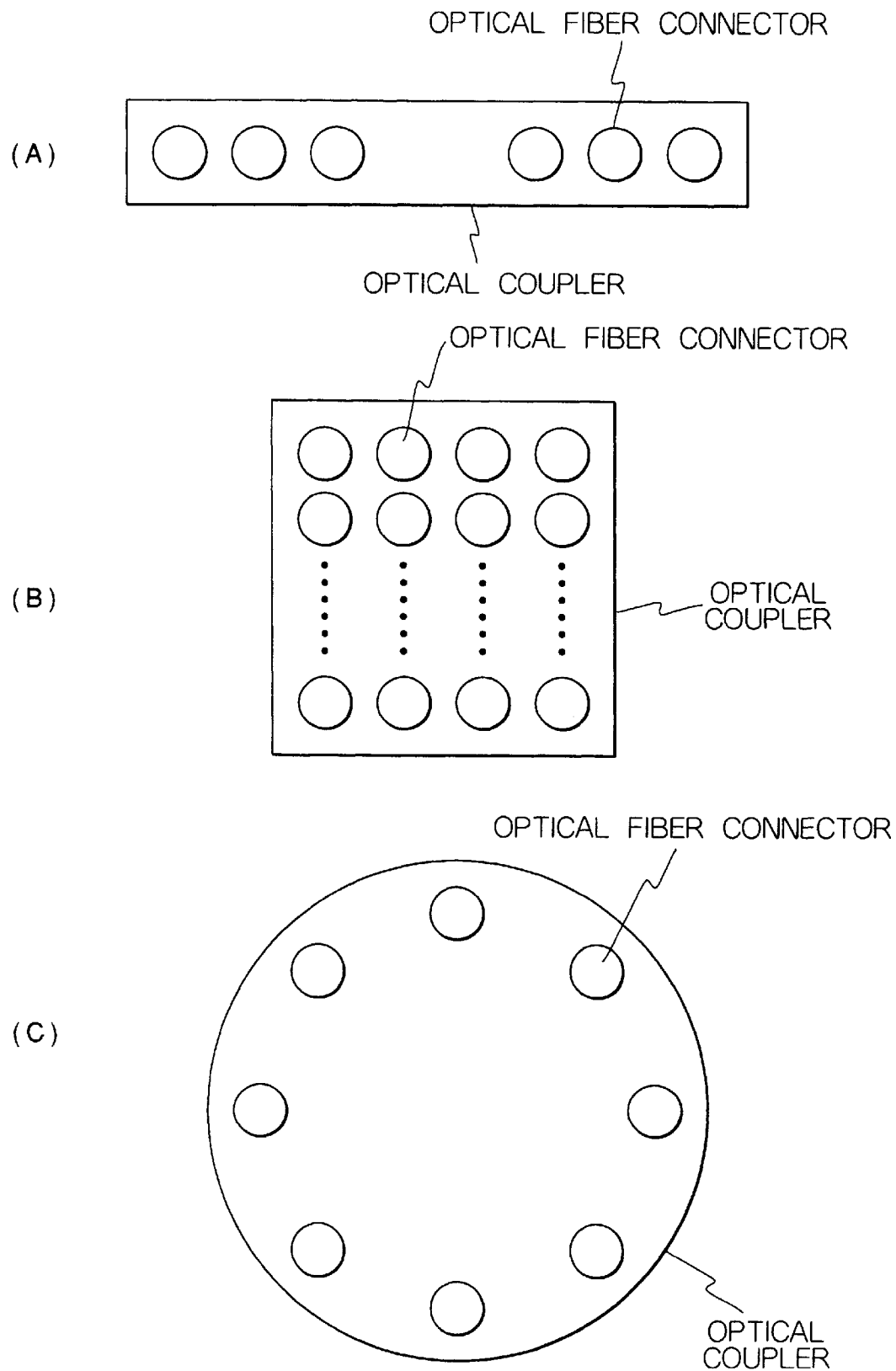
FIG. 37A shows a configuration of the optical coupler used in the Embodiment 4.2 viewed from the sensor optical fibers.
FIG. 37B and FIG. 37C show modified configurations of the optical coupler.

FIG. 37 shows some examples of arrangement of optical paths in the second optical coupler P7b viewed from the sensor optical fibers. Firstly, FIG. 37A shows an arrangement of optical paths (in cross section) in a single row. Moreover, FIG. 37B shows an arrangement of optical paths in a matrix. Furthermore, FIG. 37C shows an arrangement of optical paths in a circle. These are arrangements are given as examples, and the present invention is not to be limited to these arrangements.

It should be noted that in case the optical coupler can freely control optical paths (photoelectric effect type, temperature control type, or stress control type), the shutters Pc1, Pc2, ..., Pcn, Pcr can be removed.

[Embodiment 4.3]

Figure 38:
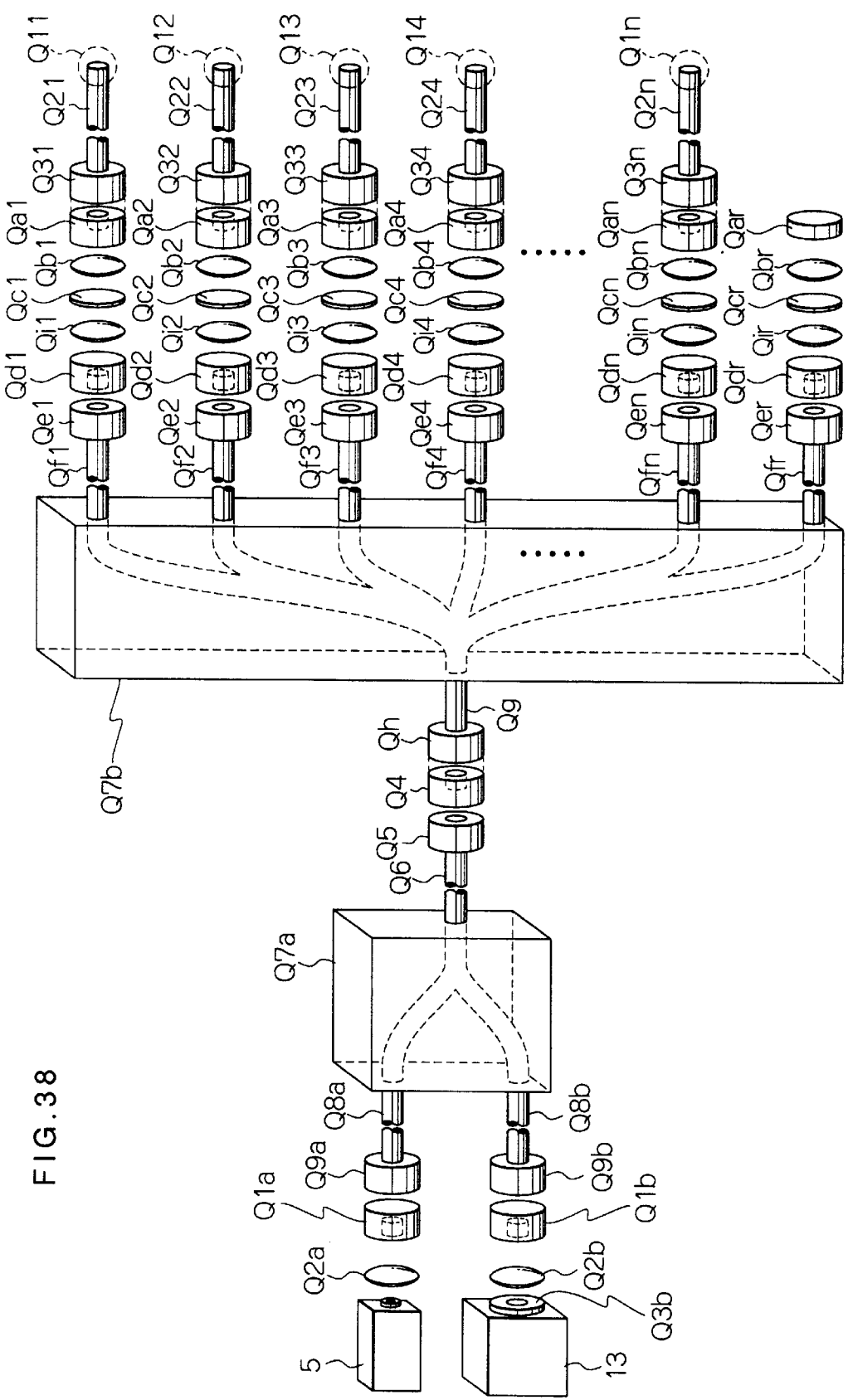
FIG. 38 is a perspective view showing a configuration of an immunoassay apparatus according to an Embodiment 4.3 of the present invention.

Next, explanation will be given on an Embodiment 4.3 with reference to FIG. 38.

This embodiment has almost identical configuration as the Embodiment 4.2 except for that converging lenses Qi1, Qi2, ..., Qin, Qir are further provided between shutters Qc1, Qc2, ..., Qcn, Qcr, and receptacles Qd1, Qd2, ..., Qdn, Qdr.

The converging lenses Qi1, Qi2, ..., Qin, Qir functions to converge the light from the receptacles Qd1, Qd2, ..., Qdn, Qdr so as to effectively transmit the light to the SPR sensors Q11, Q12, ..., Q1n as well as converge the light reflected from the SPR sensors Q11, Q12, ..., Q1n and effectively transmit the reflected light to the second optical coupler P7b.

[Embodiment 4.4]

Figure 39:
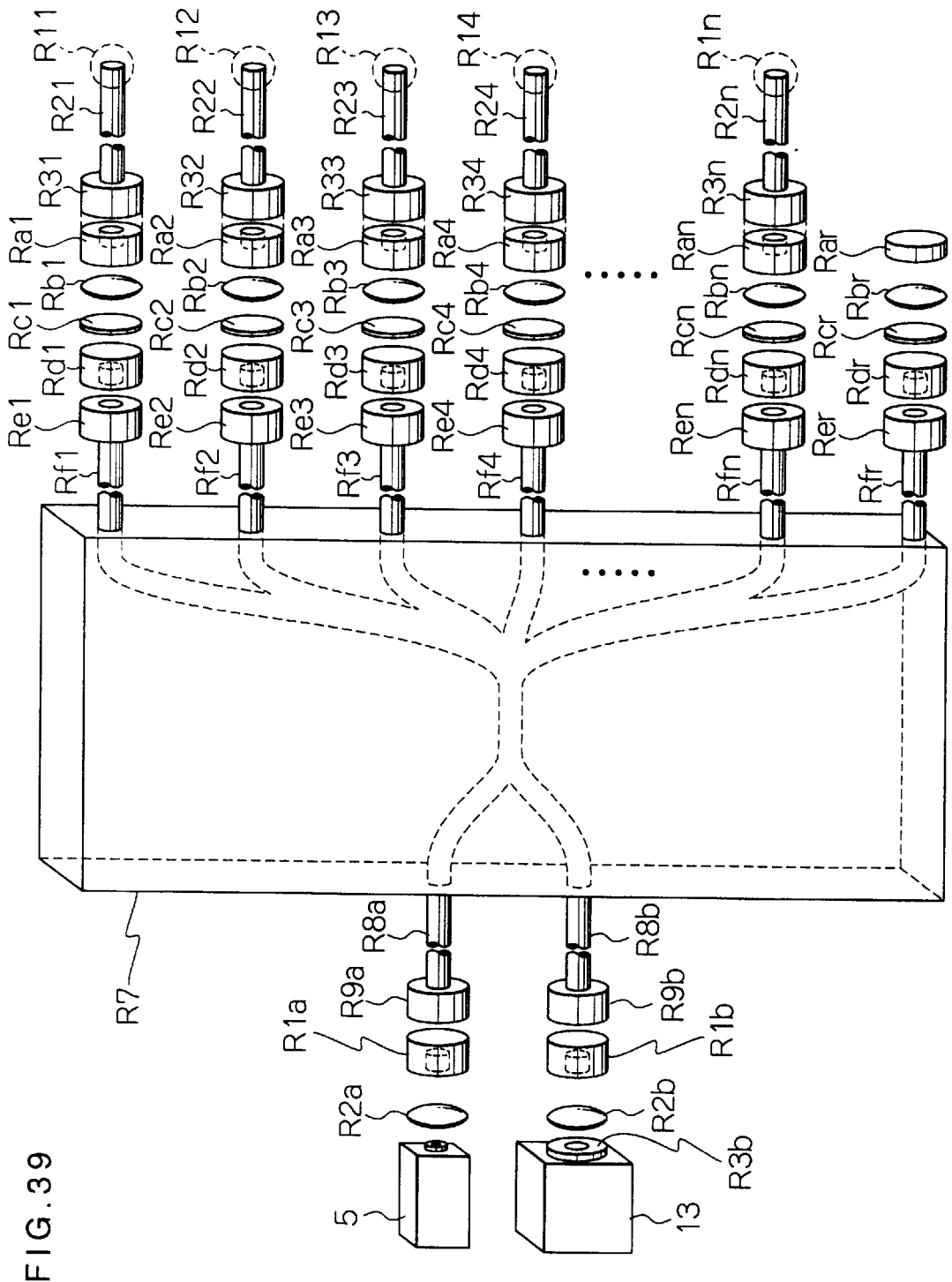
FIG. 39 is a perspective view showing a configuration of an immunoassay apparatus according to an Embodiment 4.4 of the present invention.

Next, explanation will be given on an Embodiment 4.4 with reference to FIG. 39.

This embodiment has an almost identical configuration as the aforementioned Embodiment 4.3 except for that the optical couplers P7a and P7b of the Embodiment 4.3 are combined into a single optical coupler R7 in this embodiment. That is, the optical coupler R7 has two optical paths for the light source 5 and the spectrometer 13 and n+1 optical paths for the sensor optical fibers R21, R22, ..., R2n.

A reference measurement is carried out as follows. The shutter Rcr corresponding to the reflection mirror Rar is opened and the other shutters Rc1, Rc2, ..., Rcn are all closed. Thus, the light from the light source 5 is reflected by the reflection mirror Rar to pass through the optical coupler R7, reaching the spectrometer 13, so that the light is subjected to a wavelength distribution analysis.

Next, an actual immunoassay is carried out with the first SPR sensor R11. The first (uppermost) shutter Rc1 alone is opened and the other shutters Rc2, ..., Rcn, Rcr are all closed. Accordingly, the light emitted from the light source 5 passes through the converging lens R2a and the receptacle R1a to reach the optical coupler R7. In the optical coupler R7, the light is branched into the n+1 optical paths but only the first shutter Rc1 is open. Accordingly, the light advances through the receptacle Rd1, shutter Rc1, the converging lens Rb1, and the receptacle Ra1 to reach the first SPR sensor R11, where the light is reflected by the end face of the SPR sensor. The reflected light 11 passes through the optical coupler R7 and enters the spectrometer 13 so as to be subjected an analysis.

This procedure is repeated for the second SPR sensor and after.

In this embodiment, only one optical coupler is used, which enables to reduce the number of components and to reduce the size of the entire immunoassay apparatus.

[Embodiment 4.5]

Figure 40:
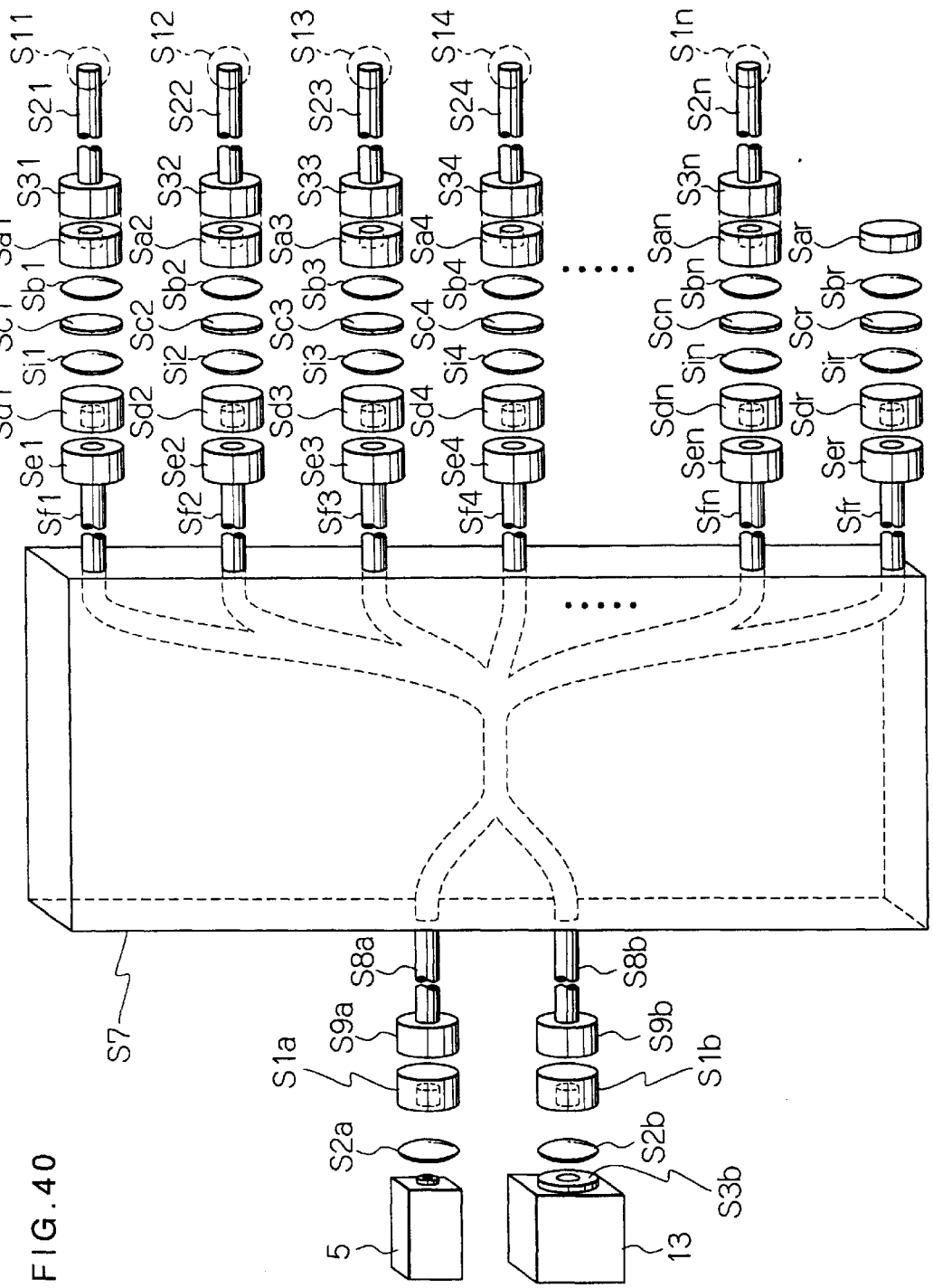
FIG. 40 is a perspective view showing a configuration of an immunoassay apparatus according to an Embodiment 4.5 of the present invention.

Next, explanation will given on an embodiment 4.5 with reference to FIG. 40.

This embodiment has an almost identical configuration as the Embodiment 4.4 except for that converging lenses Si1, Si2, ..., Sin, Sir are provided between the shutters Sc1, Sc3,..., Scn, Scr and the receptacles Sd1, Sd2, Sdn, Sdr.

The converging lenses Si1, Si2, ..., Sin, Sir serves to converge the light from the receptacles Sd1, Sd2, Sdn, Sdr and effectively transmit the light to the SPR sensors S11, S12, ..., S1n as well as to converge the reflected light from the SPR sensors S11, S12, ..., S1n and effectively transmit the reflected light to the optical coupler S7.

[Embodiment 4.6]

Figure 41:
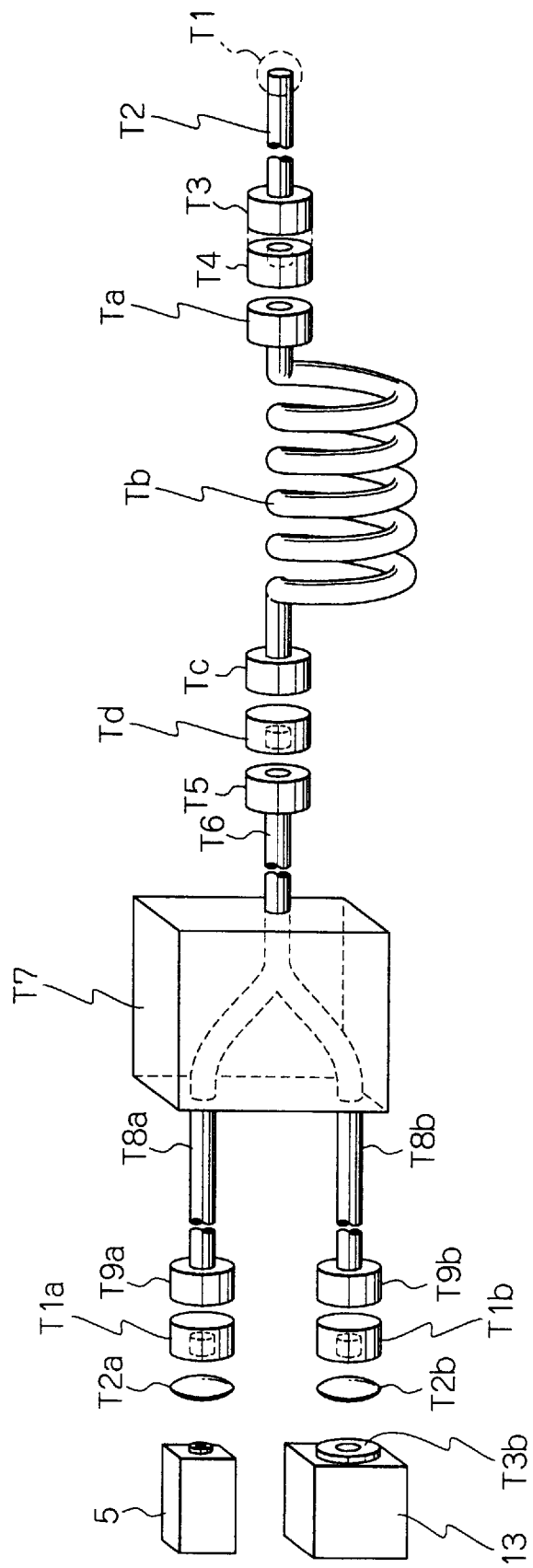
FIG. 41 is a perspective view showing a configuration of an immunoassay apparatus according to an Embodiment 4.6 of the present invention.

Next, explanation will be given on an Embodiment 4.6 with reference to FIG. 41.

This embodiment has an almost identical configuration as the Embodiment 4.1 except for that the Embodiment 4.6 comprises a predetermined length of optical cable Tb provided between a sensor optical fiber T2 and an optical coupler T7. The optical fiber cable Tb has connects Ta and Tc at its both ends. The connector Ta is connected via an adapter T4 to a connector T3 of a sensor optical fiber T2. The connector Tc is connected via an adapter Td to a connector T5 of an optical coupler T7.

Because the optical fiber cable Tb itself has a sufficient length, the sensor optical fiber T2 alone can be freely moved while the light source 5, the spectrometer 13, and the optical coupler T7 are at fixed positioned. The immunoassay apparatus according to this embodiment is convenient to be used as a stand-alone type.

[Embodiment 4.7]

Figure 42:
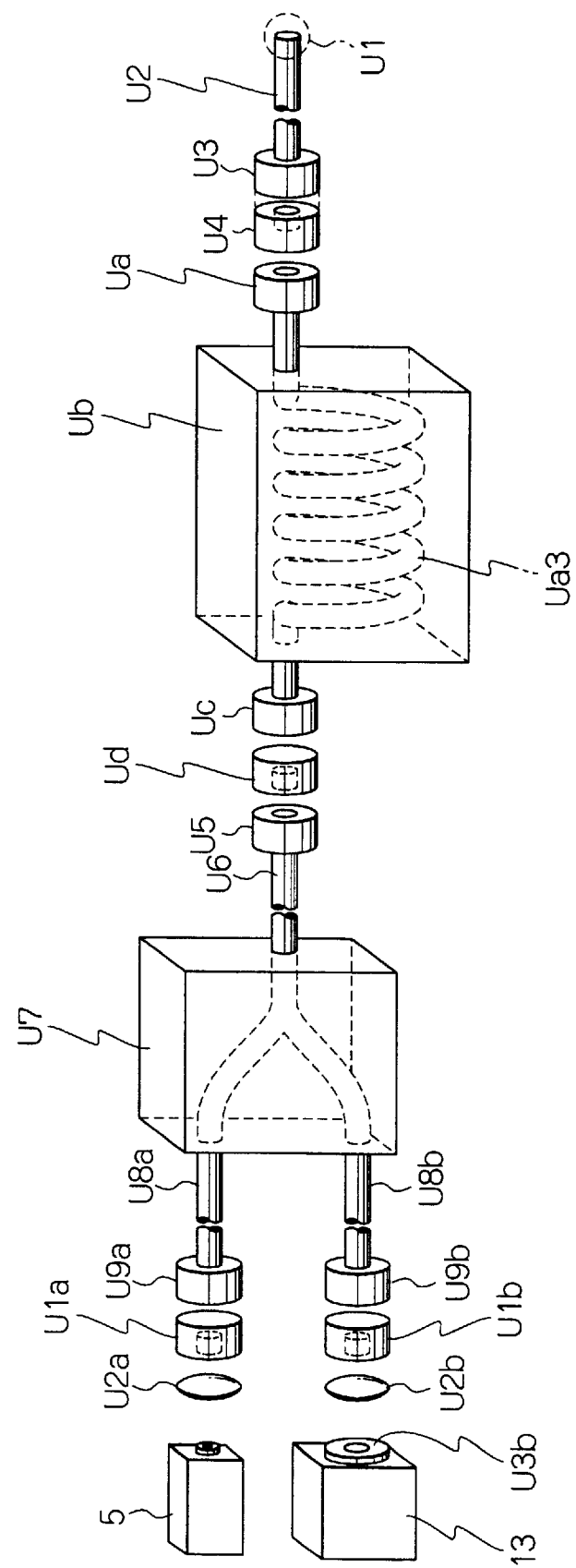
FIG. 42 is a perspective view showing a configuration of an immunoassay apparatus according to an Embodiment 4.7 of the present invention.

Next, explanation will be given on an Embodiment 4.7 with reference to FIG. 42.

This embodiment has an almost identical configuration as Embodiment 4.6 except for that in this embodiment the optical fiber cable Ua3 is contained in a winding mechanism Ub. More specifically, the winding mechanism Ub may include a drum (not depicted) which is rotatably supported so that the optical fiber cable Ua3 is wound up around the drum.

When an immunoassay is carried out in a small space, the optical fiber cable Ua3 is wound up to be contained in the winding mechanism Ub. When an immunoassay is carried out in a large space, the optical fiber cable Ua3 is pulled out of the winding mechanism Ub. After the immunoassay is complete, the optical fiber cable Ua3 is again wound up in the winding mechanism 3.

It should be noted that when the optical fiber cable Ua3 is wound up, it is preferable that the optical fiber cable have a radius of curvature greater than a predetermined value. If the optical fiber cable Ua3 is curved by a great value, the light transmission efficiency may be lowered and the optical fiber cable Ua3 itself may be damaged.

[Embodiment 4.8]

Next, explanation will be given on an Embodiment 4.8 with reference to FIG. 43.

This embodiment has an almost identical configuration as Embodiment 4.7 except for that a fiber guide Va is provided for supporting the optical fiber cable Va3. That is, the optical fiber cable Va3 is supported by the fiber guide Va when used for an immunoassay. The fiber guide Va itself can be extended and contracted.

Figure 44:
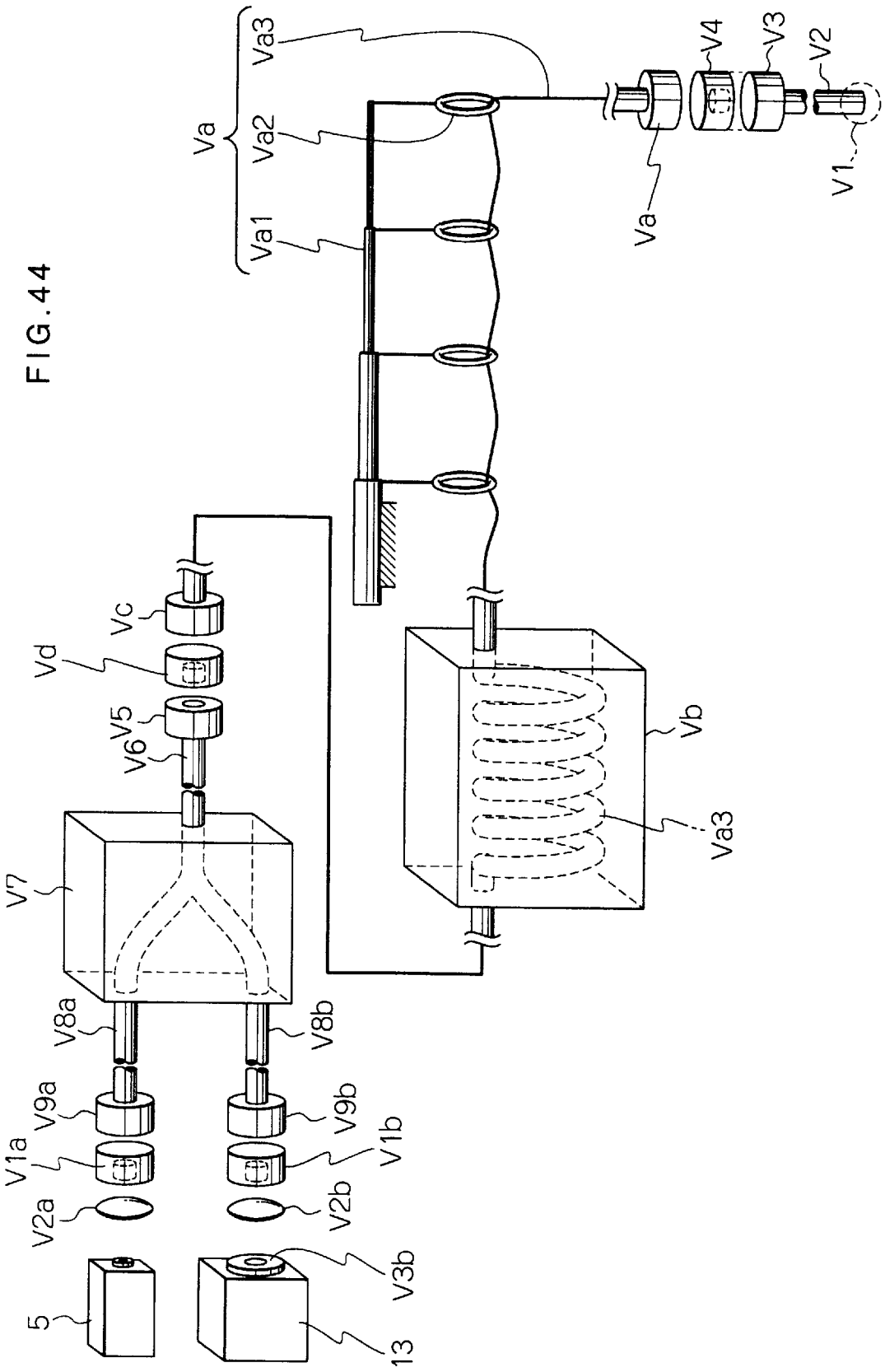
FIG. 44 shows the immunoassay apparatus disclosed in FIG. 43 with the sensor optical fiber in a shifted position.

FIG. 44 shows the fiber guide Va in an extended state. As shown in this FIG. 44, the fiber guide Va comprises a plurality of sheath members Va1 having different diameters which are positioned in one another so that they can be pulled out continuously. Each of the sheath members Va1 has a predetermined support ring Va2, through which the optical fiber cable Va3 is passed. Accordingly, the sensor optical fiber V1 can be moved in a wide range while the optical fiber cable Va3 is supported,

[Embodiment 5.1]

Explanation will be given on an immunoassay apparatus according to an Embodiment 5.1 of the present invention.

Figure 45:
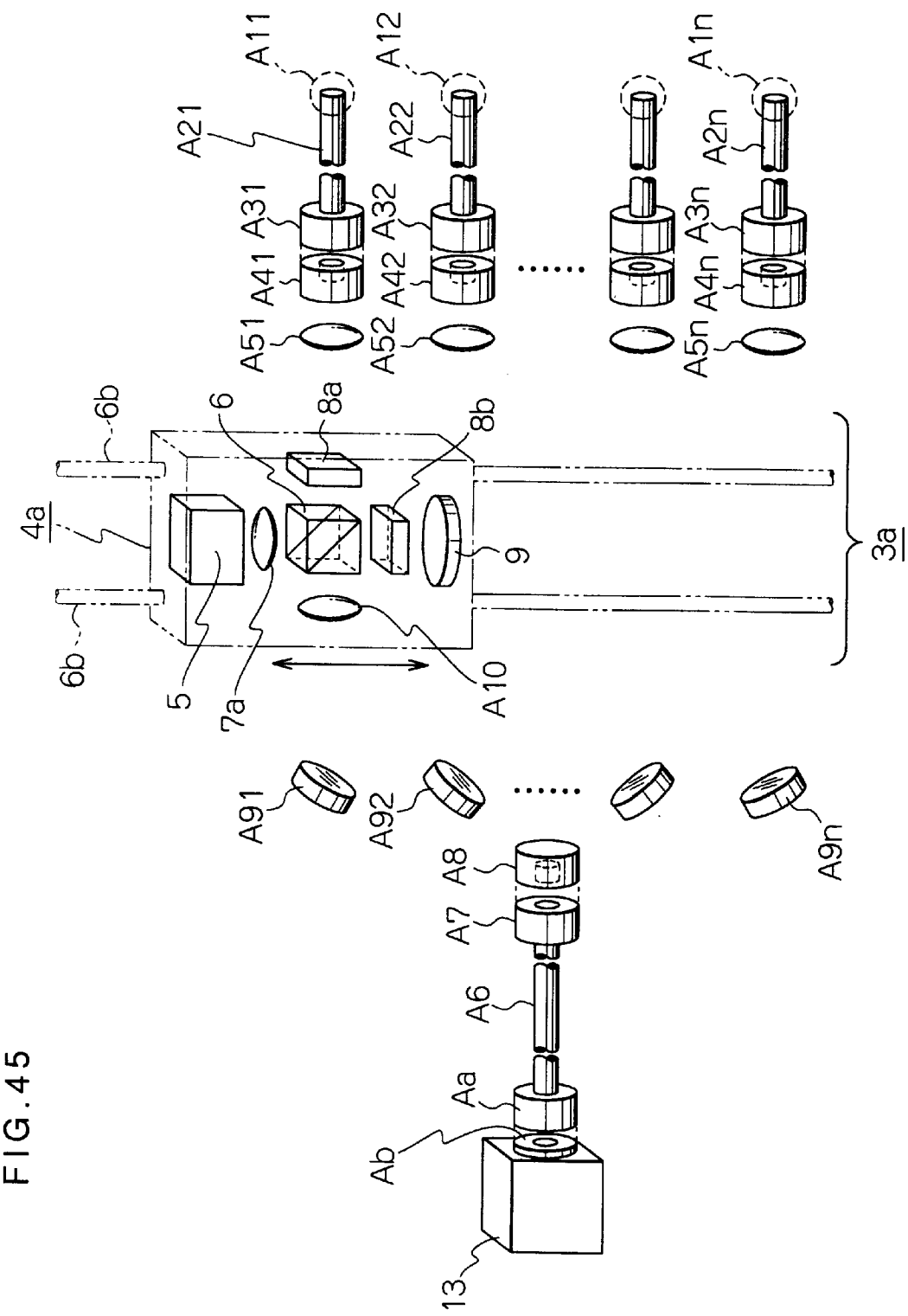
FIG. 45 is a perspective view showing a configuration of an immunoassay apparatus according to an Embodiment 5.1 of the present invention.

This embodiment is characterized by an optical path switching mechanism. FIG. 45 schematically shows a basic configuration of this embodiment that includes: sensor optical fibers A21, A22, . . . , A2a having at one end SPR sensors A11, A12, . . . , A1n and at the other end, optical fiber connectors A31, A32, . . . , A3n; light emitting means 4a for emitting a predetermined light; and a spectrometer 13 for detecting a reflected light from the SPR sensors A11, A12, . . . , A1n. For a plurality of the sensor optical fibers A21, A22, . . . , A2n, only one set of the light emitting means 4a and only one set of spectrometer 13 are used.

[SPR Sensors]

For example, one of the sensor optical fibers A21 has the connector A31 which is connected to a corresponding receptacle A41. When an immunoassay with the SPR sensor A11 is complete, the sensor optical fiber A21 can be removed to be discarded. Moreover, a converging lens A51 is provided between the receptacle A41 and the light emitting means 4a. This converging lens A51 has two functions. One of the functions is to converge a light from the light emitting means 4a and effectively transmits the light to the receptacle A41 for the SPR sensor A11. The other of the functions is to converge a reflected light from the SPR sensor A11 and effectively transmits the reflected light to the light emitting means 4a. It should be noted that a converging lens A51, A52, . . . , A5n is provided for each of the sensor optical fibers A21, A22, . . . , A2n.

[Light Emitting Means]

The light emitting means 4a emits a light of a predetermined wavlength light. More specifically, the light emitting means 4a comprises a light source 5, a converging lens 7a, a beam splitter 6, and a shutter 8a for the sensors. Moreover, the light emitting means 4a comprises a reflecting mirror 9 and a shutter 8b for the reflecting mirror 9.

The light source 5 is a halogen lamp. The halogen lamp contains lights of various wavelengths. It should be noted that the light source 5 is not to be limited to a halogen lamp but can be any light source if a predetermined wavelength band is contained. Moreover, in case a wavelength to be attenuated by an immunoassay can be predicted beforehand, it is possible to use a light source for emitting a light of the predicted wavelength alone.

The converging lens 7a serves to converge a light emitted from the light source 5, with a constant ratio for introducing the light to the beam splitter 6. The converging lens 7a is selected according to the light from the light source 5. More specifically, if the light source 5 emits a diverging light, a lens having a function of conversion is used.

The beam splitter provided at the downstream side of the converging lens 7a functions to branch the incident light. More specifically, the beam splitter 6 has a reflection plane slanting toward the sensors, so as to reflect a part of the light from the light source 5, toward the sensor5s. On the other hand, the remaining part of the light from the light source 5 transmits the beam splitter 6. The beam splitter 6 is a so-called half mirror or the like.

The reflection mirror 9 serves to reflect a light (reflected light) from the beam splitter 6 when the shutter 8b is open.

On the other hand, the shutter 8a is used to control transmission/cut-off of the light to the SPR sensors A11, A12, . . . , A1n. The shutter 8a is, for example, a liquid crystal shutter that transmits or cuts off a light according to a voltage applied to a liquid crystal panel.

Moreover, a converging lens A10 is provided so as to sandwich beam splitter 6 by incorporating with the shutter 8a. This converging lens A10 converges a light reflected by the beam splitter 6 or a light (reflected light) which has transmitted through the beam splitter 6, so that-the light is effectively transmitted to a spectrometer 13.

[Optical Path Switching Mechanism]

Next, explanation will be given on the optical path switching mechanism for the plurality of the optical fibers.

In this embodiment, the light emitting means 4a is shifted so that a reflected light from the SPR sensors A11, A12, ..., A1n is introduced to the spectrometer 13.

That is, the light emitting means 4a is carried on a predetermined optical path switching mechanism. More specifically, the optical path switching mechanism comprises a shifting frame (not depicted) which is movable along two guide shafts 6b so as to switch an optical path from one sensor to another. The shifting frame may be moved by a drive motor (not depicted) provided on the shifting frame so as to rotate rollers (not depicted) along the guide shafts 6b. Alternatively, the shifting frame may be provided with a wire (not depicted) to which tension is applied so as to directly move the shifting frame.

Moreover, deflection mirrors A91, A92, ..., A9n are provided between the light emitting means 4a and the spectrometer optical fiber A6, so as to correspond to the respective sensor optical fibers A21, A22, ..., A2n. These deflection mirrors A91, a92, ..., A9n are arranged on optical axes of the corresponding sensor optical fibers A21, A22, ..., A2n. When a reflected light is returned from the sensor optical fiber A21, A22, ..., A2n, the light passes through the light emitting means 4a and reaches the corresponding deflection mirror.

The deflection mirrors A91, A92, ..., A9n are arranged at a predetermined angle with respect to the optical axis of the corresponding sensor optical fibers A21, A22, ..., A2n so that a reflected light is introduced to a receptacle A8 connected to the spectrometer optical fiber A6.

[Immunoassay Procedure]

(1) Reference measurement

Figure 46:
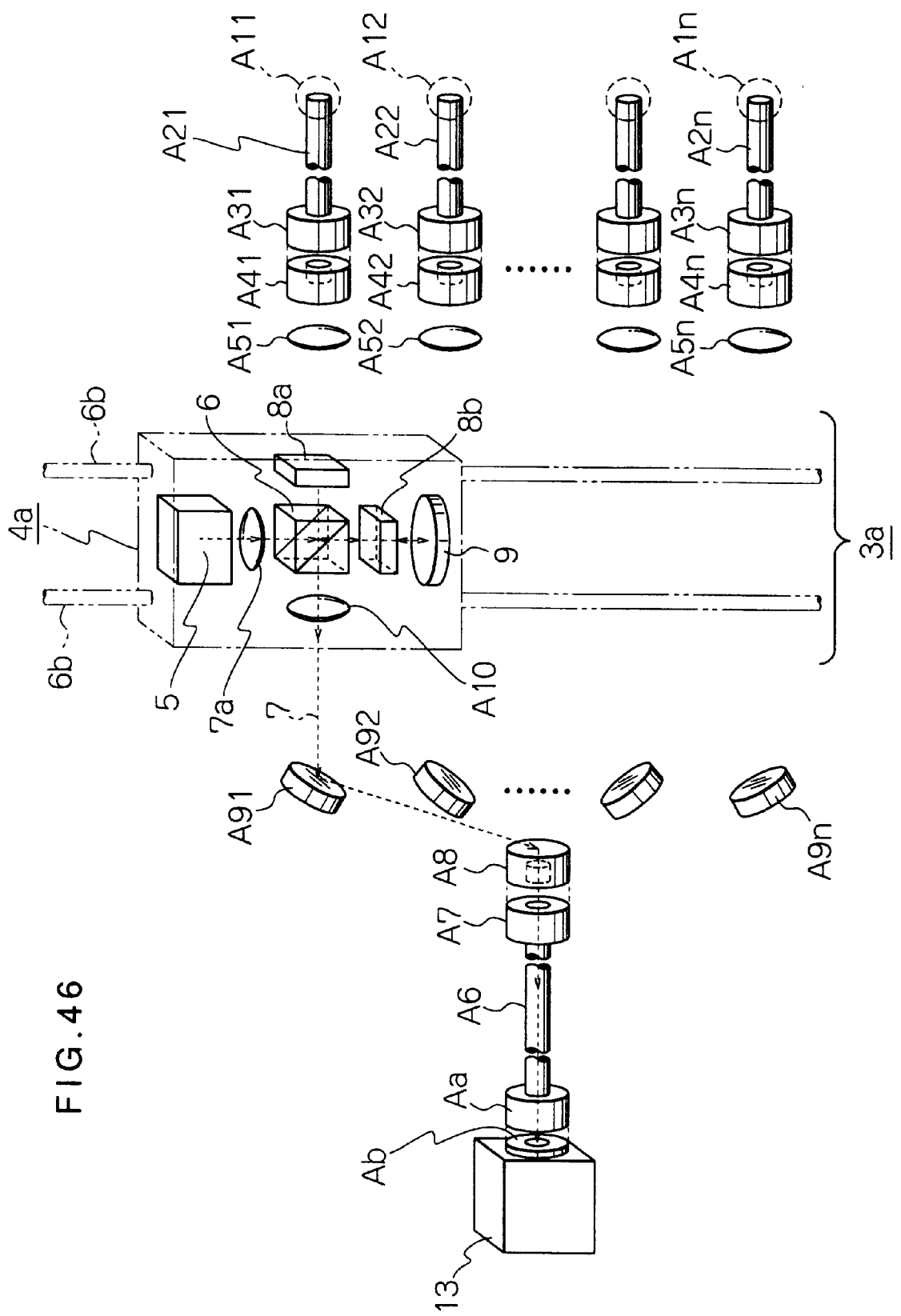
FIG. 46 is a perspective view showing the immunoassay apparatus according to Embodiment 5.1 in a state for reference measurement.

Firstly, the light emitted from the light source is directly subjected to a wavelength distribution analysis for reference. This reference measurement is carried out for evaluation of the operation of the immunoassay apparatus 1 itself. As shown in FIG. 46, the light 7 emitted from the light source 5 transmits through the convering lens 7a and reaches the beam splitter 6. In the beam splitter 6, a part of the light 7 is reflected to reach the shutter 8a. The other part of the light 7 reaching the beam splitter 6 passes through the beam splitter 6 and then the shutter 8b to reach the reflection mirror 9. Here, the light is reflected toward the beam splitter 6 where the light is reflected toward the spectrometer 13.

That is, in the reference measurement, the shutter 8a is closed and the shutter 8b is open. The light reflected by the beam splitter 6 passes through the deflection mirror A91, the receptacle A8, the connector A7, and the spectrometer optical fiber A6 to reach the spectrometer 13. Thus, it is possible to analyze a wavelength distribution of the light 7 emitted from the light source 5.

(2) Immunoassay procedure

Figure 47:
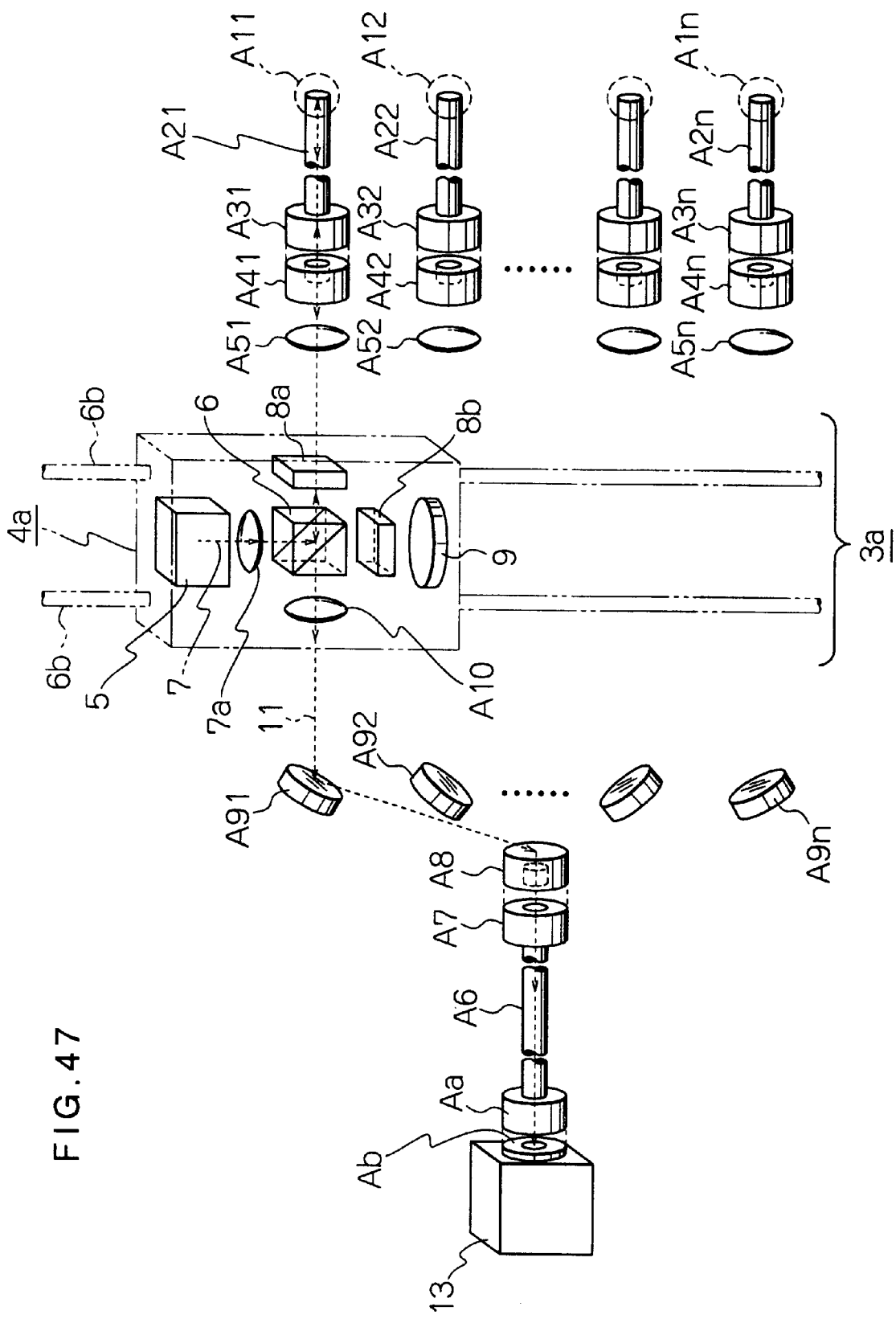
FIG. 47 is a perspective view showing the immunoassay apparatus according to Embodiment 5.1 in a state for an immunoassay with a first SPR sensor.

The SPR sensors A11, A12, ..., A1n prepared for respective check items are connected one after another with the aforementioned connectors A31, A32, ..., A3n. However, it is also possible to use a multi-connector to connect a plurality of optical fibers all at once. Moreover, as shown in FIG. 47, the shutter 8a is opened for the sensor and the shutter 8b for the mirror is closed. Here, the light emitting means 4a has been positioned so that the optical axis of the light emitting means is matched with the optical axis of the sensor optical fiber A21. The light emitted from the light source 5 is reflected by the beam splitter 6 and passes through the shutter 8a, the converging lens A51, the receptacle A41, and the connector A31 to reach the SPR sensor A11. The light 7 advances while being reflected by the outer circumference of the end portion of the SPR sensor A11 and is reflected by the reflection mirror 3b (mirror coated with a gold or silver film) at the end face of the SPR sensor A11 to return as a reflected light 11 through the sensor optical fiber A21. Here, the light 7 excites a surface plasmon resonance in the SPR sensor A11. This surface plasmon resonance is caused by a particular wavelength in the light 7. Accordingly, the intensity of this particular wavelength is attenuated and the reflection light 11 returns with this particular wavelength attenuated.

A part of the reflected light 11 passes through the beam splitter 6 and the converging lens A10 and bent by the deflection mirror A91 to reach the receptacle A8. The reflected light 11 further passes through the spectrometer optical fiber A6 and reaches the spectrometer 13, so as to be subjected to a wavelength distribution analysis by the spectrometer 13. Thus, the immunoassay with the first SPR sensor A11 is complete.

Figure 48:
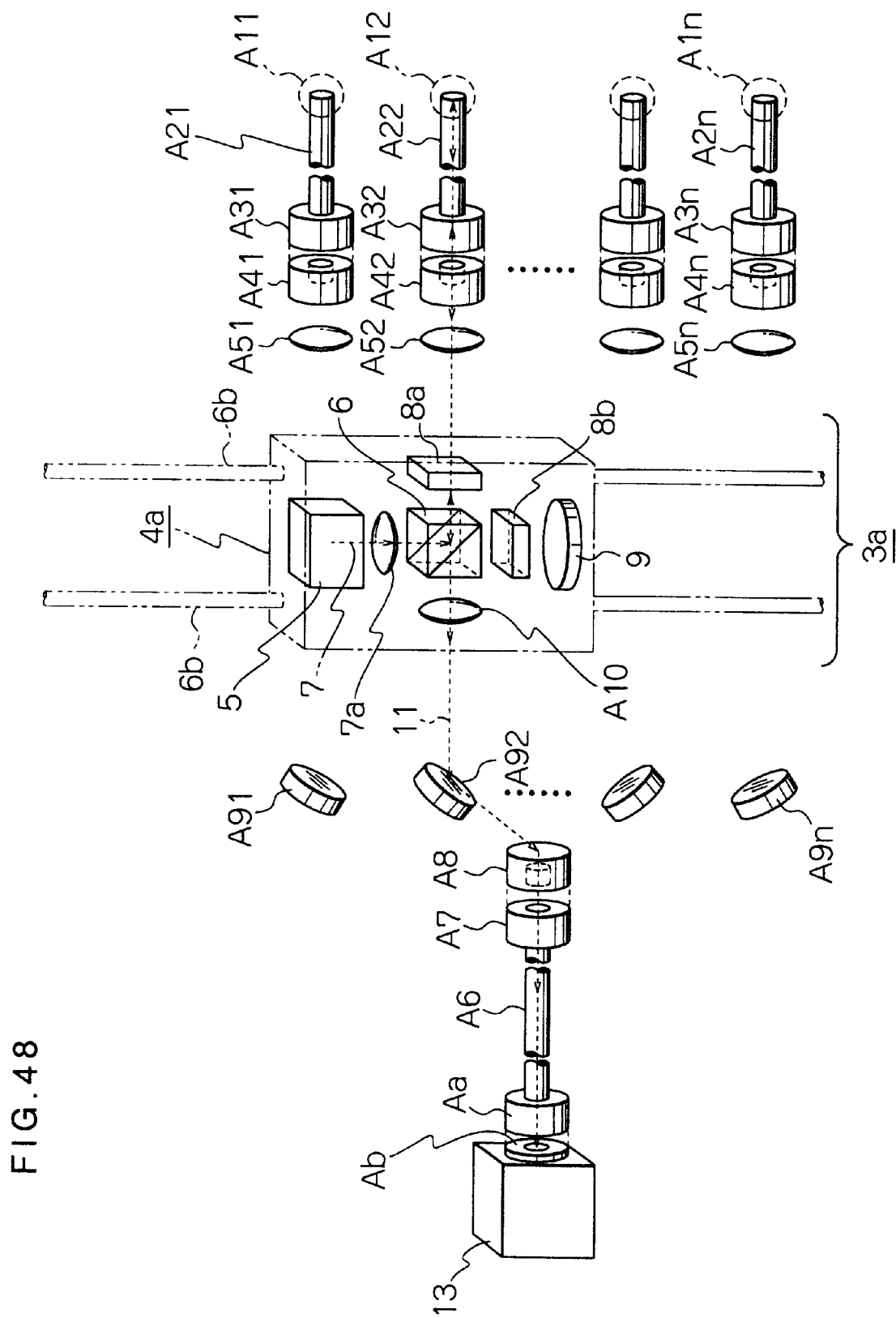
FIG. 48 is a perspective view showing the immunoassay apparatus according to Embodiment 5.1 in a state for an immunoassay with a second SPR sensor.

Next, as shown in FIG. 48, an immunoassay with the second optical fiber having the SPR sensor A12 is carried out. More specifically, the shifting frame (not depicted) is moved so that the optical axis of the light emitting means 4a is matched with the optical path of the receptacle A42 corresponding to the second sensor optical fiber A22. The light 7 from the light source 5, in the same way as the first SPR sensor, reaches the second SPR sensor A12. The reflected light 11 is bent by the deflection mirror A92 and reaches the spectrometer 13. The second SPR sensor A12 has an antibody different from the first SPR sensor A11, it is possible to detect a concentration of a different antigen.

Figure 49:
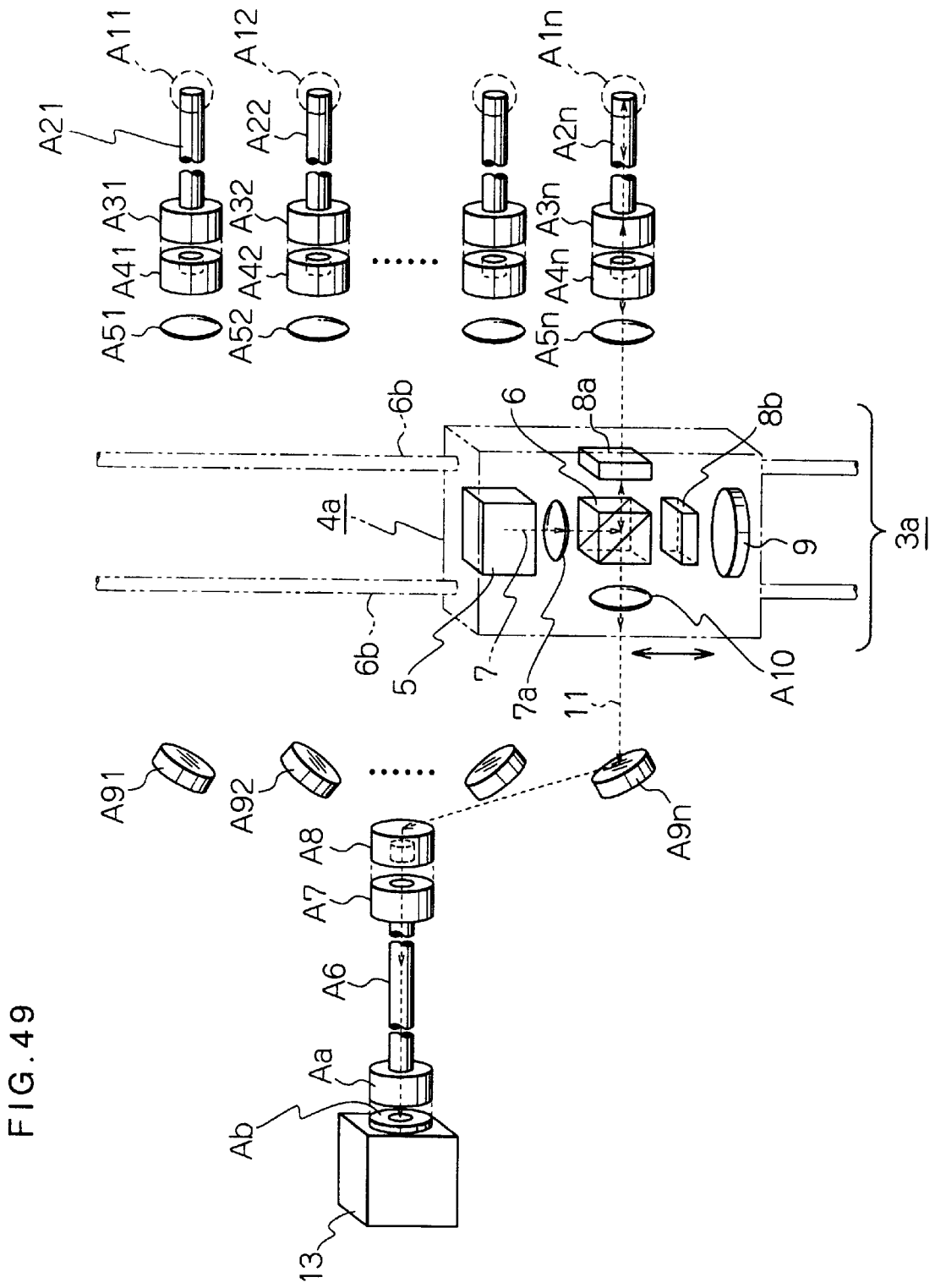
FIG. 49 is a perspective view showing the immunoassay apparatus according to Embodiment 5.1 in a state for an immunoassay with an n-th SPR sensor.

FIG. 49 shows the immunoassay apparatus in a state for a immunoassay with the n-th SPR sensor A1n formed on the n-th sensor optical fiber A2n. In this case also, the shifting frame is moved so that the light emitting means 4a is positioned on an optical axis of the n-th converging lens A5n. The reflected light 11 from the SPR sensor A1n passes through the light emitting means 4a and introduced by the deflection mirror A9n to the receptacle A8.

As has been described above, the optical path switching mechanism 3a carries out optical path switching without changing the length of the optical path for the respective optical fibers. Accordingly, there is no need of correction for the intensity change depending on the optical fibers.

It should be noted that in this embodiment the optical fibers are arranged with their cross sections in a straight line. However, the present invention is not to be limited to this arrangement. The cross sections may be arranged in a matrix and the shifting frame is constructed so as to be movable over the matrix.

When a series of immunoassays is complete, the sensor optical fibers A21, A22, ..., A2n are removed from the connectors A31, A32, ..., A3n and a new set of sensor optical fibers A21, A22, ..., A2n are connected. In this embodiment, the sensor optical fibers A21, A22, ..., A2n alone can be disconnected. This enables to suppress the assay costs. It is also possible to disconnect the connectors A31, A32, ..., A3n together with the sensor optical fibers A21, A22, ..., A2n to be discarded.

[Embodiment 5.2]

Figure 50:
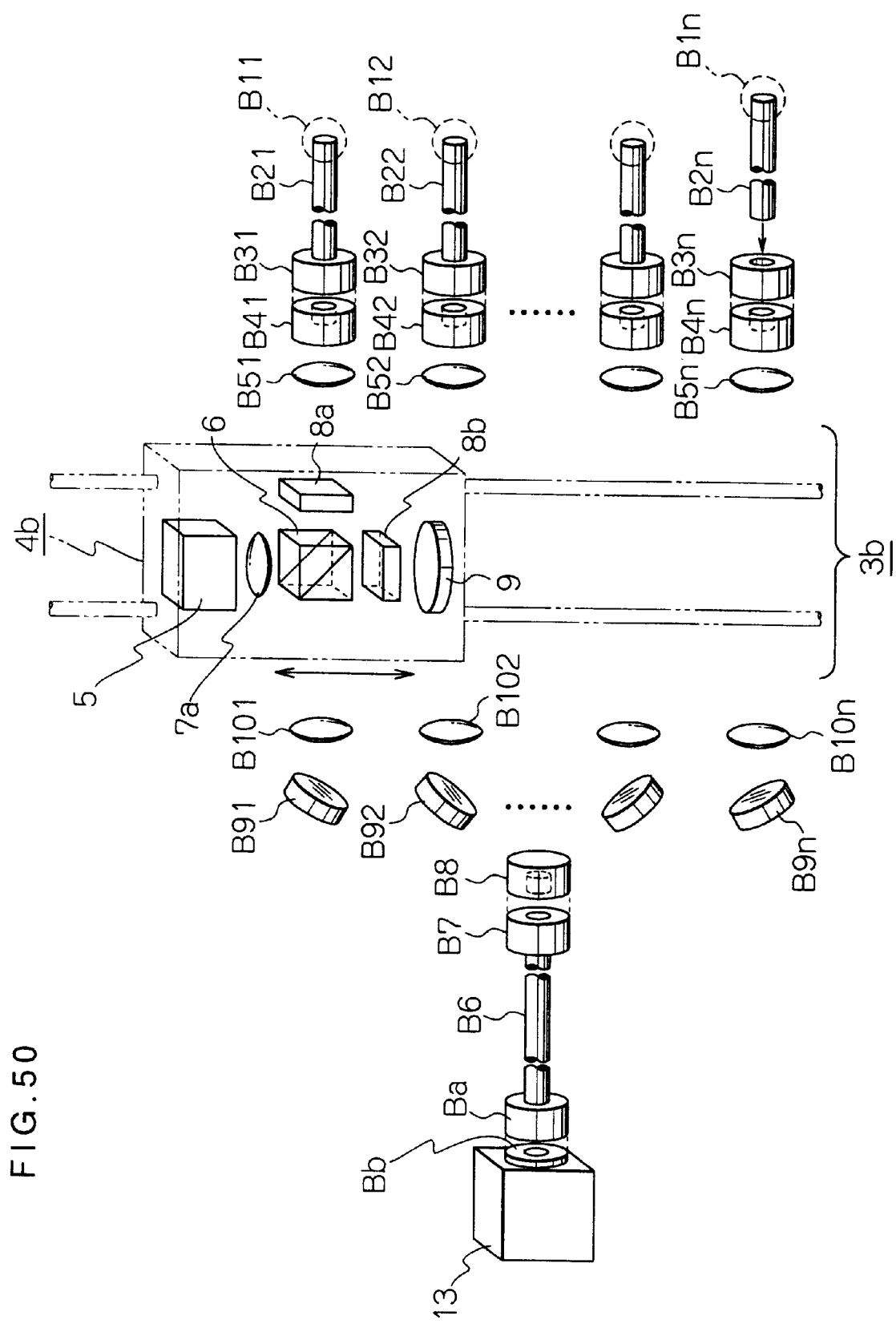
FIG. 50 is a perspective view showing a configuration of an immunoassay apparatus according to an Embodiment 5.2 of the present invention.

Explanation will be given on an Embodiment 5.2 of the present invention with reference to FIG. 50.

This embodiment has an almost identical configuration as the Embodiment 5.1 except for that instead of the single converging lens A10, a plurality of converging lenses B101, B102, ..., B10n are provided to correspond to respective polarizing mirrors B91, B92, ..., B9n.

The converging lenses provided between the light emitting means 4b and the deflection mirrors B91, B92, ..., B9n serves to converge a reflected light and effectively transmits the reflected light to the spectrometer 13. The use of the plurality of converging lenses B101, B102, ... , B10n corresponding to the sensor optical fibers B21, B22, ... , B2n increases the positioning o the optical system.

That is, as in the Embodiment 5.1, when a single fixed converging lens is provided in the light emitting means 4b and the light emitting means 4a is moved by the shifting frame, it is difficult to accurately control the optical positional relationship between the converging lens A10 and the respective deflection mirrors A91, A92, ... , A9n: On the other hand, as shown in FIG. 50, when each of the deflection mirrors B91, B92, ... , B9n has a corresponding converging lens B101, B102, ... , B10n, the positional relationship between each of the pairs can be accurately set in advance.

Next, explanation will be given on the operation of this embodiment.

Figure 51:
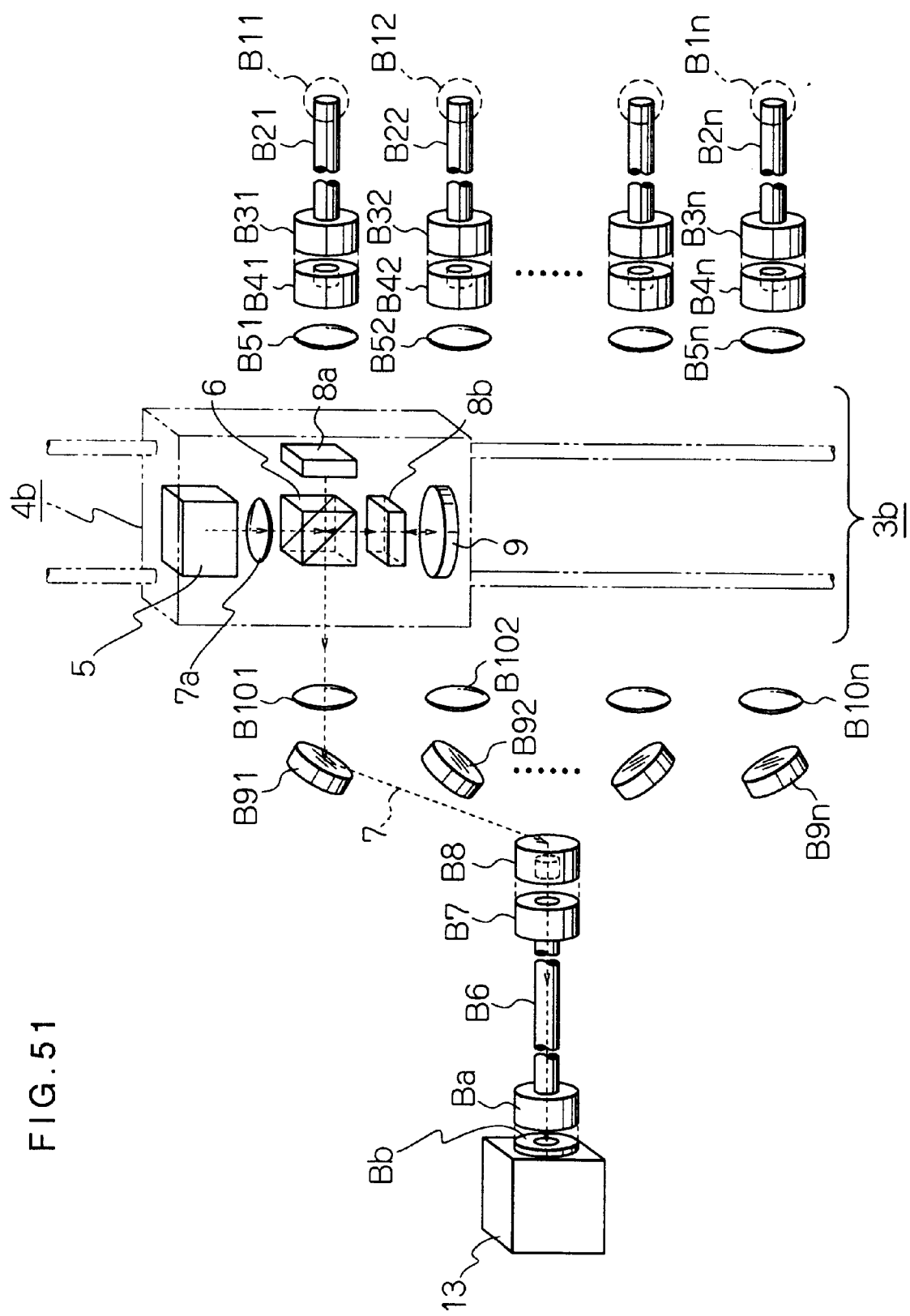
FIG. 51 is a perspective view showing the immunoassay apparatus according to Embodiment 5.2 in a state for reference measurement.

FIG. 51 shows the immunoassay apparatus according to the Embodiment 5.2 in a state for a reference measurement for analyzing a wavelength distribution of a light emitted from the light source 5. The light 7 from the light source 5 transmits through the converging lens 7a and reaches the beam splitter 6. A part of the light 7 transmits through the beam splitter 6 and the shutter 8b and is reflected by a reflection mirror 9. The light is further reflected by the beam splitter 6 to advance for the spectrometer. The light 7 passes through the converging lens B101, the deflection mirror B91, the receptacle B8, and the spectrometer optical fiber B6 to reach the spectrometer 13. Thus, the light 7 emitted from the light source 5 is subjected to a wavelength distribution analysis.

Figure 52:
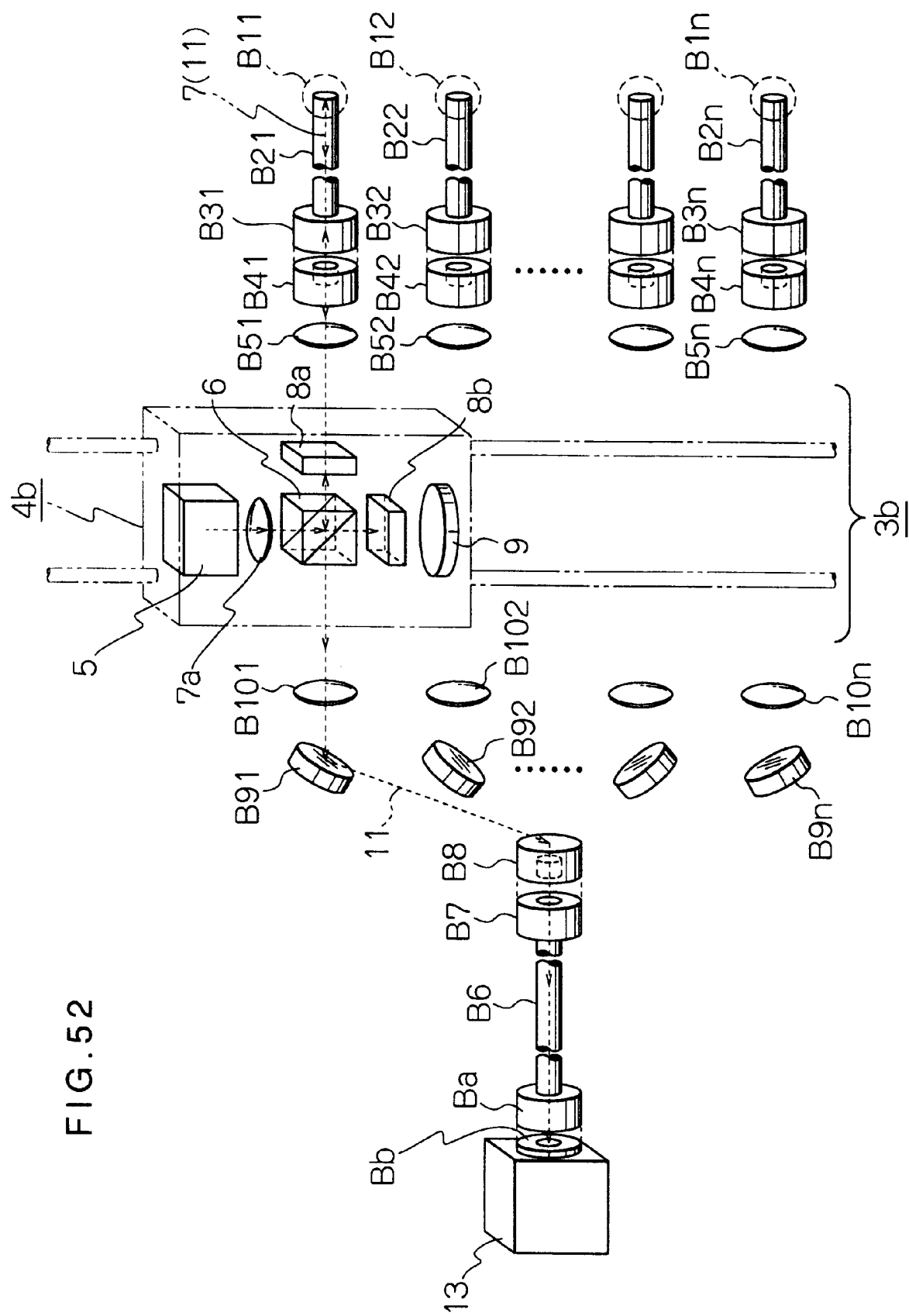
FIG. 52 is a perspective view showing the immunoassay apparatus according to Embodiment 5.2 in a state for an immunoassay with a first SPR sensor.

FIG. 52 shows the immunoassay apparatus of Embodiment 5.2 set in a state for an immunoassay with the first SPR sensor B11. When an immunoassay is carried out, the shutter 8a at the sensor side is opened and the shutter 8b for the mirror is closed. Accordingly, the light 7 from the light source 5 reaches the SPR sensor B11 and is reflected there to return as a reflected light 11 to the light emitting means 4b. The reflected light passes through the converging lens B101 and is bent by the deflection mirror B91 to enter the spectrometer 13, where an analysis of the reflected light 11 is carried out.

[Embodiment 5.3]

Figure 53:
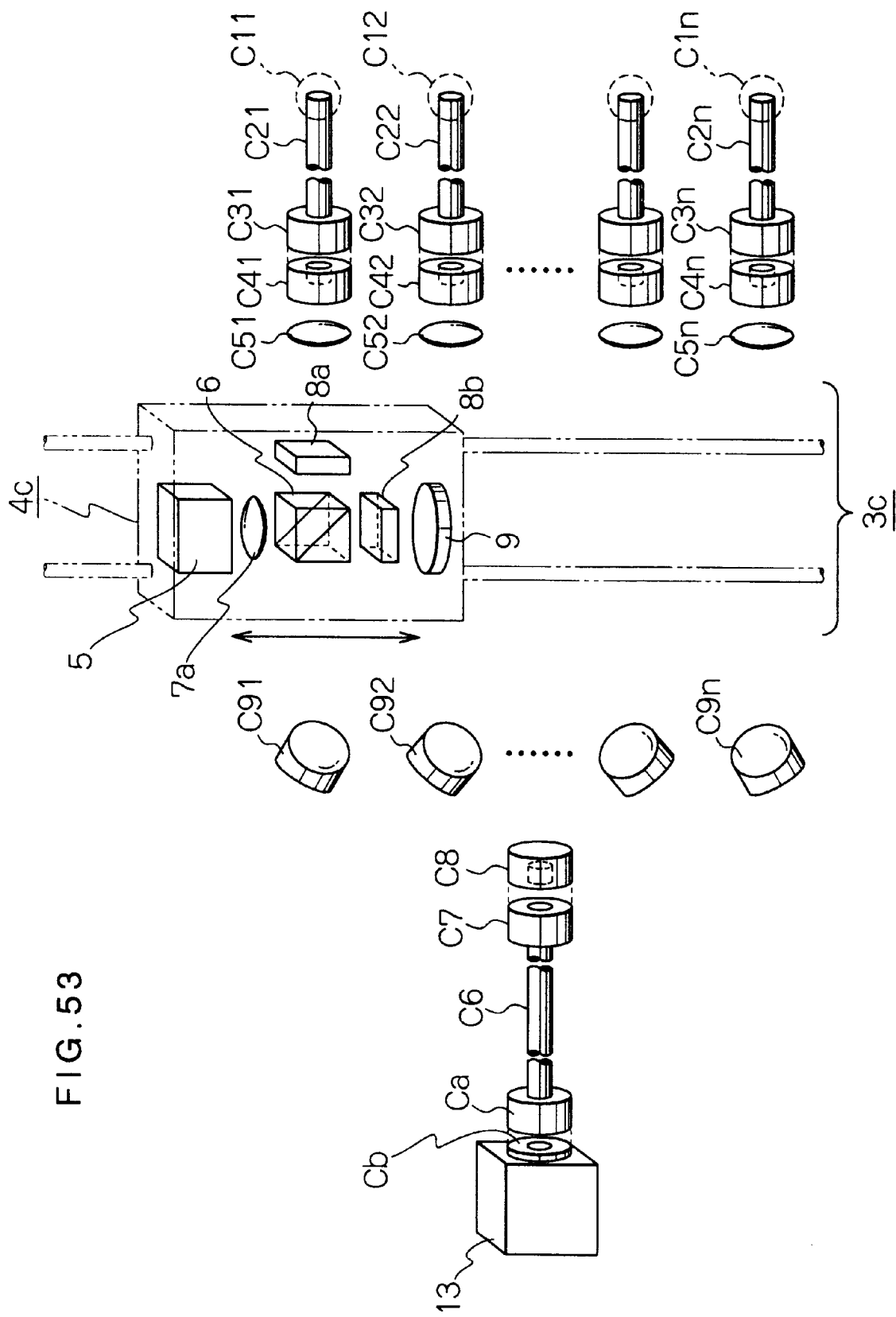
FIG. 53 is a perspective view showing a configuration of an immunoassay apparatus according to an Embodiment 5.3 of the present invention.

Explanation will be given on another embodiment 5.3 of the present invention with reference to FIG. 53. This embodiment has an almost identical configuration as embodiment 5.1 except for that between light emitting means 4a and the receptacle C8, there are provided predetermined concave mirrors C91, C92, ... , C9n corresponding to respective sensor optical fibers C21, C22, ... , C2n. Like components as in embodiment 5.1 are denoted with like reference numerals.

The aforementioned concave mirrors C91, C92, ... , C9n introduce a reflected light transmitting the light emitting means 4a, to the receptacle C8. These concave mirrors C91, C92, ... , C9n serve to converge the reflected light and deflect the light advancing direction. That is, these concave mirrors can take place of the converging lenses and the deflection mirrors in the embodiments 5.1 and 5.2. Accordingly, it is possible to reduce production costs.

Figure 54:
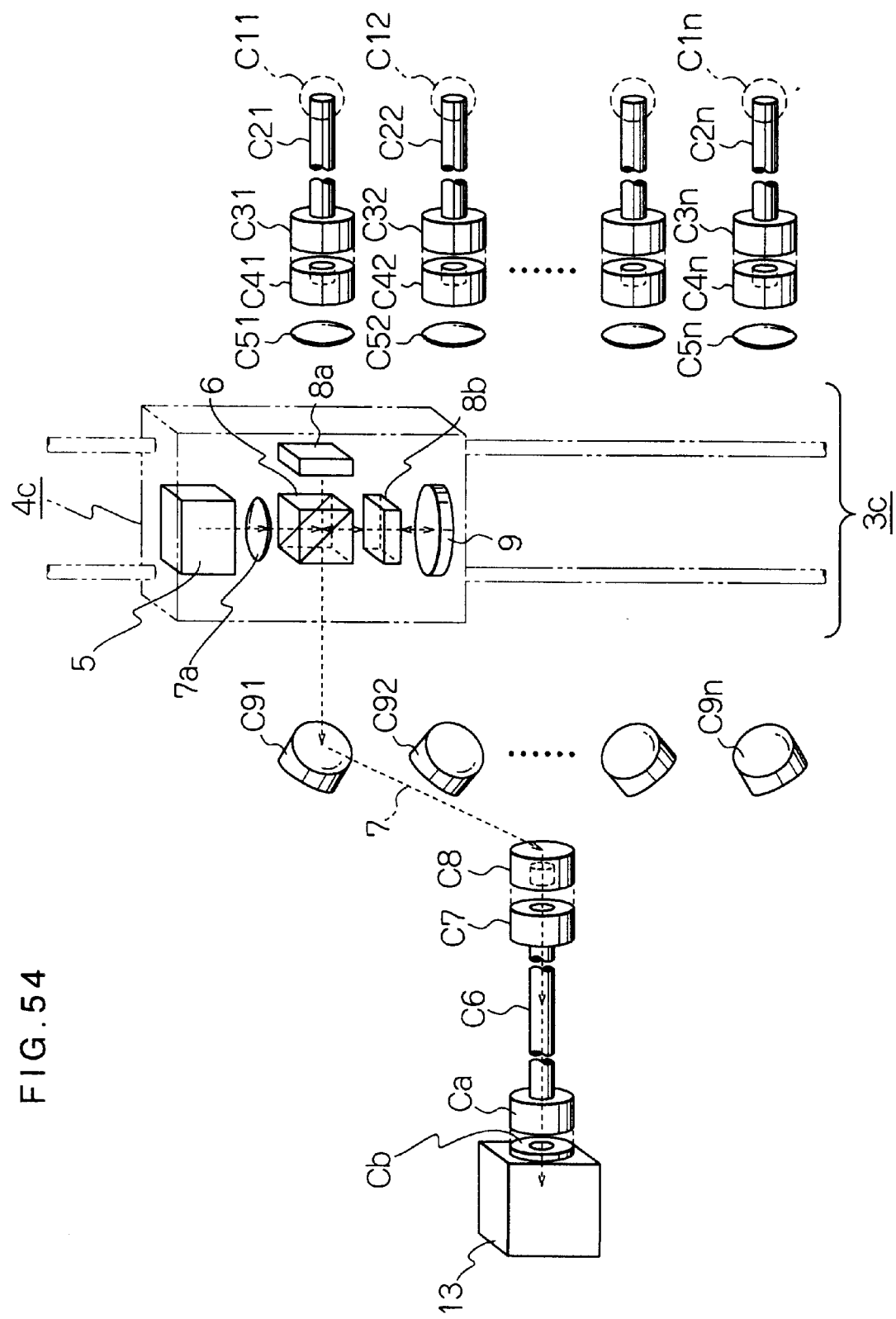
FIG. 54 is a perspective view showing the immunoassay apparatus according to Embodiment 5.3 in a state for reference measurement.

FIG. 54 shows the immunoassay apparatus of this embodiment in a state for a reference measurement, i.e., for a wavelength distribution analysis of a light emitted from a light source. As shown in FIG. 54, the light 7 emitted from the light source 5 transmits through the converging lens 7a and enters the beam splitter 6. A part of the light 7 passes through the beam splitter 6 and the shutter 8b and is reflected by the reflecting mirror 9. The reflected light is further reflected by the beam splitter 6 toward the concave mirror C91 so as to pass through the receptacle C8 and the spectrometer optical fiber C6, reaching the spectrometer 13. Thus, the light emitted from the light source 5 is subjected to a wavelength distribution analysis.

Figure 55:
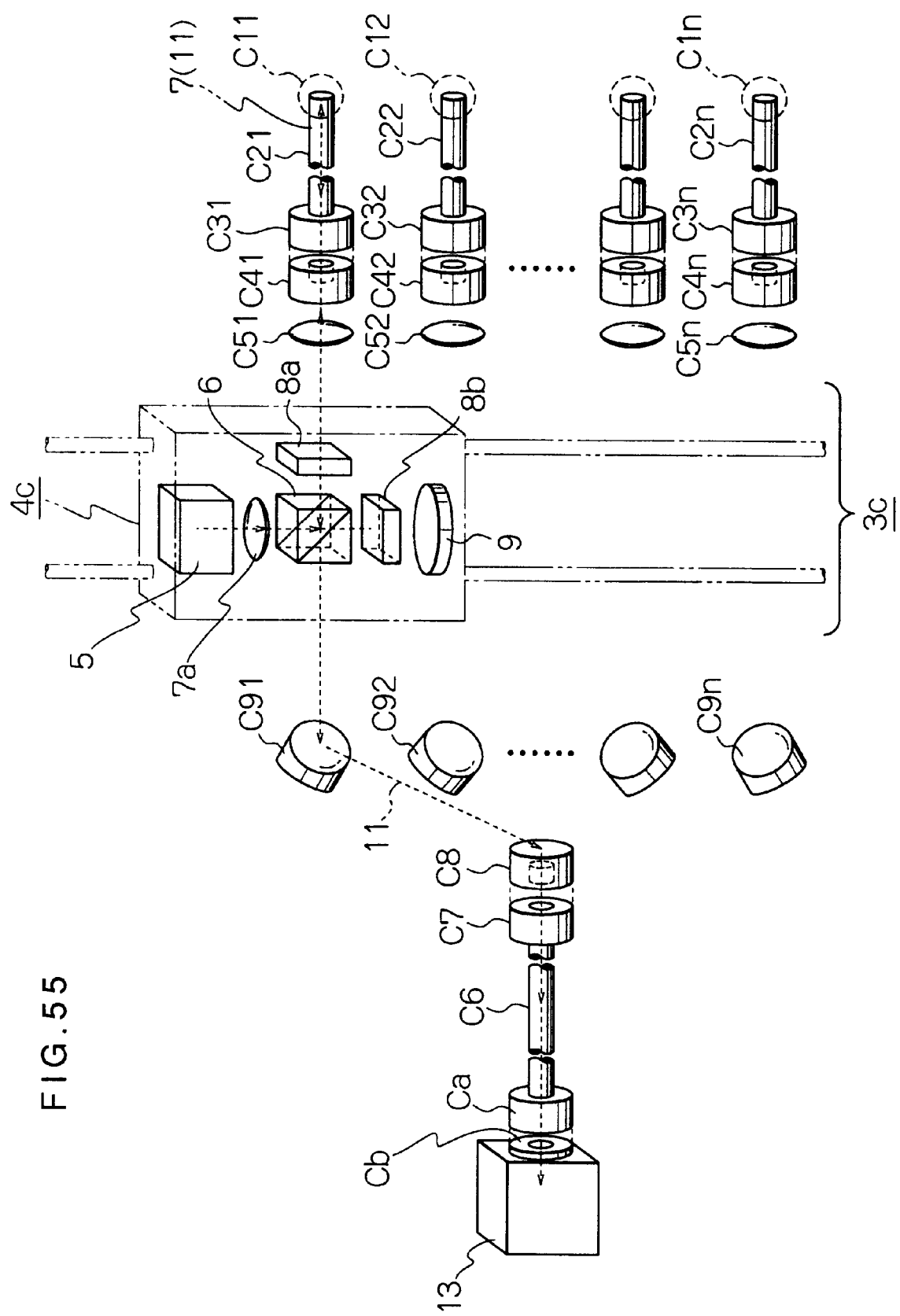
FIG. 55 is a perspective view showing the immunoassay apparatus according to Embodiment 5.3 in a state for an immunoassay with a first SPR sensor.

FIG. 55 shows the immunoassay apparatus of embodiment 5.3 in a state for an immunoassay with the SPR sensor C11. When an immunoassay is to be carried out, the shutter Ba is opened for a sensor and the shutter 1b is closed. As shown in FIG. 55, the light 7 from the light source 5 reaches the SPR sensor C11, where it is reflected to reach the light emitting means 4c and the concave mirror C91. The reflected light is converged and deflected by the concave mirror C91 so as to be introduced into the spectrometer 13 for an analysis.

[Embodiment 5.4]

Figure 56:
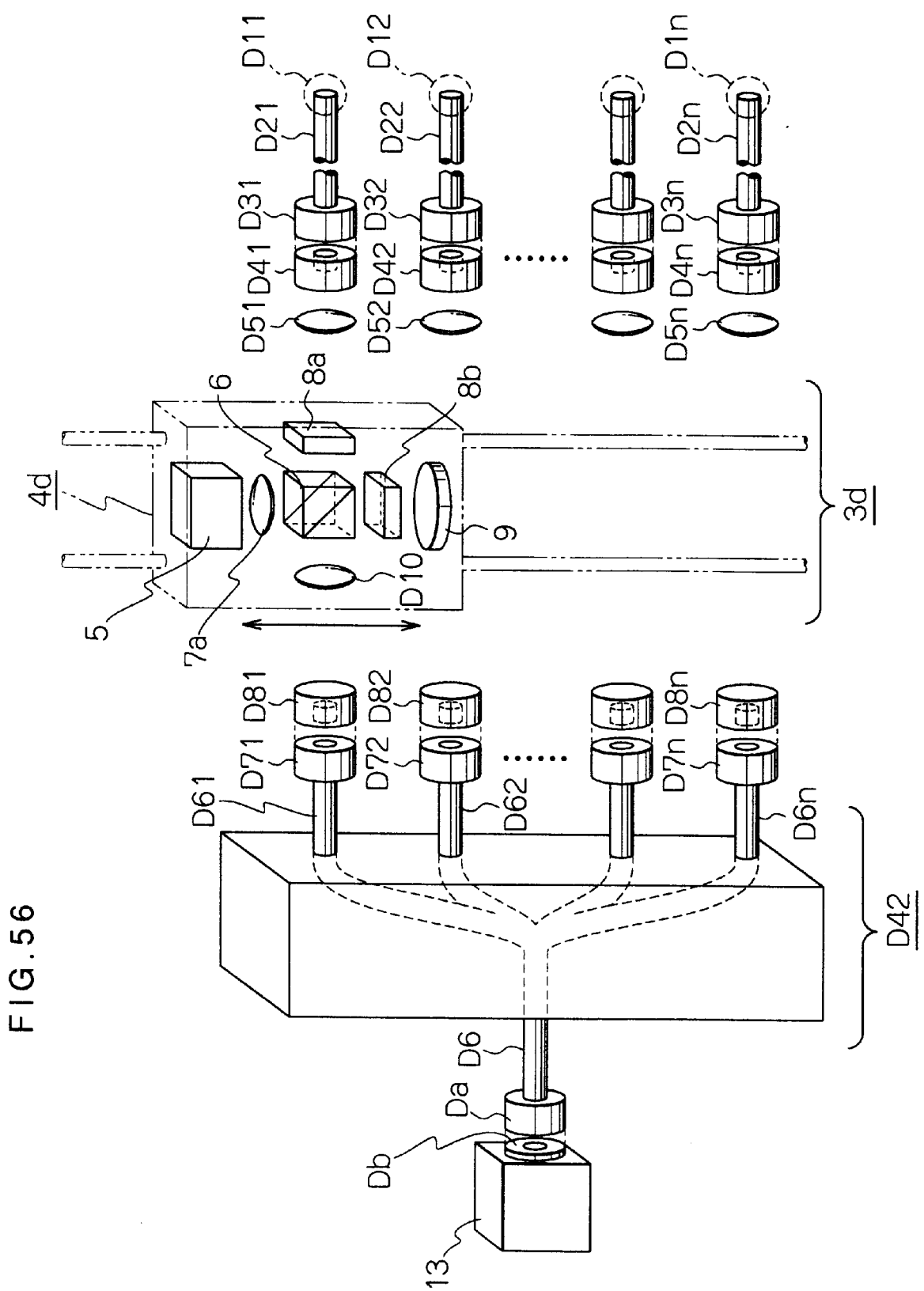
FIG. 56 is a perspective view showing a configuration of an immunoassay apparatus according to an Embodiment 5.4 of the present invention.

Next , explanation will be given on another embodiment 5.4 with reference to FIG. 56.

This embodiment has an almost identical configuration as embodiment 5.1 except for that between the light emitting means 4d and the spectrometer 13, there are provided receptacles D81, D82, ... , D8n and optical fiber connectors D71, D72, ... , D7n corresponding to sensor optical fibers D21, D22, ... , D2n. Furthermore, this embodiment comprises spectrometer optical fibers D61, D62, ... , D6n which are bound by an optical fiber coupler D42.

Figure 57:
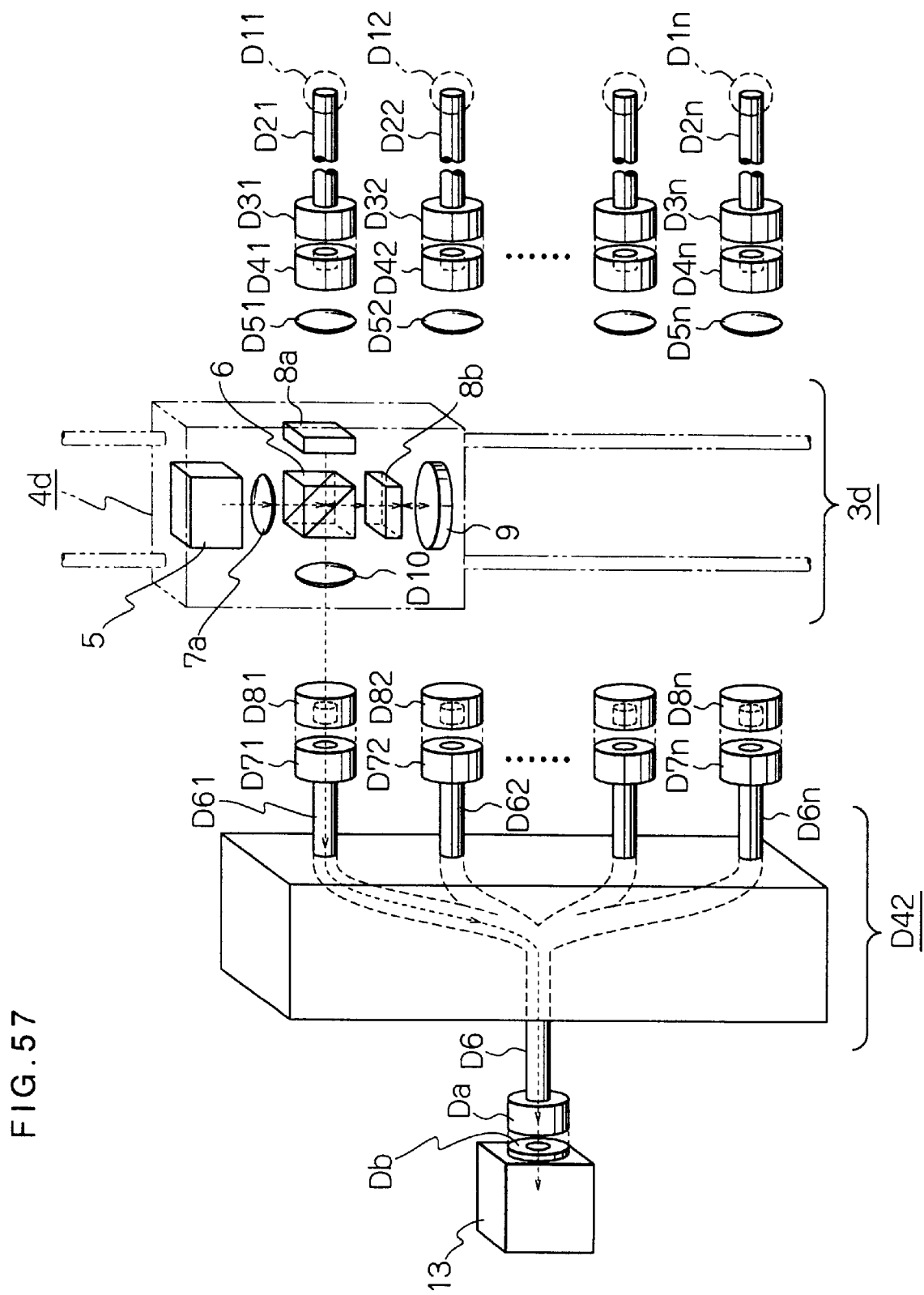
FIG. 57 is a perspective view showing the immunoassay apparatus according to Embodiment 5.4 in a state for reference measurement.

FIG. 57 shows the immunoassay apparatus of embodiment 5.4 in a state for a reference measurement, i.e., a wavelength distribution analysis of a light emitted from a light source. The light 7 from the light source 5 passes through the converging lens 7a and enters the beam splitter. A part of the light 7 directly passes through the beam splitter 6 and the shutter 8b and is reflected by the reflection mirror 9. The light is further reflected by the beam splitter 6 to pass through the converging lens D10, the receptacle D81, the connector D71, and the spectrometer optical fiber D61 to reach the spectrometer 13. Thus, the light 7 emitted from the light source 5 is subjected to a wavelength distribution analysis. Here, the optical fiber coupler D42 serves to transmit the light introduced from the receptacle D81 as it is directly to the spectrometer 13.

Figure 58:
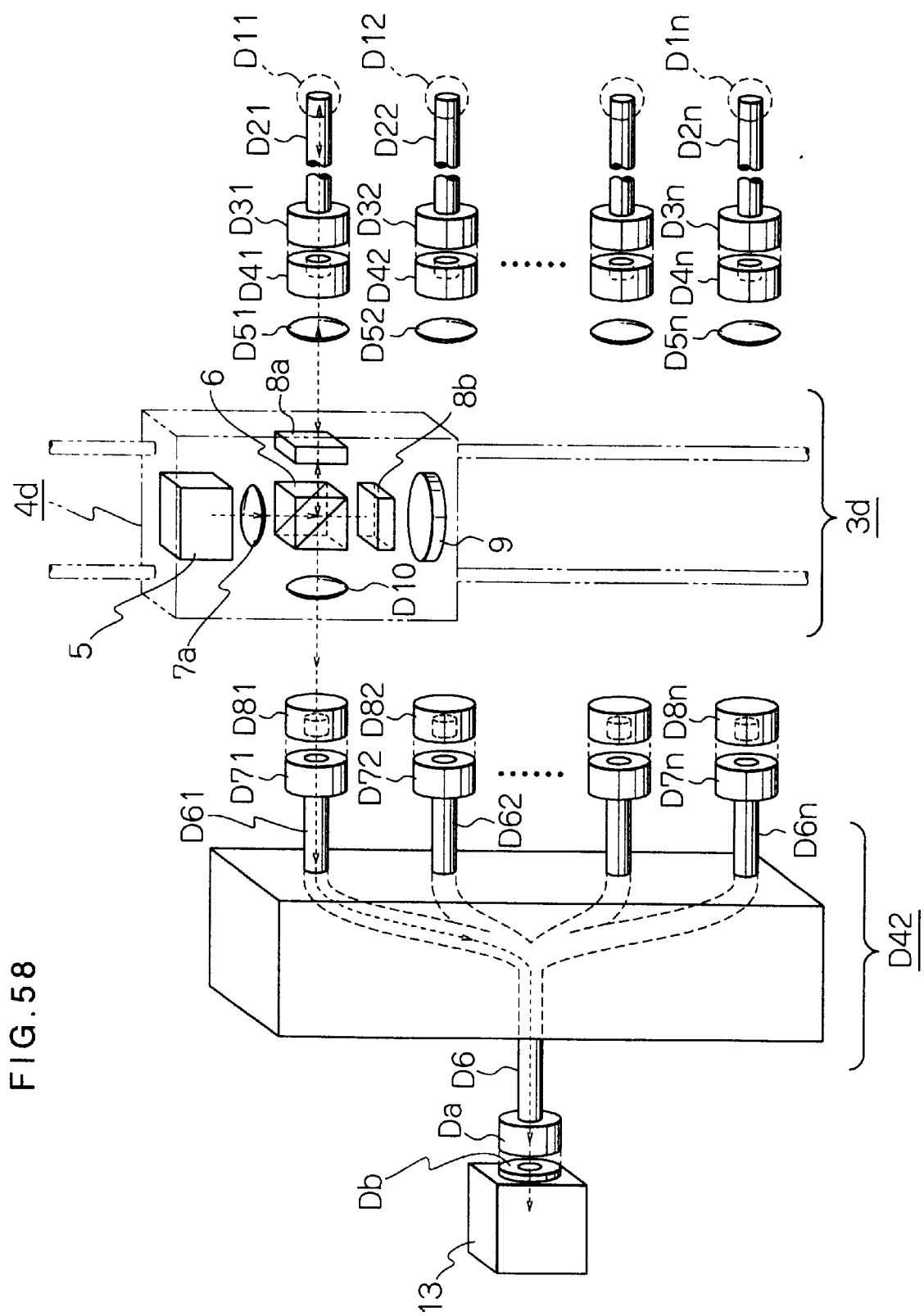
FIG. 58 is a perspective view showing the immunoassay apparatus according to Embodiment 5.4 in a state for an immunoassay with a first SPR sensor.

FIG. 58 shows the immunoassay apparatus of embodiment 5.4 in a state for an immunoassay with a first SPR sensor D11. When an immunoassay is to be carried out, the shutter 8a is opened and the shutter 8b is closed. Thus, the light 7 from the light source 5 reaches the SPR sensor D11, where it is reflected to pass through the light emitting means 4d and the receptacle D81. The reflected light 11 further passes through the optical fiber connector D71, the spectrometer optical fiber D61, and the optical fiber coupler D42 to reach the spectrometer 13 to be analyzed.

[Embodiment 5.5]

Figure 59:
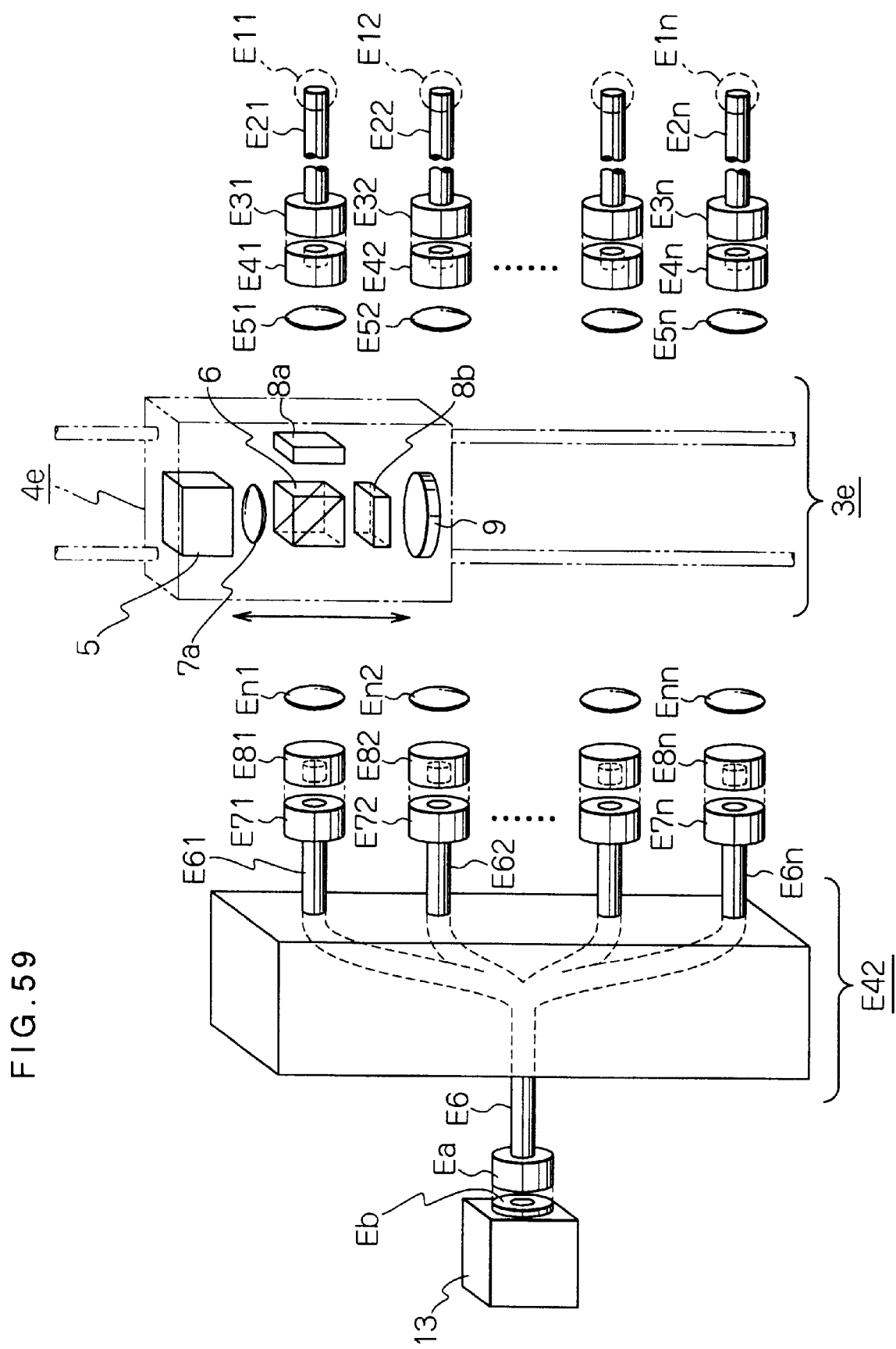
FIG. 59 is a perspective view showing a configuration of an immunoassay apparatus according to an Embodiment 5.5 of the present invention.

Next, an explanation will be given on still another embodiment 5.5 with reference to FIG. 59.

This embodiment has an almost identical configuration as the embodiment 5.4 except for that converging lens En1, En2, ... , Enn are provided corresponding to the receptacles E81, E82, ... , E8n.

Figure 60:
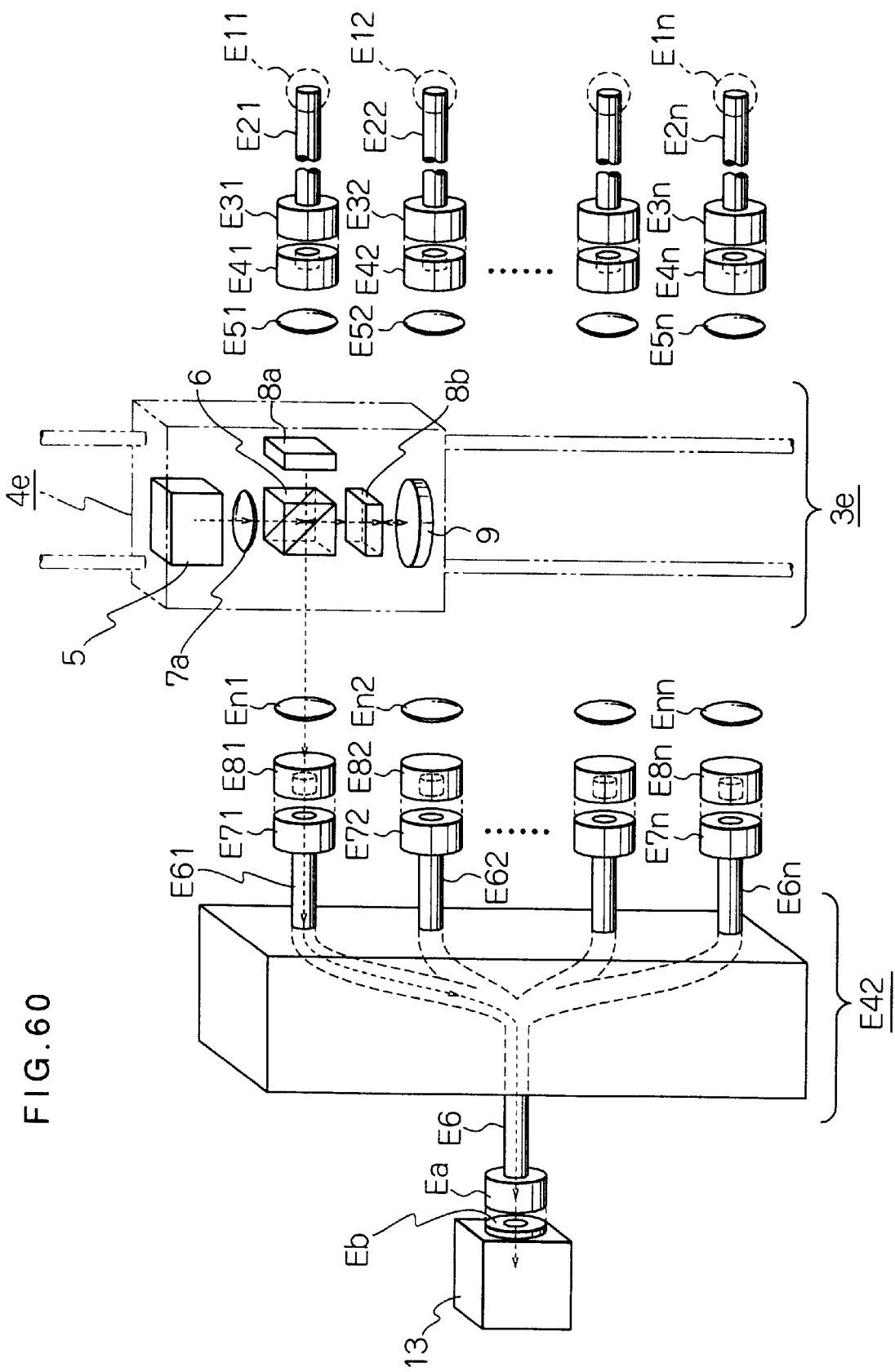
FIG. 60 is a perspective view showing the immunoassay apparatus according to Embodiment 5.5 in a state for reference measurement.

FIG. 60 shows the immunoassay apparatus of embodiment 5.5 in a state for a reference measurement, i.e., for a wavelength distribution analysis of a light emitted from a light source. The light 7 from the light source 5 passes through the converging lens 7a and enters the beam splitter 6. A part of the light 7 passes through the beam splitter 6 and shutter 8b and is reflected by the reflection mirror 9. The light 7 is further reflected by the beam splitter 6 to pass through the converging lens En1, the receptacle E81, the optical fiber connector E71, and the spectrometer optical fiber E61 to reach the spectrometer 13. Thus, the light 7 from the light source 5 is subjected to a wavelength distribution analysis.

Figure 61:
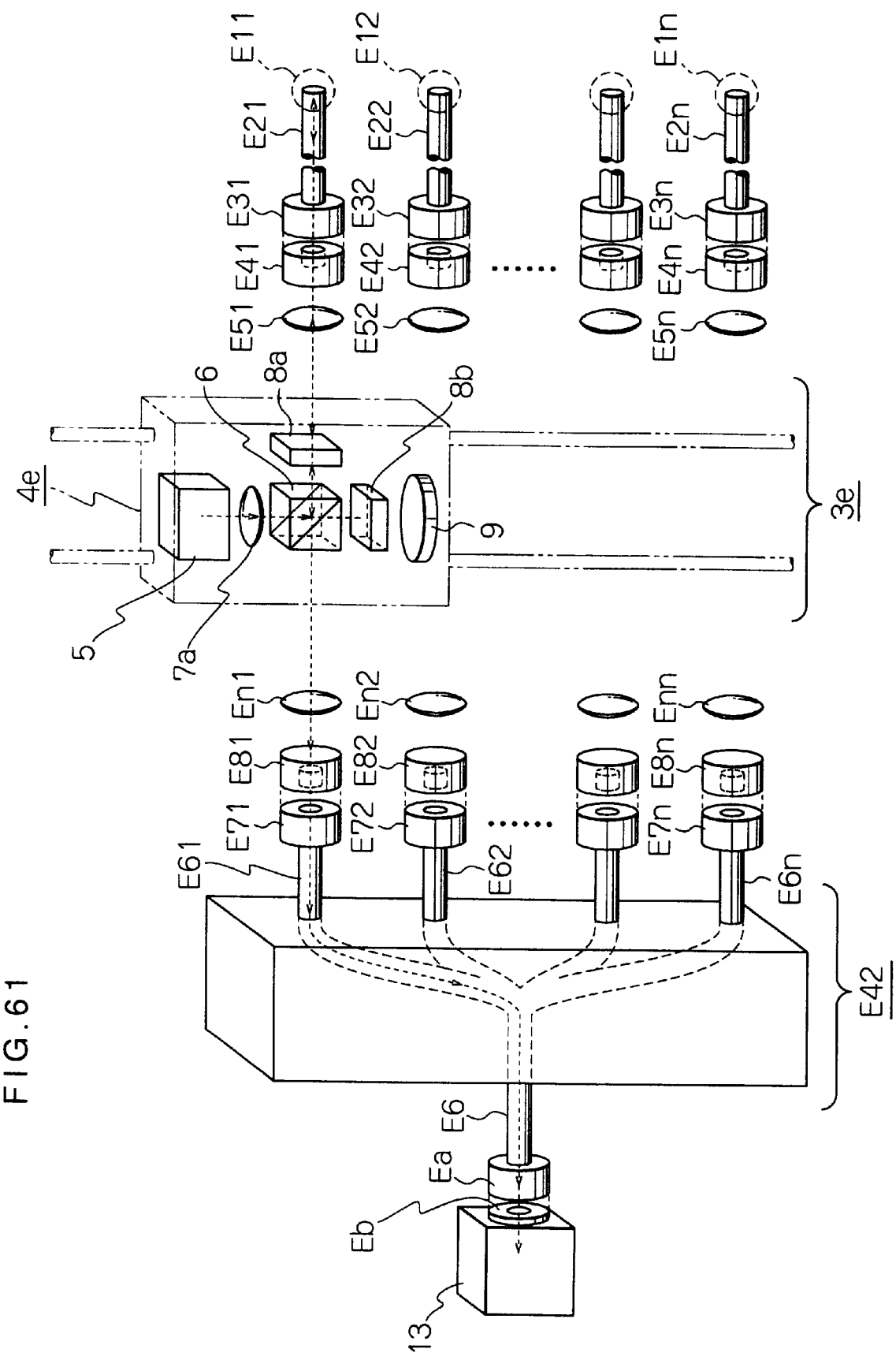
FIG. 61 is a perspective view showing the immunoassay apparatus according to Embodiment 5.5 in a state for an immunoassay with a first SPR sensor.

FIG. 61 shows the immunoassay apparatus of embodiment 5.5 in a state for an immunoassay with a first SPR sensor E11. When an immunoassay is to be carried out, the shutter 8a is opened and the shutter 8b is closed. Accordingly, the light 7 from the light source 5 reaches the first SPR sensor E11 and it is reflected there to pass through the light emitting means 4e, the converging lens En1, the receptacle E81, the optical fiber connector E71, the spectrometer optical fiber E61, and the optical fiber coupler E42 to enter the spectrometer 13 for an analysis.

[Embodiment 5.6]

Figure 62:
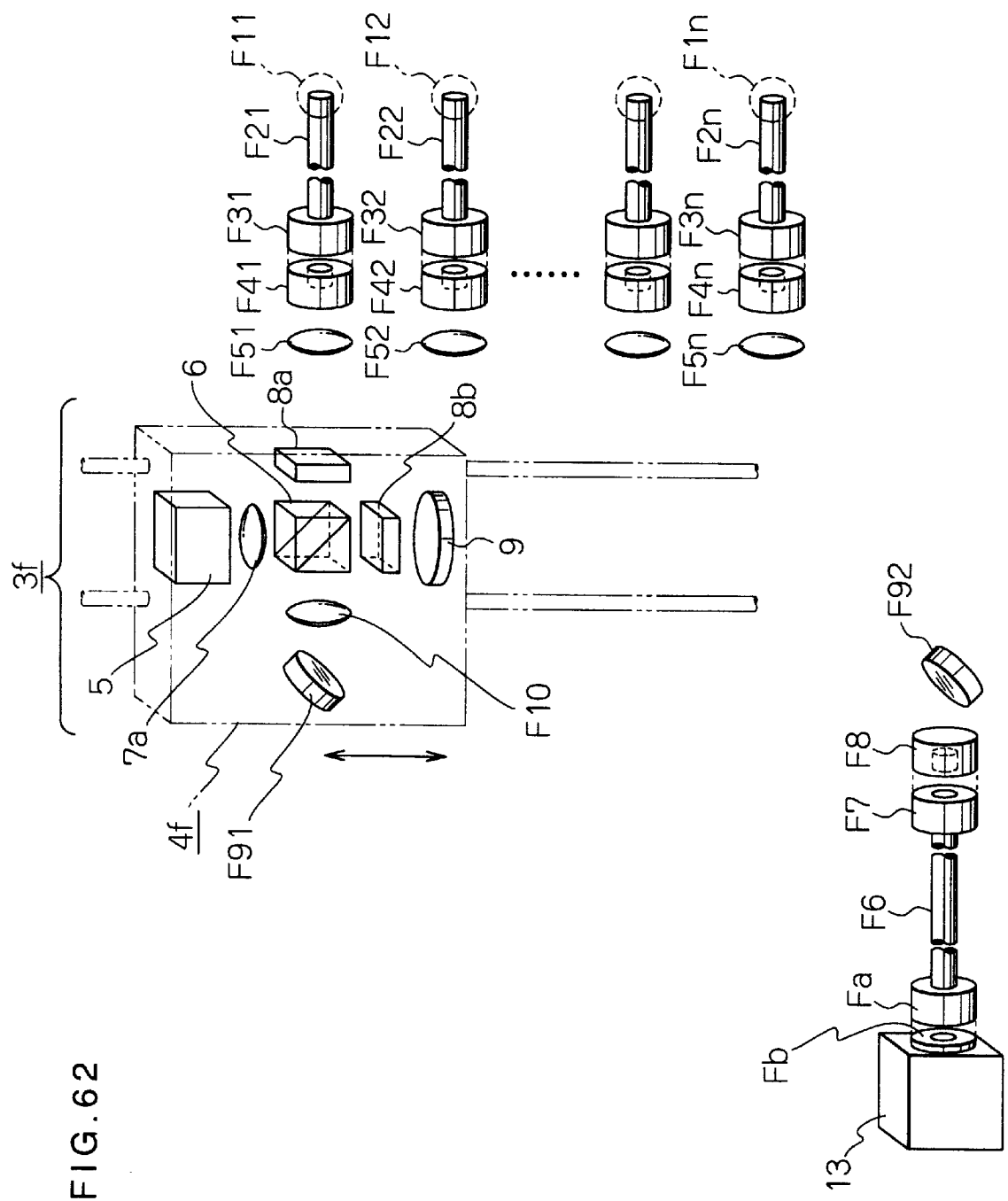
FIG. 62 is a perspective view showing a configuration of an immunoassay apparatus according to an Embodiment 5.6 of the present invention.

Next, explanation will be given on yet another embodiment 5.6 with reference to FIG. 62.

This embodiment has an almost identical configuration as embodiment 5.1 except for that the light emitting means 4f comprises a converging lens F10 and a first deflection mirror F91. Here, the first deflection mirror F91 has a reflection plane inclined by 45 degrees with respect to the optical axis of the sensor optical fibers F11, F12, . . . , F1n. This is for deflecting the light from the beam splitter, in the shifting direction of the light emitting means 4f (downward in the figure).

The light deflected downward by the deflection mirror F92 is further deflected by a second deflection mirror F92 so as to be deflected toward the spectrometer 13 which is provided at a downmost position. The line connecting the first deflection mirror and the second deflection mirror is parallel to the shifting direction of the light emitting means 4f.

Figure 63:
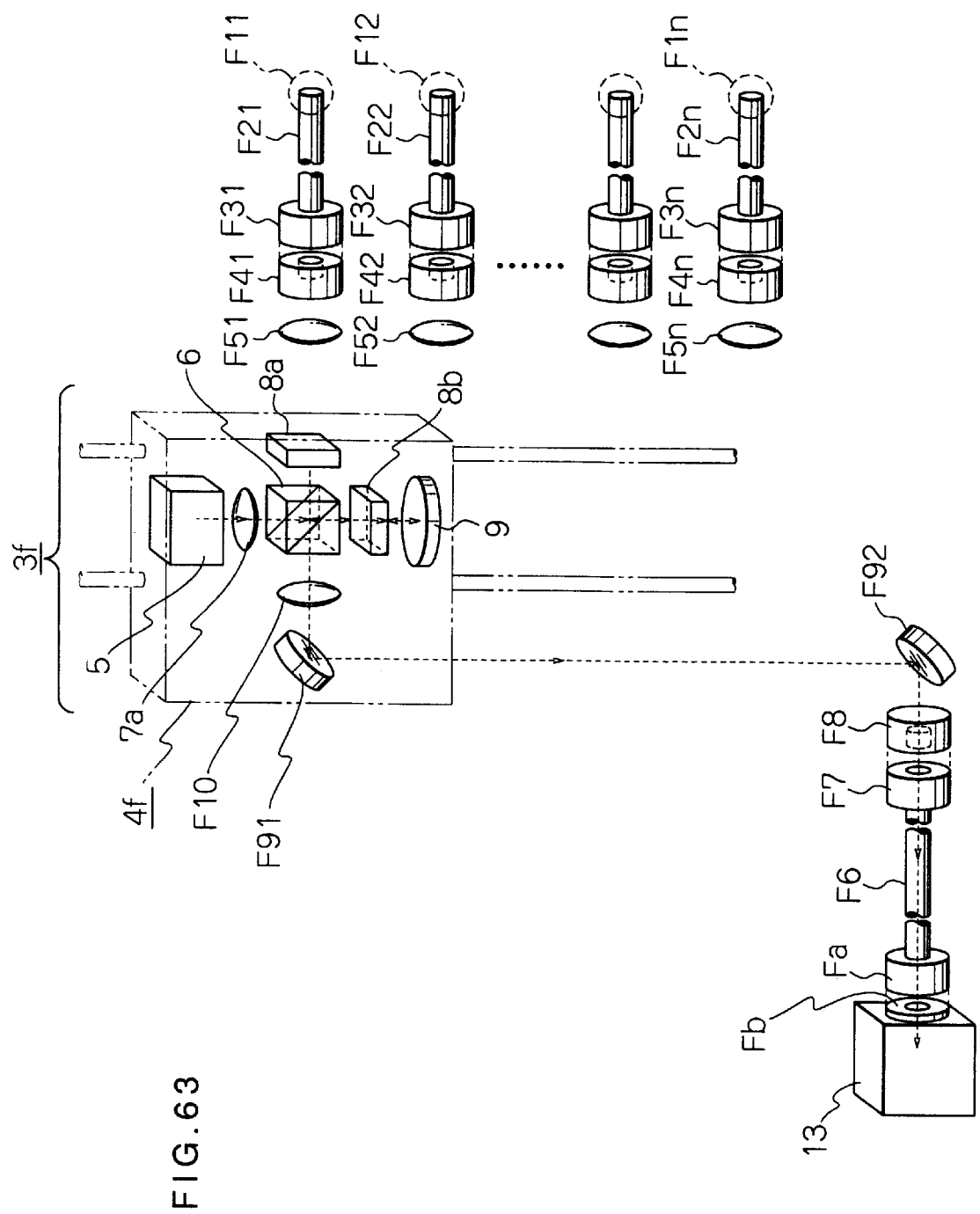
FIG. 63 is a perspective view showing the immunoassay apparatus according to Embodiment 5.6 in a state for reference measurement.

FIG. 63 shows the immunoassay apparatus of embodiment 5.6 in a state for a reference measurement, i.e., a wavelength distribution analysis of a light emitted from a light source. The light 7 emitted from the light source 5 passes through the converging lens 7a and enter s the beam splitter 6. A part of the light 7 passes through the beam splitter and the shutter 8b and is reflected by the reflection mirror 9. The light is further reflected by the beam splitter 6 to pass the converging lens F10 and is bent by the deflection mirror F91 downward. The light is further is further bent by the second deflection mirror F92 to pass through the receptacle F8, the connector F7, and the spectrometer optical fiber F6 to reach the spectrometer for an analysis.

Figure 64:
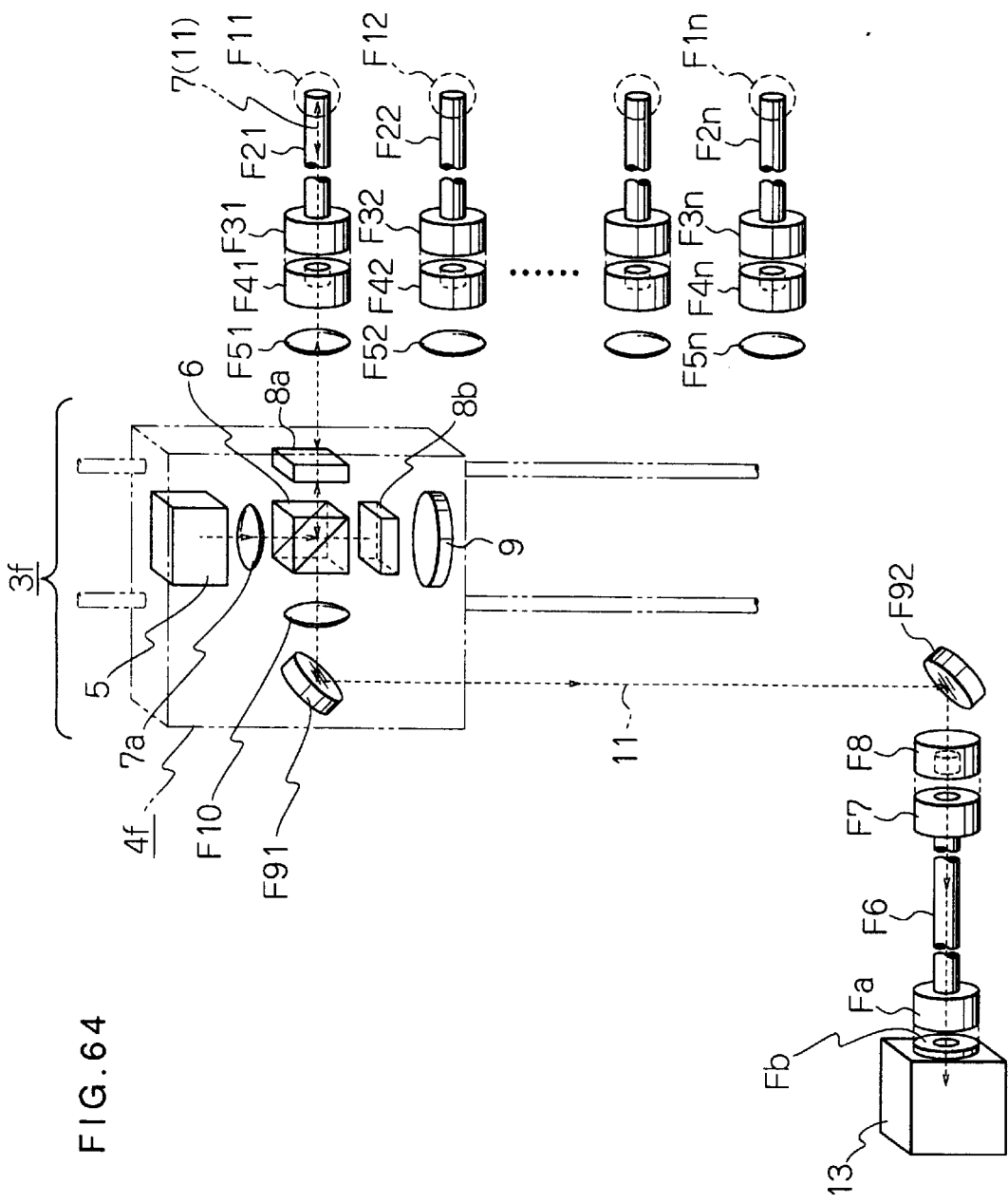
FIG. 64 is a perspective view showing the immunoassay apparatus according to Embodiment 5.6 in a state for an immunoassay with a first SPR sensor.

FIG. 64 shows the immunoassay apparatus of embodiment 5.6 in a state for an immunoassay with a first SPR sensor F11. When an immunoassay is to be carried out, the shutter 8a is opened and the shutter 8b is closed. Accordingly, the light 7 from the light source 5 reaches the SPR sensor F11, where it is reflected. The reflected light 11 passes through the light emitting means 4f and the converging lens F10 and is bent by the first deflection mirror F91 and further bent by the second deflection mirror F92 so as to pass through the receptacle F8, the connector F7, and the spectrometer optical fiber F6 to reach the spectrometer 13 for an analysis.

Thus, by providing the first deflection mirror F91 and the second deflection mirror F92, it is possible to easily switch the optical path only by shifting the light emitting means 4f.

[Embodiment 5.7]

Figure 65:
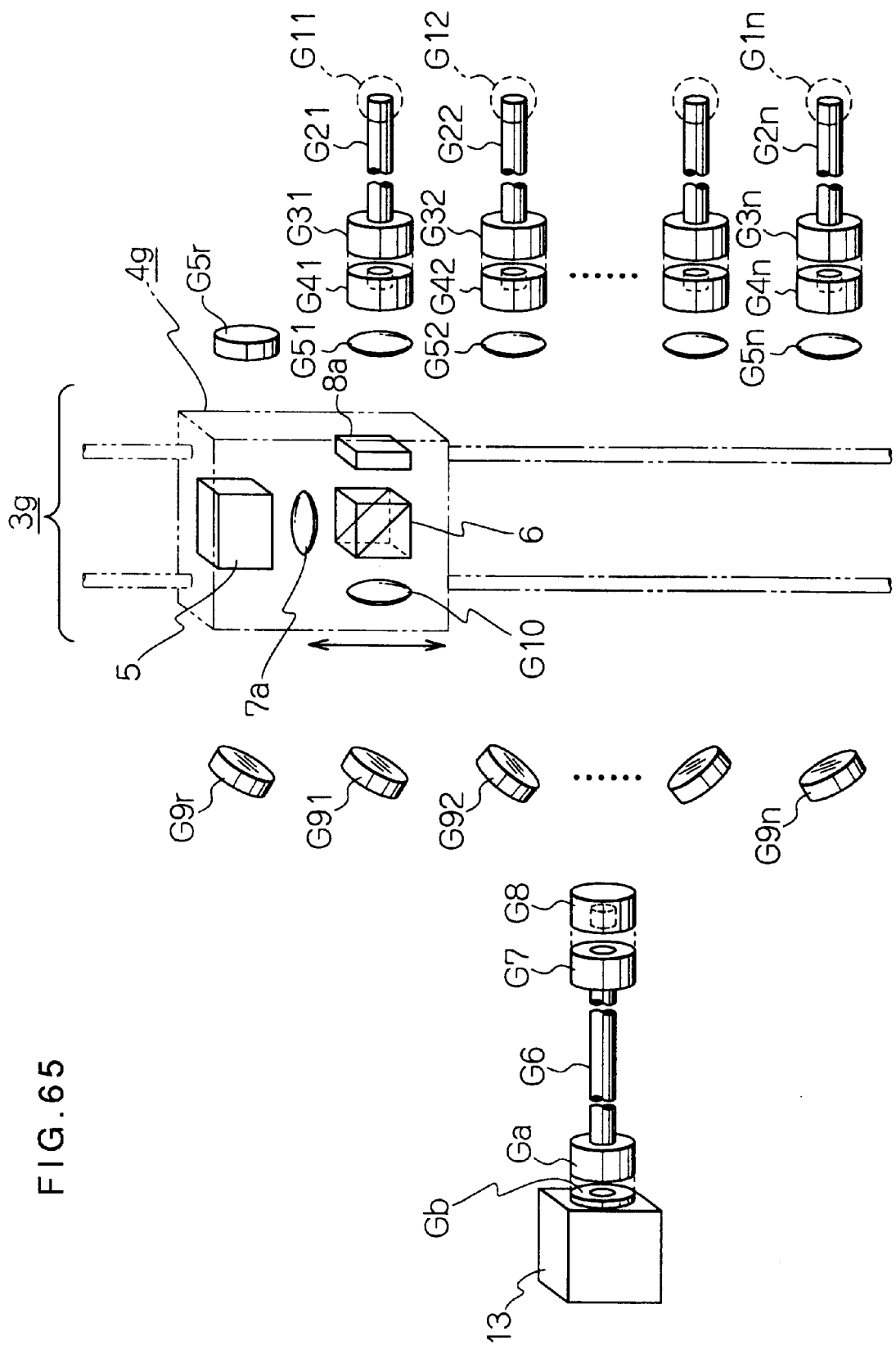
FIG. 65 is a perspective view showing a configuration of an immunoassay apparatus according to an Embodiment 5.7 of the present invention.

Next, an explanation will be given yet another embodiment 5.7 with reference to FIG. 65.

This embodiment has an almost identical configuration as embodiment 5.1 except for that a total reflection mirror G5r is provided at an upper end of the arrangement line of the converging lenses G51, G52, . . . , G5n provided corresponding to sensor optical fibers G21, G22, . . . , G2n. Moreover, this embodiment differs from embodiment 5.1 in that the light emitting means 4g does not comprises the reflection mirror 9 and the shutter 8b disclosed in the embodiment 5.1.

Figure 66:
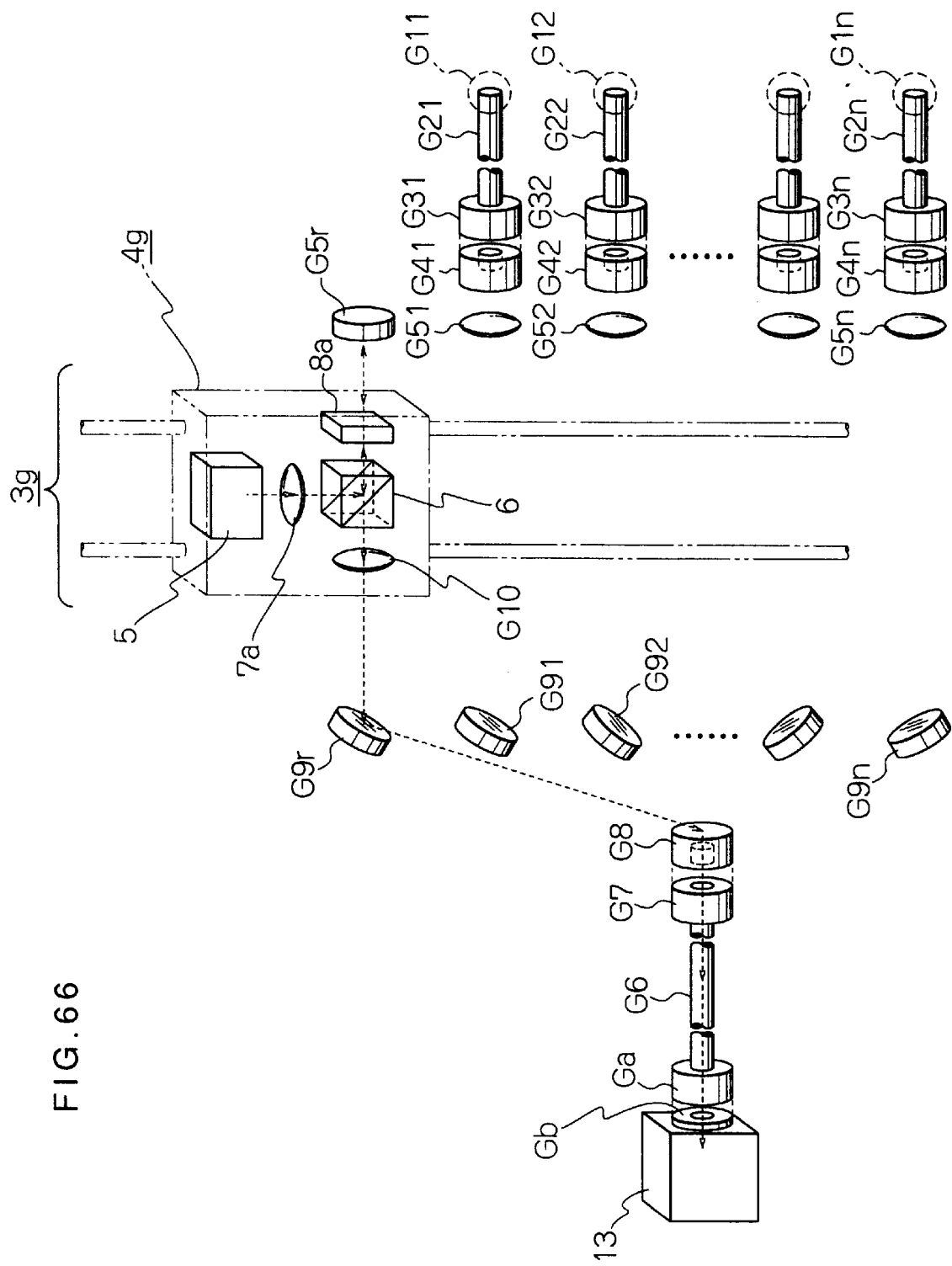
FIG. 66 is a perspective view showing the immunoassay apparatus according to Embodiment 5.7 in a state for reference measurement.

FIG. 66 shows the immunoassay apparatus of embodiment 5.7 in a state for a reference measurement, i.e. a wavelength analysis of a light emitted from a light source. The light 7 emitted from the light source 5 passes through the converging lens 7a and enters the beam splitter 6. A part of the light 7 is reflected by the beam splitter and further reflected by the aforementioned total reflection mirror G5r to return to the beam splitter 6. A part of the light 7 passes through the beam splitter 6 and introduced by the deflection mirror G9r to the receptacle G8. Further, the light 7 passes through the connector G7 and the spectrometer optical fiber G6 to reach the spectrometer 13 so as to be subjected to a wavelength distribution analysis.

Figure 67:
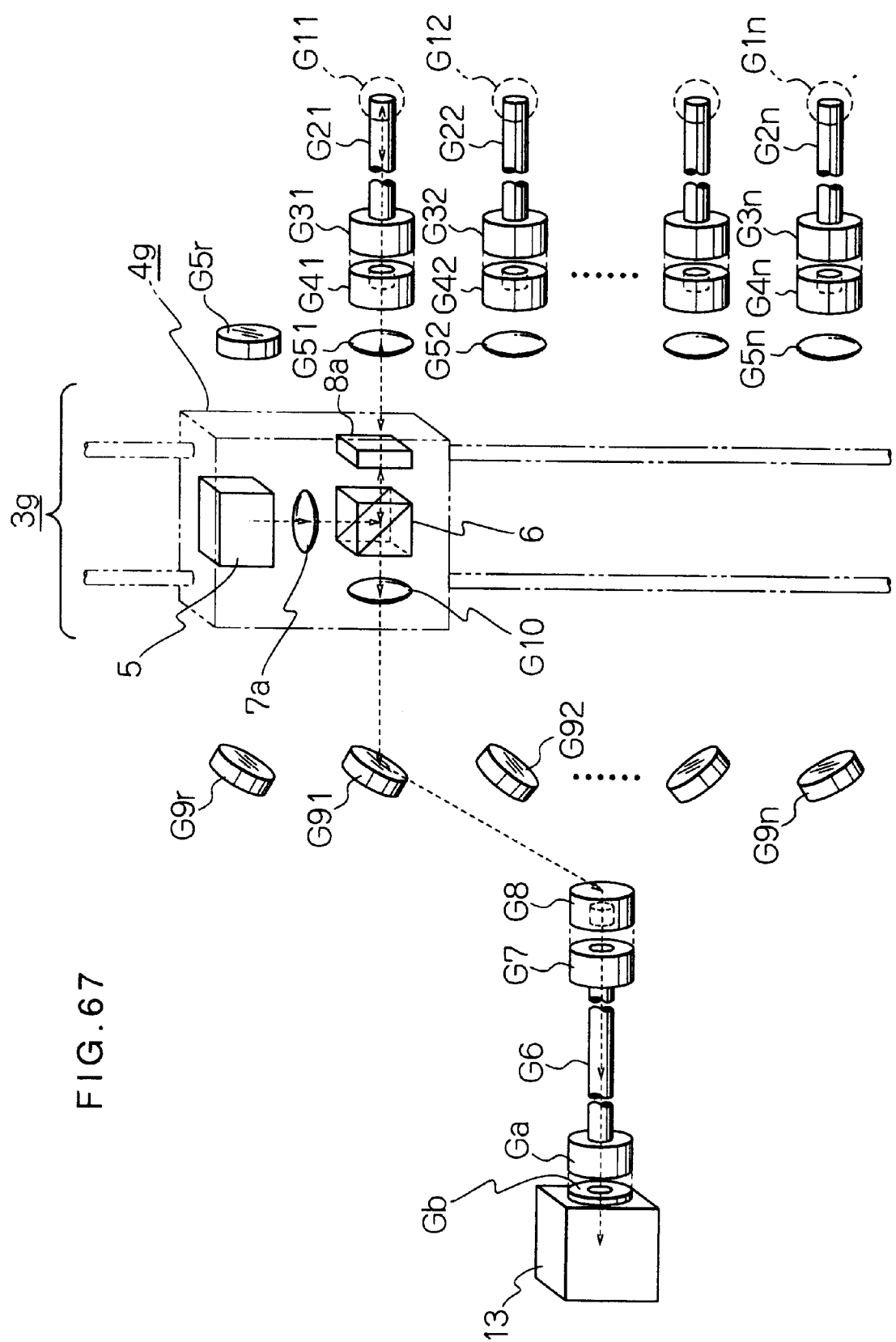
FIG. 67 is a perspective view showing the immunoassay apparatus according to Embodiment 5.7 in a state for an immunoassay with a first SPR sensor.

FIG. 67 shows the immunoassay apparatus of embodiment 5.7 in a state for an immunoassay with a first SPR sensor G11. When an immunoassay is to be carried out, the light emitting means 4g is slightly shifted (downward in the figure). The light emitting means 4g is positioned in such a manner that the light emitting means 4g has an optical axis matched with the optical axis of the converging lens G51 corresponding to the sensor optical fiber G11. Accordingly, the light 7 from the light source 5 reaches the SPR sensor G11 and is reflected there to pass through the light emitting means 4g and bent by the deflection mirror G91 to reach the receptacle G8. The reflected light 11 passes through the connector G7 and the spectrometer optical fiber G6 to reach the spectrometer 13 for an analysis.

Figure 68:
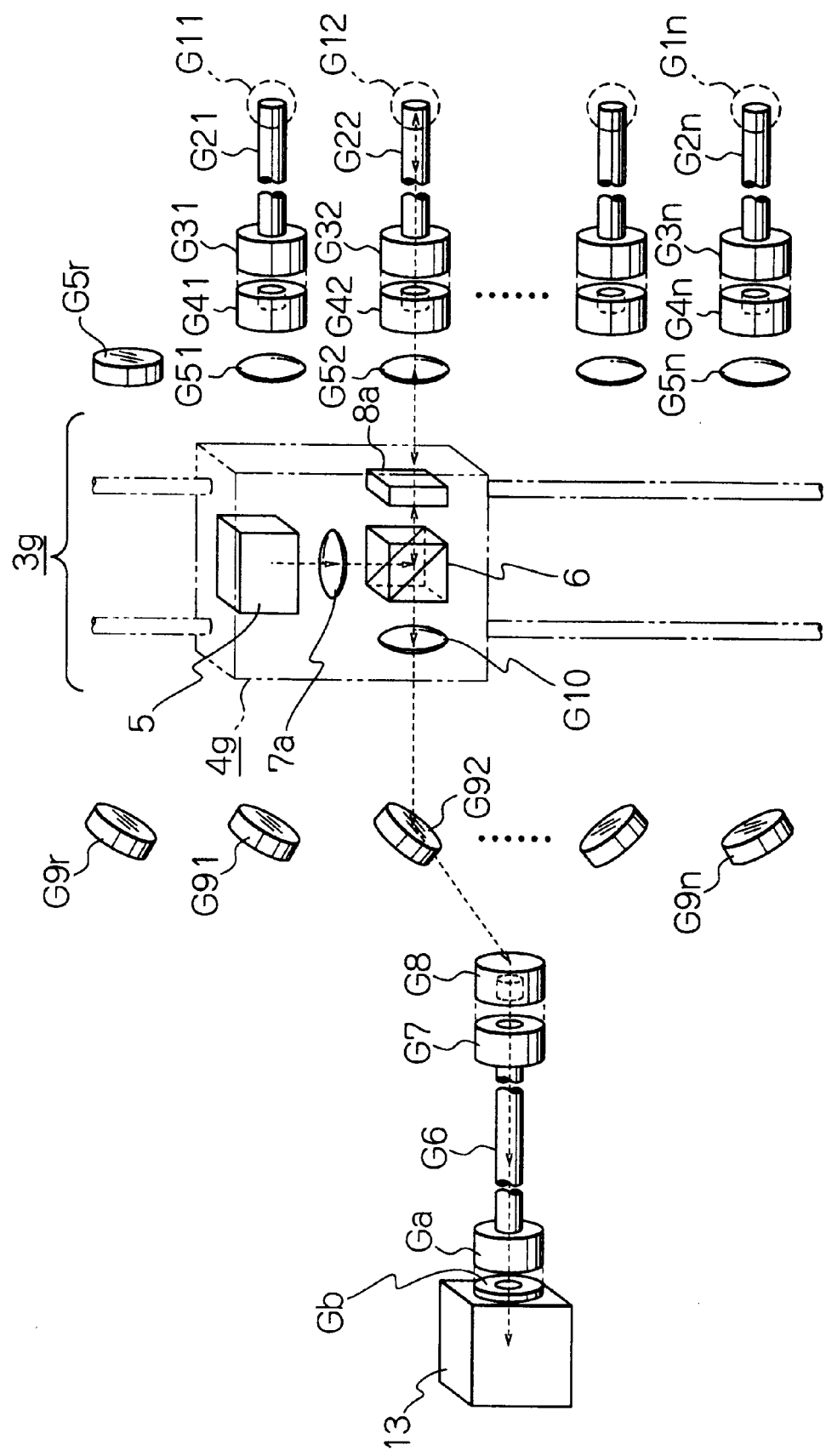
FIG. 68 is a perspective view showing the immunoassay apparatus according to Embodiment 5.7 in a state for an immunoassay with a second SPR sensor.

FIG. 68 shows the immunoassay apparatus of embodiment 5.7 in a state for an immunoassay with a second SPR sensor G12. In this case, the light emitting means 4g is further shifted (downward in the figure). The light emitting means 4g is positioned in such a manner that the light emitting means 4g has an optical axis matched with the optical axis of the converging lens G52 corresponding to the sensor optical fiber G12. Accordingly, the light 7 from the light source 5 reaches the SPR sensor G12 and is reflected so as to return a reflected light 11 passing through the light emitting means 4g and bent by the deflection mirror G92 to reach the receptacle G8. The reflected light 11 passes through the connector G7 and the spectrometer optical fiber G6 to reach the spectrometer 13 for an analysis.

Figure 69:
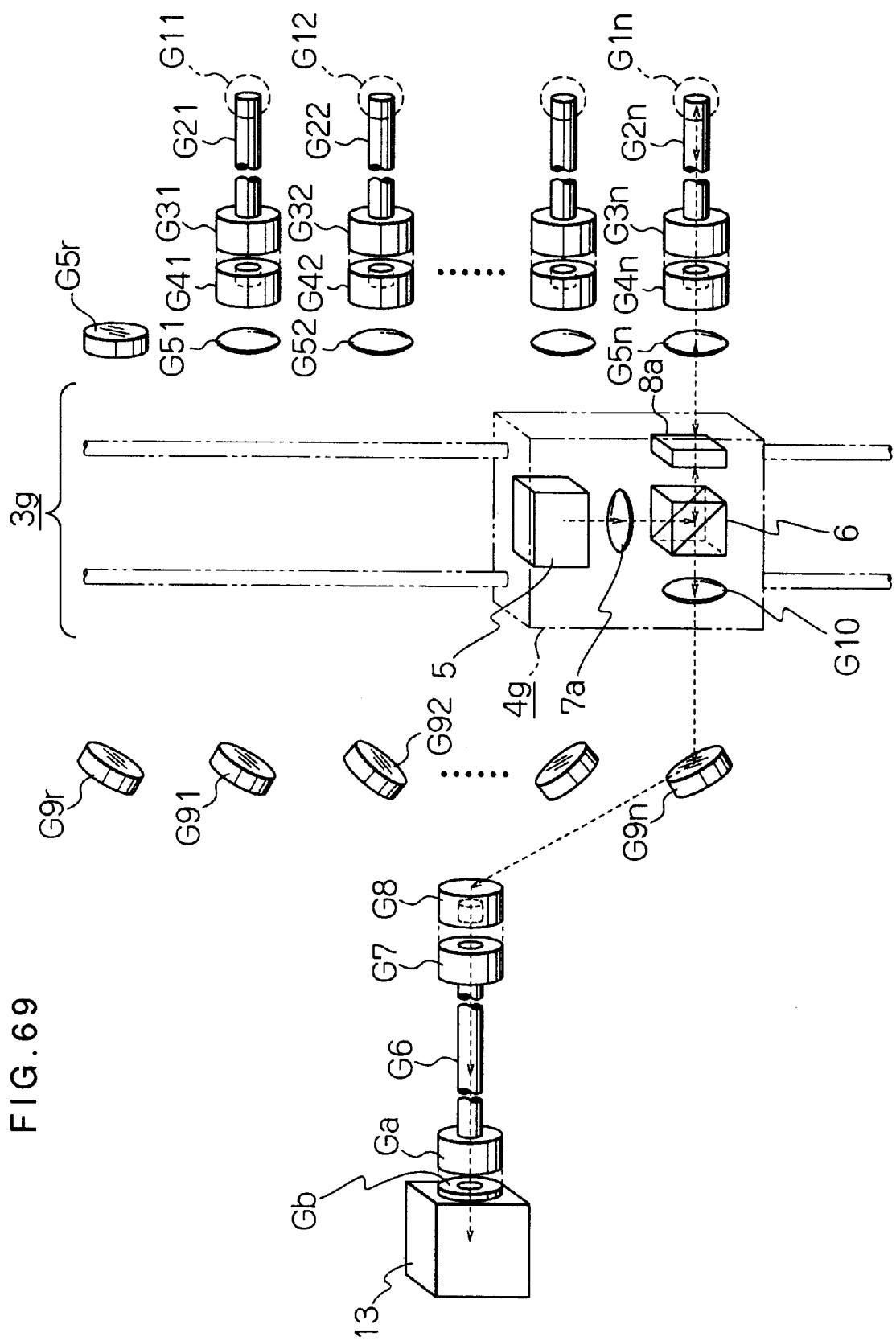
FIG. 69 is a perspective view showing the immunoassay apparatus according to Embodiment 5.7 in a state for an immunoassay with an n-th SPR sensor.

FIG. 69 shows the immunoassay apparatus of embodiment 5.7 in a state for an immunoassay with an n-th SPR sensor G1n. In this case, the light emitting means 4g is further shifted to a downmost position (lower end in the figure). The light emitting means 4g is positioned in such a manner that the light emitting means 4g has an optical axis matched with the optical axis of the converging lens G5n corresponding to the sensor optical fiber G2n. Accordingly, the light 7 from the light source 5 reaches the SPR sensor G1n and is reflected so as to return a reflected light 11 passing through the light emitting means 4g and bent by the deflection mirror G9n to reach the receptacle G8. The reflected light 11 passes through the connector G7 and the spectrometer optical fiber G6 to reach the spectrometer 13 for an analysis.

[Embodiment 5.8]

Figure 70:
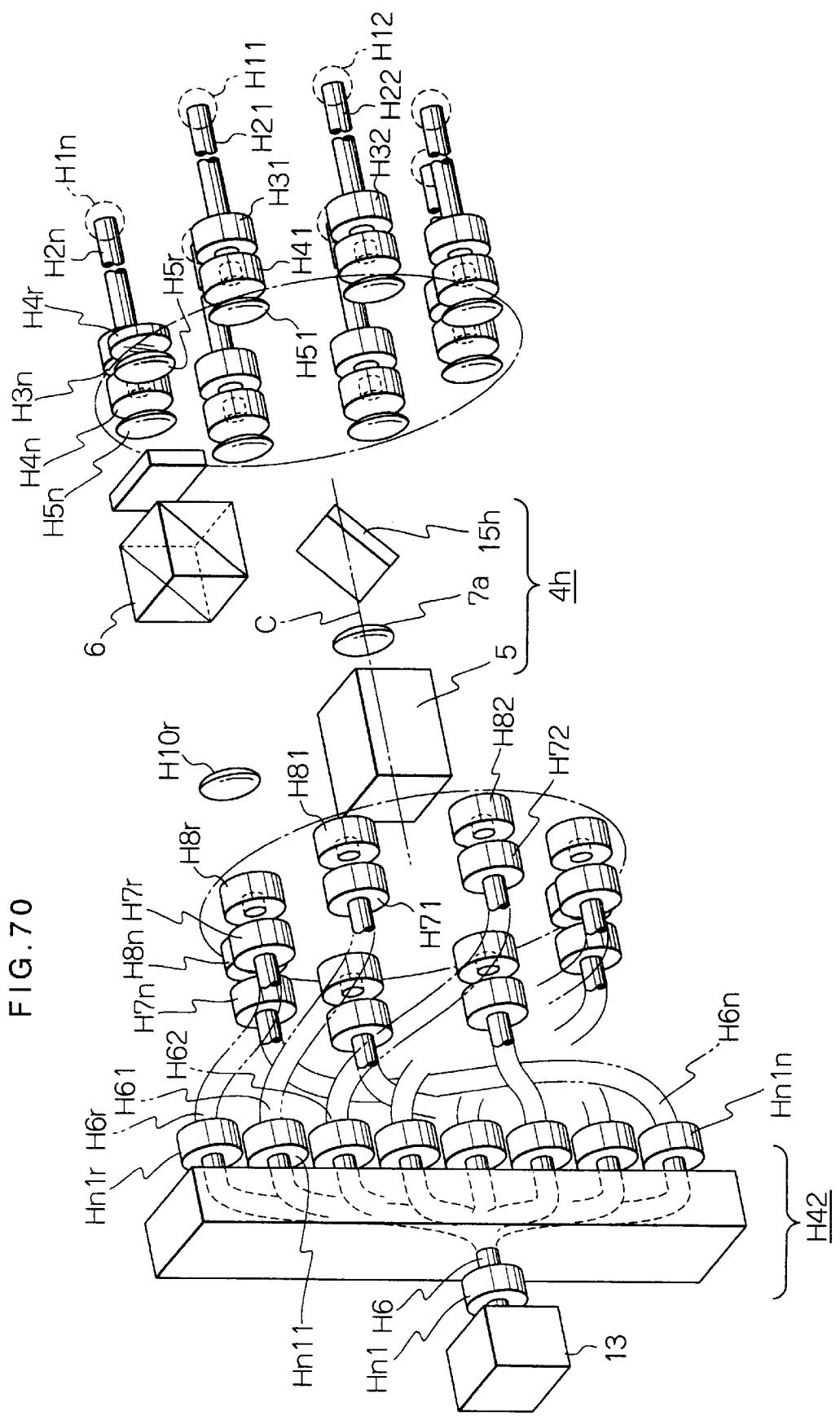
FIG. 70 is a perspective view showing a configuration of an immunoassay apparatus according to an Embodiment 5.8 of the present invention.

Next, explanation will be given on yet another embodiment 5.8 with reference to FIG. 70.

This embodiment differs from the aforementioned embodiments in that the apparatus comprises a plurality of sensor optical fibers H21, H22, ..., H2n having connectors H31, H32, ..., H3n and arranged in a circle in cross section. The sensor optical fibers H21, H22, ..., H2n may also be constructed so as to be removed from the connectors H31, H32, ..., H3n.

Moreover, the connectors H31, H32, ..., H3n are connected to predetermined receptacles H41, H42, ..., H4n. It should be noted that in this embodiment, a total reflection mirror H4r is arranged together with the receptacles H41, H42, ..., H4n arranged on a circumference. This total reflection mirror H4r serves to totally reflect the light coming from light emitting means which will be detailed later.

In the vicinity of the respective receptacles H41, h42, ..., H4n, there are provided converging lenses H51, H52, ..., H5n. Moreover, for the aforementioned total reflection mirror H4r, there is provided a converging lens H5r. These converging lenses H51, H52, ..., H5n, and H5r serve to converge the light emitted and effectively transmit the light.

Moreover, light emitting means 4h is provided between the sensor optical fibers H21, H22, ..., H2n and the spectrometer 13. This light emitting means 4h comprises a predetermined light source 5, a converging lens 7a for converging light from the light source 5, light source mirror 15h for reflecting the light which has transmitted the converging lens 7a, and a beam splitter 6 capable of branching the light. Here, the light source 5, the converging lens 7a, and the light source mirror 15h are arranged on a line, i.e., a rotation shaft C, matched with the center axis of the circle where the sensor optical fibers H21, H22, ..., H2n are arranged. A distance from the rotation shaft C to the beam splitter is identical to a radius of the aforementioned circle. The light emitting means 4h can be rotated around the optical axis of the converging lens 7a. Accordingly, the light emitting means 4h including the beam splitter 6 and a converging lens H10r can be positioned for each of the sensor optical fibers H21, H22, ..., H2n.

On the other hand, between the light emitting means 4h and the spectrometer 13, there are provided receptacles H81, H82, ..., H8n corresponding to the sensor optical fibers H21, H22, ..., H2n, for which are provided connectors H71, H72, ..., H7n. From the respective connectors H71, H72, ..., H7n extend intermediate optical fibers H61, H62, ..., H6n. These intermediate optical fibers have at the other end, connectors Hn11, Hn12, ..., Hn1n which are connected to an optical coupler H42. This optical coupler H42 can be connected to n optical fibers.

The optical coupler H42 has at the other end, a single optical fiber H6 and an optical fiber connector Hn1. The optical coupler H42 is connected via this connector to the spectrometer 13.

Figure 71:
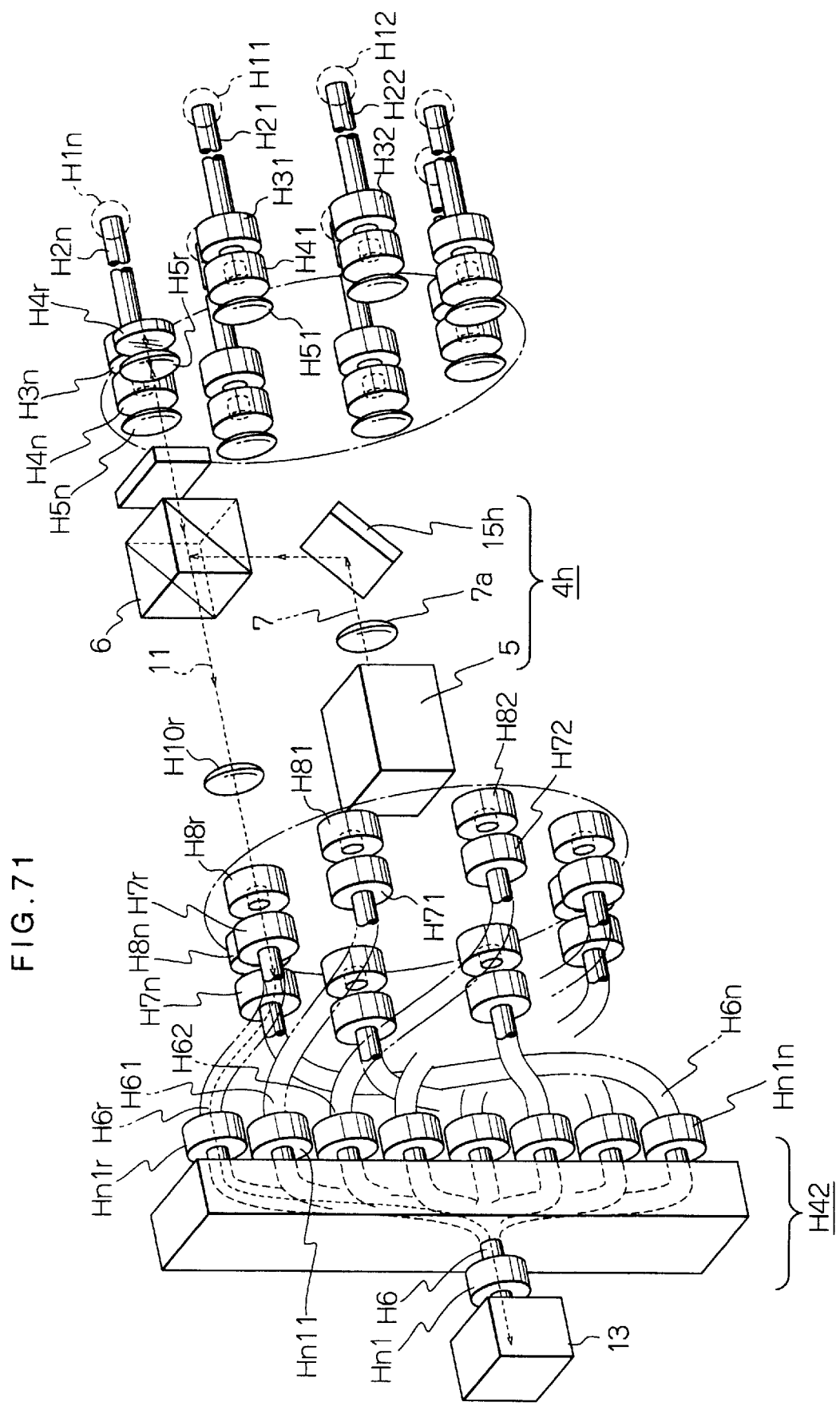
FIG. 71 is a perspective view showing the immunoassay apparatus according to Embodiment 5.8 in a state for reference measurement.

FIG. 71 shows the immunoassay apparatus of embodiment 5.8 in a state for a reference measurement, i.e., a wavelength distribution analysis of a light emitted from the light source 5. The light 7 from the light source 5 is reflected by the mirror 15h to be introduced to the beam splitter 6. A part of the light 7 is branched to pass the shutter and reach the total reflection mirror H4r. The light 7 reflected by the total reflection mirror H4r returns to the beam splitter 6 and a part of the light passes through the beam splitter 6 and the converging lens H10r to reach the receptacle H8r.

The light further passes through the connector H7r, the intermediate optical fiber H6r and the optical coupler H42 to enter the spectrometer 13 for a wavelength distribution analysis.

Figure 72:
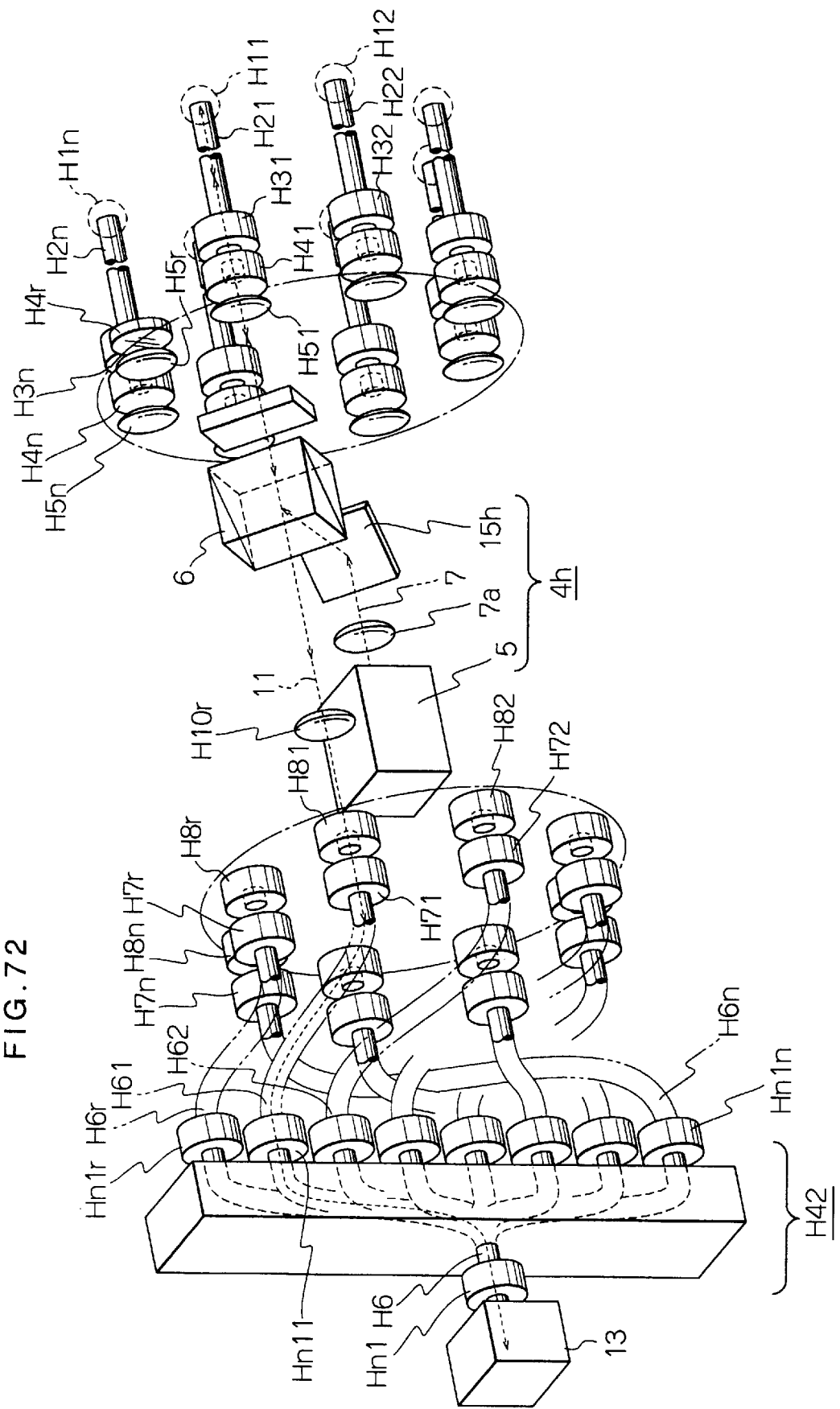
FIG. 72 is a perspective view showing the immunoassay apparatus according to Embodiment 5.8 in a state for an immunoassay with a first SPR sensor.

FIG. 72 shows the immunoassay apparatus of this embodiment in a state for an immunoassay with a first SPR sensor H11. When an immunoassay is to be carried out, the light emitting means 4h is rotated around the aforementioned rotation shaft C so that the beam splitter 6 is moved to a position corresponding to the first sensor optical fiber H21. The light 7 from the light source 5 reaches the SPR sensor H11 and is reflected to pass the beam splitter 6 to reach the receptacle H81. The reflected light 11 further passes through the connector H71, the intermediate optical fiber H61 and the optical coupler H42 to enter the spectrometer for an analysis.

Figure 73:
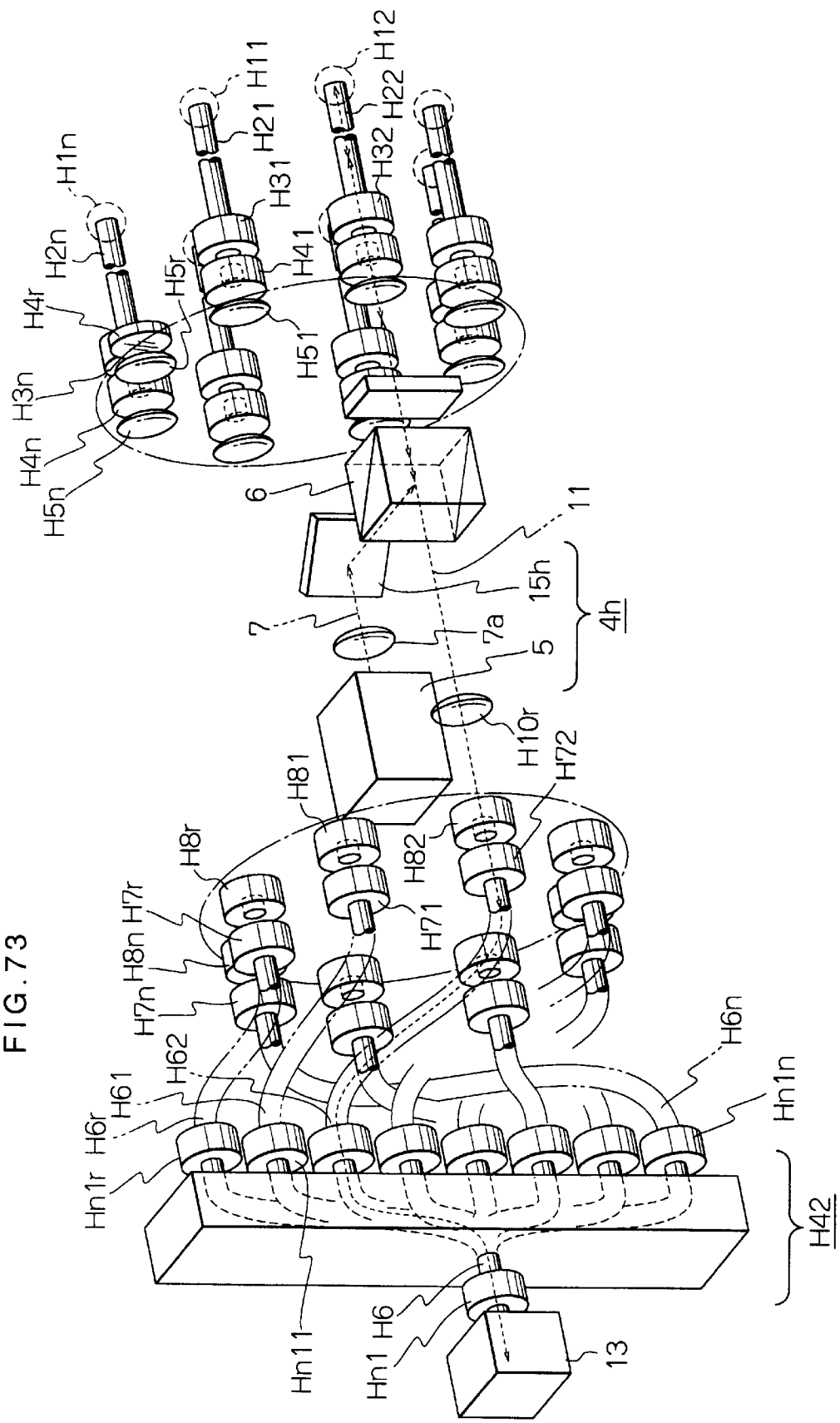
FIG. 73 is a perspective view showing the immunoassay apparatus according to Embodiment 5.8 in a state for an immunoassay with a second SPR sensor.

FIG. 73 shows the immunoassay apparatus of this embodiment in a state for an immunoassay with a second SPR sensor H12. In this case, the light emitting means 4h is further rotated around the aforementioned rotation shaft C so that the beam splitter 6 is moved to a position corresponding to the second sensor optical fiber H22. In the same way as in the immunoassay with the first SPR sensor H11, the light 7 from the light source 5 reaches the SPR sensor H12 and is reflected to reach the spectrometer for an analysis.

Figure 74:
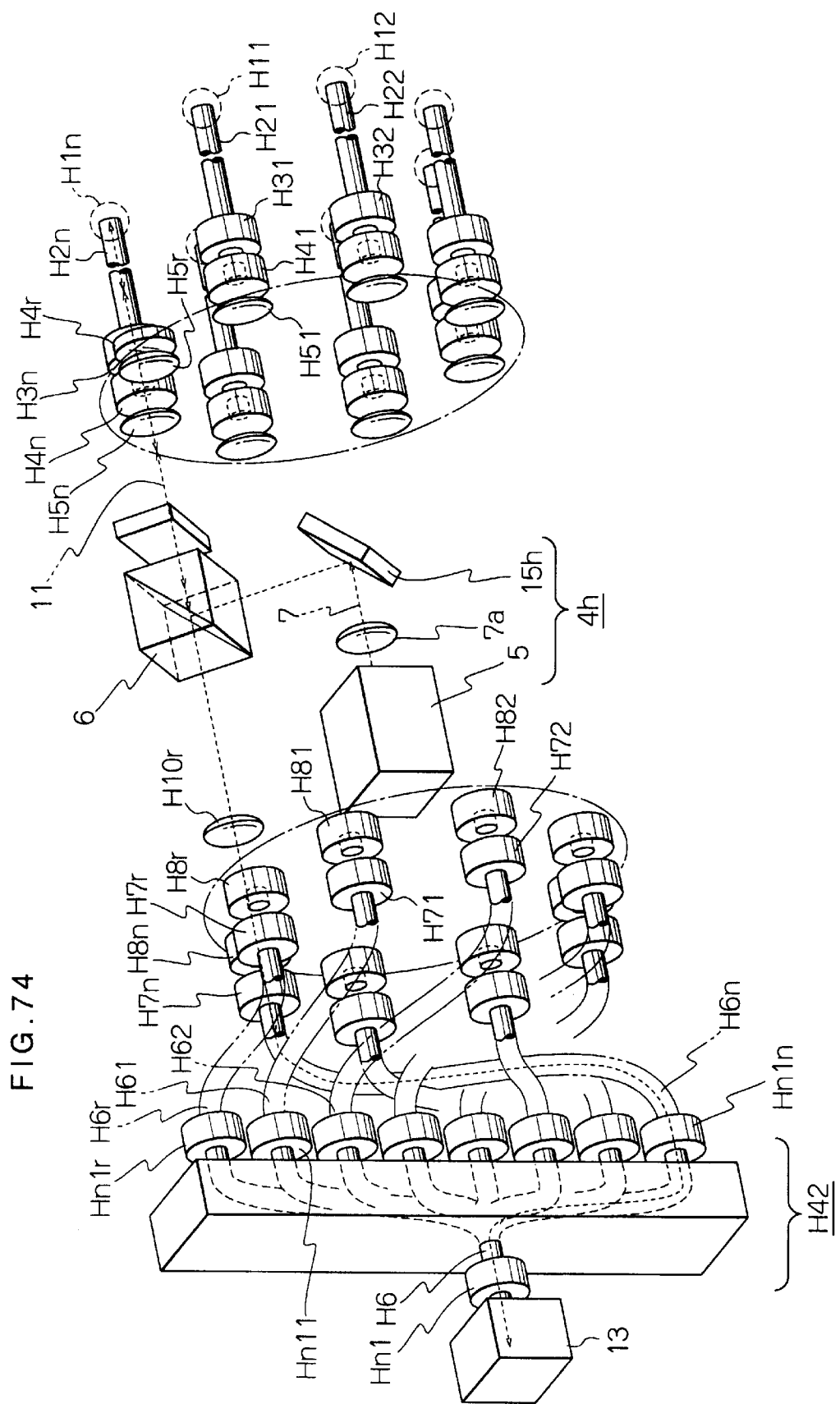
FIG. 74 is a perspective view showing the immunoassay apparatus according to Embodiment 5.8 in a state for an immunoassay with an n-th SPR sensor.

FIG. 74 shows the immunoassay apparatus of this embodiment in a state for an immunoassay with an n-th SPR sensor H1n.

[Embodiment 5.9]

Figure 75:
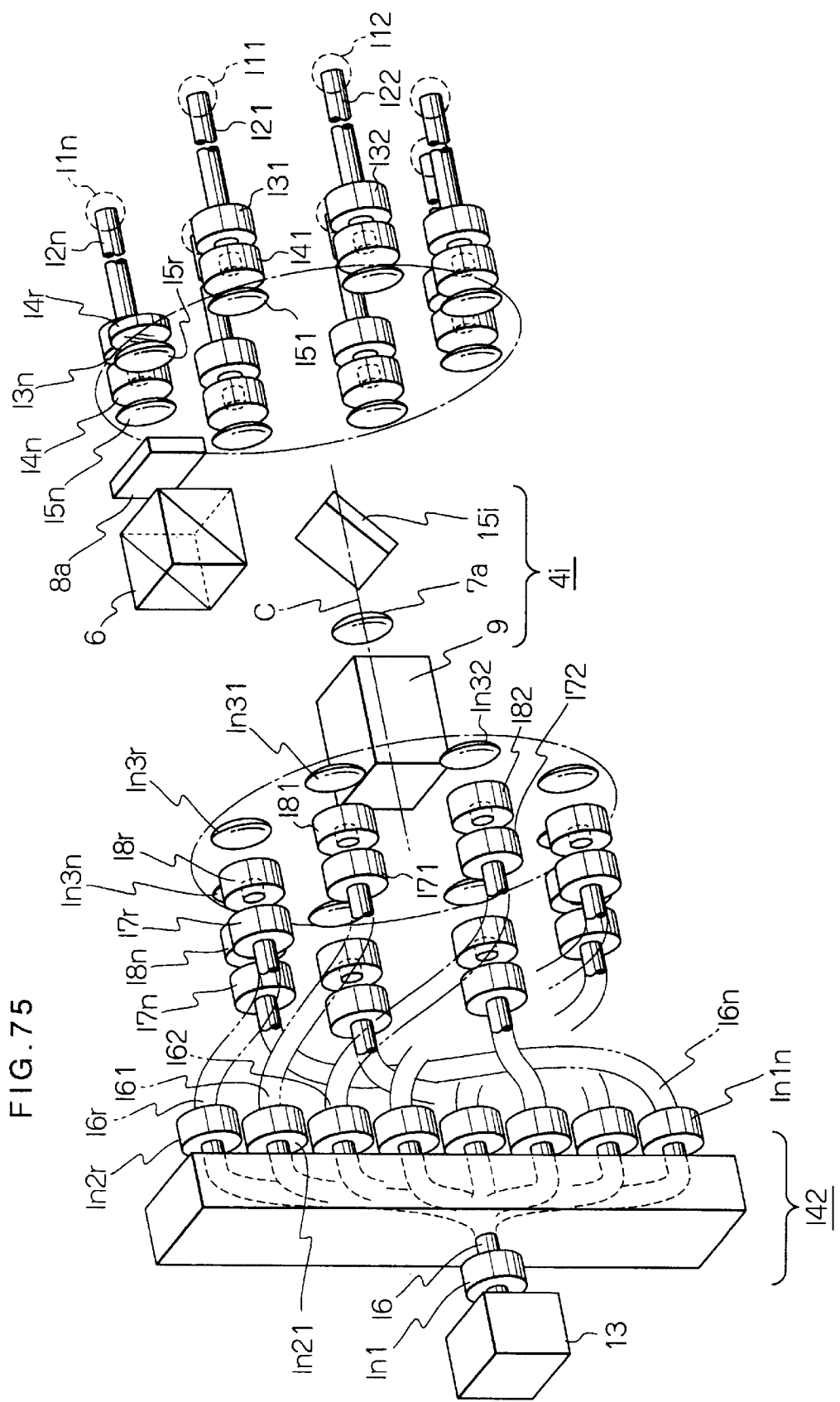
FIG. 75 is a perspective view showing a configuration of an immunoassay apparatus according to an Embodiment 5.9 of the present invention.

FIG. 75 shows an immunoassay apparatus according to an embodiment 5.9. This immunoassay apparatus has an almost identical configuration as embodiment 5.8 except for that converging lenses In31, In32, ..., In3n, In3r are provided for receptacles I81, I82, ..., I8n, I8r, respectively. When the light emitting means 4i is rotated, the converging lenses In31, In 32, ..., In3n, In3r do not change their positions with respect to the receptacles I81, I82, ..., I8n, I8r. Thus, the converging lenses In31, In32, ..., In3n, In3r are at fixed positions with respect to the receptacles I81, I82, ..., I8n, I8r, which enables to increase the optical system setting accuracy.

[Embodiment 5.10]

Figure 76:
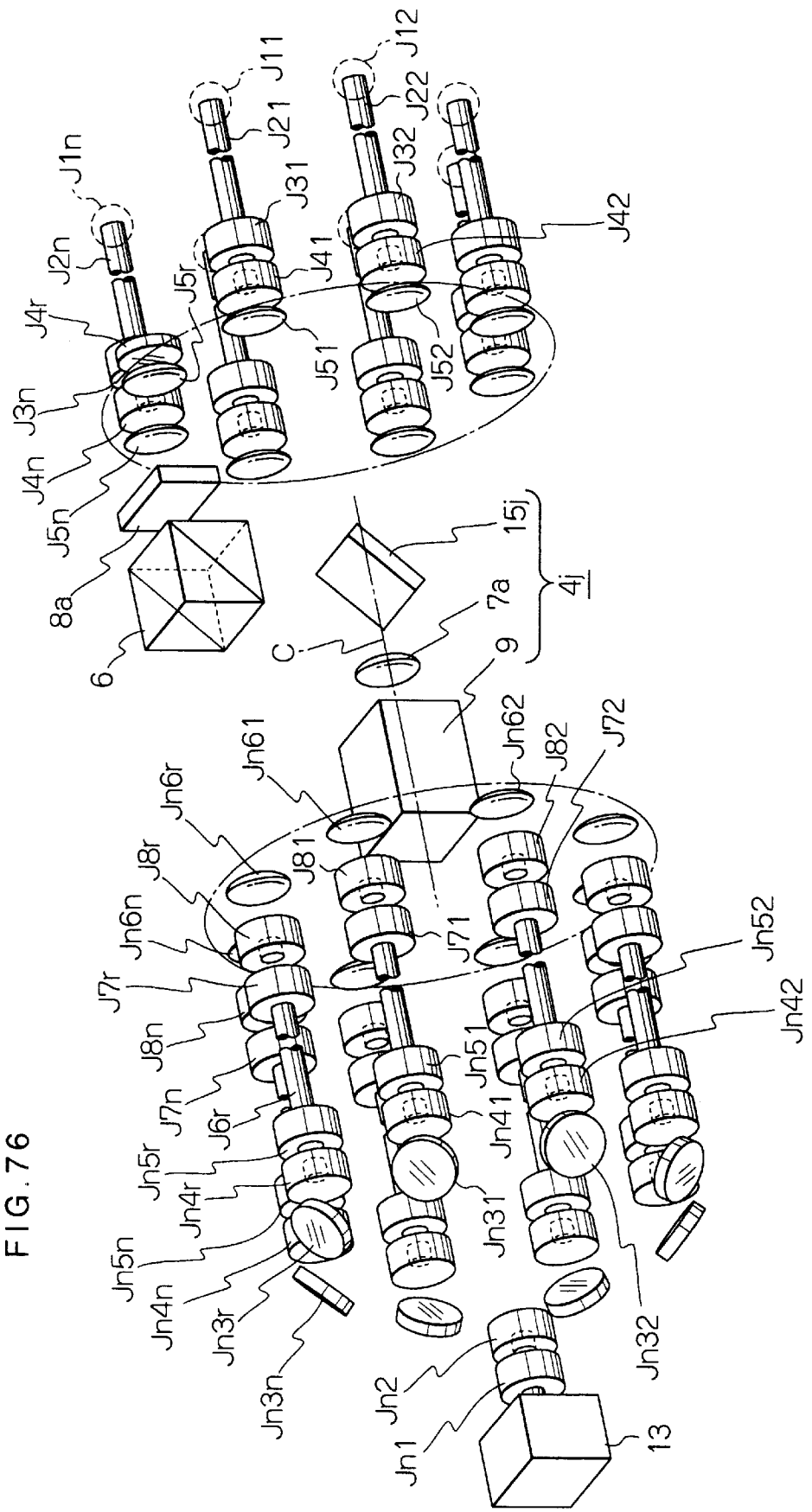
FIG. 76 is a perspective view showing a configuration of an immunoassay apparatus according to an Embodiment 5.10 of the present invention.

FIG. 76 shows an immunoassay apparatus according to an embodiment 5.10. This embodiment has an almost identical configuration as the embodiment 5.9 except for that no optical coupler is used and instead, deflection mirrors Jn31, Jn32, ..., Jn3n, Jn3r are used corresponding to sensor optical fibers J21, J22, ..., J2n, Jnr. That is, each of the sensor optical fibers J21, J22, ..., J2n, J2r has a corresponding intermediate fiber J61, J62, ..., J6n, J6r. A light emitted from the end of the intermediate fiber J61, J62, ..., J6n, J6r is introduced to the receptacle Jn2 by a corresponding deflection mirror Jn31, Jn32, ..., Jn3n, Jn3r.

[Embodiment 5.11]

Figure 77:
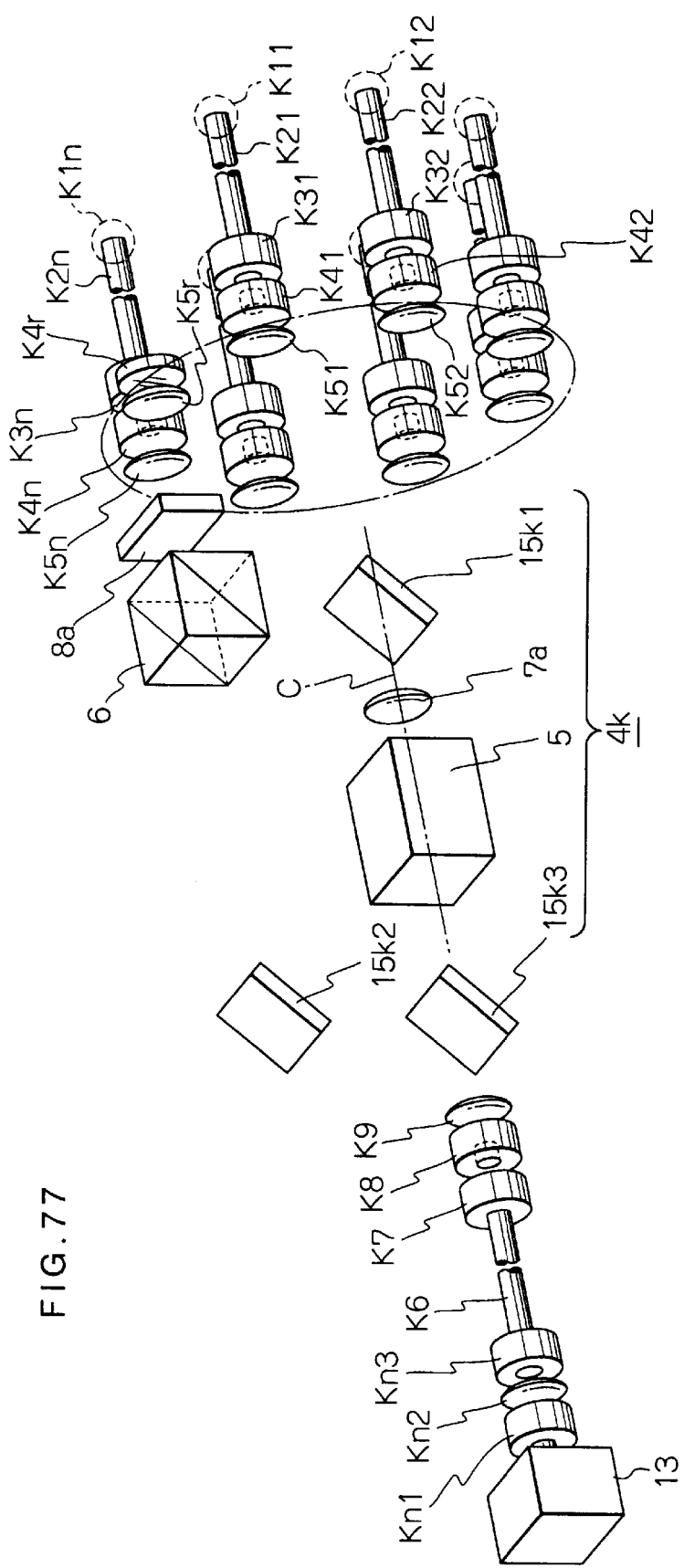
FIG. 77 is a perspective view showing a configuration of an immunoassay apparatus according to an Embodiment 5.11 of the present invention.

FIG. 77 shows an immunoassay apparatus according to an embodiment 5.11 which is a modification of embodiment 5.8. That is, in this embodiment also, the sensor optical fibers K21, K22, ..., K2n are arranged with their cross sections in a circle and the light emitting means 4k is constituted so as to be rotatable. However, this embodiment differs from the embodiment 5.8 in that the optical system for the spectrometer is a single system.

That is, the light emitting means 4k comprises the light source 5, the converging lens 7a, the first deflection mirror 15k1, and the beam splitter 6, and further comprises a second deflection mirror 15k2 and a third deflection mirror 15k3. The first deflection mirror 15k1 is provided at a position corresponding to the beam splitter 6. The second deflection mirror 15k2 is positioned on a line connecting the beam splitter to one of the sensor optical fibers which is set for an immunoassay, whereas the first deflection mirror 15k1 and the third deflection mirror 15k3 are positioned on the rotary shaft C of the light emitting means 4k at the side of the spectrometer 13.

Figure 78:
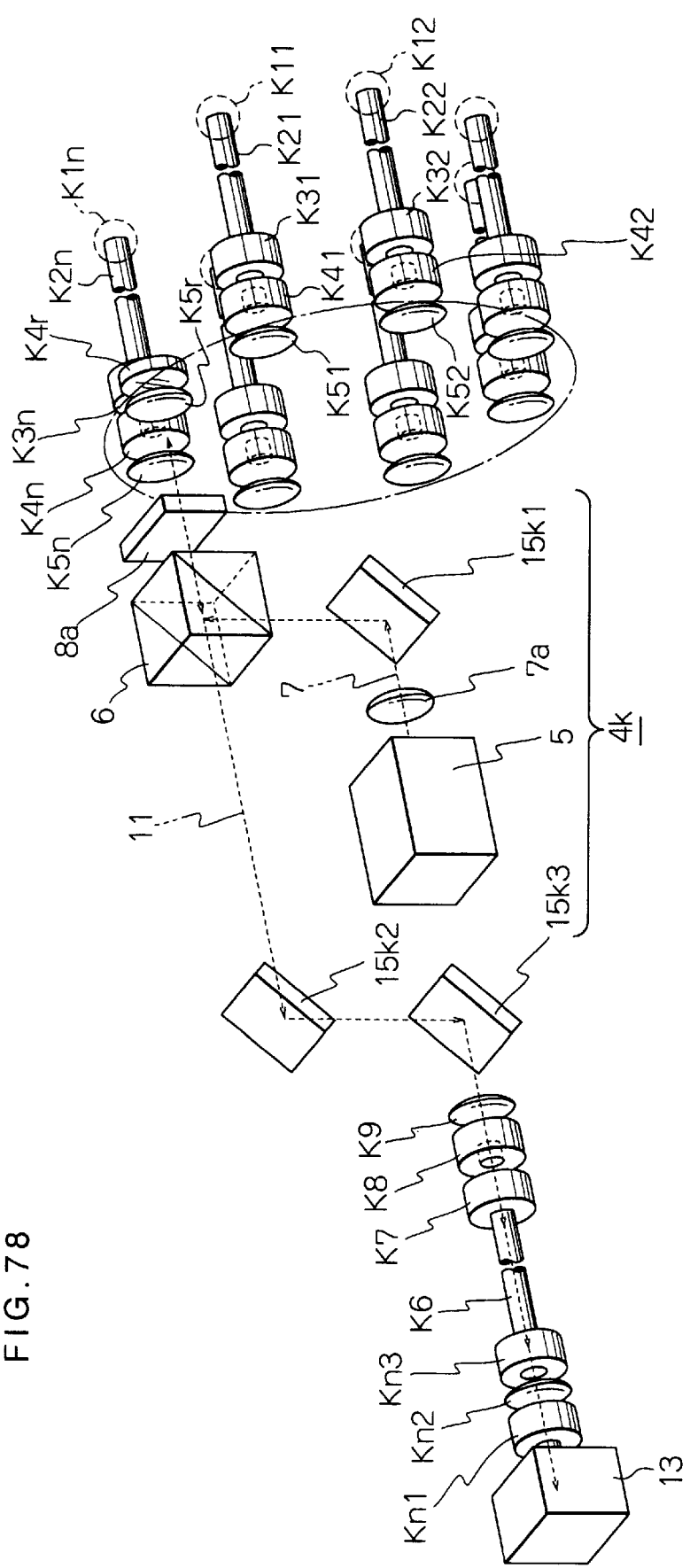
FIG. 78 is a perspective view showing the immunoassay apparatus according to Embodiment 5.11 in a state for reference measurement.

FIG. 78 shows the immunoassay apparatus of this embodiment in a state for a reference measurement, i.e., a wavelength distribution analysis of the light emitted from the light source. The light 7 emitted from the light source 5 is reflected by the first deflection mirror 15k1 so as to be introduced to the beam splitter 6. In the beam splitter 6, a part of the light 7 is branched toward the shutter 8a. The light which has passed through the shutter 8a is reflected by the total reflection mirror K4r to return to the beam splitter 6. A part of the light 7 passes through the beam splitter 6 and is reflected by the second deflection mirror 15k2 toward the rotary shaft C of the light emitting means 4k. The light 7 is further reflected by the third deflection mirror 15k3 toward the spectrometer 3.

The light 7 reflected by the third deflection mirror 15k3 passes through the converging lens K9 to reach the receptacle K8. The light introduced to the receptacle K8 further passes through the connector K7, the spectrometer optical fiber K6, the connector Kn3, the converging lens Kn2, and the connector Kn1 to reach the spectrometer 13. Thus, the light 7 emitted from the light source 5 is subjected to a wavelength distribution analysis.

Figure 79:
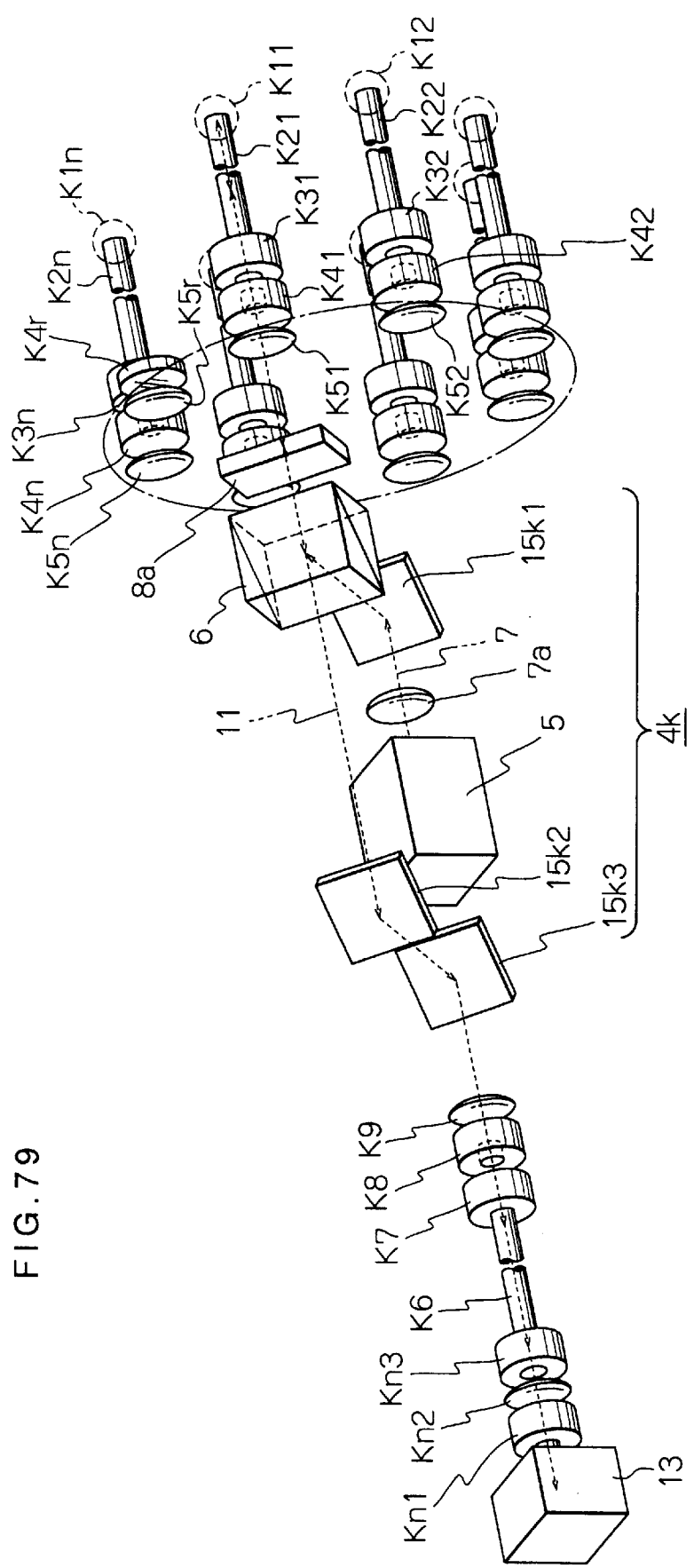
FIG. 79 is a perspective view showing the immunoassay apparatus according to Embodiment 5.11 in a state for an immunoassay with a first SPR sensor.

FIG. 79 shows the immunoassay apparatus of this embodiment in a sate for an immunoassay with a first SPR sensor K11. When an immunoassay is to be carried out, the light emitting means 4k is rotated around the aforementioned rotary shaft C so that the beam splitter 6 is moved to a position corresponding to the first sensor optical fiber K21. Thus, the light 7 emitted from the light source 5 reaches the SPR sensor K11 and reflected to return as the reflected light 11. The reflected light 11 passes through the beam splitter 6 and reflected by the second deflection mirror 15k2 and the third deflection mirror 15k3 so as to be introduced to the receptacle K8. The reflected light 11 further passes through the connector K7 and the spectrometer optical fiber K6 to reach the spectrometer 13 for an analysis.

Figure 80:
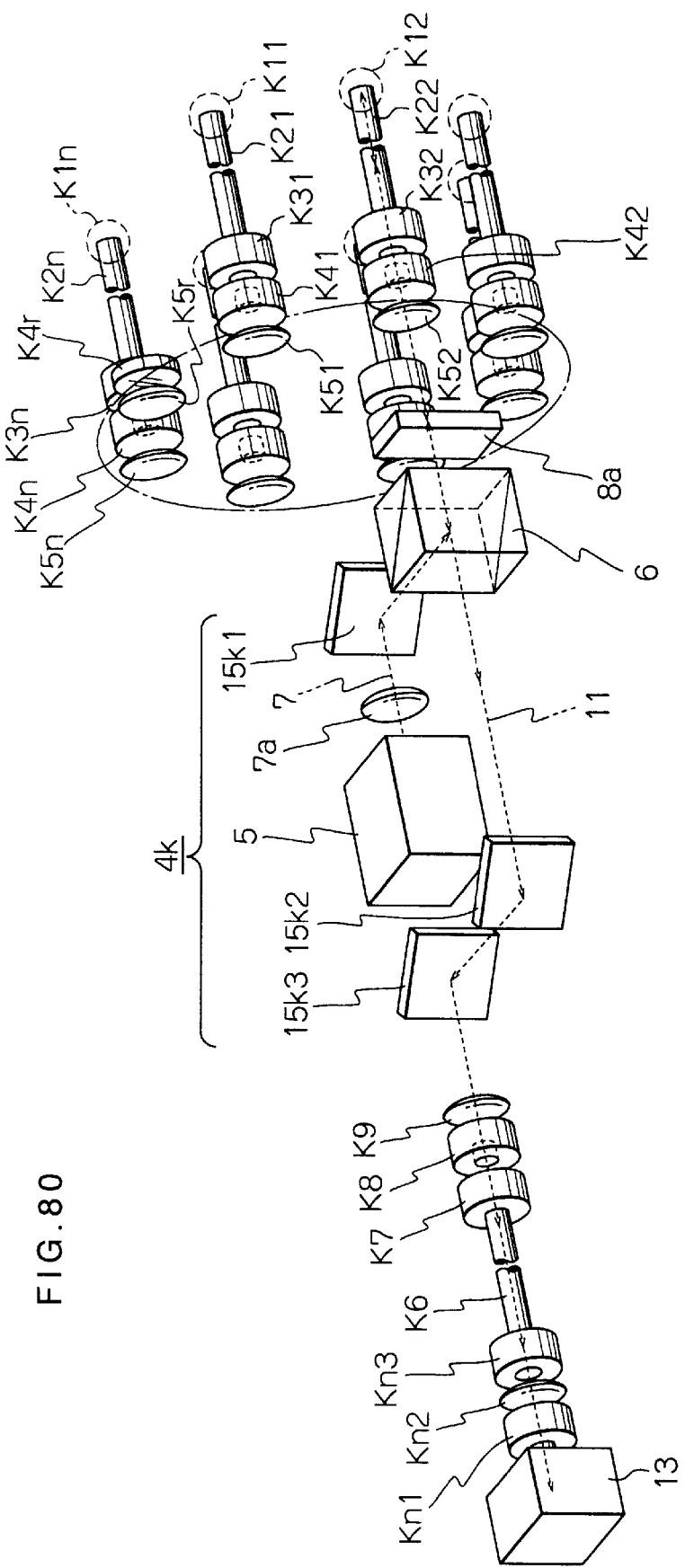
FIG. 80 is a perspective view showing the immunoassay apparatus according to Embodiment 5.11 in a state for an immunoassay with a second SPR sensor.

FIG. 80 shows the immunoassay apparatus of this embodiment in a state for an immunoassay with a second SPR sensor K12. In this case, the light emitting means 4k is further rotated around the aforementioned rotary shaft C so that the beam splitter 6 is moved to a position corresponding to the second sensor optical fiber K22. The following operation is identical as in the immunoassay with the first SPR sensor 3K11.

Figure 81:
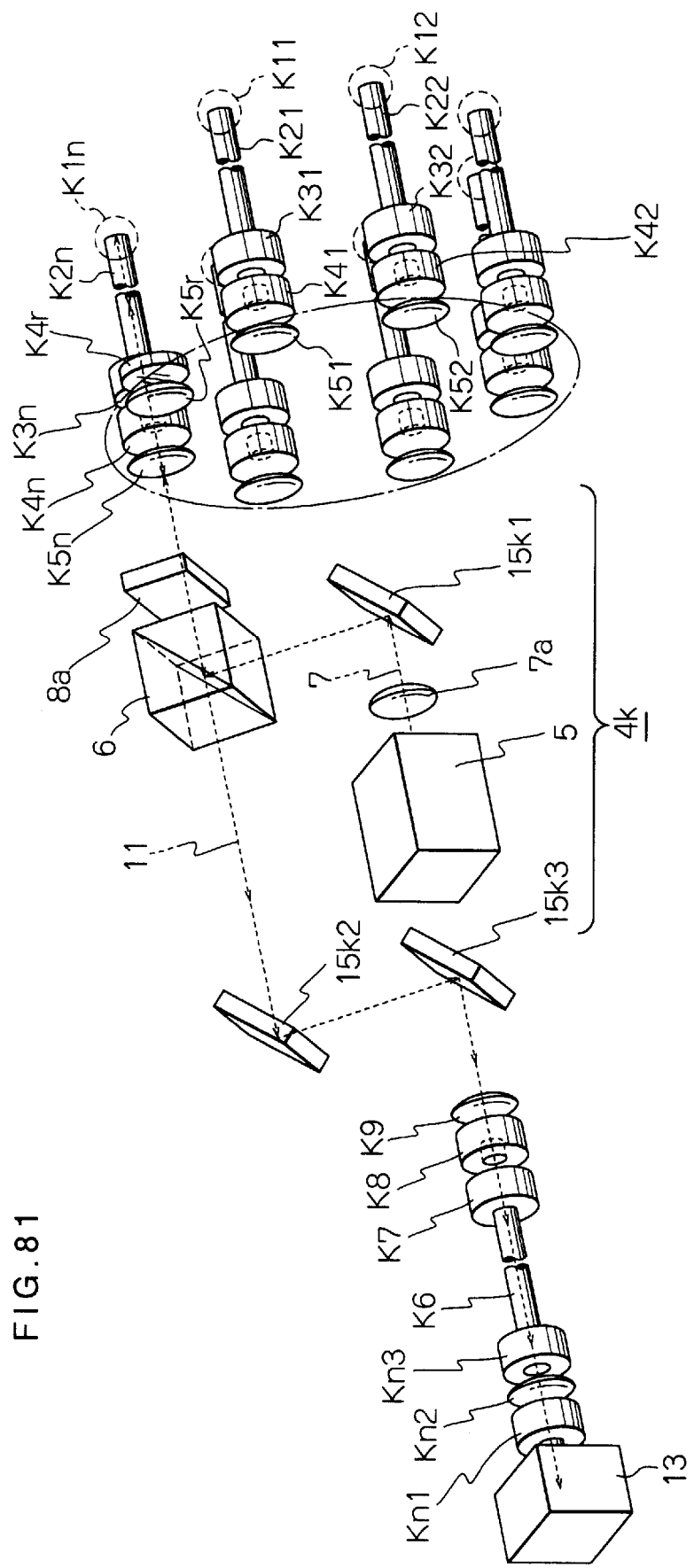
FIG. 81 is a perspective view showing the immunoassay apparatus according to Embodiment 5.11 in a state for an immunoassay with an n-th SPR sensor.

FIG. 81 shows the immunoassay apparatus of this embodiment in a state for an immunoassay with an n-th SPR sensor K1n.

[Embodiment 5.12]

Figure 82:
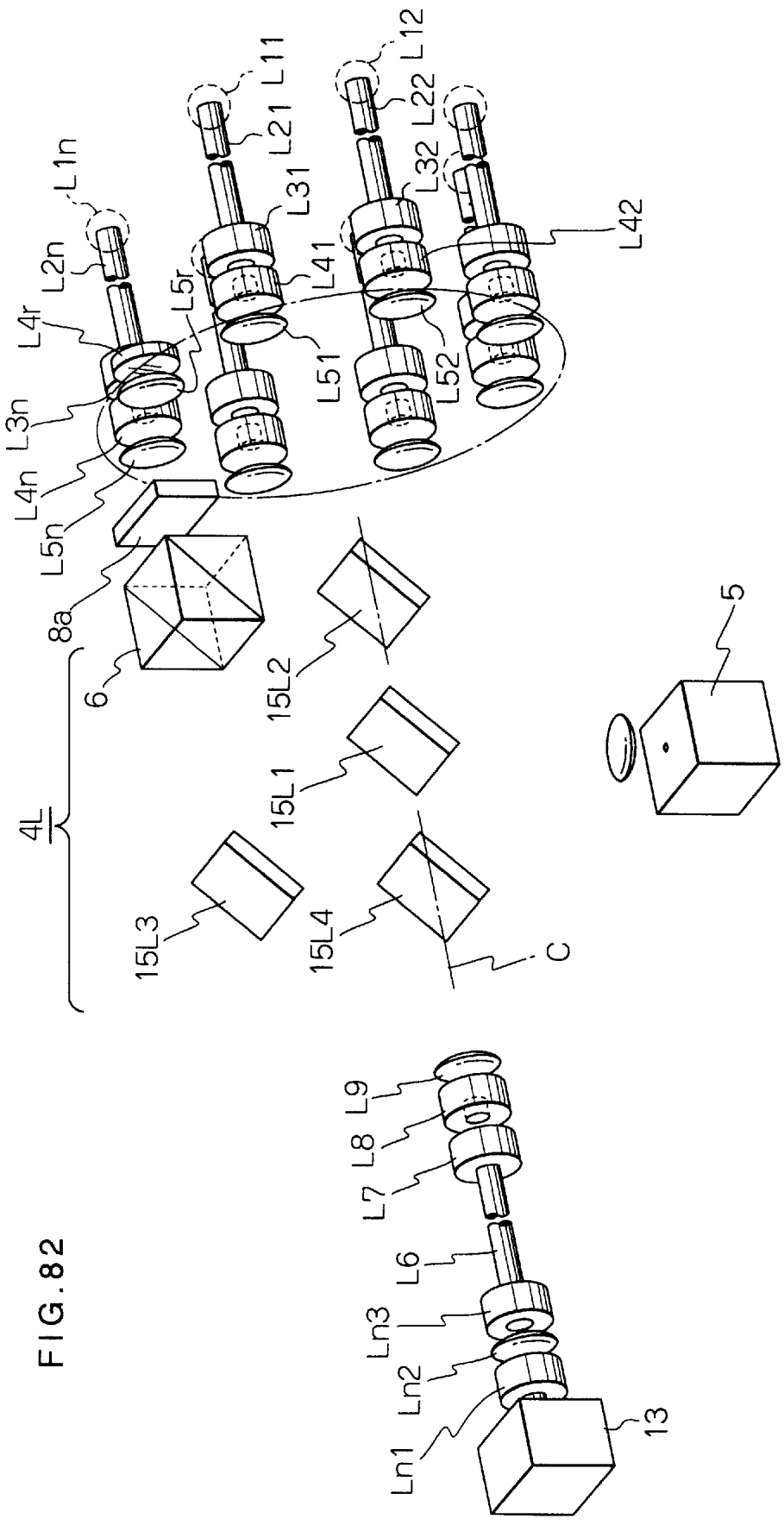
FIG. 82 is a perspective view showing a configuration of an immunoassay apparatus according to an Embodiment 5.12 of the present invention.

FIG. 82 shows an immunoassay apparatus according to an embodiment 5.12. This embodiment has an almost identical configuration as the embodiment 5.11 except for light emitting means 4L. That is, in this embodiment, a light source is located outside the light emitting means 4L. The light emitting means 4L itself comprises four reflection mirrors 15L1, 15L2, 15L3, 15L4 and the beam splitter 6.

Here, three of the reflection mirrors 15L1, 15L2, and 15L4 are arranged in a line along the rotary shaft C of the light emitting means 31d. The remaining reflection mirror 15L3 is arranged on an optical axis of one of the sensor optical fibers L21, L22, . . . , L2n set for a measurement.

Figure 83:
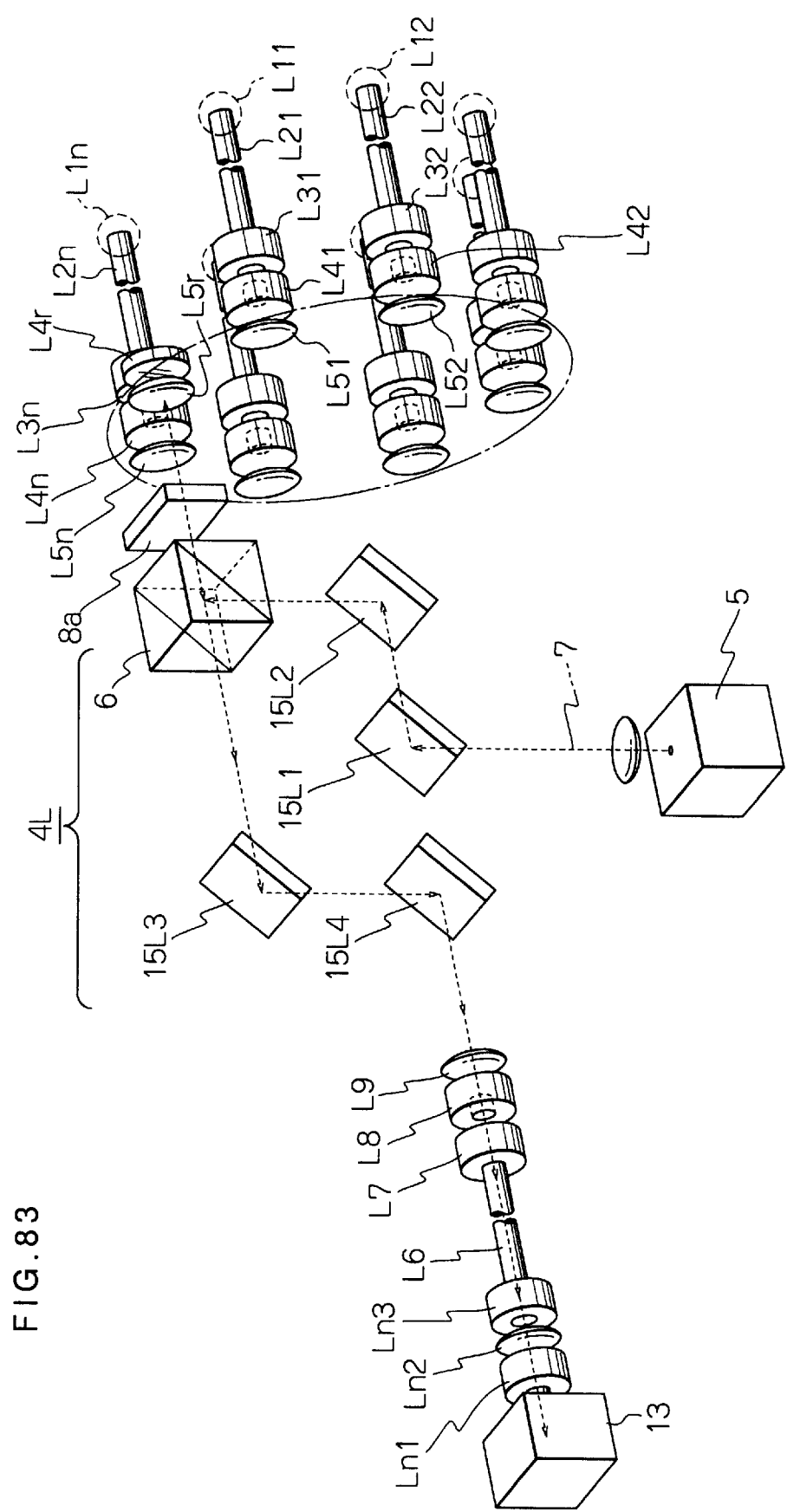
FIG. 83 is a perspective view showing the immunoassay apparatus according to Embodiment 5.12 in a state for reference measurement.

FIG. 83 shows the immunoassay apparatus of this embodiment in a state for a reference measurement, i.e., a wavelength distribution analysis of the light emitted from the light source 5. The light 7 emitted from the light source 5 passes through the converging lens and reaches the first deflection mirror 15L1, where the light is reflected toward the second deflection mirror 15L2. The light 7 is further reflected by the second deflection mirror 15L2 toward the beam splitter 6. A part of the light 7 passes through the shutter 8a and is reflected by the total reflection mirror L4r to return to the beam splitter 6. A part of the light 7 passes through the beam splitter 6 and is reflected by the third deflection mirror 15L3 toward the rotary shaft C of the light emitting means 4L. The light 7 is further reflected by the fourth deflection mirror 15L4 toward the spectrometer 13.

The light 7 reflected by the fourth deflection mirror 15L4 passes through the converging lens L9 to reach the receptacle L8. The light 7 introduced to the receptacle L8 further passes through the optical fiber connector L7, spectrometer optical fiber L6, the optical fiber connector Ln3, the converging lens Ln2, and the optical fiber connector Ln1 to reach the spectrometer 13. Thus, the light emitted from the light source 5 is subjected to a wavelength analysis.

Figure 84:
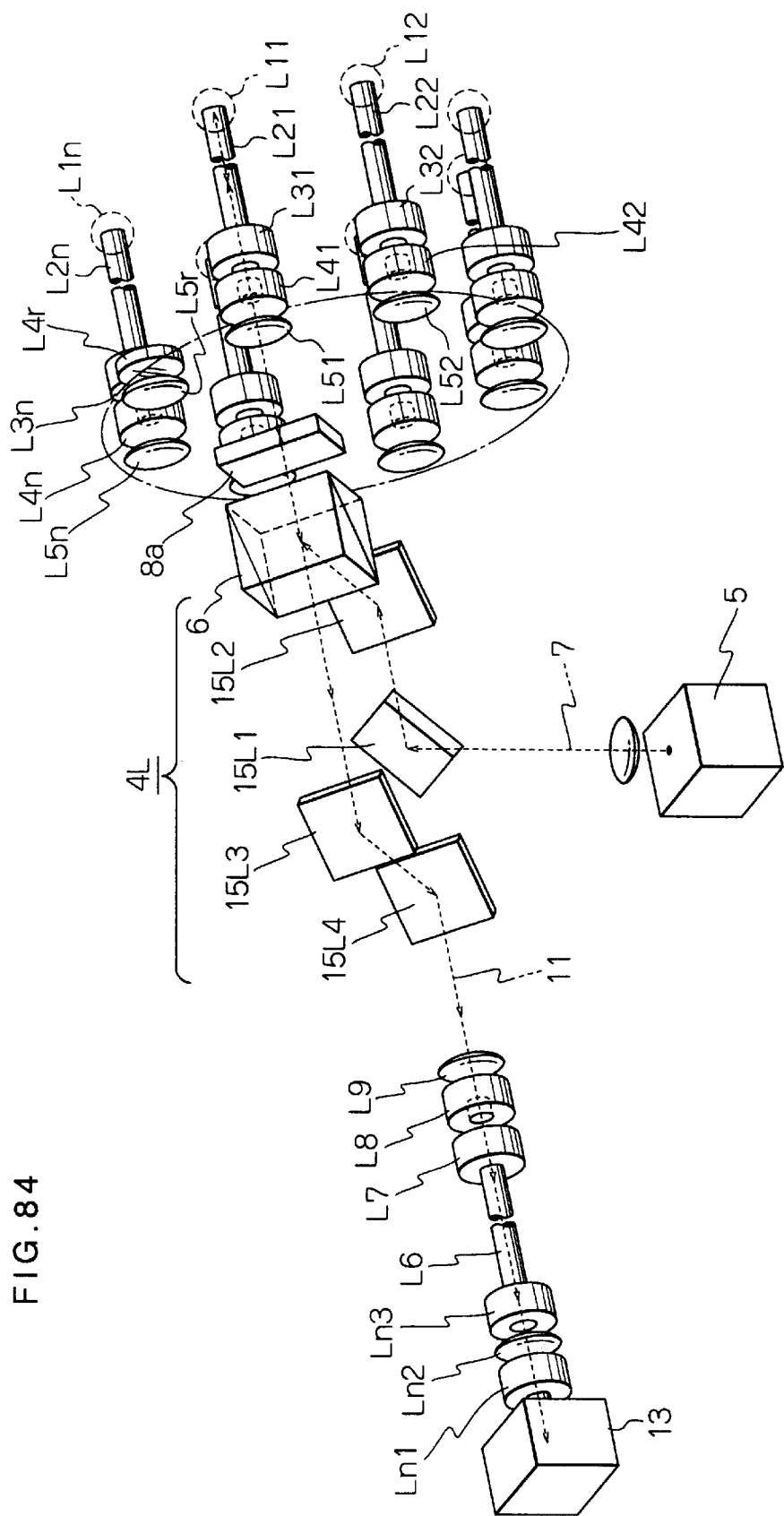
FIG. 84 is a perspective view showing the immunoassay apparatus according to Embodiment 5.12 in a state for an immunoassay with a first SPR sensor.

FIG. 84 shows the immunoassay apparatus of this embodiment in a state for an immunoassay with a first SPR sensor L11. When an immunoassay is to be carried out, the light emitting means 4L is rotated around the aforementioned rotary shaft C so that the beam splitter 6 is moved to a position corresponding to the first sensor optical fiber L21. Here, the first deflection mirror 15L1 is not moved. The light 7 from the light source 5 reaches the SPR sensor L11 and reflected to return as a reflected light 11. The reflected light passes through the beam splitter 6 and introduced to the receptacle L8 by the third deflection mirror 15L3 and the fourth deflection mirror 15L4. The reflected light 11 further passes through the connector L7 and the spectrometer optical fiber L6 to reach the spectrometer 13 for an analysis.

Figure 85:
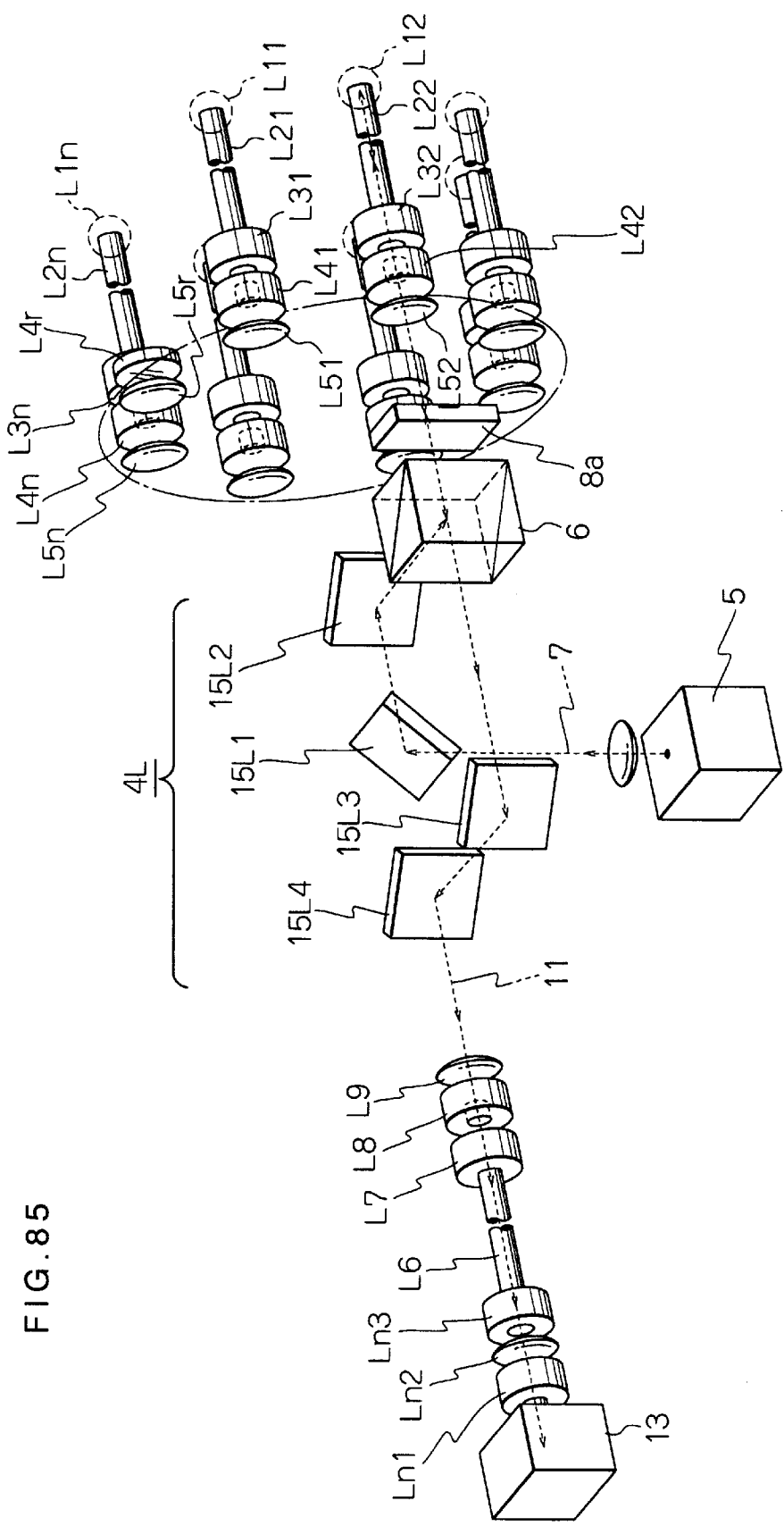
FIG. 85 is a perspective view showing the immunoassay apparatus according to Embodiment 5.12 in a state for an immunoassay with a second SPR sensor.

FIG. 85 shows the immunoassay apparatus of this embodiment in a state for an immunoassay with a second SPR sensor L12. In this case, the light emitting means 4L is further rotated around the aforementioned rotary shaft C so that the beam splitter 6 is moved to a position corresponding to the second sensor optical fiber L22. Here, the first deflection mirror 15L1 is not moved. The immunoassay is carried out in the same way as in the immunoassay with the first SPR sensor L11

Figure 86:
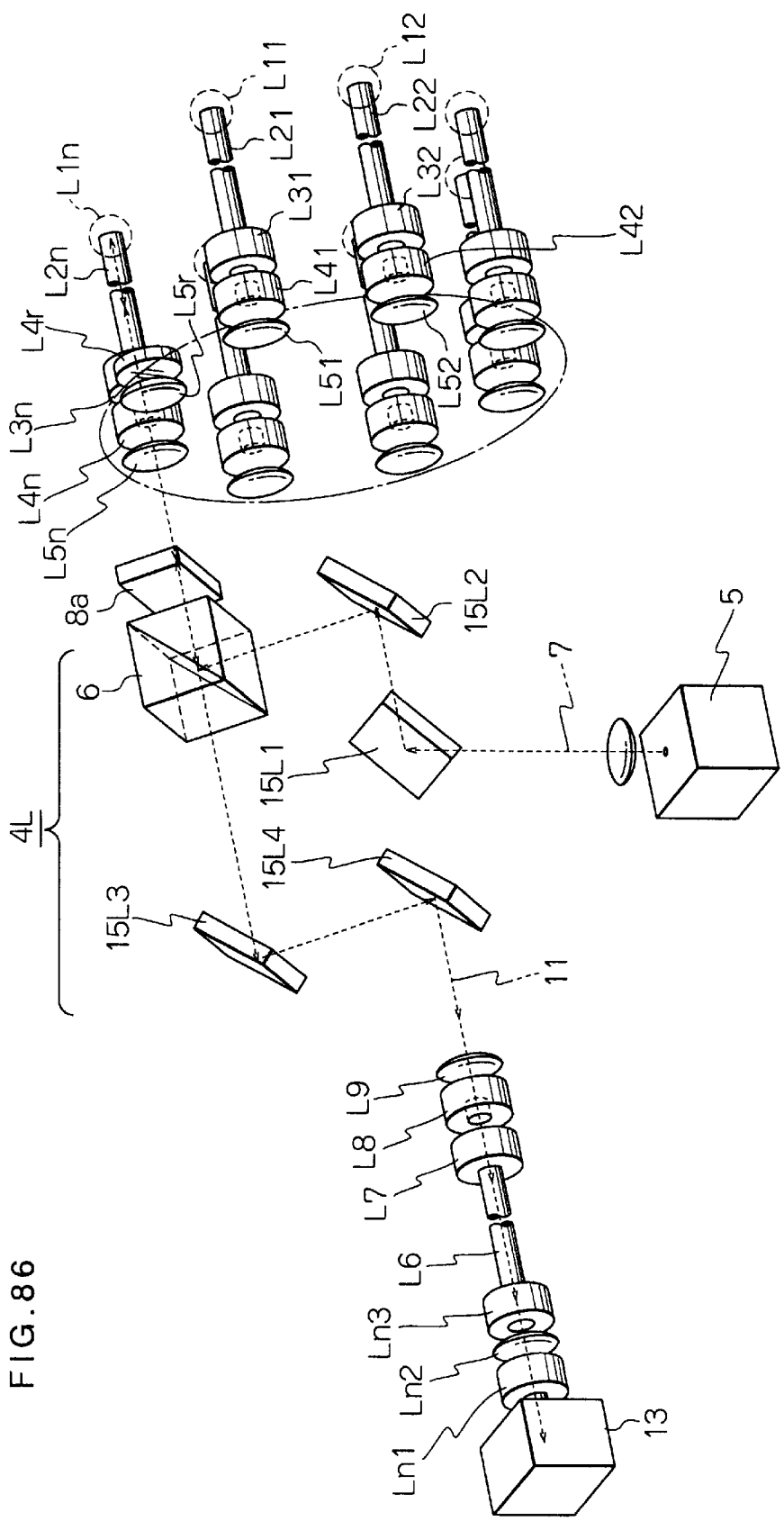
FIG. 86 is a perspective view showing the immunoassay apparatus according to Embodiment 5.12 in a state for an immunoassay with an n-th SPR sensor.

FIG. 86 shows the immunoassay apparatus in a state for an immunoassay with an n-th SPR sensor L1n.

[Embodiment 5.13]

Figure 87:
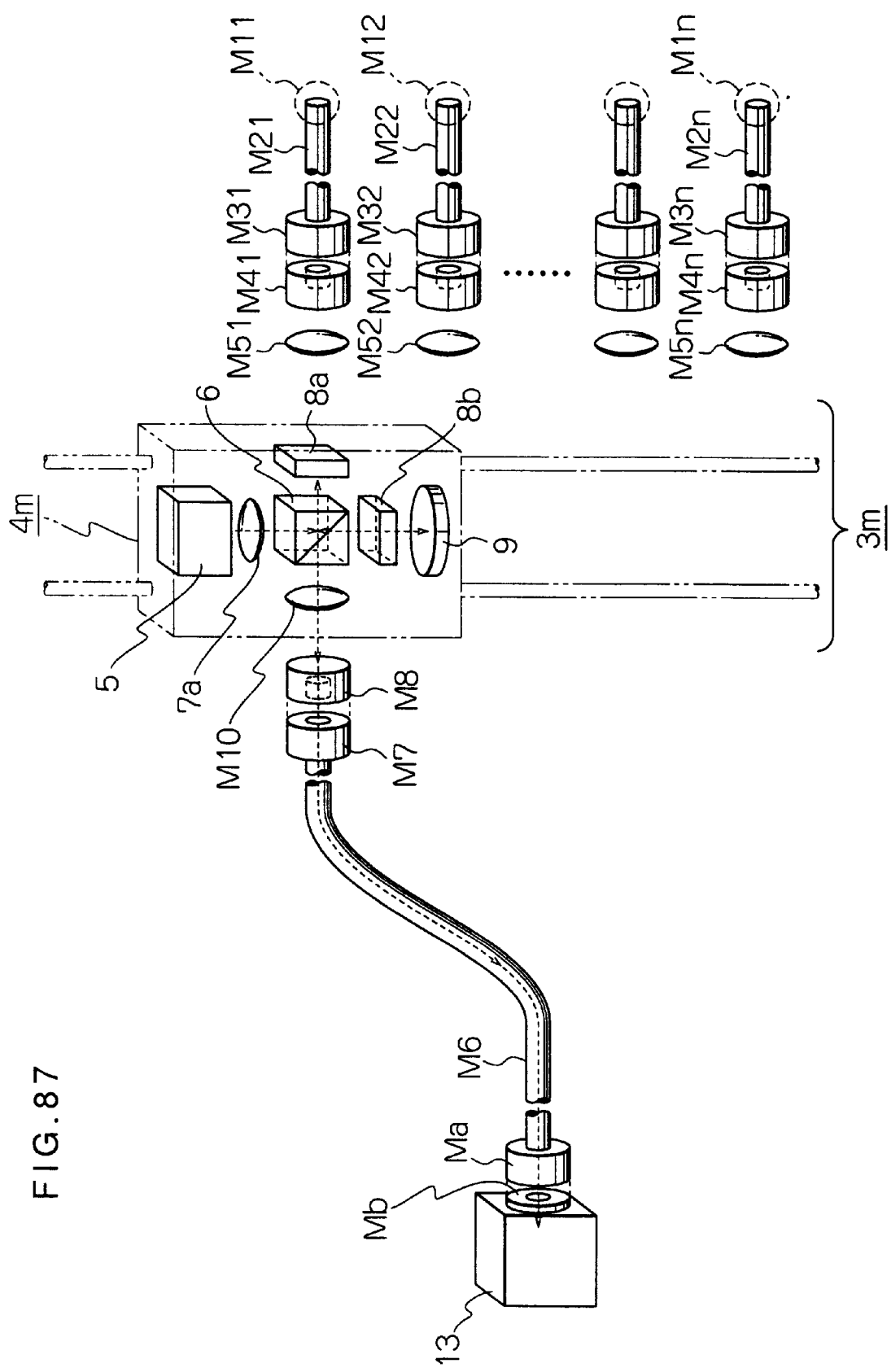
FIG. 87 is a perspective view showing a configuration of an immunoassay apparatus according to an Embodiment 5.13 of the present invention, which is set to a state for reference measurement.

FIG. 87 shows an immunoassay apparatus according to an embodiment 5.13. This embodiment has an almost identical configuration as the embodiment 5.1 except for that one end of the spectrometer optical fiber M6 is connected to the light emitting means 4m. That is, this embodiment uses the spectrometer optical fiber M6 having a sufficient length compared to a distance between the light emitting means 4m and the spectrometer 13. Accordingly, even if the light emitting means 4m is moved, the spectrometer optical fiber M6 can follow the movement.

Figure 88:
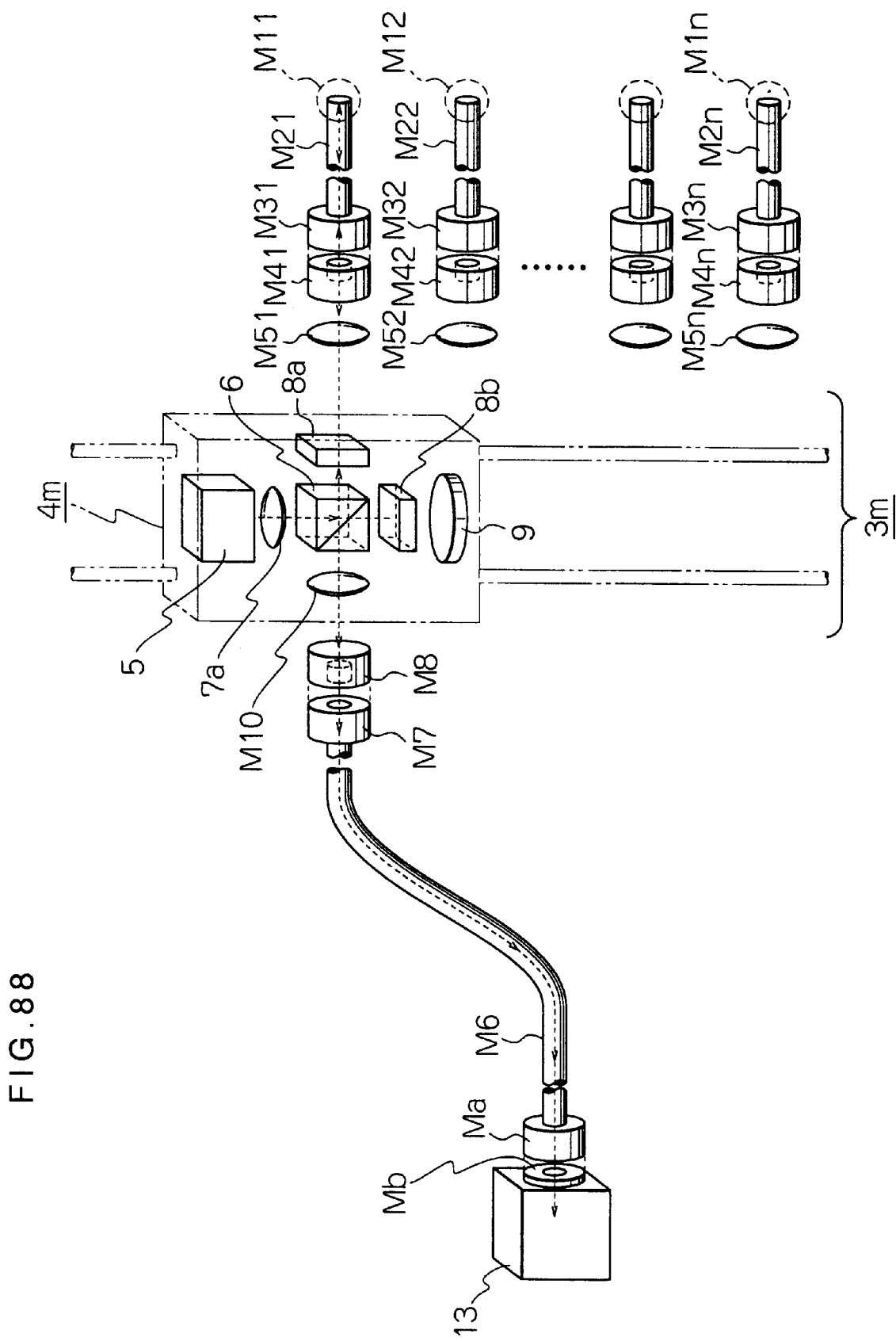
FIG. 88 is a perspective view showing the immunoassay apparatus according to Embodiment 5.13 in a state for an immunoassay with a first SPR sensor.

FIG. 88 shows the immunoassay apparatus of embodiment 5.13 in a state for a reference measurement. As shown in FIG. 88, the light 7 emitted from the light source 5 passes through the converging lens 7a to enter the beam splitter 6. A part of the light 7 is reflected by the beam splitter 6 toward the sensor shutter 8a. The light 7 is shaded by the shutter without reaching any of the SPR sensors M11, M12, . . . , M1n.

On the other hand, a part of the light 7 which has reached the beam splitter passes through the beam splitter 6 and the mirror shutter 8b to reach the reflection mirror 9. The light 7 is reflected by the reflection mirror 9 toward the beam splitter 6, and a part of the light is reflected toward the spectrometer 13. That is, in a reference measurement, the sensor shutter 8a is closed and the mirror shutter 8b is opened. The light 7 reflected by the bean splitter 6 passes through the converging lens M10, the receptacle M8, the optical fiber connector M7, and the spectrometer optical fiber M6 to reach the spectrometer. Thus, it is possible to carry out a wavelength distribution analysis of the light 7 emitted from the light source 5.

FIG. 88 shows the immunoassay apparatus of this embodiment in a state for an immunoassay with a first SPR sensor M11. As shown in the figure, the sensor shutter 8a is opened and the mirror shutter 8b is closed. The light emitting means 4m is positioned so that the optical axis of the light emitting means 4m is matched with the optical axis of the sensor optical fiber M21. Thus, the light 7 emitted from the light source 5 is reflected by the beam splitter 6 and bent toward the SPR sensor M11.

The light 7 passes through the sensor shutter 8a, the converging lens M51, the receptacle M41, and the optical fiber connector M31 to reach the SPR sensor M11. The light 7 advances through the SPR sensor M11 while being reflected by the outer circumference of the end portion of the SPR sensor and reflected by the reflection mirror 3b (mirror coated by a gold or silver film) at the end face of the SPR sensor M11 to return as a reflected light 11 through the sensor optical fiber M21 to the light emitting means 4m. A part of the reflected light 11 passes through the beam splitter 6 and the converging lens M10 as well as the receptacle M8, the optical fiber connector M7, and the spectrometer optical fiber M6 to reach the spectrometer 13. Thus, a wavelength distribution analysis of the reflected light 11 is carried out, terminating the immunoassay with the first SPR sensor M11.

Figure 89:
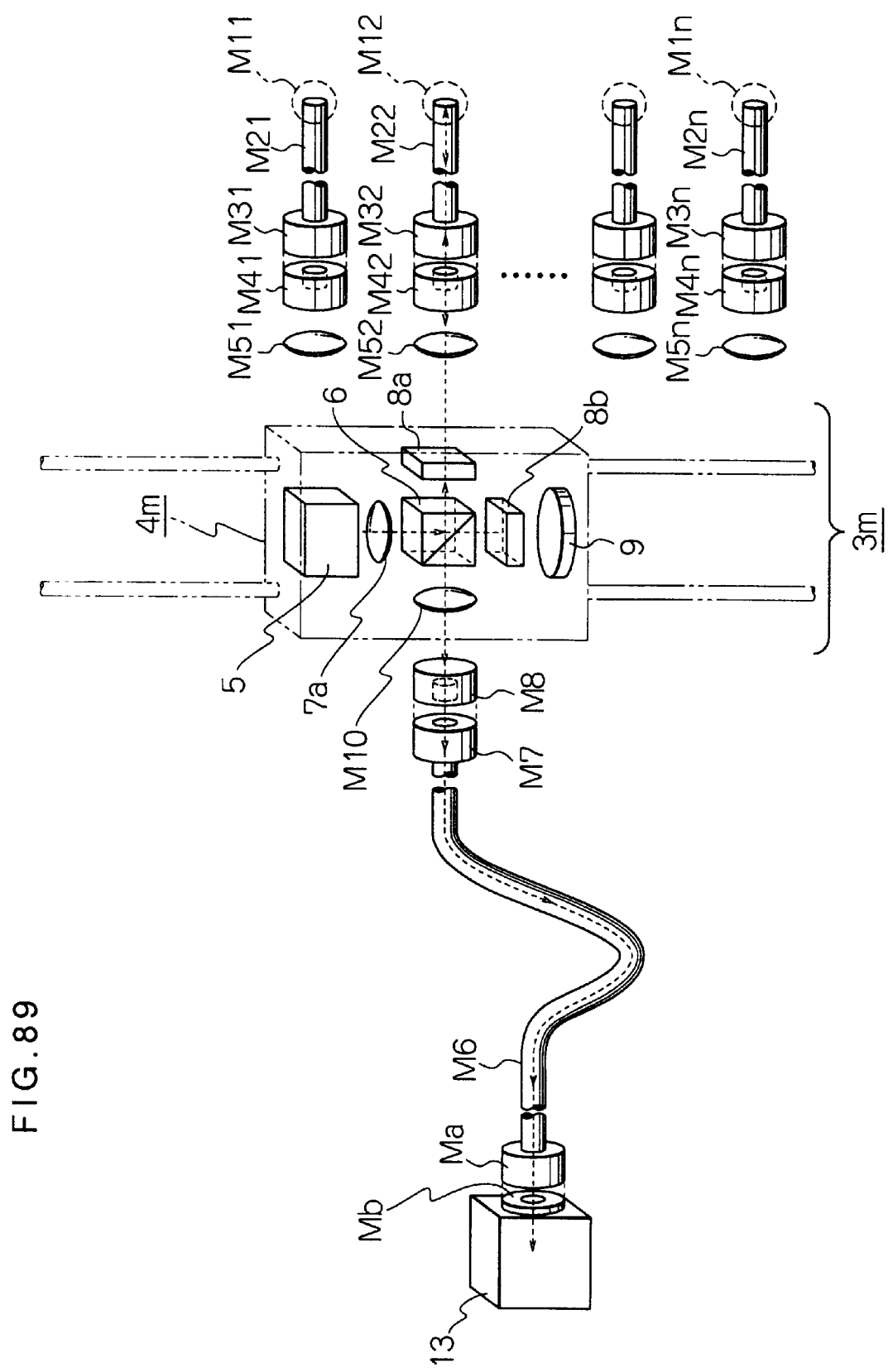
FIG. 89 is a perspective view showing the immunoassay apparatus according to Embodiment 5.13 in a state for an immunoassay with a second SPR sensor.

Next, FIG. 89 shows the immunoassay apparatus in a state for an immunoassay with a second SPR sensor M12. More specifically, the shifting frame is moved to a position where the optical axis of the light emitting means 4m is matched with the optical path of the receptacle M42 which corresponds to the second sensor optical fiber M22. The light 7 from the light source 5, in the same way as in the first SPR sensor, reaches the second SPR sensor M12, where the light is reflected to return as a reflected light 11 which passes through the spectrometer optical fiber M6 to reach the spectrometer 13.

Figure 90:
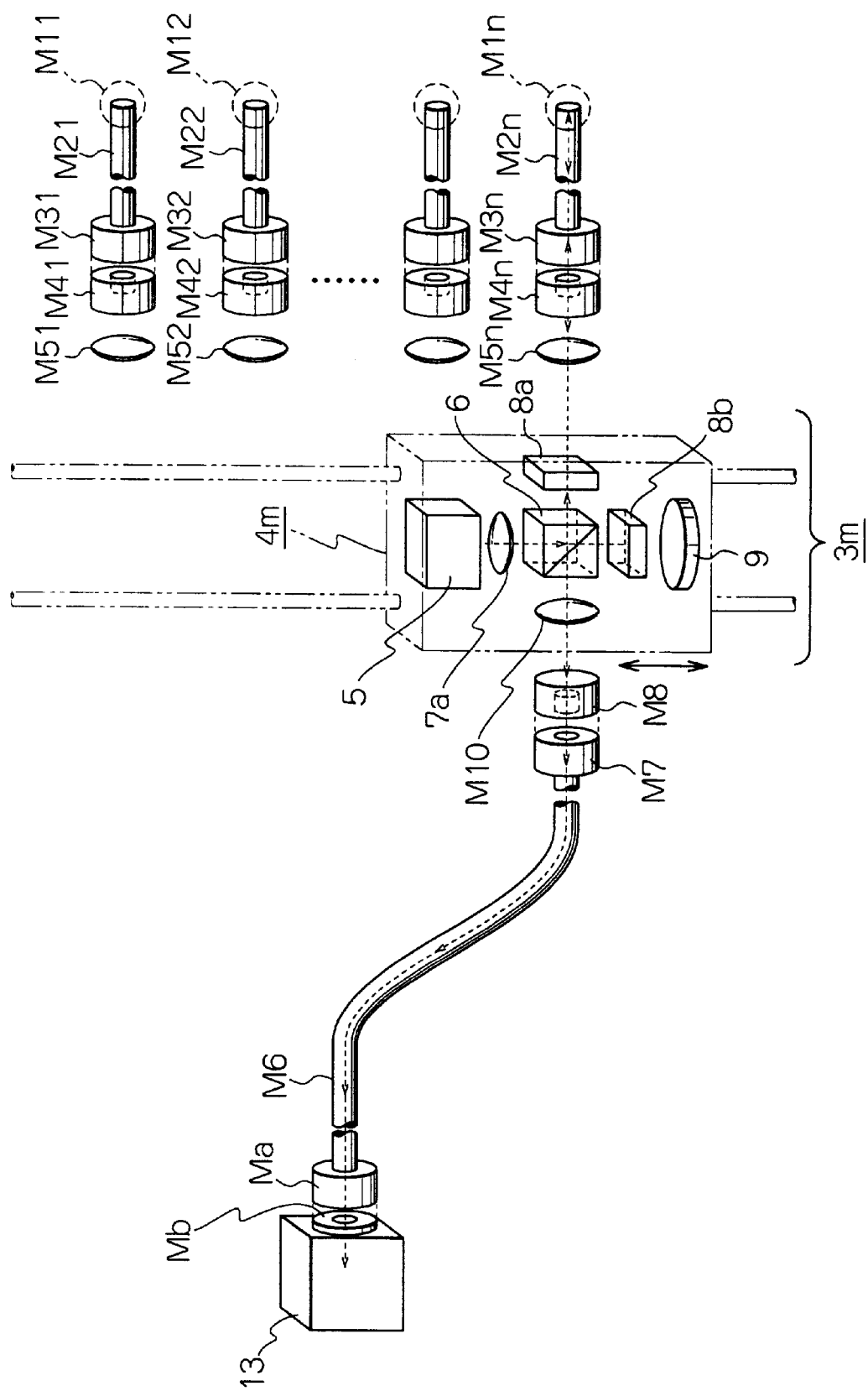
FIG. 90 is a perspective view showing the immunoassay apparatus according to Embodiment 5.13 in a state for an immunoassay with an n-th SPR sensor.

FIG. 90 shows the immunoassay apparatus in a state for an immunoassay with an n-th SPR sensor M1n. In this case also, the shifting frame is moved to a position where the light emitting means 4m is positioned on an optical axis of the n-th converging lens M5n. The reflected light 11 from the SPR sensor M1n passes through the light emitting means 4m and the spectrometer optical fiber M6 to enter the spectrometer 13.

It should be noted that in the aforementioned embodiments, explanation was given on the optical path switching by shifting or rotating the light source. However, in any of the embodiments, the light source may be fixed at a position for emitting a light.

As has been described above, the immunoassay apparatus according to the invention carries out an immunoassay with a SPR sensor using an optical fiber, an excellent effect can be obtained that it is possible to carry out a measurement with a small quantity of a sample at a real time. Besides, use of a plurality of optical fibers enables to carry out a number of immunoassays in a short time.

Moreover, the optical path selecting means provided between the light source and the optical fibers enables to switch the optical path from one to another corresponding to the respective optical fibers so that a plurality of immunoassays can be carried out by a single spectrometer. Besides, the optical path selecting means is constituted by a liquid crystal mask and accordingly, it is possible to make the optical path selecting means with a small size. Because no mechanical drive member is involved, the optical path selecting means can have a high reliability.

Moreover, the SPR sensors connected via the multi-fiber connector can easily be replaced with new ones for an immunoassay of another sample. Because all the portions in contact with a sample are replaced, there is no danger from the biohazard viewpoint.

Moreover, the immunoassay apparatus comprises a light switch for switching between transmission and cut-off the light, thus enabling to easily switch the optical path from one to another. The optical path switching means using a liquid crystal may cause a leak of some light but the light switch can cut-off the light completely.

Moreover, branching means is provided between the light source and the light switches for branching a light to the SPR sensors and to the spectrometer. This enables to obtain a simple configuration of the upstream side of the light switches as well as a simple configuration as a whole compared when splitters are provided in the respective optical fibers.

Moreover, the immunoassay apparatus comprises a suction pump for introducing a sample into a cap member provided for each of the SPR sensors, and it is possible to introduce an accurate quantity of the sample required for an immunoassay.

Moreover, a preservation buffer filled in the cap member enables to retain an antibody fixed on the SPR sensor in a stable state. Besides, this preservation buffer enables to carry out an accuracy test of the immunoassay apparatus.

Furthermore, the immunoassay apparatus comprises a transmission equipment for transmitting an output of the spectrometer to an upper node apparatus. This enables to enhance the operationability of the immunoassay apparatus by evading restrictions caused by a cable or the like.

Moreover, antibodies as a positive control and a negative control are fixed to the SPR sensors. This enables to detect a possible defect of the immunoassay system or non-specific reaction, thus enabling to enhance the measurement accuracy.

The immunoassay apparatus described in claim 11 comprises optical path selecting means having a beam splitter positioned on an optical path of a light from a light source to an SPR sensor; a first shutter positioned at the downstream side of the beam splitter; and a second shutter and mirror positioned on a line which intersects the optical path at a right angle. An incident end of the spectrometer optical fiber is connected to the line on which the beam splitter and the mirror of the optical path selecting means are arranged. Accordingly, by controlling opening/closing of the shutters, it is possible to introduce to the spectrometer a light from the light source and a reflected light from the SPR sensor, thus enabling to alternately analyze the light from the light source and the reflected light in a wavelength distribution. Moreover, by using the beam splitter and the shutter in combination, it is possible to constitute the optical path selecting means with a simplified configuration in a small size.

In the immunoassay apparatus described in claim 12, only an optical fiber portion having an SPR sensor is connected via a connector. When a predetermined immunoassay is complete, the optical fiber having the SPR sensor can be disconnected from the optical path selecting means so that another optical fiber having an SPR sensor can be connected for another immunoassay. Thus, the SPR sensors can be used as a disposable type not requiring a washing step. Moreover, by providing a light switch, it is possible to switch between plurality of optical fibers, enabling to rapidly carry out several immunoassays.

In the immunoassay apparatus described in claim 13, all the optical fibers to be connected to the optical path selecting means are connected via a predetermined connector. This enables to easily replace the SPR sensors as well as to disconnect an optical fiber from the light source and an optical fiber leading to the spectrometer. This enables to use the immunoassay apparatus in such a manner that the apparatus is assembled only when an immunoassay is to be carried out. Any part which has been deteriorated can be replaced independently of the other parts.

In the immunoassay apparatus described in claim 14, the second ends of the optical fibers are held on a predetermined shifting mechanism which is moved so that one of the second ends is matched with the optical path to the spectrometer. Thus, even the immunoassay apparatus has only one spectrometer, the shifting mechanism enables to rapidly switch the optical path from one to another. Accordingly, it is possible to mount a plurality of SPR sensors so that a series of immunoassay is carried out in a short time.

Moreover, in the immunoassay apparatus described in claim 15, a predetermined converging lens is provided between the optical fibers and the optical path leading to the spectrometer. Accordingly, when transmitting a light to an SPR sensor and a light reflected from the SPR sensor to the spectrometer, the light can be converted and transmitted effectively.

In the immunoassay apparatus described in claim 16, a plurality of converging lenses are held on the shifting mechanism so as to correspond to the second ends of the optical fibers. Thus, the converging lenses are also shifted when the shifting mechanism is moved. Accordingly, it is possible to fix beforehand the optical path between the converging lenses and the corresponding optical fibers having the SPR sensors, thus eliminating a complicated positioning control.

In the immunoassay apparatus described in claim 17, each of the optical fibers is divided into a sensor optical fiber having the SPR sensor and an intermediate optical fiber which are connected to each other by an optical fiber connector. When a series of immunoassay is complete, the SPR sensors can be disconnected as having the shortest possible length. This contributes to reduce the immunoassay costs by the immunoassay apparatus. Moreover, it is possible to quickly replace the SPR sensors, thus enabling to complete a number of immunoassays in a short time.

The immunoassay apparatus described in claim 18, each of the sensor optical fibers has an optical fiber connector which is connected via an adapter to a corresponding optical fiber connector provided in each of the intermediate optical fibers.

The immunoassay apparatus described in claim 19, the sensor optical fibers can be disconnected from the optical fiber connectors. When a series of immunoassays is complete, the sensor optical fibers used can be disconnected from the connectors. That is the connectors can be used again. This enables to further suppress the immunoassay costs.

The immunoassay apparatus described in claim 20, the intermediate optical fibers have an identical length. Accordingly, the optical length is not changed when the SPR sensors are switched from one to another, and there is no need of correction for the light intensity for the respective optical fibers.

In the immunoassay apparatus described in claim 21, an optical coupler is provided between the sensor optical fiber and the light source. The optical coupler has an optical path from the light source to the sensor optical fiber and an optical path from the sensor optical fiber to the spectrometer. This enables to easily constitute an optical path from the light source to the sensor optical fiber and an optical path from the sensor optical fiber to the spectrometer. As a result, it is possible to make the immunoassay apparatus small as well as to reduce the production cost.

Moreover, in the immunoassay apparatus described in claim 22, at least two sensor optical fibers are provided and the optical coupler has an optical path from the light source branched to the sensor optical fibers and optical paths leading from the sensor optical fibers to the spectrometer. Besides, in the immunoassay apparatus described in claim 23, each of the sensor optical fibers is provided with a shutter located between the optical coupler and the sensor optical fiber. In the immunoassay apparatus described in claim 24, the optical coupler has an optical path switching function for transmitting only one of the sensor optical fibers.

Thus, it is possible to constitute the immunoassay apparatus with a simple configuration as well as to carry out in a short time an immunoassay for a plurality of samples or a series of immunoassays for a single sample. Because the optical coupler is used, no complicated optical system is required for rapidly switching an optical path to a number of sensor optical fibers.

In the immunoassay apparatus described in claim 25, each of the sensor optical fibers is provided with an optical fiber cable located between the sensor optical fiber and the optical coupler. Accordingly, even when the light source and the spectrometer are located at a fixed position, the sensor optical fibers alone can be moved for samples arranged at separate positions.

Furthermore, in the immunoassay apparatus described in claim 26, the sensor optical fiber is connected to a predetermined optical fiber connector which is connected via a predetermined adapter to the optical coupler. Accordingly, it is possible to quickly replace the sensor optical fiber for a different sample. This is also preferable from the sanitary viewpoint.

In the immunoassay apparatus described in claim 27, light emitting means is held on an optical path switching mechanism so that the light emitting means is positioned at the second end of one of the sensor optical fibers to be used. When an immunoassay with one sensor optical fiber is complete, the optical path switching mechanism operates to position the optical path with the next sensor optical fiber to be used. Thus, it is possible to carry out a number of immunoassays with a simple configuration.

In the immunoassay apparatus described in claim 28, each of the sensor optical fibers is provided with a predetermined deflection mirror for reflecting the light from the sensor optical fiber, toward the spectrometer. Thus, it is possible to introduce a light into the spectrometer with a simple configuration.

In the immunoassay apparatus described in claim 29, the deflection mirrors are concave mirrors. That is, no converging lenses are required. Thus, it is possible to reduce the number of necessary components.

In the immunoassay apparatus described in claim 30, at least two spectrometer optical fibers are provided between the light emitting means and the spectrometer. These spectrometer optical fibers are positioned according to the sensor optical fibers. The sensor optical fibers are united in a predetermined optical coupler into a single optical path connected to the spectrometer. Thus, it is possible to ensure introduction of a reflected light from a sensor optical fiber into the spectrometer.

In the immunoassay apparatus described in claim 31, each of the spectrometer optical fibers is provided with a predetermined converging lens located between the spectrometer optical fiber and the light emitting means. This enables to converge and effectively transmit the light into the spectrometer.

In the immunoassay apparatus described in claim 32, a first deflection mirror is provided in the light emitting means for reflecting a light from a sensor optical fiber, to a direction parallel to a shifting direction of the light emitting means; and a second deflection mirror is provided in the vicinity of the spectrometer for reflecting the light from the first deflection mirror, toward the spectrometer. Accordingly, it is possible to switch the SPR sensors from one to another only by moving the light emitting means.

The immunoassay apparatus described in claim 33, a total reflection mirror is provided in the vicinity of the sensor optical fibers so as to totally reflect the light from the light emitting means, and a deflection mirror is provided between the light emitting means and the spectrometer so as to deflect the light reflected by the total reflection mirror, toward the spectrometer. Accordingly, it is possible to easily carry out a reference measurement only by positioning the light emitting means at a position of this total reflection mirror without providing a reflection mirror or a shutter in the light emitting means.

The immunoassay apparatus described in claim 34, the sensor optical fibers are arranged so as to arrange their cross sections in a circle; the light emitting means is constituted to be rotatable and has a rotary shaft matched with a center axis of the circle of the sensor optical fiber arrangement, and a light emitting member is provided in the light emitting means at a position corresponding to the sensor optical fibers, for emitting a light toward the sensor optical fibers. Accordingly, it is possible to switch between the SPR sensors to be used only by rotating the light emitting means.

The immunoassay apparatus described in claim 35, spectrometer optical fibers are provided between the light emitting means and the spectrometer so as to correspond to the sensor optical fibers; and converging lenses are provided between the spectrometer optical fibers and the light emitting means, so as to correspond to the spectrometer optical fibers. Thus, the light is converged and effectively transmitted to the spectrometer.

The immunoassay apparatus described in claim 36, deflection mirrors are provided between the spectrometer optical fibers and the spectrometer, for deflecting the light from the spectrometer optical fibers, toward the spectrometer. Thus, it is possible to introduce a light from the spectrometer optical fibers to the spectrometer with a simple configuration.

In the immunoassay apparatus described in claim 37, the light emitting means comprises: a light source for emitting a light along the rotary shaft; a first deflection mirror for deflecting the light from the light source, toward the light emitting member; a second deflection mirror for deflecting the light from the SPR sensors toward the rotary shaft; and a third deflection mirror provided on the rotary shaft for deflecting the light toward the spectrometer. Accordingly, it is possible to introduce a light to the spectrometer with a simple configuration. Moreover, because the optical path lengths from the light emitting means to the spectrometer are identical, there is no need of light intensity correction because of the optical path length.

In the immunoassay apparatus described in claim 38, the light emitting means comprises: a first deflection mirror for deflecting a light from a light source provided outside, along the rotary shaft to the SPR sensors; a second deflection mirror for deflecting the light advancing along the rotary shaft, toward the light emitting member; a third deflection mirror for deflecting the light from the SPR sensor toward the rotary shaft; and a fourth deflection mirror provided on the rotary shaft for deflecting the light toward the spectrometer. Accordingly, there is no need of light intensity correction because of the optical path length. Besides, because the light source is provided outside, it is easy to provide a wiring for the light source.

In the immunoassay apparatus described in claim 39, the light emitting means is connected to the spectrometer by a predetermined spectrometer optical fiber. Thus, even when the light emitting means is moved, the optical path length will not be changed. Accordingly, there is no need of light intensity correction because of the optical path length. Besides, the spectrometer is connected by the spectrometer optical fiber, without requiring a complicated optical setting.

Furthermore, in the immunoassay apparatus described in claim 40, the sensor optical fibers are connected via predetermined optical fiber connectors to the immunoassay apparatus and the optical fibers are constituted so that they can be disconnected from the optical fiber connectors. Accordingly, when a predetermined series of immunoassays is complete, the sensor optical fibers having the SPR sensors alone can be removed from the apparatus for connecting another set of sensor optical fibers having SPR sensors. Thus, the sensor optical fibers can be used as a disposable type not requiring a washing step. Moreover, it is possible to carry out a series of immunoassays in a short time.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Applications No. 9-239055 (Filed on Aug. $20^{th}$, 1997), No. 9-342200(Filed on Nov. $27^{th}$, 1997), No. 10-100447 (Filed on Mar. $27^{th}$, 1998), No. 10-166325 (Filed on May $29^{th}$, 1998), No. 10-181693 (Filed on Jun. $12^{th}$, 1998), including specification, claims, drawings and summary are incorporated herein by reference in its entirety.

What is claimed is:

1. An immunoassay apparatus comprising:

at least two optical fibers, each having a first end serving as a surface plasmon resonance (SPR) sensor;

a light source for emitting a predetermined light to a second end of said optical fibers;

optical path selecting means provided between said light source and said second end of said optical fibers;

a spectrometer for analyzing a wavelength distribution of a reflected light reflected by said SPR sensors;

a main control block for controlling operation of said light source and said spectrometer; and an apparatus main body for containing the aforementioned components.

2. An immunoassay apparatus as claimed in claim 1, wherein said optical path selecting means comprises a liquid crystal mask having a function to transmit said light only to one of said optical fibers.

3. An immunoassay apparatus as claimed in claim 1, wherein a multi-fiber connector is provided for simultaneously disconnecting and connecting said optical fibers with said SPR sensors.

4. An immunoassay apparatus as claimed in claim 1, wherein
    each of said SPR sensors is provided with a cap member having a suction hole for introducing a sample into said cap member; and
    a suction pump is provided at a predetermined position in said apparatus main body, for introducing said sample into said cap members.

5. An immunoassay apparatus as claimed in claim 1, wherein a predetermined transmission apparatus is provided in said apparatus main body and an output of said spectrometer is transmitted to said transmission apparatus so that said output of said spectrometer is transmitted from said transmission apparatus to an upper node apparatus.

6. An immunoassay apparatus as claimed in claim 1, wherein antibodies as a positive sensor and a negative sensor are fixed to said SPR sensors.

7. An immunoassay apparatus, comprising:
    at least two optical fibers, each having a first end serving as a surface plasmon resonance (SPR) sensor;
    a light source for emitting a predetermined light to a second end of said optical fibers;
    a spectrometer for analyzing a wavelength distribution of a reflected light reflected by said SPR sensors,
    a main control block for controlling operation of said light source and said spectrometer;
    light switches provided at said second end of said optical fibers for switching between transmission and cut-off of said light; and
    an apparatus main body for containing the aforementioned components.

8. An immunoassay apparatus as claimed in claim 7, said apparatus further comprising branching means provided between said light source and said light switches.

9. An immunoassay apparatus as claimed in claim 7, wherein each of said cap members is filled with a preservation buffer.

10. An immunoassay apparatus comprising: at least two optical fibers, each having a first end serving as an SPR sensor; a light source for emitting a predetermined light to a second end of said optical fibers; a spectrometer for analyzing a wavelength distribution of a reflected light reflected by said SPR sensors; a main control block for controlling operation of said light source and said spectrometer; and optical path selecting means provided between said light source and said SPR sensors for introducing to said spectrometer one of a light from said light source or a reflected light from said SPR sensors,
    said optical path selecting means having: a beam splitter provided on an optical path of the light from said light source to said SPR sensors; a first shutter provided at a downstream side of said beam splitter; and a second shutter and a mirror which are provided on a line intersecting at a right angle said optical path, and
    said spectrometer being connected to a spectrometer optical fiber having an incident end on said line on which said beam splitter and said mirror are provided.

11. An immunoassay apparatus as claimed in claim 10, wherein at least said SPR sensors of said optical fibers are connected via a predetermined connector to said optical path selecting means.

12. An immunoassay apparatus as claimed in claim 10, wherein all the optical fibers connected to said optical path selecting means are connected via predetermined connectors.

13. An immunoassay apparatus comprising: at least two optical fibers, each having a first end serving as an SPR sensor; a light source for emitting a predetermined light to a second end of said optical fibers; and a spectrometer for analyzing a wavelength distribution of a reflected light reflected by said SPR sensors,
    wherein said second ends of said optical fibers are held on a predetermined shifting mechanism which positions one of said second ends of said optical fibers on an optical path leading to said spectrometer.

14. An immunoassay apparatus as claimed in claim 13, wherein a predetermined converging lens is provided between said optical fibers and said optical path leading to said spectrometer.

15. An immunoassay apparatus as claimed in claim 14, wherein a plurality of converging lenses are held on said shifting mechanism so as to correspond to said second ends of said optical fibers.

16. An immunoassay apparatus as claimed in claim 13, wherein each of said optical fibers is divided into a sensor optical fiber having the SPR sensor and an intermediate optical fiber which are connected to each other by an optical fiber connector.

17. An immunoassay apparatus as claimed in claim 16, wherein each of said sensor optical fibers has an optical fiber connector which is connected via an adapter to a corresponding optical fiber connector provided in each of said intermediate optical fibers.

18. An immunoassay apparatus as claimed in claim 16, wherein said sensor optical fibers are detachably connected to said optical fiber connectors.

19. An immunoassay apparatus as claimed in claim 16, wherein said intermediate optical fibers have an identical length.

20. An immunoassay apparatus comprising:
    a sensor optical fiber having at its first end a surface plasmon resonance (SPR) sensor;
    a light source for emitting a predetermined light to second end of said sensor optical fiber;
    a spectrometer for receiving and analyzing a light reflected from said SPR sensor; and
    an optical coupler provided between said sensor optical fiber and said light source, said optical coupler having an optical path from said light source to said sensor optical fiber and an optical path from said sensor optical fiber to said spectrometer, and
    at least two sensor optical fibers, wherein said optical coupler has an optical path from said light source branched to said sensor optical fibers and optical paths leading from said sensor optical fibers to said spectrometer, and
    wherein said optical coupler has an optical path switching function for transmitting only one of said sensor optical fibers.

21. An immunoassay apparatus as claimed in claim 20, wherein each of said sensor optical fibers is provided with an optical fiber cable located between said sensor optical fiber and said optical coupler.

22. An immunoassay apparatus as claimed in claim 20, wherein said sensor optical fiber is connected to a predetermined optical fiber connector which is connected via a predetermined adapter to said optical coupler.

23. An immunoassay apparatus, comprising:
    a sensor optical fiber having at its first end a surface plasmon resonance (SPR) sensor;
    a light source for emitting a predetermined light to second end of said sensor optical fiber;

a spectrometer for receiving and analyzing a light reflected from said SPR sensor; and an optical coupler provided between said sensor optical fiber and said light source, said optical coupler having an optical path from said light source to said sensor optical fiber and an optical path from said sensor optical fiber to said spectrometer, wherein at least two sensor optical fibers are provided and said optical coupler has an optical path from said light source branched to said sensor optical fibers and optical paths leading from said sensor optical fibers to said spectrometer, wherein each of said sensor optical fibers is provided with a shutter located between said optical coupler and said sensor optical fiber.

24. An immunoassay apparatus comprising: at least two sensor optical fibers, each having at its first end an SPR sensor; light emitting means for emitting a predetermined light to second ends of said sensor optical fibers; and a spectrometer for receiving and analyzing a light returned from said SPR sensors, wherein said light emitting means is held on an optical path switching mechanism so that said light emitting means is positioned at the second end of one of said sensor optical fibers.

25. An immunoassay apparatus as claimed in claim 24, said apparatus further comprising a first deflection mirror provided in said light emitting means and a second deflection mirror provided in the vicinity of said spectrometer, wherein said first deflection mirror reflects a light from said sensor optical fibers, into a direction parallel to a shifting direction of said light emitting means, and said second deflection mirror reflects the light from said first deflection mirror, toward said spectrometer.

26. An immunoassay apparatus as claimed in claim 24, said apparatus further comprising a total reflection mirror provided in the vicinity of said sensor optical fibers and a deflection mirror provided between said light emitting means and said spectrometer, wherein said total reflection mirror totally reflects the light from said light emitting means, and said deflection mirror deflects the light reflected by said total reflection mirror, toward said spectrometer.

27. An immunoassay apparatus as claimed in claim 24, wherein said light emitting means is connected to said spectrometer by a predetermined spectrometer optical fiber.

28. An immunoassay apparatus as claimed in claim 24, wherein said sensor optical fibers are connected via predetermined optical fiber connectors to said immunoassay apparatus and said optical fibers are constituted so that they can be disconnected from said optical fiber connectors.

29. An immunoassay apparatus as claimed in claim 24, wherein each of said sensor optical fibers is provided with a predetermined deflection mirror for reflecting the light from said sensor optical fiber, toward said spectrometer.

30. An immunoassay apparatus as claimed in claim 29, wherein said deflection mirrors are concave mirrors.

31. An immunoassay apparatus as claimed in claim 24, wherein each of said sensor optical fibers is provided with a corresponding spectrometer optical fiber which is positioned according to the position of said sensor optical fiber and is connected to an optical coupler where said sensor optical fibers are united into a single optical path connected to said spectrometer.

32. An immunoassay apparatus as claimed in claim 31, wherein each of said spectrometer optical fibers is provided with a predetermined converging lens located between said spectrometer optical fiber and said light emitting means.

33. An immunoassay apparatus as claimed in claim 24, wherein said sensor optical fibers are arranged so as to arrange their cross sections in a circle, said light emitting means is constituted to be rotatable and has a rotary shaft matched with a center axis of said circle of said sensor optical fiber arrangement, and a light emitting member is provided in said light emitting means at a position corresponding to said sensor optical fibers, for emitting a light toward said sensor optical fibers.

34. An immunoassay apparatus as claimed in claim 33, wherein said light emitting means comprises: a light source for emitting a light along said rotary shaft; a first deflection mirror for deflecting said light from said light source, toward said light emitting member; a second deflection mirror for deflecting the light from said SPR sensors toward said rotary shaft; and a third deflection mirror provided on said rotary shaft for deflecting the light toward said spectrometer.

35. An immunoassay apparatus as claimed in claim 33, wherein said light emitting means comprises: a first deflection mirror for deflecting a light from a light source provided outside, along said rotary shaft to said SPR sensors; a second deflection mirror for deflecting said light advancing along said rotary shaft, toward said light emitting member; a third deflection mirror for deflecting the light from said SPR sensor toward said rotary shaft; and a fourth deflection mirror provided on said rotary shaft for deflecting said light toward said spectrometer.

36. An immunoassay apparatus as claimed in claim 33, said apparatus further comprising: spectrometer optical fibers provided between said light emitting means and said spectrometer so as to correspond to said sensor optical fibers; and converging lenses provided between said spectrometer optical fibers and said light emitting means, so as to correspond to said spectrometer optical fibers.

37. An immunoassay apparatus as claimed in claim 36, said apparatus further comprising deflection mirrors provided between said spectrometer optical fibers and said spectrometer, for deflecting said light from said spectrometer optical fibers, toward said spectrometer.

* * * * *